United States Patent
Breuer et al.

(10) Patent No.: US 10,190,112 B2
(45) Date of Patent: Jan. 29, 2019

(54) METHOD FOR THE BIOCATALYTIC CYCLIZATION OF TERPENES AND CYCLASE MUTANTS EMPLOYABLE THEREIN

(71) Applicant: BASF SE, Ludwigshafen (DE)

(72) Inventors: Michael Breuer, Darmstadt (DE); Bernhard Hauer, Fußgönheim (DE); Dieter Jendrossek, Tübingen (DE); Gabriele Siedenburg, Stuttgart (DE); Juergen Pleiss, Asperg (DE); Demet Sirim, Stuttgart (DE); Silvia Fadenrecht, Stuttgart (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/234,529

(22) Filed: Aug. 11, 2016

(65) Prior Publication Data
US 2016/0340666 A1 Nov. 24, 2016

Related U.S. Application Data

(62) Division of application No. 14/560,263, filed on Dec. 4, 2014, now Pat. No. 9,447,404, which is a division of application No. 13/297,798, filed on Nov. 16, 2011, now Pat. No. 8,932,839.

(60) Provisional application No. 61/540,028, filed on Sep. 28, 2011, provisional application No. 61/499,228, filed on Jun. 21, 2011, provisional application No. 61/414,434, filed on Nov. 17, 2010.

(51) Int. Cl.
| | |
|---|---|
| *C12N 9/88* | (2006.01) |
| *C12N 9/10* | (2006.01) |
| *C12N 15/00* | (2006.01) |
| *C12P 7/02* | (2006.01) |
| *C12P 5/00* | (2006.01) |
| *C12N 9/90* | (2006.01) |
| *C12P 7/22* | (2006.01) |

(52) U.S. Cl.
CPC .................. *C12N 9/88* (2013.01); *C12N 9/90* (2013.01); *C12P 5/007* (2013.01); *C12P 7/02* (2013.01); *C12P 7/22* (2013.01); *C12Y 406/01* (2013.01); *C12Y 504/99017* (2013.01); *Y02P 20/52* (2015.11)

(58) Field of Classification Search
CPC .. C12N 9/88; C12N 9/90; C12P 5/007; C12Y 504/9901
USPC ........................... 435/233, 252, 254.2, 320.1
See application file for complete search history.

(56) References Cited

FOREIGN PATENT DOCUMENTS

WO WO-2010/139719 A2 12/2010

OTHER PUBLICATIONS

"Nomenclature Committee of the International Union of Biochemistry and Molecular Biology (NC-IUBMB). Enzyme Supplement 5 (1999)", Eur. J. Biochem., 1999, vol. 264, pp. 610-650.
Daum et al., "Genes and Enzymes Involved in Bacterial Isoprenoid Biosynthesis", Current Opinion in Chemical Biology, 2009, vol. 13, pp. 180-188.
Devos et al., "Practical Limits of Function Prediction", Proteins: Structure, Function and Genetics, 2000, vol. 41, pp. 98-107.
Kisselev, L., "Polypeptide Release Factors in Prokaryotes and Eukaryotes: Same Function, Different Strucutre", Structure, 2002, vol. 10, pp. 8-9.
Neumann et al, "Purification, Partial Characterization and Substrate Specificity of a Squalene Cyclase from *Bacillus acidocaldarius*", Biol. Chem., 1986, vol. 367, pp. 723-729.
Seo et al., "The Genome Sequence of the Ethanologenic Bacterium *Zymomonas mobilis* ZM4" Nature Biotechnology, 2005, vol. 23, No. 1, pp. 63-68.
Whisstock et al., "Prediction of Protein Function From Protein Sequence and Structure", Quarterly Reviews of Biophysics, 2003, vol. 36, No. 3, pp. 307-340.
Witkowski et al., "Conversion of a β-Ketoacyl Synthase to a Malonyl Decarboxylase by Replacement of the Active-Site Cysteine with Glutamine", Biochemistry, 1999, vol. 38, pp. 11643-11650.

*Primary Examiner* — Robert B Mondesi
*Assistant Examiner* — Mohammad Y Meah
(74) *Attorney, Agent, or Firm* — Drinker Biddle & Reath LLP

(57) ABSTRACT

The present invention relates to novel mutants with cyclase activity and use thereof in a method for biocatalytic cyclization of terpenes, such as in particular for the production of isopulegol by cyclization of citronellal; a method for the preparation of menthol and methods for the biocatalytic conversion of further compounds with structural motifs similar to terpene.

4 Claims, 4 Drawing Sheets
Specification includes a Sequence Listing.

```
  1 MGIDRMNSLS RLLMKKIFGA EKTSYKPASD TIIGTDTLKR PNRRPEPTAK
 51 VDKTIFKTMG NSLNNTLVSA CDWLIGQQKP DGHWVGAVES NASMEAEWCL
101 ALWFLGLEDH PLRPRLGNAL LEMQREDGSW GVYFGAGNGD INATVEAYAA
151 LRSLGYSADN PVLKKAAAWI AEKGGLKNIR VFTRYWLALI GEWPWEKTPN
201 LPPEIIWFPD NFVFSIYNFA QWARATMVPI AILSARRPSR PLRPQDRLDE
251 LFPEGRARFD YELPKKEGID LWSQFFRTTD RGLHWVQSNL LKRNSLREAA
301 IRHVLEWIIR HQDADGGWGG IQPPWVYGLM ALHGEGYQLY HPVMAKALSA
351 LDDPGWRHDR GESSWIQATN SPVWDTMLAL MALKDAKAED RFTPEMDKAA
401 DWLLARQVKV KGDWSIKLPD VEPGGWAFEY ANDRYPDTDD TAVALIALSS
451 YRDKEEWQKK GVEDAITRGV NWLIAMQSEC GGWGAFDKDN NRSILSKIPF
501 CDFGESIDPP SVDVTAHVLE AFGTLGLSRD MPVIQKAIDY VRSEQEAEGA
551 WFGRWGVNYI YGTGAVLPAL AAIGEDMTQP YITKACDWLV AHQQEDGGWG
601 ESCSSYMEID SIGKGPTTPS QTAWALMGLI AANRPEDYEA IAKGCHYLID
651 RQEQDGSWKE EEFTGTGFPG YGVGQTIKLD DPALSKRLLQ GAELSRAFML
701 RYDFYRQFFP IMALSRAERL IDLNN
```

Fig. 1a

```
   1 atgggtattg acagaatgaa tagcttaagt cgcttgttaa tgaagaagat
  51 tttcggggct gaaaaaacct cgtataaacc ggcttccgat accataatcg
 101 gaacggatac cctgaaaaga cgaaccggc ggcctgaacc gacggcaaaa
 151 gtcgacaaaa cgatattcaa gactatgggg aatagtctga ataataccct
 201 tgtttcagcc tgtgactggt tgatcggaca caaaagccc gatggtcatt
 251 gggtcggtgc cgtggaatcc aatgcttcga tggaagcaga atggtgtctg
 301 gccttgtggt ttttgggtct ggaagatcat ccgcttcgtc caagattggg
 351 caatgctctt ttggaaatgc agcgggaaga tggctcttgg ggagtctatt
 401 tcggcgctgg aaatggcgat atcaatgcca cggttgaagc ctatgcggcc
 451 ttgcggtctt tggggtattc tgccgataat cctgttttga aaaagcggc
 501 agcatggatt gctgaaaaag cggattaaaa aaatatccgt gtctttaccc
 551 gttattggct ggcgttgatc ggggaatggc cttgggaaaa gacccctaac
 601 cttcccctg aaattatctg gttccctgat aattttgtct tttcgattta
 651 taattttgcc caatgggcgc gggcaaccat ggtgccgatt gctattctgt
 701 ccgcgagacg accaagccgc cgctgcgcc ctcaagaccg attggatgaa
 751 ctgtttccag aaggccgcgc tcgctttgat tatgaattgc cgaaaaaga
 801 aggcatcgat ctttggtcgc aatttttccg aaccactgac cgtggattac
 851 attgggttca gtccaatctg ttaaagcgca atagcttgcg tgaagccgct
 901 atccgtcatg ttttggaatg gattatccgg catcaggatg ccgatggcgg
 951 ttggggtgga attcagccac cttgggtcta tggtttgatg gcgttacatg
1001 gtgaaggcta tcagctttat catccggtga tggccaaggc tttgtcggct
1051 ttggatgatc ccggttggcg acatgacaga ggcgagtctt cttggataca
1101 ggccaccaat agtccggtat gggatacaat gttggccttg atggcgttaa
1151 aagacgccaa ggccgaggat cgttttacgc cggaaatgga taaggccgcc
1201 gattggcttt ggctcgaca ggtcaaagtc aaaggcgatt ggtcaatcaa
1251 actgccgat gttgaacccg gtggatgggc atttgaatat gccaatgatc
1301 gctatcccga taccgatgat accgccgtcg ctttgatcgc cttttcctct
1351 tatcgtgata aggaggagtg gcaaaagaaa ggcgttgagg acgccattac
1401 ccgtggggtt aattggttga tcgccatgca aagcgaatgt ggcggttggg
1451 gagcctttga taaggataat aacagaagta tcctttccaa aattccttt
1501 tgtgatttcg gagaatctat tgatccgcct tcagtcgatg taacggcgca
1551 tgttttagag gcctttggca ccttgggact gtcccgcgat atgccggtca
1601 tccaaaaagc gatcgactat gtccgttccg aacaggaagc cgaaggcgcg
1651 tggtttggtc gttggggcgt taattatatc tatggcaccg gtgcggttct
1701 gcctgctttg gcggcatcg gtgaagatat gacccagcct tacatcacca
1751 aggcttgcga ttggctggtc gcacatcagc aggaagacgg cggttggggc
1801 gaaagctgct cttcctatat ggagattgat tccattggga agggcccaac
1851 cacgccgtcc cagactgctt gggctttgat ggggttgatc gcggccaatc
1901 gtcccgaaga ttatgaagcc attgccaagg gatgccatta tctgattgat
1951 cgccaagagc aggatggtag ctggaaagaa gaagaattca ccggcaccgg
2001 attccccggt tatggcgtgg gtcagacgat caagttggat gatccggctt
2051 tatcgaaacg attgcttcaa ggcgctgaac tgtcacgggc gtttatgctg
2101 cgttatgatt tttatcggca attcttcccg attatggcgt taagtcgggc
2151 agagagactg attgatttga ataattga
```

Fig. 1b

METHOD FOR THE BIOCATALYTIC CYCLIZATION OF TERPENES AND CYCLASE MUTANTS EMPLOYABLE THEREIN

RELATED APPLICATIONS

This application is a divisional of U.S. application Ser. No. 14/560,263, filed Dec. 4, 2014, U.S. Pat. No. 9,447,404, which is a divisional of U.S. application Ser. No. 13/297,798, filed Nov. 16, 2011, now U.S. Pat. No. 8,932,839, which claims the benefit under 35 U.S.C. § 119(e) of U.S. Provisional Application No. 61/414,434, filed Nov. 17, 2010, U.S. Provisional Application No. 61/499,228, filed Jun. 21, 2011, and U.S. Provisional Application No. 61/540,028, filed Sep. 28, 2011. The entire content of each aforementioned application is hereby incorporated by reference in its entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_074012_0194_02. The size of the text file is 1,428 KB, and the text file was created on Aug. 11, 2016.

BRIEF DESCRIPTION OF THE INVENTION

The present invention relates to novel methods for cyclizing terpenes using cyclases and to novel mutants with cyclase activity and use thereof in a method for biocatalytic cyclization of terpenes, such as in particular for the production of isopulegol by cyclization of citronellal; a method for the preparation of menthol and methods for the biocatalytic conversion of further compounds with structural motifs similar to terpene.

BACKGROUND OF THE INVENTION

Isopulegol of formula (II) (2-isopropenyl-5-methyl-cyclohexanol) is a terpene that is used as an aroma compound, to generate "flower notes". Moreover, it is an intermediate in the synthesis of menthol from citral.

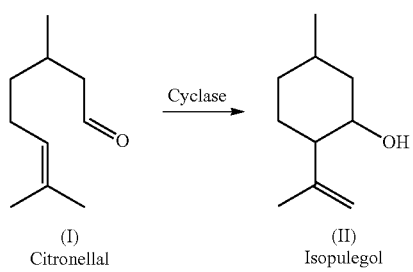

(I) Citronellal
(II) Isopulegol

Isopulegol isomers occur in nature in a large number of essential oils. As isopulegol is formed relatively easily from citronellal, the compound of formula (I) (3,7-dimethyloct-6-en-1-al), it often occurs accompanying citronellal or is formed during extraction of the essential oil. Isopulegol, which is produced industrially from (+)-citronellal, is as a rule a mixture of different isomers with a high proportion of (−)-isopulegol.

The industrial production of isopulegol is mainly carried out by the chemical cyclization of (+)-citronellal. Originally 80-85% pure raw material obtained from citronella oil was used. Since the 1990s this has increasingly been replaced with the optically purer (+)-citronellal (97.5%) from the so-called Takasago process. Here, geranyldiethyldiamine is isomerized asymmetrically to (+)-citronellal using an Rh-BINAP-complex catalyst (Rh-complex with 2,2′-bis-(diphenylphosphino)-1,1′-binaphthyl).

The chemical synthesis of isopulegol starting from citronellal has been described many times. (+)-Citronellal can be cyclized using a copper-chromium catalyst, zinc bromide, alkylaluminum chloride, a rhodium complex, a solid acid-base catalyst, zeolite or silica gel. In recent times the silica gel method has increasingly been superseded by the method with zinc bromide, as the latter has higher selectivity.

The cyclization of terpenes with the aid of special cyclases is generally known. For example, in nature squalene is cyclized by a squalene-hopene cyclase (SHC) to the pentacyclic hopene.

The gene and protein sequences of squalene-hopene cyclase derived from the bacterium *Zymomonas mobilis* (Zm-SHC) are known (Genpept Accession No AAV90172 2004 and Nat Biotechnol 2005, 23:63-68, cf. SEQ ID NO: 1 and 2).

In international application PCT/EP2010/057696 (WO2010139719 A2), to the complete disclosure of which reference is expressly made herein, polypeptides are proposed as biocatalysts for the cyclization of homofarnesol to ambroxan.

The biosynthesis of numerous monoterpenes in the corresponding production organisms has already been elucidated. Frequently this involves cyclization of linear precursor molecules by highly specific biocatalysts. The precursors are generally esters of linear terpene alcohols and diphosphoric acid. One typical example of such a precursor is geranyl pyrophosphate. The pyrophosphate group is eliminated from the molecule enzymatically, and is subsequently hydrolyzed into two phosphate ions. On the other side, a carbocation is formed, which is then able to undergo further intramolecular reaction and which recombines to form a cyclic monoterpene, with elimination of a proton, for example (Curr. Opin. Chem. Biol. 2009, 13: 180-188).

A problem to be solved by the present invention, furthermore, was to find an alternative to the known chemical cyclization methods for terpenes, allowing terpene compounds to be cyclized by means of enzymatic catalysis, such as the linear citronellal to be cyclized to isopulegol, for example.

The problem to be solved by the present invention was furthermore to provide novel biocatalysts that can be used for the cyclization of terpenes, for example of citronellal with formation of isopulegol.

SUMMARY OF THE INVENTION

The above first problem is solved by a method of production of isopulegol of general formula (I)

(I)

comprising one reaction step, wherein citronellal of general formula (II)

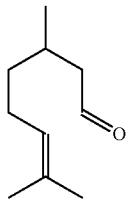

is cyclized biocatalytically to the corresponding isopulegol of formula (I) by means of an enzyme having the activity of citronellal-isopulegol cyclase.

The above second problem could, surprisingly, be solved by providing mutants of wild-type enzymes, such as Zm-SHC-1 (SEQ ID NO:2). In particular it was in fact found that through targeted introduction of mutations in at least one highly conserved sequence position in said cyclases, in particular squalene-hopene cyclases (cf. alignment of SEQ ID NOs. 2 to 326, below) the enzymatic activity can be influenced in the desired manner.

DESCRIPTION OF THE FIGURES

FIG. 1a shows the wild-type amino acid sequence (SEQ ID NO: 2) of squalene-hopene cyclase 1 from *Zymomonas mobilis* (Zm-SHC-1). Position 486 of saturation mutagenesis is marked.

FIG. 1b shows the wild-type nucleic acid sequence (SEQ ID NO: 1) of Zm-SHC-1. Positions 1456-1458 of saturation mutagenesis are marked.

DETAILED DESCRIPTION OF THE INVENTION

A. General Definitions

Figure 2:
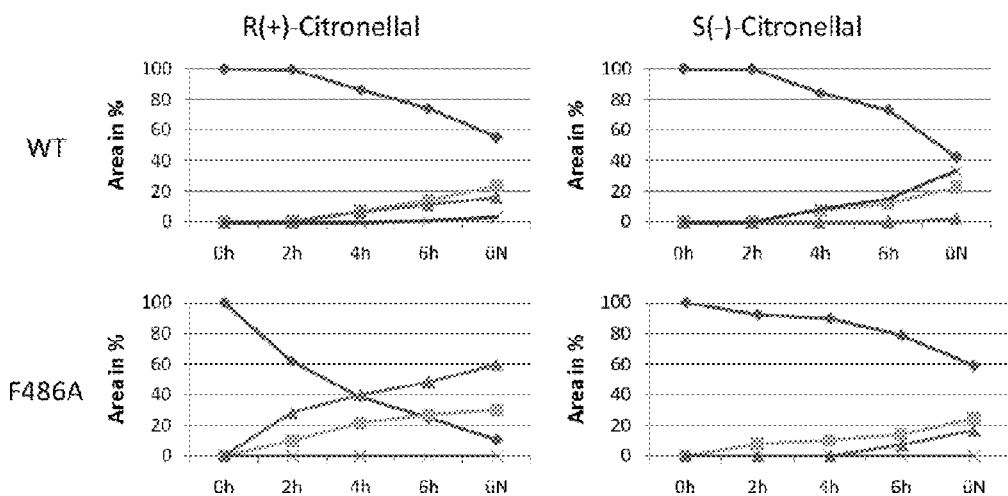
FIG. 2 shows the turnover of the SHC_1 WT protein compared with the F486A mutant as a function of time with 10 mM R(+)- and S(−)-citronellal as substrate. The percentage distribution of substrate and isopulegol product isomers after incubation for various times at 30° C. is shown in each case. Citronellal (diamonds), isopulegol I (squares), isopulegol II (triangles) and isopulegol III (crosses).

"Cyclases" in the sense of the present invention are generally enzymes or enzyme mutants, which in particular display the activity of a citronellal-isopulegol cyclase. Intramolecular transferases from the isomerase subclass are suitable as enzymes with the activity of a citronellal-isopulegol cyclase; i.e. proteins with the EC number EC 5.4. (Enzyme code according to Eur. J. Biochem. 1999, 264, 610-650). In particular they are representatives of EC 5.4.99.17. Suitable enzymes with the activity of a citronellal-isopulegol cyclase are in particular those cyclases that also bring about the cyclization of homofarnesol to ambroxan or of squalene to hopene (hence sometimes also designated "SHC": squalene hopene cyclase) and which are described in detail in international application PCT/EP2010/057696, to which reference is expressly made here. In particular, cyclases according to the invention are those that are derived by mutation of SHCs.

On the basis of the reversibility of enzymatic reactions, the present invention relates to the enzymatic reactions described herein in both directions of reaction.

"Functional mutants" of a "cyclase" include the "functional equivalents" of such enzymes defined below.

The term "biocatalytic process" refers to any process carried out in the presence of catalytic activity of a "cyclase" according to the invention or of an enzyme with "cyclase activity", i.e. processes in the presence of raw, or purified, dissolved, dispersed or immobilized enzyme, or in the presence of whole microbial cells, which have or express such enzyme activity. Biocatalytic processes therefore include both enzymatic and microbial processes.

The term "stereospecific" means that one of several possible stereoisomers of a compound produced according to the invention is produced with at least one asymmetry center by the action of an enzyme according to the invention in high "enantiomeric excess" or high "enantiomeric purity", for example at least 90% ee, in particular at least 95% ee, or at least 98% ee, or at least 99% ee. The ee % value is calculated from the following formula:

$$ee\% = [X_A - X_B]/[X_A + X_B] * 100,$$

in which $X_A$ and $X_B$ stand for the mole fraction of enantiomers A and B respectively.

"First sphere residues" and "second sphere residues" are amino acid residues which, based on structural analyses of the protein, are assigned a special proximity to the reactive center of the cyclase. The criterion for the first sphere is the distance from the ligand 2-azasqualene, which is given in a published x-ray structure (pdb: 1 ump). These residues were determined automatically with a computer program (ligin.weizmann.ac.il/cgi-bin/lpccsu/LpcCsu.cgi; Sobolev V, Sorokine A, Prilusky J, Abola E E, Edelman M. Automated analysis of interatomic contacts in proteins. Bioinformatics 1999; 15(4):327-332.). This program assumes that two molecules are in contact with each other when the distance between their atoms corresponds to the sum of their van der Waals radii±1 Å. The second sphere includes all amino acids that are located in a radius of 5 Å to each residue of the first sphere. Such residues therefore appear to be especially suitable for undertaking directed mutation, for further targeted modification of the enzyme activity.

"Cyclase activity", determined with a "reference substrate under standard conditions", is e.g. an enzyme activity that describes the formation of a cyclic product from a noncyclic substrate. Standard conditions are e.g. substrate concentrations from 10 mM to 0.2 M, in particular 15 to 100 mM, for example about 20 to 25 mM; at pH 4 to 8, and at temperatures of e.g. 15 to 30 or 20 to 25° C. It can be determined with recombinant cyclase-expressing cells, lysed cyclase-expressing cells, fractions thereof or enriched or purified cyclase enzyme. In particular the reference substrate is a citronellal of formula (II); in particular R(+)-citronellal, or a citronellal racemate, in a concentration from 15 to 100 mM or about 20 to 25 mM, at 20 to 25° C. and pH 4-6, such as 4.5; as is also described in more detail in the examples.

An "F486-analog" position corresponds to position F486 according to SEQ ID NO:2 from the functional standpoint and can be determined by sequence alignment of SHCs from organisms other than *Zymomonas mobilis* as explained herein. For example the F486-analog position of SEQ ID NO:3 is position F449 and of SEQ ID NO:4 position F481 and of SEQ ID NO:5 position F447 and of SEQ ID NO:6 position F438. Corresponding analogies apply to the other sequence positions described concretely for SEQ ID NO: 2 herein, such as the so-called "first sphere residues" and "second sphere residues" or of the DXDD motif and their analogous positions in SEQ ID NO:3 to 326).

"Terpenes" are hydrocarbons that are made up of isoprene units (C5 units), in particular noncyclic terpenes, for example squalene, the carbon number of which is divisible by 5.

"Terpenoids" are substances that are derived from terpenes, in particular noncyclic terpenes, e.g. by additional insertion of carbon atoms and/or heteroatoms, for example citronellal.

"Terpene-like" compounds for the purposes of the present invention comprise in particular those compounds which fall within the general structural formula (IV) as defined below.

Generally encompassed in accordance with the invention are all isomeric forms of the compounds described herein, such as constitutional isomers and more particularly stereoisomers and mixtures thereof, such as optical isomers or geometric isomers, such as E- and Z-isomers, and also combinations thereof. Where there are two or more centers of asymmetry in a molecule, the invention encompasses all combinations of different conformations of these centers of asymmetry, such as pairs of enantiomers, for example.

"Menthol" encompasses all stereoisomeric forms such as (+)-menthol, (+)-isomenthol, (+)-neomenthol, (+)-neoisomentol, (−)-menthol, (−)-isomenthol, (−)-neomenthol, (−)-neoisomenthol and any desired mixtures thereof.

Citronellal of formula (II) is commercially available both as R(+)-citronellal of formula (R-II) and as S(−)-citronellal of formula (S-II) and as racemate of formula (II).

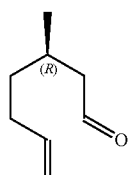

(R-II)

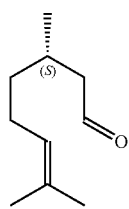

(S-II)

Isopulegol of formula (I)

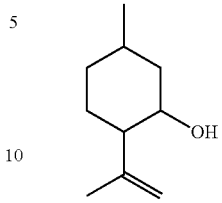

(I)

has in positions 1, 3 and 6 in each case an optically active center, so that in principle 4 different diastereomers with in each case 2 enantiomers, thus altogether 8 stereoisomers, are conceivable, starting from the racemate of citronellal of formula (I).

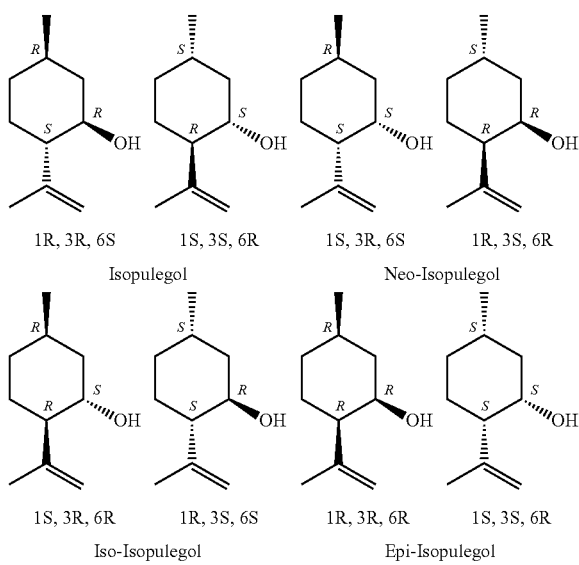

Isopulegol is also called isopulegol I, neo-isopulegol is also called isopulegol II; iso-isopulegol is also called isopulegol III; epi-isopulegol or neo-iso-isopulegol is also called isopulegol IV.

Unless indicated otherwise, the general chemical definitions that apply herein are as follows:

Alkyl and also all alkyl moieties in radicals derived therefrom, such as hydroxyalkyl, for example: saturated, straight-chain or branched hydrocarbon radicals having 1 to 4, 1 to 6, 1 to 8 or 1 to 10 carbon atoms, e.g.

$C_1$-$C_6$-alkyl: such as methyl, ethyl, propyl, 1-methylethyl, butyl, 1-methylpropyl, 2-methylpropyl and 1,1-dimethylethyl as exemplary representatives of $C_1$-$C_4$-alkyl; and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Hydroxy-$C_1$-$C_6$-alkyl, comprising hydroxy-$C_1$-$C_4$-alkyl, such as e.g. hydroxymethyl, 1- or 2-hydroxyethyl, 1-, 2- or 3-hydroxypropyl, 1-hydroxymethylethyl, 1-, 2-, 3- or 4-hydroxybutyl, 1-hydroxymethylpropyl and 2-hydroxymethylpropyl.

Alkenyl stands for mono- or polyunsaturated, more particularly monounsaturated, straight-chain or branched hydrocarbon radicals having 2 to 4, 2 to 6, 2 to 8, 2 to 10 or 2 to 20 carbon atoms and one double bond in any desired position, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Oxo", for example, is a radical which together with the C atom to which it is bonded forms a keto group (C=O).

"Methylene" (=$CH_2$), for example, is a radical which together with the C atom to which it is bonded forms a vinyl radical (—CH=$CH_2$).

B. Special Embodiments of the Invention

The present invention relates in particular to the following special embodiments:

1. Enzyme mutant with cyclase activity, selected from mutants of a wild-type enzyme, which comprises an amino acid sequence, selected from SEQ ID NO: 2 to 326 or a partial sequence thereof; wherein the mutant catalyzes at least the cyclization of at least one citronellal isomer (or a mixture of isomers, for example racemate) according to the above definition to at least one isopulegol isomer (or to a pair of diastereomers I to IV, for example I and/or II) according to the above definition, wherein the partial sequence or short form of the cyclase comprises e.g. at least 50, 100, 150, 200, 250, 300, 350, 400, 450, 500, 550, 600, 650 or 700 continuous amino acid residues of one of these sequences, and is accessible e.g. by N- and/or C-terminal shortening of the concrete sequences.

2. Enzyme mutant according to embodiment 1, comprising
   a) a mutation in position F486 of SEQ ID NO: 2 or
   b) a mutation in a sequence selected from SEQ ID NO: 3 to 326, wherein the mutated position corresponds to position F486 of SEQ ID NO: 2 (i.e. is an "F486-analog" position);
   wherein at least the cyclization of at least one citronellal isomer to at least one isopulegol isomer is made possible by the mutation (i.e. the corresponding original or wild-type protein did not catalyze this reaction) or is modified (i.e. the corresponding original or wild-type protein catalyzed this reaction, but e.g. at lower product yield, turnover rate and/or stereospecificity). Moreover, the partial sequence or short form of the cyclase also has this cyclase-typical mutation in a position corresponding to F486 from SEQ ID NO: 2. For example, an N-terminally shortened version of the cyclase according to SEQ ID NO: 2 is an example of said short version. This is characterized by the following N-terminus: (M)<u>K</u>IFGAEKTSYKPASDTIIGTDTLKRPN . . . wherein the N-terminal <u>K</u> corresponds to position 16 of SEQ ID NO:2.

3. Enzyme mutant according to one of the preceding embodiments in which up to 25% or up to 20, 15, 10, 9, 8, 7, 6, 5, 4, 3, 2 or 1% of the amino acid residues, for example 1 to 30, 2 to 25, 3 to 20 or 4 to 15 or 5 to 10 of the amino acid residues, are in each case altered relative to the unmutated wild-type sequence according to SEQ ID NO: 2 to 326, by deletion, insertion, substitution, addition, inversion or a combination thereof.

4. Enzyme mutant according to one of the preceding embodiments, in which the mutation in position F486 of SEQ ID NO:2 or in a position corresponding to this position in one of the sequences according to SEQ ID NO: 3 to 326, is a substitution selected from F486N, F486Q, F486L, F486M, F486E, F486G, F486S, F486V, F486T, F486C, F486I and F486A or optionally selected from F486H, F486Y, F486W and F486D.

5. Enzyme mutant according to one of the preceding embodiments, in which additionally (or alternatively, but in particular additionally) at least one, for example 1, 2, 3, 4, 5, 6, 7, or 8, mutations in one of the positions W374, D437, D440, F428, W555, Y561, Y702, Y705 (the so-called "first sphere residues") of SEQ ID NO: 2 or in at least one corresponding position selected from these positions, is present in one of the sequences according to SEQ ID NO: 3 to 326.

6. Enzyme mutant according to one of the preceding embodiments, in which there is no mutation in position D437 and/or D439 and/or D440 of SEQ ID NO: 2 (DXDD motif) or the respective corresponding position in one of the sequences according to SEQ ID NO: 3 to 326.

7. Enzyme mutant according to one of the preceding embodiments, in which there is no mutation in position Y702 of SEQ ID NO: 2 or in the corresponding position in one of the sequences according to SEQ ID NO: 3 to 326, or if a mutation is present, this is a substitution Y702F or optionally Y702E or Y702D or corresponding substitution.

8. Enzyme mutant according to one of the preceding embodiments, which optionally is further mutated in at least one, for example 1 to 15, 1 to 10 or 1 to 5, such as 1, 2, 3 or 4, of positions P229, D439, D508, E601, G553, G556, N432, P436, P499, R224, S371, T376, T563, W414 or W624 (the so-called "second sphere residues") of SEQ ID NO: 2 or in at least one corresponding position selected from these positions, in one of the sequences according to SEQ ID NO: 3 to 326; and optionally a further mutation in position E429, L700 and R554 of SEQ ID NO: 2 or the analogous positions of SEQ ID NO: 3 to 326.

9. Enzyme mutant according to one of the preceding embodiments, selected from
   a) the single mutants
      F486X with X=N, Q, L, M, E, G, S, V, T, C, I or A according to SEQ ID NO: 2 or a short version thereof;
      Y702X with X=F, A, C or S according to SEQ ID NO: 2 or a short version thereof;

Y561X with X=A or S according to SEQ ID NO: 2 or a short version thereof;
wherein the short version comprises e.g. the following N-terminal sequence:

(M) KIFGAEKTSYKPASDTIIGTDTLKRPN...

b) the multiple mutants F486A/Y702A, F486A/Y561A or F486A/Y705A according to SEQ ID NO: 2
c) the mutants corresponding to a) or b), derived from one of SEQ ID NO: 3 to 325.
10. Enzyme mutant according to one of the preceding embodiments, which comprises at least 50%, for example 50 to 100% or more than 100%, for example >100 to 1000%, in each case determined under standard conditions using a reference substrate that displays citronellal-isopulegol cyclase activity of an enzyme, which has an amino acid sequence according to SEQ ID NO: 2 from position 1 to 725, 2 to 725 or 16 to 725, optionally extended N-terminally with a methionine residue.
11. Enzyme mutant according to embodiment 10, wherein the citronellal-isopulegol cyclase activity is determined under standard conditions using a citronellal, for example the racemate or the R(+) form, as reference substrate.
12. Enzyme mutant according to one of the preceding embodiments, wherein the mutation takes place in an enzyme, and comprises an amino acid sequence according to SEQ ID NO: 2 from position 1 to 725, 2 to 725 or 16 to 725, optionally extended N-terminally with a methionine residue.
13. Nucleic acid sequence coding for a mutant according to one of the preceding embodiments.
14. Expression cassette, comprising a nucleic acid sequence according to embodiment 13.
15. Recombinant vector, comprising, under the control of at least one regulatory element, at least one nucleic acid sequence according to embodiment 13 or at least one expression cassette according to embodiment 14.
16. Recombinant microorganism, comprising at least one nucleic acid sequence according to embodiment 13 or at least one expression cassette according to embodiment 14 or at least one vector according to embodiment 15.
17. Biocatalytic process for producing isopulegol of general formula (I)

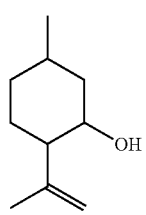

(I)

wherein citronellal of general formula (II)

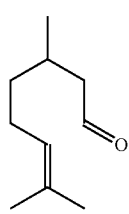

(II)

is cyclized to isopulegol of formula (I) by means of an enzyme of EC class EC 5.4.99, in particular of EC class EC 5.4.99.17, or in the presence of a microorganism expressing this enzyme.
18. Biocatalytic process for producing isopulegol of general formula (I)

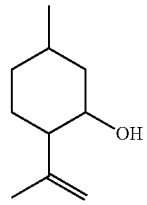

(I)

wherein citronellal of general formula (II)

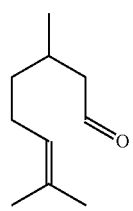

(II)

is cyclized to isopulegol of formula (I) by means of an enzyme mutant according to one of embodiments 1 to 12, or in the presence of a microorganism expressing this enzyme mutant according to embodiment 16.
19. A method of production of menthol of formula III

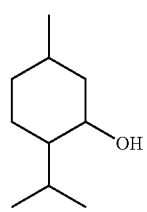

(III)

by
a) cyclizing citronellal to isopulegol by a method according to embodiment 17 or 18, and
b) catalytically hydrogenating isopulegol to menthol.
20. The method according to embodiment 19, where the hydrogenation takes place in the presence of hydrogen and a catalyst comprising
30% to 70% by weight of oxygen-containing compounds of nickel, calculated as NiO,
15% to 45% by weight of oxygen-containing compounds of zirconium, calculated as $ZrO_2$,
5% to 30% by weight of oxygen-containing compounds of copper, calculated as CuO, and
0.1% to 10% by weight of oxygen-containing compounds of molybdenum, calculated as $MoO_3$,
the % by weight figures being based on the dry, unreduced catalyst.
21. A method for enzymatic or biocatalytic conversions of compounds of general formula IV (IV)

[Structure showing a carbon chain with substituents $R_1$ through $R_{10}$ and bonds labeled a, b, c, d]

in which
"a", "b", "c" and "d", in each case independently of one another, represent a single or double C—C bond, with the proviso that cumulative double bonds are excluded; and with the following provisos:
$R_1$ possesses the following definitions:
  (1) when "a" is a double bond:
    $R_1$ is selected from
      oxo (=O), or
      CH—$(CH_2)_n$—Z,
        in which n is 0, 1 or 2 and
        Z is OH, CHO, C(O)alkyl, such as $C(O)C_1$-$C_4$-alkyl, in particular C(O)—$CH_3$ or C(O)—$CH_2CH_3$; COOH, $C(CH_2)$—CH=$CH_2$; $C(OH)(CH_3)$—CH=$CH_2$; $C(CH_3)$=CH—CH=$CH_2$; or a radical of the formula $C(CH_3)$=CH—$CH_2Y$
        in which
          Y is OH, $CH_2OH$, COOH, or $CH_2C(O)CH_3$; or
  (2) when "a" is a single bond:
    $R_1$ is selected from
      $CH_3$; CHO; $CH_2CH_2OH$; CH=$CH_2$; $CH_2C(O)OH$; $CH_2CHO$ or $C_3H_6CH(CH_3)CHO$;
  wherein, when "a" is a double bond, it has E or Z configuration;
$R_2$ and $R_3$ possess the following definitions:
  (1) when "a" and "b" are each a single bond:
    $R_2$ and $R_3$ independently of one another are H, alkyl, such as $C_1$-$C_4$-alkyl or OH, or $R_2$ and $R_3$ together are a methylene (=$CH_2$) or oxo (=O) group; or
  (2) when "a" or "b" is a double bond, one of the radicals $R_2$ and $R_3$ is absent and the other of the two radicals is H, $C_1$-$C_4$-alkyl, in particular methyl, or OH;
$R_4$ is H or hydroxy-$C_1$-$C_4$-alkyl, in particular Hydroxymethyl;
$R_5$ and $R_6$ possess the following definitions:
  (1) when "c" is a single bond:
    $R_5$ and $R_6$ are each H, or $R_5$ and $R_6$ together are an oxo (=O) group; or
  (2) when "c" is a double bond, one of the radicals $R_5$ and $R_6$ is absent and the other of the two radicals is H;
$R_7$, $R_8$ and $R_9$ possess the following definitions:
  (1) when "d" is a single bond:
    two of the radicals $R_7$, $R_8$ and $R_9$ in each case independently of one another are H or alkyl, such as $C_1$-$C_4$-alkyl, in particular methyl or ethyl, and the other of the radicals is OH; or
  (2) when "d" is a double bond, one of the radicals $R_7$, $R_8$ and $R_9$ is absent and the other two radicals in each case independently of one another are H or alkyl, such as $C_1$-$C_4$-alkyl, in particular methyl or ethyl;

$R_{10}$ is H or hydroxy-$C_1$-$C_6$-alkyl, such as hydroxy-$C_1$-$C_4$-alkyl, or mono- or polyunsaturated $C_2$-$C_6$-alkenyl, such as, in particular, H or CH=CH—$C(CH_3)$=$CH_2$;
where a compound of the formula IV in stereoisomerically pure form, or a stereoisomer mixture thereof, is reacted using an enzyme of class EC 5.4.99, in particular of class EC 5.4.99.17, or an enzyme mutant according to one of embodiments 1 to 12 or in the presence of a microorganism according to embodiment 16 expressing these enzymes or enzyme mutants.

22. The method according to embodiment 21, in which a compound is converted which is selected from compounds of the formula IVa (IVa)

[Structure of compound IVa with $R_1$ substituent]

in which $R_1$ possesses the definitions indicated above and in particular is the radical CH—$(CH_2)_n$—Z
in which
  n=0 and Z=CHO, or COOH; or
  n=1 and Z=OH; or
  n=2 and Z=$C(O)CH_3$; COOH, $C(CH_2)$—CH=$CH_2$; $C(CH_3)$=CH—CH=$CH_2$;
    or is a radical of the formula $C(CH_3)$=CH—$CH_2Y$
    in which Y is OH, $CH_2OH$, COOH, or $CH_2C(O)CH_3$;
and "a" optionally has E or Z configuration;
or of the formula IVb (IVb)

[Structure of compound IVb with $R_1$ substituent]

in which $R_1$ possesses the definitions indicated above and in particular is $CH_2CHO$;
or of the formula IVc (IVc)

[Structure of compound IVc with $R_1$, $R_7$, $R_8$ substituents and bonds a, d]

in which
$R_1$ possesses the definitions indicated above, and in particular is CH—CHO; and one of the radicals $R_7$ and $R_8$ is H and the other is $C_1$-$C_4$-alkyl, where in particular $R_7$ is ethyl and the double bonds "a" and "d" have Z configuration.

23. The method according to one of embodiments 20 to 22, in which the compound of the formula IV is selected from citronellal; citral; farnesol; homofarnesol; homofarnesol derivatives, such as homofarnesylic acid; geranylacetone, melonal; nonadienal; and trimethyldecatetraene.

24. Use of an enzyme from EC class EC 5.4.99, in particular from EC class EC 5.4.99.17 for the cyclization of terpenes and/or terpenoids, in particular for the conversion of citronellal to isopulegol.

25. Use of an enzyme mutant according to one of embodiments 1 to 12, a nucleic acid according to embodiment 13, an expression construct according to embodiment 14, a recombinant vector according to embodiment 15 or a recombinant microorganism according to embodiment 1 for the cyclization of terpenes and/or terpenoids, and for the conversion of compounds of the general formula IV according to the definition in one of the embodiments 20 to 23.

25. Use according to embodiment 25 for the conversion of citronellal to isopulegol; or for the conversion of squalene to hopene.

26. A method of production of isopulegol of general formula (I)

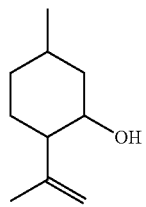

(I)

comprising one reaction step,
wherein citronellal of general formula (II)

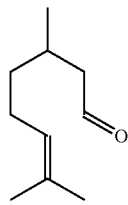

(II)

is cyclized biocatalytically to the corresponding isopulegol of formula (I) by means of an enzyme having the activity of a citronellal-isopulegol cyclase.

27. The method according to embodiment 26, wherein the enzyme possesses a polypeptide sequence which either
a) is SEQ ID NO: 2, or
b) in which up to 25%, such as, for example, up to 20, 15, 10, 9, 8, 7, 6, 5, 4, 3, 2 or 1% of the amino acid residues are altered relative to SEQ ID NO: 2 by deletion, insertion, substitution or a combination thereof, and which still has at least 50%, such as, for example, at least 60, 65, 70, 75, 80, 85, 90 or 95%, of the enzymatic activity of SEQ ID NO: 2.

28. The method according to embodiment 26 or 27, wherein the enzyme is encoded by a nucleic acid sequence according to SEQ ID NO: 1 or a functional equivalent thereof.

29. The method according to one of embodiments 26 to 28, wherein the enzyme is encoded by a nucleic acid sequence according to SEQ ID NO: 1 or a functional equivalent thereof, the nucleic acid sequence being part of a gene construct or vector.

30. The method according to one of embodiments 26 to 29, wherein the enzyme is encoded by a nucleic acid sequence according to SEQ ID NO: 1 or a functional equivalent thereof, the nucleic acid sequence being part of a gene construct or vector which are present in a host cell.

31. The method according to one of embodiments 26 to 30, wherein the enzyme is present in a form selected from the group consisting of:
a) free, optionally purified or partly purified polypeptide having the activity of a citronellal-isopulegol cyclase;
b) immobilized polypeptide having the activity of a citronellal-isopulegol cyclase;
c) polypeptide according to a) or b) which is isolated from cells;
d) whole cell, optionally resting or digested cells, comprising at least one polypeptide having the activity of a citronellal-isopulegol cyclase;
e) cell lysate or cell homogenate of the cells described under d).

32. The method according to embodiment 31, wherein the cells are microorganisms, preferably transgenic microorganisms expressing at least one heterologous nucleic acid molecule coding for a polypeptide having the activity of a citronellal-isopulegol cyclase.

33. The method according to one of embodiments 26 to 32, wherein the production of isopulegol takes place in one-phase aqueous systems or in two-phase systems.

34. The method according to one of embodiments 26 to 33, in which the reaction of citronellal to isopulegol takes place at a temperature in the range from 20 to 40° C. and/or at a pH in the range from 4 to 8.

35. The method according to one of embodiments 26 to 34, wherein the enzyme having the activity of a citronellal-isopulegol cyclase is encoded by a gene which has been isolated from a microorganism selected from the group of microorganisms consisting of *Zymomonas mobilis*, *Methylococcus capsulatus*, *Rhodopseudomonas palustris*, *Bradyrhizobium japonicum*, *Frankia* spec. and *Streptomyces coelicolor*, in particular *Zymomonas mobilis*.

36. The method according to one of embodiments 26 to 35, wherein the enzyme having the activity of a citronellal-isopulegol cyclase has been produced by a microorganism which overproduces the enzyme having the activity of a citronellal-isopulegol cyclase and which has been selected from the group of microorganisms consisting of the genera *Escherichia*, *Corynebacterium*, *Ralstonia*, *Clostridium*, *Pseudomonas*, *Bacillus*, *Zymomonas*, *Rhodobacter*, *Streptomyces*, *Burkholderia*, *Lactobacillus* and *Lactococcus*.

37. The method according to one of embodiments 26 to 36, wherein the enzyme having the activity of a citronellal-isopulegol cyclase has been produced by transgenic microorganisms of the species *Escherichia coli*, *Pseudomonas putida*, *Burkholderia glumae*, *Corynebacterium glutamicum*, *Saccharomyces cerevisiae*, *Pichia pastoris*, *Streptomyces lividans*, *Streptomyces coelicolor*, *Bacillus subtilis* or *Zymomonas mobilis* which overproduce the enzyme having the activity of a citronellal-isopulegol cyclase.

38. Use of an enzyme having the activity of a citronellal-isopulegol cyclase for the biocatalytic conversion of citronellal to isopulegol.

39. Use according to embodiment 38, wherein the enzyme possesses a polypeptide sequence which either
   a) is SEQ ID NO: 2, or
   b) in which up to 25%, such as, for example, up to 20, 15, 10, 9, 8, 7, 6, 5, 4, 3, 2 or 1% of the amino acid residues are altered relative to SEQ ID NO: 2 by deletion, insertion, substitution or a combination thereof, and which still has at least 50%, such as, for example, at least 60, 65, 70, 75, 80, 85, 90 or 95%, of the enzymatic activity of SEQ ID NO: 2.
40. Use according to embodiment 38 or 39, wherein the enzyme is encoded by a nucleic acid sequence according to SEQ ID NO: 1 or a functional equivalent thereof.
41. Use of a gene construct or vector comprising a nucleic acid sequence according to SEQ ID NO: 1 or a functional equivalent thereof, which encode a polypeptide having the activity of a citronellal-isopulegol cyclase, which serves for the biocatalytic conversion of citronellal to isopulegol, in a method of production of isopulegol by cyclization of citronellal.
42. Use of a host cell which comprises a gene construct or a vector comprising a nucleic acid sequence according to SEQ ID NO: 1 or a functional equivalent thereof, for preparing an enzyme having the activity of a citronellal-isopulegol cyclase for the biocatalytic conversion of citronellal to isopulegol.

C. Further Embodiments of the Invention

1. Especially Suitable Wild-Type Sequences

SHC wild-type sequences usable according to the invention, whose SEQ ID NO, source organism, GenBank reference number, the amino acid residue "corresponding" to position F486 of SEQ ID NO:2, i.e. F486-analog ("Aa") and whose sequence position are presented in the following table. The information is based on a sequence alignment, which was set up as follows:

| Program: CLUSTALW, Default parameters: | |
|---|---|
| Protein Gap Open Penalty | 10.0 |
| Protein Gap Extension Penalty | 0.2 |
| Protein weight matrix: | Gonnet series |

| S_ID DB | SEQ ID NO | Organism | GI No. of the reference sequences | Aa | Position |
|---|---|---|---|---|---|
| s1 | seq_ID 2 | Zymomonas mobilis | AAV90172.1 | F | 486 |
| s20 | seq_ID 3 | Streptomyces coelicolor | CAB39697.1 | F | 449 |
| s911 | seq_ID 4 | Acetobacter pasteurianus | BAH99456.1 | F | 481 |
| s2 | seq_ID 5 | Bradyrhizobium sp. | ABQ33590.1 | F | 447 |
| s940 | seq_ID 6 | Zymomonas mobilis | EER62728.1 | F | 438 |
| s949 | seq_ID 7 | Acidithiobacillus caldus | EET25937.1 | Y | 432 |
| s167 | seq_ID 8 | Acidithiobacillus ferrooxidans | ACH84004.1 | Y | 429 |
| s41 | seq_ID 9 | Acidobacterium capsulatum | ACO34244.1 | F | 458 |
| s36 | seq_ID 10 | Acidothermus cellulolyticus | ABK53469.1 | F | 426 |
| s83 | seq_ID 11 | Adiantum capillus-veneris | BAF93209.1 | Y | 436 |
| s143 | seq_ID 12 | Ajellomyces capsulatus | EDN09769.1 | F | 496 |
| s995 | seq_ID 13 | Ajellomyces capsulatus | EER40510.1 | — | 432 |
| s163 | seq_ID 14 | Ajellomyces capsulatus | EEH02950.1 | F | 429 |
| s13 | seq_ID 15 | Alicyclobacillus acidocaldarius | EED08231.1 | Y | 420 |
| s14 | seq_ID 16 | Alicyclobacillus acidocaldarius | P33247.4 | Y | 420 |
| s1193 | seq_ID 17 | Alicyclobacillus acidocaldarius | AAT70690.1 | Y | 116 |
| s21 | seq_ID 18 | Alicyclobacillus acidoterrestris | CAA61950.1 | Y | 420 |
| s1189 | seq_ID 19 | Alicyclobacillus acidoterrestris | AAT70691.1 | Y | 121 |
| s51 | seq_ID 20 | Anabaena variabilis | ABA24268.1 | F | 423 |
| s76 | seq_ID 21 | Anaeromyxobacter sp. | ABS28257.1 | F | 440 |
| s159 | seq_ID 22 | Aspergillus clavatus | EAW07713.1 | F | 446 |
| s131 | seq_ID 23 | Aspergillus flavus | EED48353.1 | F | 444 |
| s176 | seq_ID 24 | Aspergillus fumigatus | EDP50814.1 | F | 502 |
| s126 | seq_ID 25 | Aspergillus fumigatus | EAL84865.1 | F | 449 |
| s178 | seq_ID 26 | Aspergillus fumigatus | EAL86291.2 | F | 406 |
| s121 | seq_ID 27 | Aspergillus niger | CAK43501.1 | F | 441 |
| s115 | seq_ID 28 | Aspergillus niger | CAK45506.1 | F | 440 |
| s124 | seq_ID 29 | Aspergillus oryzae | BAE63941.1 | F | 444 |
| s119 | seq_ID 30 | Azotobacter vinelandii | EAM07611.1 | F | 442 |
| s223 | seq_ID 31 | Bacillus amyloliquefaciens | ABS74269.1 | F | 413 |
| s221 | seq_ID 32 | Bacillus anthracis | AAP27368.1 | F | 409 |
| s976 | seq_ID 33 | Bacillus cereus | EEK66523.1 | F | 423 |
| s225 | seq_ID 34 | Bacillus cereus | EAL12758.1 | F | 423 |
| s972 | seq_ID 35 | Bacillus cereus | EEL44583.1 | F | 412 |
| s977 | seq_ID 36 | Bacillus cereus | EEK43841.1 | F | 412 |
| s985 | seq_ID 37 | Bacillus cereus | EEK82938.1 | F | 412 |
| s988 | seq_ID 38 | Bacillus cereus | EEK99528.1 | F | 412 |
| s981 | seq_ID 39 | Bacillus cereus | EEK77935.1 | F | 412 |
| s987 | seq_ID 40 | Bacillus cereus | EEL81079.1 | F | 412 |
| s960 | seq_ID 41 | Bacillus cereus | EEK88307.1 | F | 412 |
| s979 | seq_ID 42 | Bacillus cereus | EEL63943.1 | F | 412 |
| s974 | seq_ID 43 | Bacillus cereus | EEL59884.1 | F | 412 |
| s956 | seq_ID 44 | Bacillus cereus | EEL69857.1 | F | 412 |
| s951 | seq_ID 45 | Bacillus cereus | EEL92663.1 | F | 412 |
| s986 | seq_ID 46 | Bacillus cereus | EEL49968.1 | F | 411 |
| s227 | seq_ID 47 | Bacillus cereus | AAU16998.1 | F | 409 |
| s224 | seq_ID 48 | Bacillus cereus | AAS42477.1 | F | 409 |

-continued

| S_ID DB | SEQ ID NO | Organism | GI No. of the reference sequences | Aa | Position |
|---|---|---|---|---|---|
| s212 | seq_ID 49 | *Bacillus cereus* | ACK95843.1 | F | 409 |
| s289 | seq_ID 50 | *Bacillus coahuilensis* | 205373680 | F | 276 |
| s219 | seq_ID 51 | *Bacillus cytotoxicus* | ABS22481.1 | F | 411 |
| s230 | seq_ID 52 | *Bacillus licheniformis* | AAU23777.1 | F | 414 |
| s955 | seq_ID 53 | *Bacillus mycoides* | EEL98438.1 | F | 412 |
| s990 | seq_ID 54 | *Bacillus mycoides* | EEM04821.1 | F | 411 |
| s989 | seq_ID 55 | *Bacillus pseudomycoides* | EEM16144.1 | F | 411 |
| s247 | seq_ID 56 | *Bacillus pumilus* | ABV62529.1 | F | 409 |
| s250 | seq_ID 57 | *Bacillus pumilus* | EDW21137.1 | F | 409 |
| s249 | seq_ID 58 | *Bacillus sp.* | EAR64404.1 | F | 425 |
| s218 | seq_ID 59 | *Bacillus sp.* | EDL66148.1 | F | 412 |
| s241 | seq_ID 60 | *Bacillus subtilis* | Q796C3.1 | F | 415 |
| s284 | seq_ID 61 | *Bacillus subtilis* | AAB84441.1 | F | 415 |
| s215 | seq_ID 62 | *Bacillus thuringiensis* | ABK86448.1 | F | 423 |
| s984 | seq_ID 63 | *Bacillus thuringiensis* | EEM21409.1 | F | 412 |
| s957 | seq_ID 64 | *Bacillus thuringiensis* | EEM82653.1 | F | 412 |
| s980 | seq_ID 65 | *Bacillus thuringiensis* | EEM52372.1 | F | 412 |
| s961 | seq_ID 66 | *Bacillus thuringiensis* | EEM27851.1 | F | 412 |
| s969 | seq_ID 67 | *Bacillus thuringiensis* | EEM40716.1 | F | 412 |
| s959 | seq_ID 68 | *Bacillus thuringiensis* | EEM46814.1 | F | 409 |
| s965 | seq_ID 69 | *Bacillus thuringiensis* | EEM94969.1 | F | 409 |
| s202 | seq_ID 70 | *Bacillus weihenstephanensis* | ABY44436.1 | F | 409 |
| s63 | seq_ID 71 | Bacterium Ellin514 | EEF57225.1 | F | 461 |
| s72 | seq_ID 72 | Bacterium Ellin514 | EEF59508.1 | Y | 435 |
| s87 | seq_ID 73 | *Beijerinckia indica* | ACB96717.1 | F | 441 |
| s69 | seq_ID 74 | *Blastopirellula marina* | EAQ81955.1 | F | 475 |
| s543 | seq_ID 75 | *Blastopirellula marina* | EAQ78122.1 | F | 389 |
| s156 | seq_ID 76 | *Bradyrhizobium japonicum* | CAA60250.1 | F | 439 |
| s938 | seq_ID 77 | *Acetobacter pasteurianus* | BAH98349.1 | F | 437 |
| s3 | seq_ID 78 | *Bradyrhizobium sp.* | CAL79893.1 | F | 447 |
| s201 | seq_ID 79 | *Brevibacillus brevis* | BAH44778.1 | F | 448 |
| s148 | seq_ID 80 | *Burkholderia ambifaria* | EDT05097.1 | F | 450 |
| s158 | seq_ID 81 | *Burkholderia ambifaria* | EDT37649.1 | F | 450 |
| s149 | seq_ID 82 | *Burkholderia ambifaria* | ACB68303.1 | F | 446 |
| s100 | seq_ID 83 | *Burkholderia ambifaria* | EDT42454.1 | F | 436 |
| s146 | seq_ID 84 | *Burkholderia cenocepacia* | EAY66961.1 | F | 451 |
| s139 | seq_ID 85 | *Burkholderia cenocepacia* | ACA95661.1 | F | 451 |
| s147 | seq_ID 86 | *Burkholderia cenocepacia* | CAR57099.1 | F | 451 |
| s95 | seq_ID 87 | *Burkholderia cenocepacia* | CAR56694.1 | F | 436 |
| s102 | seq_ID 88 | *Burkholderia dolosa* | EAY71311.1 | F | 437 |
| s941 | seq_ID 89 | *Burkholderia glumae* | ACR32572.1 | F | 555 |
| s945 | seq_ID 90 | *Burkholderia glumae* | ACR30752.1 | F | 449 |
| s132 | seq_ID 91 | *Burkholderia graminis* | EDT12320.1 | F | 462 |
| s104 | seq_ID 92 | *Burkholderia mallei* | ABM48844.1 | F | 436 |
| s140 | seq_ID 93 | *Burkholderia multivorans* | ABX19650.1 | F | 450 |
| s116 | seq_ID 94 | *Burkholderia multivorans* | ABX16859.1 | F | 436 |
| s91 | seq_ID 95 | *Burkholderia oklahomensis* | 167567074 | F | 447 |
| s111 | seq_ID 96 | *Burkholderia phymatum* | ACC73258.1 | F | 456 |
| s127 | seq_ID 97 | *Burkholderia phytofirmans* | ACD21317.1 | F | 455 |
| s120 | seq_ID 98 | *Burkholderia pseudomallei* | EEC32728.1 | F | 436 |
| s137 | seq_ID 99 | *Burkholderia sp.* | EEA03553.1 | F | 460 |
| s144 | seq_ID 100 | *Burkholderia sp.* | ABB06563.1 | F | 450 |
| s98 | seq_ID 101 | *Burkholderia sp.* | ABB10136.1 | F | 436 |
| s944 | seq_ID 102 | *Burkholderia sp. CCGE1002* | EFA54357.1 | F | 473 |
| s89 | seq_ID 103 | *Burkholderia thailandensis* | 167840988 | F | 451 |
| s113 | seq_ID 104 | *Burkholderia thailandensis* | 167617352 | F | 442 |
| s154 | seq_ID 105 | *Burkholderia ubonensis* | 167589807 | F | 445 |
| s93 | seq_ID 106 | *Burkholderia ubonensis* | 167584986 | F | 436 |
| s96 | seq_ID 107 | *Burkholderia vietnamiensis* | ABO56791.1 | F | 436 |
| s150 | seq_ID 108 | *Burkholderia xenovorans* | ABE35912.1 | F | 457 |
| s54 | seq_ID 109 | *Candidatus Koribacter* | ABF40741.1 | F | 435 |
| s171 | seq_ID 110 | *Candidatus Kuenenia* | CAJ71215.1 | F | 273 |
| s79 | seq_ID 111 | *Candidatus Solibacter* | ABJ82180.1 | F | 439 |
| s99 | seq_ID 112 | *Candidatus Solibacter* | ABJ82254.1 | F | 429 |
| s917 | seq_ID 113 | *Catenulispora acidiphila* | ACU75510.1 | F | 418 |
| s65 | seq_ID 114 | *Chthoniobacter flavus* | EDY15838.1 | F | 433 |
| s637 | seq_ID 115 | *Chthoniobacter flavus* | EDY22035.1 | F | 384 |
| s38 | seq_ID 116 | *Crocosphaera watsonii* | EAM53094.1 | F | 426 |
| s186 | seq_ID 117 | *Cupriavidus taiwanensis* | CAQ72562.1 | F | 454 |
| s32 | seq_ID 118 | *Cyanothece sp.* | ACB53858.1 | F | 441 |
| s40 | seq_ID 119 | *Cyanothece sp.* | ACK71719.1 | F | 430 |
| s30 | seq_ID 120 | *Cyanothece sp.* | EDY02410.1 | F | 429 |
| s29 | seq_ID 121 | *Cyanothece sp.* | ACK66841.1 | F | 429 |
| s47 | seq_ID 122 | *Cyanothece sp.* | EDX97382.1 | F | 428 |
| s35 | seq_ID 123 | *Cyanothece sp.* | EAZ91809.1 | F | 426 |

-continued

| S_ID DB | SEQ ID NO | Organism | GI No. of the reference sequences | Aa | Position |
|---|---|---|---|---|---|
| s39 | seq_ID 124 | Cyanothece sp. | ACL45896.1 | F | 423 |
| s925 | seq_ID 125 | Cyanothece sp. PCC 8802 | ACV02092.1 | F | 429 |
| s64 | seq_ID 126 | Desulfovibrio salexigens | EEC62384.1 | F | 475 |
| s74 | seq_ID 127 | Dryopteris crassirhizoma | BAG68223.1 | F | 444 |
| s59 | seq_ID 128 | Frankia alni | CAJ61140.1 | Y | 533 |
| s48 | seq_ID 129 | Frankia alni | CAJ60090.1 | F | 493 |
| s56 | seq_ID 130 | Frankia sp. | ABD10207.1 | F | 530 |
| s60 | seq_ID 131 | Frankia sp. | ABW15063.1 | F | 512 |
| s31 | seq_ID 132 | Frankia sp. | ABW14125.1 | Y | 481 |
| s948 | seq_ID 133 | Frankia sp. Eul1c | EFA59873.1 | F | 557 |
| s919 | seq_ID 134 | Frankia sp. Eul1c | EFA59089.1 | F | 553 |
| s628 | seq_ID 135 | Gemmata obscuriglobus | 168700710 | F | 387 |
| s209 | seq_ID 136 | Geobacillus sp. | EED61885.1 | F | 404 |
| s206 | seq_ID 137 | Geobacillus sp. | EDY05760.1 | F | 403 |
| s964 | seq_ID 138 | Geobacillus sp. Y412MC52 | EEN95021.1 | F | 404 |
| s993 | seq_ID 139 | Geobacillus sp. Y412MC61 | ACX79399.1 | F | 404 |
| s205 | seq_ID 140 | Geobacillus thermodenitrificans | ABO67242.1 | F | 403 |
| s15 | seq_ID 141 | Geobacter bemidjiensis | ACH40355.1 | F | 468 |
| s8 | seq_ID 142 | Geobacter lovleyi | ACD95949.1 | F | 470 |
| s62 | seq_ID 143 | Geobacter metallireducens | ABB30662.1 | F | 493 |
| s12 | seq_ID 144 | Geobacter metallireducens | ABB33038.1 | F | 467 |
| s73 | seq_ID 145 | Geobacter sp. | ACM21577.1 | F | 487 |
| s10 | seq_ID 146 | Geobacter sp. | EDV72707.1 | F | 468 |
| s11 | seq_ID 147 | Geobacter sp. | ACM22003.1 | F | 467 |
| s913 | seq_ID 148 | Geobacter sp. M18 | EET34621.1 | F | 468 |
| s914 | seq_ID 149 | Geobacter sp. M21 | ACT16952.1 | F | 468 |
| s58 | seq_ID 150 | Geobacter sulfurreducens | AAR36453.1 | F | 493 |
| s7 | seq_ID 151 | Geobacter sulfurreducens | AAR34018.1 | F | 467 |
| s9 | seq_ID 152 | Geobacter uraniireducens | ABQ25226.1 | F | 467 |
| s46 | seq_ID 153 | Gloeobacter violaceus | BAC91998.1 | F | 425 |
| s67 | seq_ID 154 | Gluconacetobacter diazotrophicus | ACI51585.1 | F | 444 |
| s165 | seq_ID 155 | Gluconacetobacter diazotrophicus | CAP55563.1 | F | 444 |
| s68 | seq_ID 156 | Gluconobacter oxydans | AAW61994.1 | F | 445 |
| s80 | seq_ID 157 | Granulibacter bethesdensis | ABI63005.1 | F | 429 |
| s937 | seq_ID 158 | Hyphomicrobium denitrificans | EET65847.1 | F | 444 |
| s932 | seq_ID 159 | Leptospirillum ferrodiazotrophum | EES53667.1 | F | 460 |
| s24 | seq_ID 160 | Leptospirillum rubarum | EAY57382.1 | F | 448 |
| s25 | seq_ID 161 | Leptospirillum sp. | EDZ38599.1 | F | 448 |
| s174 | seq_ID 162 | Magnaporthe grisea | EDK02551.1 | F | 445 |
| s153 | seq_ID 163 | Magnetospirillum magnetotacticum | 46203107 | F | 447 |
| s49 | seq_ID 164 | Methylacidiphilum infernorum | ACD82457.1 | F | 456 |
| s169 | seq_ID 165 | Methylobacterium chloromethanicum | ACK83067.1 | F | 447 |
| s75 | seq_ID 166 | Methylobacterium chloromethanicum | ACK86232.1 | F | 426 |
| s946 | seq_ID 167 | Methylobacterium extorquens | CAX24364.1 | F | 447 |
| s141 | seq_ID 168 | Methylobacterium nodulans | ACL61886.1 | F | 442 |
| s152 | seq_ID 169 | Methylobacterium populi | ACB79998.1 | F | 447 |
| s162 | seq_ID 170 | Methylobacterium radiotolerans | ACB27373.1 | F | 445 |
| s180 | seq_ID 171 | Methylobacterium sp. | ACA20611.1 | F | 442 |
| s175 | seq_ID 172 | Methylocella silvestris | ACK52150.1 | F | 451 |
| s181 | seq_ID 173 | Methylococcus capsulatus | CAA71098.1 | F | 439 |
| s55 | seq_ID 174 | Microcystis aeruginosa | CAO86472.1 | F | 423 |
| s101 | seq_ID 175 | Neosartorya fischeri | EAW20752.1 | F | 448 |
| s129 | seq_ID 176 | Nitrobacter hamburgensis | ABE63461.1 | F | 433 |
| s161 | seq_ID 177 | Nitrobacter sp. | EAQ34404.1 | F | 430 |
| s160 | seq_ID 178 | Nitrobacter winogradskyi | ABA05523.1 | F | 433 |
| s157 | seq_ID 179 | Nitrococcus mobilis | EAR22397.1 | F | 436 |
| s164 | seq_ID 180 | Nitrosococcus oceani | ABA57818.1 | F | 446 |
| s170 | seq_ID 181 | Nitrosomonas europaea | CAD85079.1 | F | 452 |
| s173 | seq_ID 182 | Nitrosomonas eutropha | ABI59752.1 | F | 456 |
| s943 | seq_ID 183 | Nitrosomonas sp. AL212 | EET32702.1 | F | 452 |
| s142 | seq_ID 184 | Nitrosospira multiformis | ABB75845.1 | F | 439 |
| s52 | seq_ID 185 | Nostoc punctiforme | ACC84529.1 | F | 423 |
| s45 | seq_ID 186 | Nostoc sp. | BAB72732.1 | F | 423 |
| s122 | seq_ID 187 | Oligotropha carboxidovorans | ACI93782.1 | F | 433 |
| s233 | seq_ID 188 | Paenibacillus sp. | EDS49994.1 | F | 399 |
| s991 | seq_ID 189 | Paenibacillus sp. JDR-2 | ACS99948.1 | F | 399 |
| s950 | seq_ID 190 | Paenibacillus sp. oral taxon 786 | EES74793.1 | F | 428 |
| s1280 | seq_ID 191 | Paramecium tetraurelia | 145542269 | F | 400 |
| s71 | seq_ID 192 | Pelobacter carbinolicus | ABA87701.1 | F | 494 |
| s5 | seq_ID 193 | Pelobacter carbinolicus | ABA87615.1 | F | 435 |
| s66 | seq_ID 194 | Pelobacter propionicus | ABK98395.1 | F | 486 |
| s16 | seq_ID 195 | Pelobacter propionicus | ABK98811.1 | F | 467 |
| s136 | seq_ID 196 | Penicillium chrysogenum | CAP99707.1 | F | 440 |
| s936 | seq_ID 197 | Planctomyces limnophilus | EEO67214.1 | F | 490 |
| s1158 | seq_ID 198 | Planctomyces limnophilus | EEO68341.1 | F | 412 |

-continued

| S_ID DB | SEQ ID NO | Organism | GI No. of the reference sequences | Aa | Position |
|---|---|---|---|---|---|
| s526 | seq_ID 199 | *Planctomyces maris* | EDL58855.1 | F | 392 |
| s992 | seq_ID 200 | *Polypodiodes niponica* | BAI48071.1 | Y | 521 |
| s942 | seq_ID 201 | *Polypodiodes niponica* | BAI48070.1 | F | 443 |
| s1202 | seq_ID 202 | *Populus trichocarpa* | EEF12098.1 | F | 162 |
| s168 | seq_ID 203 | *Ralstonia eutropha* | AAZ64302.1 | F | 452 |
| s190 | seq_ID 204 | *Ralstonia eutropha* | CAJ96989.1 | F | 451 |
| s81 | seq_ID 205 | *Ralstonia metallidurans* | ABF11015.1 | F | 448 |
| s110 | seq_ID 206 | *Ralstonia metallidurans* | ABF11268.1 | F | 430 |
| s123 | seq_ID 207 | *Rhizobium* sp. | P55348.1 | F | 433 |
| s657 | seq_ID 208 | *Rhodopirellula baltica* | CAD74517.1 | F | 428 |
| s4 | seq_ID 209 | *Rhodopseudomonas palustris* | ABJ08391.1 | F | 445 |
| s130 | seq_ID 210 | *Rhodopseudomonas palustris* | CAA71101.1 | F | 433 |
| s155 | seq_ID 211 | *Rhodopseudomonas palustris* | ABD06434.1 | F | 433 |
| s97 | seq_ID 212 | *Rhodopseudomonas palustris* | ABD87279.1 | F | 433 |
| s135 | seq_ID 213 | *Rhodopseudomonas palustris* | ACF02757.1 | F | 432 |
| s84 | seq_ID 214 | *Rhodospirillum rubrum* | ABC20867.1 | F | 437 |
| s1279 | seq_ID 215 | *Rubrobacter xylanophilus* | ABG05671.1 | F | 372 |
| s915 | seq_ID 216 | *Saccharomonospora viridis* | ACU97316.1 | F | 428 |
| s42 | seq_ID 217 | *Saccharopolyspora erythraea* | CAM03596.1 | F | 421 |
| s82 | seq_ID 218 | *Schizosaccharomyces japonicus* | EEB08219.1 | F | 437 |
| s923 | seq_ID 219 | *Sphaerobacter thermophilus* | ACZ39437.1 | F | 404 |
| s924 | seq_ID 220 | *Streptomyces albus* | 239983547 | F | 371 |
| s23 | seq_ID 221 | *Streptomyces avermitilis* | BAC69361.1 | F | 450 |
| s44 | seq_ID 222 | *Acaryochloris marina* | ABW29816.1 | F | 423 |
| s921 | seq_ID 223 | *Streptomyces filamentosus* | 239945642 | F | 447 |
| s934 | seq_ID 224 | *Streptomyces flavogriseus* | EEW70811.1 | F | 447 |
| s920 | seq_ID 225 | *Streptomyces ghanaensis* | 239927462 | F | 448 |
| s922 | seq_ID 226 | *Streptomyces griseoflavus* | 256812310 | F | 448 |
| s28 | seq_ID 227 | *Streptomyces griseus* | BAG17791.1 | F | 447 |
| s926 | seq_ID 228 | *Streptomyces hygroscopicus* | 256775136 | F | 414 |
| s916 | seq_ID 229 | *Streptomyces lividans* | 256783789 | F | 449 |
| s33 | seq_ID 230 | *Streptomyces peucetius* | ACA52082.1 | F | 455 |
| s27 | seq_ID 231 | *Streptomyces pristinaespiralis* | EDY61772.1 | F | 455 |
| s933 | seq_ID 232 | *Streptomyces scabiei* | CBG68454.1 | F | 447 |
| s37 | seq_ID 233 | *Streptomyces* sp. | EDX25760.1 | F | 453 |
| s34 | seq_ID 234 | *Streptomyces* sp. | EDY46371.1 | F | 453 |
| s931 | seq_ID 235 | *Streptomyces* sp. AA4 | 256668250 | F | 428 |
| s918 | seq_ID 236 | *Streptomyces* sp. C | 256770952 | F | 454 |
| s929 | seq_ID 237 | *Streptomyces* sp. Mg1 | 254385931 | F | 453 |
| s928 | seq_ID 238 | *Streptomyces* sp. SPB74 | 254379682 | F | 453 |
| s930 | seq_ID 239 | *Streptomyces* sp. SPB78 | 256680470 | F | 404 |
| s26 | seq_ID 240 | *Streptomyces sviceus* | EDY55942.1 | F | 453 |
| s927 | seq_ID 241 | *Streptomyces viridochromogenes* | 256805984 | F | 447 |
| s61 | seq_ID 242 | *Synechococcus* sp. | EDX84551.1 | F | 426 |
| s935 | seq_ID 243 | *Synechococcus* sp. PCC 7335 | 254422098 | F | 426 |
| s53 | seq_ID 244 | *Synechocystis* sp. | BAA17978.1 | F | 428 |
| s22 | seq_ID 245 | *Syntrophobacter fumaroxidans* | ABK18414.1 | F | 478 |
| s6 | seq_ID 246 | *Syntrophobacter fumaroxidans* | ABK17672.1 | F | 457 |
| s912 | seq_ID 247 | *Teredinibacter turnerae* | ACR13362.1 | F | 438 |
| s57 | seq_ID 248 | *Thermosynechococcus elongatus* | BAC09861.1 | F | 425 |
| s43 | seq_ID 249 | *Trichodesmium erythraeum* | ABG50159.1 | F | 418 |
| s1178 | seq_ID 250 | Uncultured organism | ACA58560.1 | F | 118 |
| s1176 | seq_ID 251 | Uncultured organism | ABL07557.1 | F | 118 |
| s1165 | seq_ID 252 | Uncultured organism | ACA58559.1 | F | 116 |
| s1166 | seq_ID 253 | Uncultured organism | ACA58558.1 | F | 116 |
| s1168 | seq_ID 254 | Uncultured organism | ABL07560.1 | F | 116 |
| s1169 | seq_ID 255 | Uncultured organism | ABL07565.1 | F | 116 |
| s1170 | seq_ID 256 | Uncultured organism | ABL07566.1 | F | 116 |
| s1167 | seq_ID 257 | Uncultured organism | ACA58545.1 | F | 116 |
| s1171 | seq_ID 258 | Uncultured organism | ACA58535.1 | F | 116 |
| s1180 | seq_ID 259 | Uncultured organism | ACA58549.1 | F | 116 |
| s1179 | seq_ID 260 | Uncultured organism | ACA58554.1 | F | 116 |
| s1181 | seq_ID 261 | Uncultured organism | ACA58555.1 | F | 116 |
| s1182 | seq_ID 262 | Uncultured organism | ACA58556.1 | F | 116 |
| s1235 | seq_ID 263 | Uncultured organism | ACA58530.1 | F | 116 |
| s1188 | seq_ID 264 | Uncultured organism | ACA58534.1 | F | 115 |
| s1237 | seq_ID 265 | Uncultured organism | ACA58552.1 | F | 115 |
| s1223 | seq_ID 266 | Uncultured organism | ABL07558.1 | F | 115 |
| s1200 | seq_ID 267 | Uncultured organism | ABL07542.1 | F | 115 |
| s1236 | seq_ID 268 | Uncultured organism | ACA58539.1 | F | 114 |
| s1238 | seq_ID 269 | Uncultured organism | ACA58537.1 | F | 114 |
| s1233 | seq_ID 270 | Uncultured organism | ACA58543.1 | F | 114 |
| s1173 | seq_ID 271 | Uncultured organism | ABL07553.1 | F | 114 |
| s1241 | seq_ID 272 | Uncultured organism | ABL07540.1 | F | 114 |
| s1242 | seq_ID 273 | Uncultured organism | ABL07544.1 | F | 114 |

-continued

| S_ID DB | SEQ ID NO | Organism | GI No. of the reference sequences | Aa | Position |
|---------|-----------|----------|-----------------------------------|----|----------|
| s1225 | seq_ID 274 | Uncultured organism | ACA58557.1 | F | 114 |
| s1183 | seq_ID 275 | Uncultured organism | ACA58520.1 | F | 113 |
| s1197 | seq_ID 276 | Uncultured organism | ACA58524.1 | F | 113 |
| s1185 | seq_ID 277 | Uncultured organism | ACA58522.1 | F | 113 |
| s1190 | seq_ID 278 | Uncultured organism | ACA58525.1 | F | 113 |
| s1187 | seq_ID 279 | Uncultured organism | ACA58523.1 | F | 113 |
| s1184 | seq_ID 280 | Uncultured organism | ACA58521.1 | F | 113 |
| s1204 | seq_ID 281 | Uncultured organism | ACA58547.1 | F | 113 |
| s1221 | seq_ID 282 | Uncultured organism | ACA58544.1 | F | 113 |
| s1198 | seq_ID 283 | Uncultured organism | ACA58546.1 | F | 112 |
| s1226 | seq_ID 284 | Uncultured organism | ACA58527.1 | F | 112 |
| s1227 | seq_ID 285 | Uncultured organism | ABL07537.1 | F | 112 |
| s1232 | seq_ID 286 | Uncultured organism | ACA58510.1 | F | 112 |
| s1230 | seq_ID 287 | Uncultured organism | ACA58538.1 | F | 112 |
| s1229 | seq_ID 288 | Uncultured organism | ACA58542.1 | F | 112 |
| s1231 | seq_ID 289 | Uncultured organism | ACA58540.1 | F | 112 |
| s1207 | seq_ID 290 | Uncultured organism | ABL07564.1 | F | 112 |
| s1212 | seq_ID 291 | Uncultured organism | ABL07563.1 | F | 112 |
| s1208 | seq_ID 292 | Uncultured organism | ABL07562.1 | F | 112 |
| s1209 | seq_ID 293 | Uncultured organism | ABL07559.1 | F | 112 |
| s1214 | seq_ID 294 | Uncultured organism | ABL07556.1 | F | 112 |
| s1216 | seq_ID 295 | Uncultured organism | ACA58528.1 | F | 112 |
| s1219 | seq_ID 296 | Uncultured organism | ACA58536.1 | F | 112 |
| s1192 | seq_ID 297 | Uncultured organism | ABL07533.1 | F | 112 |
| s1195 | seq_ID 298 | Uncultured organism | ABL07536.1 | F | 112 |
| s1174 | seq_ID 299 | Uncultured organism | ABL07545.1 | F | 112 |
| s1186 | seq_ID 300 | Uncultured organism | ABL07548.1 | F | 112 |
| s1196 | seq_ID 301 | Uncultured organism | ACA58561.1 | F | 112 |
| s1172 | seq_ID 302 | Uncultured organism | ABL07555.1 | F | 112 |
| s1194 | seq_ID 303 | Uncultured organism | ABL07541.1 | F | 112 |
| s1211 | seq_ID 304 | Uncultured organism | ABL07554.1 | F | 112 |
| s1220 | seq_ID 305 | Uncultured organism | ABL07547.1 | F | 112 |
| s1203 | seq_ID 306 | Uncultured organism | ABL07550.1 | F | 112 |
| s1199 | seq_ID 307 | Uncultured organism | ABL07551.1 | F | 112 |
| s1228 | seq_ID 308 | Uncultured organism | ACA58509.1 | F | 111 |
| s1201 | seq_ID 309 | Uncultured organism | ACA58514.1 | F | 111 |
| s1205 | seq_ID 310 | Uncultured organism | ABL07543.1 | F | 111 |
| s1206 | seq_ID 311 | Uncultured organism | ABL07534.1 | F | 111 |
| s1177 | seq_ID 312 | Uncultured organism | ABL07546.1 | F | 111 |
| s1210 | seq_ID 313 | Uncultured organism | ABL07535.1 | F | 111 |
| s1175 | seq_ID 314 | Uncultured organism | ABL07552.1 | F | 111 |
| s1191 | seq_ID 315 | Uncultured organism | ABL07549.1 | F | 111 |
| s1222 | seq_ID 316 | Uncultured organism | ACA58553.1 | F | 111 |
| s1244 | seq_ID 317 | Uncultured organism | ABL07539.1 | F | 111 |
| s1213 | seq_ID 318 | Uncultured organism | ACA58532.1 | F | 110 |
| s1239 | seq_ID 319 | Uncultured organism | ACA58548.1 | F | 110 |
| s1215 | seq_ID 320 | Uncultured organism | ABL07561.1 | F | 110 |
| s1240 | seq_ID 321 | Uncultured organism | ACA58533.1 | F | 110 |
| s1234 | seq_ID 322 | Uncultured organism | ABL07538.1 | F | 109 |
| s1224 | seq_ID 323 | Uncultured organism | ACA58541.1 | F | 109 |
| s1217 | seq_ID 324 | Uncultured organism | ACA58529.1 | F | 109 |
| s596 | seq_ID 325 | *Verrucomicrobium spinosum* | 171910093 | F | 395 |
| s70 | seq_ID 326 | *Acidiphilium cryptum* | ABQ30890.1 | F | 430 |

Further potential cyclase mutants with the desired substrate properties can be produced starting from these, on the basis of the findings for mutants of Zm-SHC-1.

2. Further Proteins/Enzyme Mutants According to the Invention

The present invention is not limited to the mutants with cyclase activity concretely disclosed herein, but rather also extends to functional equivalents thereof.

"Functional equivalents" or analogs of the concretely disclosed enzymes and enzyme mutants (F486 and "F486-analog" mutants, derived from SEQ ID NO: 2 to 326, in particular SEQ ID NO: 2 to 6) are, within the scope of the present invention, various polypeptides thereof, which furthermore possess the desired biological activity, for example cyclase activity.

For example "functional equivalents" are understood to include enzymes and mutants that have, in a test applied for "cyclase activity" in the sense of the invention (i.e. with a reference substrate under standard conditions), an at least 1%, in particular at least about 5 to 10%, for example at least 10% or at least 20%, for example at least 50% or 75% or 90% higher or lower activity of an enzyme, comprising an amino acid sequence concretely defined herein (e.g. an F486 and "F486-analog" mutant, derived from SEQ ID NO: 2 to 326; in particular SEQ ID NO: 2 to 6).

The activity information for functional equivalents refers herein, unless stated otherwise, to activity determinations, performed by means of a reference substrate under standard conditions, as defined herein.

The "cyclase activity" in the sense of the invention can be detected by means of various known tests. Without being limited to this, we may mention a test using a reference substrate, for example citronellal racemate or R(+) form, under standard conditions, as described above and explained in the experimental section.

Functional equivalents are moreover stable e.g. between pH 4 to 11 and advantageously possess a pH optimum in a range from pH 5 to 10, such as in particular 6.5 to 9.5 or 7 to 8 or at about 7.5, and a temperature optimum in the range from 15° C. to 80° C. or 20° C. to 70° C., for example about 30 to 60° C. or about 35 to 45° C., such as at 40° C.

"Functional equivalents" are to be understood according to the invention to include in particular also "mutants", which, as well as the concretely stated mutation(s) (e.g. an F486 and "F486-analog" mutant, derived from SEQ ID NO: 2 to 326, in particular SEQ ID NO: 2 to 6), have in at least one sequence position of the aforementioned amino acid sequences, an amino acid other than that concretely stated, but nevertheless possess one of the aforementioned biological activities.

"Functional equivalents" comprise the mutants obtainable by one or more, for example 1 to 50, 2 to 30, 2 to 15, 4 to 12 or 5 to 10 "additional mutations", such as amino acid additions, substitutions, deletions and/or inversions, wherein the stated changes can occur in any sequence position, provided they lead to a mutant with the property profile according to the invention. Functional equivalence is in particular also present when the reactivity profiles between mutant and unaltered polypeptide coincide qualitatively, i.e. for example the same substrates are converted at a different rate.

"Additional mutations" of this kind occur at a position of the respective amino acid sequence different from position F486 according to SEQ ID NO: 2 or from the F486-analog position according to one of SEQ ID NOs: 3 to 326, in particular SEQ ID NO: 3 to 6.

Nonlimiting examples of suitable amino acid substitutions are given in the following table:

| Original residue | Examples of substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described as well as "functional derivatives" and "salts" of the polypeptides.

"Precursors" are natural or synthetic precursors of the polypeptides with or without the desired biological activity.

The term "salts" means both salts of carboxyl groups and salts of acid addition of amino groups of the protein molecules according to the invention. Salts of carboxyl groups can be produced in a manner known per se and comprise inorganic salts, for example sodium, calcium, ammonium, iron and zinc salts, and salts with organic bases, for example amines, such as triethanolamine, arginine, lysine, piperidine and the like. Salts of acid addition, for example salts with mineral acids, such as hydrochloric acid or sulfuric acid and salts with organic acids, such as acetic acid and oxalic acid, are also objects of the invention.

"Functional derivatives" of polypeptides according to the invention can also be produced on functional amino acid side groups or at their N- or C-terminal end by known techniques. Derivatives of this kind comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxyl groups, produced by reaction with acyl groups.

"Functional equivalents" naturally also comprise polypeptides that are accessible from other organisms, and naturally occurring variants. For example areas of homologous sequence regions can be established by sequence comparison and equivalent enzymes can be determined based on the concrete information of the invention.

"Functional equivalents" also comprise fragments, preferably individual domains or sequence motifs, of the polypeptides according to the invention, which for example have the desired biological function.

"Functional equivalents" are moreover fusion proteins, which have one of the aforementioned polypeptide sequences or functional equivalents derived therefrom and at least one further, functionally different therefrom, heterologous sequence in functional N- or C-terminal linkage (i.e. without mutual substantial functional impairment of the fusion protein parts). Nonlimiting examples of heterologous sequences of this kind are e.g. signal peptides, histidine anchors or enzymes.

"Functional equivalents" that are also included according to the invention are homologs to the concretely disclosed proteins. These possess at least 60%, preferably at least 75%, especially at least 85%, for example 90, 91, 92, 93, 94, 95, 96, 97, 98 or 99%, homology (or identity) to one of the concretely disclosed amino acid sequences, calculated using the algorithm of Pearson and Lipman, Proc. Natl. Acad. Sci. (USA) 85(8), 1988, 2444-2448. A percentage homology or identity of a homologous polypeptide according to the invention means in particular percentage identity of the amino acid residues relative to the total length of one of the amino acid sequences concretely described herein. In particular, however, these homologs also have the F486 or "F486-analog" mutation, derived from SEQ ID N0:2 to 326, in particular SEQ ID NO: 2 to 6.

The percentage identity values can also be determined on the basis of BLAST alignments, blastp algorithms (protein-protein BLAST), or using the Clustal settings given below.

In the case of a possible protein glycosylation, "functional equivalents" according to the invention comprise proteins of the type designated above in deglycosylated or glycosylated form as well as modified forms obtainable by changing the glycosylation pattern.

Homologs of the proteins or polypeptides according to the invention can be produced by mutagenesis, e.g. by point mutation, lengthening or shortening of the protein.

Homologs of the proteins according to the invention can be identified by screening combinatorial databases of mutants, for example shortened mutants. For example a variegated database of protein variants can be produced by combinatorial mutagenesis at nucleic acid level, for example by enzymatic ligation of a mixture of synthetic oligonucleotides. There are a great many methods that can be used for producing databases of potential homologs from a degenerated oligonucleotide sequence. The chemical synthesis of a degenerated gene sequence can be carried out in an automatic DNA synthesizer, and the synthetic gene can then be ligated into a suitable expression vector. The use of a degenerated set of genes makes it possible to provide all sequences, in one mixture, which code for the desired set of potential protein sequences. Methods for the synthesis of degenerated oligonucleotides are known by a person skilled in the art (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

Several techniques for screening gene products of combinatorial databases, which were produced by point mutations or shortening, and for screening cDNA databases for gene products with a chosen property, are known in the prior art. These techniques can be adapted for rapid screening of gene banks that have been produced by combinatorial mutagenesis of homologs according to the invention. The techniques used most often for screening large gene banks, as the basis for high-throughput analysis, comprise cloning the gene bank into replicatable expression vectors, transforming suitable cells with the resultant vector bank and expressing the combinatorial genes in conditions in which detection of the desired activity facilitates the isolation of the vector that codes for the gene whose product was detected. Recursive ensemble mutagenesis (REM), a technique that increases the frequency of functional mutants in the databases, can be used in combination with the screening tests, to identify homologs (Arkin and Yourvan (1992) PNAS 89:7811-7815; Delgrave et al. (1993) Protein Engineering 6(3):327-331).

3. Nucleic Acids and Constructs 3.1 Nucleic Acids

The invention also relates to nucleic acid sequences that code for an enzyme as described above or a mutant thereof described above with cyclase activity.

The present invention also relates to nucleic acids with a specified degree of identity to the concrete sequences described herein.

"Identity" between two nucleic acids means identity of the nucleotides in each case over the whole length of nucleic acid, in particular the identity that is calculated by comparison by means of the Vector NTI Suite 7.1 software from the company Informax (USA) using the Clustal method (Higgins D G, Sharp P M. Fast and sensitive multiple sequence alignments on a microcomputer. Comput Appl. Biosci. 1989 April; 5(2):151-1), setting the following parameters:

Multiple Alignment Parameters:

| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighting | 0 |

Pairwise Alignment Parameter:

| FAST algorithm | on |
| K-tuple size | 1 |

-continued

| Gap penalty | 3 |
| Window size | 5 |
| Number of best diagonals | 5 |

As an alternative, the identity can also be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, according to Internet address: ebi-.ac.uk/Tools/clustalw/index.html# and with the following parameters:

| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All nucleic acid sequences mentioned herein (single-stranded and double-stranded DNA and RNA sequences, for example cDNA and mRNA) can be produced in a manner known per se by chemical synthesis from the nucleotide building blocks, for example by fragment condensation of individual overlapping, complementary nucleic acid building blocks of the double helix. The chemical synthesis of oligonucleotides can for example be carried out in a known manner, by the phosphoroamidite technique (Voet, Voet, 2nd edition, Wiley Press New York, pages 896-897). The adding-on of synthetic oligonucleotides and filling of gaps using the Klenow fragment of DNA polymerase and ligation reactions as well as general cloning techniques are described in Sambrook et al. (1989), Molecular Cloning: A Laboratory Manual, Cold Spring Harbor Laboratory Press.

The invention also relates to nucleic acid sequences (single-stranded and double-stranded DNA and RNA sequences, for example cDNA and mRNA), coding for one of the above polypeptides and functional equivalents thereof, which are accessible e.g. using artificial nucleotide analogs.

The invention relates both to isolated nucleic acid molecules, which code for polypeptides or proteins according to the invention or biologically active segments thereof, and to nucleic acid fragments, which can be used for example as hybridization probes or primers for the identification or amplification of coding nucleic acids according to the invention.

The nucleic acid molecules according to the invention can in addition contain untranslated sequences of the 3'- and/or 5'-end of the coding gene region.

The invention further comprises the nucleic acid molecules complementary to the concretely described nucleotide sequences, or a segment thereof.

The nucleotide sequences according to the invention make it possible to produce probes and primers that can be used for the identification and/or cloning of homologous sequences in other cell types and organisms. Said probes or primers usually comprise a nucleotide sequence region which hybridizes under "stringent" conditions (see below) to at least about 12, preferably at least about 25, for example about 40, 50 or 75 successive nucleotides of a sense strand of a nucleic acid sequence according to the invention or of a corresponding antisense strand.

An "isolated" nucleic acid molecule is separate from other nucleic acid molecules that are present in the natural source of the nucleic acid, and moreover can be essentially free of other cellular material or culture medium, when it is produced by recombinant techniques, or free of chemical precursors or other chemicals, when it is chemically synthesized.

A nucleic acid molecule according to the invention can be isolated by standard techniques of molecular biology and the sequence information provided according to the invention. For example, cDNA can be isolated from a suitable cDNA-bank, using one of the concretely disclosed complete sequences or a segment thereof as hybridization probe and standard hybridization techniques (as described for example in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). Moreover, a nucleic acid molecule, comprising one of the disclosed sequences or a segment thereof, can be isolated by polymerase chain reaction, using the oligonucleotide primers that were constructed on the basis of this sequence. The nucleic acid thus amplified can be cloned into a suitable vector and can be characterized by DNA sequence analysis. The oligonucleotides according to the invention can moreover be produced by standard methods of synthesis, e.g. with an automatic DNA synthesizer.

Nucleic acid sequences according to the invention or derivatives thereof, homologs or parts of these sequences, can be isolated for example with usual hybridization methods or PCR techniques from other bacteria, e.g. via genomic or cDNA databases. These DNA sequences hybridize under standard conditions to the sequences according to the invention.

"Hybridization" means the capacity of a poly- or oligonucleotide to bind to an almost complementary sequence under standard conditions, whereas under these conditions nonspecific binding between noncomplementary partners does not occur. For this, the sequences can be up to 90-100% complementary. The property of complementary sequences of being able to bind specifically to one another is utilized for example in Northern or Southern blotting or in primer binding in PCR or RT-PCR.

Short oligonucleotides of the conserved regions are used advantageously for hybridization. However, longer fragments of the nucleic acids according to the invention or the complete sequences can also be used for hybridization. These standard conditions vary depending on the nucleic acid used (oligonucleotide, longer fragment or complete sequence) or depending on which type of nucleic acid, DNA or RNA, is used for hybridization. Thus, for example, the melting temperatures for DNA:DNA hybrids are approx. 10° C. lower than those of DNA:RNA hybrids of the same length.

Standard conditions mean for example, depending on the nucleic acid, temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are for example calculated melting temperature values for a nucleic acid with a length of approx. 100 nucleotides and a G+C content of 50% in the absence of formamide. The experimental conditions for DNA hybridization are described in relevant textbooks on genetics, for example Sambrook et al., "Molecular Cloning", Cold Spring Harbor Laboratory, 1989, and can be calculated using formulas known by a person skilled in the art, for example depending on the length of the nucleic acids, the type of hybrids or the G+C content. Further information on hybridization can be obtained by a person skilled in the art from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

"Hybridization" can in particular take place under stringent conditions. Said hybridization conditions are described for example by Sambrook, J., Fritsch, E. F., Maniatis, T. in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions mean in particular: Incubation at 42° C. overnight in a solution consisting of 50% formamide, 5×SSC (750 mM NaCl, 75 mM trisodium citrate), 50 mM sodium phosphate (pH7.6), 5×Denhardt solution, 10% dextran sulfate and 20 g/ml denatured, sheared salmon sperm DNA, followed by a step of washing the filters with 0.1×SSC at 65° C.

The invention also relates to derivatives of the concretely disclosed or derivable nucleic acid sequences.

Thus, further nucleic acid sequences according to the invention coding for cyclase mutants can be derived e.g. from SEQ ID NO: 1 or from the coding sequences for SEQ ID NO: 2 to 326, in particular SEQ ID NO: 2 to 6, by an F486 or F486-analog mutation and differ from them by addition, substitution, insertion or deletion of single or several nucleotides, but furthermore code for polypeptides with the desired property profile.

The invention also includes nucleic acid sequences that comprise so-called silent mutations or are altered corresponding to the codon-usage of a special original or host organism, compared with a concretely stated sequence, as well as naturally occurring variants, for example splice variants or allele variants, thereof.

It also relates to sequences obtainable by conservative nucleotide substitutions (i.e. the amino acid in question is replaced with an amino acid of the same charge, size, polarity and/or solubility).

The invention also relates to the molecules derived by sequence polymorphisms from the concretely disclosed nucleic acids. These genetic polymorphisms can exist between individuals within a population owing to natural variation. These natural variations usually bring about a variance of 1 to 5% in the nucleotide sequence of a gene.

Derivatives of the nucleic acid sequences according to the invention coding for cyclase mutants derived from sequence SEQ ID NO: 1 or from one of the coding sequences for SEQ ID NO: 2 to 326, in particular SEQ ID NO: 2 to 6, include for example allele variants that have at least 60% homology at the derived amino acid level, preferably at least 80% homology, quite especially preferably at least 90% homology over the whole sequence region (regarding homology at the amino acid level, reference should be made to the above account relating to polypeptides). The homologies can advantageously be higher over partial regions of the sequences.

Furthermore, derivatives also mean homologs of the nucleic acid sequences according to the invention, for example fungal or bacterial homologs, shortened sequences, single-strand DNA or RNA of the coding and noncoding DNA sequence.

Moreover, derivatives mean for example fusions with promoters. The promoters, which are added to the given nucleotide sequences, can be altered by at least one nucleotide exchange, at least one insertion, inversion and/or deletion, without the functionality or efficacy of the promoters being impaired. Moreover, the efficacy of the promoters can be increased by altering their sequence or they can be exchanged completely for more effective promoters even of organisms of a different species.

3.2 Generation of Functional Mutants

Furthermore, methods for producing functional mutants of enzymes according to the invention are known by a person skilled in the art.

Depending on the technology used, a person skilled in the art can introduce completely random or even more-directed mutations in genes or also noncoding nucleic acid regions (which for example are important for the regulation of expression) and then prepare gene libraries. The necessary methods of molecular biology are known by a person skilled in the art and for example are described in Sambrook and Russell, Molecular Cloning. 3rd edition, Cold Spring Harbor Laboratory Press 2001.

Methods for altering genes and therefore for altering the proteins that they encode have long been familiar to a person skilled in the art, for example site-directed mutagenesis, in which single or several nucleotides of a gene are deliberately exchanged (Trower M K (Ed.) 1996; In vitro mutagenesis protocols. Humana Press, New Jersey), saturation mutagenesis, in which a codon for any amino acid can be exchanged or added at any point of a gene (Kegler-Ebo D M, Docktor C M, DiMaio D (1994) Nucleic Acids Res 22:1593; Barettino D, Feigenbutz M, Valcárel R, Stunnenberg H G (1994) Nucleic Acids Res 22:541; Bank S (1995) Mol Biotechnol 3:1), the error-prone polymerase chain reaction (error-prone PCR), in which nucleotide sequences are mutated by error-prone DNA polymerases (Eckert K A, Kunkel T A (1990) Nucleic Acids Res 18:3739);

the SeSaM method (sequence saturation method), in which preferred exchanges are prevented by the polymerase. Schenk et al., Biospektrum, Vol. 3, 2006, 277-279 the passaging of genes in mutator strains, in which, for example owing to defective DNA repair mechanisms, there is an increased mutation rate of nucleotide sequences (Greener A, Callahan M, Jerpseth B (1996) An efficient random mutagenesis technique using an *E. coli* mutator strain. In: Trower M K (Ed.) In vitro mutagenesis protocols. Humana Press, New Jersey), or DNA shuffling, in which a pool of closely related genes is formed and digested and the fragments are used as templates for a polymerase chain reaction, in which, by repeated strand separation and bringing together again, finally mosaic genes of full length are produced (Stemmer W P C (1994) Nature 370:389; Stemmer W P C (1994) Proc Natl Acad Sci USA 91:10747).

Using so-called directed evolution (described for instance in Reetz M T and Jaeger K-E (1999), Topics Curr Chem 200:31; Zhao H, Moore J C, Volkov A A, Arnold F H (1999), Methods for optimizing industrial enzymes by directed evolution, in: Demain A L, Davies J E (Ed.) Manual of industrial microbiology and biotechnology. American Society for Microbiology), a person skilled in the art can produce functional mutants in a directed manner and on a large scale. For this, in a first step, gene libraries of the respective proteins are first produced, for example using the methods given above. The gene libraries are expressed in a suitable way, for example by bacteria or by phage display systems.

The relevant genes of host organisms that express functional mutants with properties that largely correspond to the desired properties can be submitted to another round of mutation. The steps of mutation and selection or screening can be repeated iteratively until the present functional mutants have the desired properties to a sufficient extent. Using this iterative procedure, a limited number of mutations, for example 1, 2, 3, 4 or 5 mutations, can be effected in stages and can be assessed and selected for their influence on the enzyme property in question. The selected mutant can then be submitted to a further mutation step in the same way. In this way the number of individual mutants to be investigated can be reduced significantly.

The results according to the invention also provide important information relating to structure and sequence of the relevant enzymes, which is required for deliberately generating further enzymes with desired modified properties. In particular so-called "hot spots" can be defined, i.e. sequence segments that are potentially suitable for modifying an enzyme property by introducing targeted mutations.

Information can also be deduced regarding amino acid sequence positions, in the region of which mutations can be carried out that should probably have little effect on enzyme activity, and can be designated as potential "silent mutations".

3.3 Constructs

The invention further relates to, in particular recombinant, expression constructs, containing, under the genetic control of regulatory nucleic acid sequences, a nucleic acid sequence coding for a polypeptide according to the invention; and, in particular recombinant, vectors, comprising at least one of these expression constructs.

An "expression unit" means, according to the invention, a nucleic acid with expression activity, which comprises a promoter, as defined herein, and after functional linkage with a nucleic acid to be expressed or a gene, regulates the expression, i.e. the transcription and the translation of said nucleic acid or said gene. Therefore in this connection it is also called a "regulatory nucleic acid sequence". In addition to the promoter, other regulatory elements, for example enhancers, can also be present.

An "expression cassette" or "expression construct" means, according to the invention, an expression unit that is functionally linked to the nucleic acid to be expressed or the gene to be expressed. In contrast to an expression unit, an expression cassette therefore comprises not only nucleic acid sequences that regulate transcription and translation, but also the nucleic acid sequences that are to be expressed as protein as a result of the transcription and translation.

The terms "expression" or "overexpression" describe, in the context of the invention, the production or increase in intracellular activity of one or more enzymes in a microorganism, which are encoded by the corresponding DNA. For this, it is possible for example to introduce a gene into an organism, replace an existing gene with another gene, increase the copy number of the gene or genes, use a strong promoter or use a gene that codes for a corresponding enzyme with a high activity; optionally, these measures can be combined.

Preferably said constructs according to the invention comprise a promoter 5'-upstream of the respective coding sequence and a terminator sequence 3'-downstream and optionally other usual regulatory elements, in each case operatively linked with the coding sequence.

A "promoter", of a "nucleic acid with promoter activity" or of a "promoter sequence" means, according to the invention, a nucleic acid which, functionally linked to a nucleic acid to be transcribed, regulates the transcription of said nucleic acid.

A "functional" or "operative" linkage means, in this connection, for example the sequential arrangement of one of the nucleic acids with promoter activity and of a nucleic acid sequence to be transcribed and optionally further regulatory elements, for example nucleic acid sequences that ensure the transcription of nucleic acids, and for example a terminator, in such a way that each of the regulatory elements can perform its function during transcription of the nucleic acid sequence. This does not necessarily require a direct linkage in the chemical sense. Genetic control sequences, for example enhancer sequences, can even exert their function on the target sequence from more remote positions or even from other DNA molecules. Arrangements are preferred in which the nucleic acid sequence to be transcribed is positioned behind (i.e. at the 3'-end of) the promoter sequence, so that the two sequences are joined together covalently. The distance between the promoter sequence and the nucleic acid sequence to be expressed transgenically can be smaller than 200 base pairs, or smaller than 100 base pairs or smaller than 50 base pairs.

In addition to promoters and terminator, the following may be mentioned as examples of other regulatory elements: targeting sequences, enhancers, polyadenylation signals, selectable markers, amplification signals, replication origins and the like. Suitable regulatory sequences are described for example in Goeddel, Gene Expression Technology: Methods in Enzymology 185, Academic Press, San Diego, Calif. (1990).

Nucleic acid constructs according to the invention comprise in particular a sequence coding for a cyclase mutant, e.g. derived from SEQ ID NO: 1 or coding for a mutant of SEQ ID NO: 2 to 326 or derivatives and homologs thereof, and the nucleic acid sequences derivable therefrom, which have been linked operatively or functionally with one or more regulatory signals advantageously for controlling, e.g. increasing, gene expression.

In addition to these regulatory sequences, the natural regulation of these sequences can still be present before the actual structural genes and optionally can have been genetically altered, so that the natural regulation has been switched off and expression of the genes has been increased. The nucleic acid construct can, however, also be of simpler construction, i.e. no additional regulatory signals have been inserted before the coding sequence and the natural promoter, with its regulation, has not been removed. Instead, the natural regulatory sequence is mutated so that regulation no longer takes place and gene expression is increased.

A preferred nucleic acid construct advantageously also contains one or more of the "enhancer" sequences already mentioned, functionally linked to the promoter, which make increased expression of the nucleic acid sequence possible. Additional advantageous sequences can also be inserted at the 3'-end of the DNA sequences, such as further regulatory elements or terminators. One or more copies of the nucleic acids according to the invention can be contained in the construct. The construct can also contain other markers, such as antibiotic resistances or auxotrophy complementing genes, optionally for selection on the construct.

Examples of suitable regulatory sequences are contained in promoters such as cos-, tac-, trp-, tet-, trp-tet-, lpp-, lac-, lpp-lac-, lacI$^{q-}$, T7-, T5-, T3-, gal-, trc-, ara-, rhaP (rhaP$_{BAD}$) SP6-, lambda-P$_R$- or in the lambda-P$_L$-promoter, which advantageously find application in gram-negative bacteria. Further advantageous regulatory sequences are contained for example in the gram-positive promoters amy and SPO2, in the yeast or fungal promoters ADC1, MFalpha, AC, P-60, CYC1, GAPDH, TEF, rp28, ADH. Artificial promoters can also be used for regulation.

For expression in a host organism, the nucleic acid construct is advantageously inserted into a vector, for example a plasmid or a phage, which makes optimal expression of the genes in the host possible. Apart from plasmids and phage, vectors are also to be understood as all other vectors known by a person skilled in the art, e.g. viruses, such as SV40, CMV, baculovirus and adenovirus, transposons, IS elements, phasmids, cosmids, and linear or circular DNA. These vectors can be replicated autonomously in the host organism or can be replicated chromosomally. These vectors represent a further embodiment of the invention.

Suitable plasmids are for example in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCl, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac$^+$, pBIN19, pAK2004 or pDH51. The stated plasmids represent a small selection of the possible plasmids. Further plasmids are well known by a person skilled in the art and can for example be found in the book Cloning Vectors (Eds. Pouwels P. H. et al. Elsevier, Amsterdam-New York-Oxford, 1985, ISBN 0 444 904018).

In another embodiment of the vector, the vector containing the nucleic acid construct according to the invention or the nucleic acid according to the invention can also advantageously be introduced in the form of a linear DNA into the microorganisms and integrated via heterologous or homologous recombination into the genome of the host organism. This linear DNA can consist of a linearized vector such as a plasmid or only of the nucleic acid construct or the nucleic acid according to the invention.

For optimal expression of heterologous genes in organisms, it is advantageous to alter the nucleic acid sequences corresponding to the specific "codon usage" used in the organism. The "codon usage" can easily be determined on the basis of computer evaluations of other known genes of the organism in question.

An expression cassette according to the invention is produced by fusion of a suitable promoter with a suitable coding nucleotide sequence and a terminator signal or polyadenylation signal. Common recombination and cloning techniques are used, as described for example in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y.

(1984) and in Ausubel, F. M. et al., Current Protocols in Molecular Biology, Greene Publishing Assoc. and Wiley Interscience (1987).

For expression in a suitable host organism, advantageously the recombinant nucleic acid construct or gene construct is inserted into a host-specific vector, which makes optimal expression of the genes in the host possible. Vectors are well known by a person skilled in the art and are given for example in "Cloning vectors" (Pouwels P. H. et al., Ed., Elsevier, Amsterdam-New York-Oxford, 1985).

4. Microorganisms

Depending on the context, the term "microorganism" can mean the wild-type microorganism or a genetically altered, recombinant microorganism or both.

Using the vectors according to the invention, recombinant microorganisms can be produced, which are for example transformed with at least one vector according to the invention and can be used for producing the polypeptides according to the invention. Advantageously, the recombinant constructs according to the invention, described above, are introduced into a suitable host system and expressed. Preferably common cloning and transfection methods, known by a person skilled in the art, are used, for example coprecipitation, protoplast fusion, electroporation, retroviral transfection and the like, for expressing the stated nucleic acids in the respective expression system. Suitable systems are described for example in Current Protocols in Molecular Biology, F. Ausubel et al., Ed., Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

In principle, all prokaryotic or eukaryotic organisms may be considered as recombinant host organisms for the nucleic acid according to the invention or the nucleic acid construct. Advantageously, microorganisms such as bacteria, fungi or yeasts are used as host organisms. Advantageously, gram-positive or gram-negative bacteria are used, preferably bacteria of the families Enterobacteriaceae, Pseudomonadaceae, Rhizobiaceae, Streptomycetaceae or Nocardiaceae, especially preferably bacteria of the genera *Escherichia, Pseudomonas, Streptomyces, Nocardia, Burkholderia, Salmonella, Agrobacterium, Clostridium* or *Rhodococcus*. The genus and species *Escherichia coli* is quite especially preferred. Furthermore, other advantageous bacteria are to be found in the group of alpha-Proteobacteria, beta-Proteobacteria or gamma-Proteobacteria.

The host organism or the host organisms according to the invention preferably contain at least one of the nucleic acid sequences, nucleic acid constructs or vectors described in the present invention, which code for an enzyme with phenylethanol dehydrogenase activity according to the above definition.

Depending on the host organism, the organisms used in the method according to the invention are grown or cultured in a manner known by a person skilled in the art. Microorganisms are as a rule grown in a liquid medium, which contains a carbon source generally in the form of sugars, a nitrogen source generally in the form of organic nitrogen sources such as yeast extract or salts such as ammonium sulfate, trace elements such as iron, manganese and magnesium salts and optionally vitamins, at temperatures between 0° C. and 100° C., preferably between 10° C. to 60° C. with oxygen aeration. The pH of the liquid nutrient can be kept at a fixed value, i.e. regulated or not during culture. Culture can be batchwise, semi-batchwise or continuous. Nutrients can be present at the beginning of fermentation or can be supplied later, semicontinuously or continuously.

5. Recombinant Production of Enzymes According to the Invention

The invention further relates to methods for recombinant production of polypeptides according to the invention or functional, biologically active fragments thereof, wherein a polypeptide-producing microorganism is cultured, optionally the expression of the polypeptides is induced and these are isolated from the culture. The polypeptides can also be produced in this way on an industrial scale, if desired.

The microorganisms produced according to the invention can be cultured continuously or discontinuously in the batch method or in the fed-batch method or repeated fed-batch method. A summary of known cultivation methods can be found in the textbook by Chmiel (Bioprozesstechnik 1. Einführung in die Bioverfahrenstechnik [Bioprocess technology 1. Introduction to bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Braunschweig/Wiesbaden, 1994)).

The culture medium to be used must suitably meet the requirements of the respective strains. Descriptions of culture media for various microorganisms are given in the manual "Manual of Methods for General Bacteriology" of the American Society for Bacteriology (Washington D. C., USA, 1981).

These media usable according to the invention usually comprise one or more carbon sources, nitrogen sources, inorganic salts, vitamins and/or trace elements.

Preferred carbon sources are sugars, such as mono-, di- or polysaccharides. Very good carbon sources are for example glucose, fructose, mannose, galactose, ribose, sorbose, ribulose, lactose, maltose, sucrose, raffinose, starch or cellulose. Sugars can also be added to the media via complex compounds, such as molasses, or other by-products of sugar refining. It can also be advantageous to add mixtures of different carbon sources. Other possible carbon sources are oils and fats, for example soybean oil, sunflower oil, peanut oil and coconut oil, fatty acids, for example palmitic acid, stearic acid or linoleic acid, alcohols, for example glycerol, methanol or ethanol and organic acids, for example acetic acid or lactic acid.

Nitrogen sources are usually organic or inorganic nitrogen compounds or materials that contain these compounds. Examples of nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as corn-steep liquor, soya flour, soya protein, yeast extract, meat extract and others. The nitrogen sources can be used alone or as a mixture.

Inorganic salt compounds that can be present in the media comprise the chloride, phosphorus or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, as well as organic sulfur compounds, such as mercaptans and thiols, can be used as the sulfur source.

Phosphoric acid, potassium dihydrogen phosphate or dipotassium hydrogen phosphate or the corresponding sodium-containing salts can be used as the phosphorus source.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention usually also contain other growth factors, such as vitamins or growth promoters, which include for example biotin, riboflavin, thiamine, folic acid, nicotinic acid, pantothenate and pyridoxine. Growth factors and salts often originate from the components of complex media, such as yeast extract, molasses, corn-steep liquor and the like. Moreover, suitable precursors can be added to the culture medium. The exact composition of the compounds in the medium is strongly dependent on the respective experiment and is decided for each specific case individually. Information on media optimization can be found in the textbook "Applied Microbiol. Physiology, A Practical Approach" (Ed. P. M. Rhodes, P. F. Stanbury, IRL Press (1997) p. 53-73, ISBN 0 19 963577 3). Growth media can also be obtained from commercial suppliers, such as Standard 1 (Merck) or BHI (brain heart infusion, DIFCO) and the like.

All components of the medium are sterilized, either by heat (20 min at 1.5 bar and 121° C.) or by sterile filtration. The components can either be sterilized together, or separately if necessary. All components of the medium can be present at the start of culture or can be added either continuously or batchwise.

The culture temperature is normally between 15° C. and 45° C., preferably 25° C. to 40° C. and can be varied or kept constant during the experiment. The pH of the medium should be in the range from 5 to 8.5, preferably around 7.0. The pH for growing can be controlled during growing by adding basic compounds such as sodium hydroxide, potassium hydroxide, ammonia or ammonia water or acid compounds such as phosphoric acid or sulfuric acid. Antifoaming agents, for example fatty acid polyglycol esters, can be used for controlling foaming. To maintain the stability of plasmids, suitable selective substances, for example antibiotics, can be added to the medium. To maintain aerobic conditions, oxygen or oxygen-containing gas mixtures, for example ambient air, are fed into the culture. The temperature of the culture is normally in the range from 20° C. to 45° C. The culture is continued until a maximum of the desired product has formed. This target is normally reached within 10 hours to 160 hours.

The fermentation broth is then processed further. Depending on requirements, the biomass can be removed from the fermentation broth completely or partially by separation techniques, for example centrifugation, filtration, decanting or a combination of these methods or can be left in it completely.

If the polypeptides are not secreted in the culture medium, the cells can also be lysed and the product can be obtained from the lysate by known methods for isolation of proteins. The cells can optionally be disrupted with high-frequency ultrasound, high pressure, for example in a French press, by osmolysis, by the action of detergents, lytic enzymes or organic solvents, by means of homogenizers or by a combination of several of the aforementioned methods.

The polypeptides can be purified by known chromatographic techniques, such as molecular sieve chromatography (gel filtration), such as Q-sepharose chromatography, ion exchange chromatography and hydrophobic chromatography, and with other usual techniques such as ultrafiltration, crystallization, salting-out, dialysis and native gel electrophoresis. Suitable methods are described for example in Cooper, T. G., Biochemische Arbeitsmethoden [Biochemical processes], Verlag Walter de Gruyter, Berlin, N.Y. or in Scopes, R., Protein Purification, Springer Verlag, New York, Heidelberg, Berlin.

For isolating the recombinant protein, it can be advantageous to use vector systems or oligonucleotides, which lengthen the cDNA by defined nucleotide sequences and therefore code for altered polypeptides or fusion proteins, which for example serve for easier purification. Suitable modifications of this type are for example so-called "tags" functioning as anchors, for example the modification known as hexa-histidine anchor or epitopes that can be recognized as antigens of antibodies (described for example in Harlow, E. and Lane, D., 1988, Antibodies: A Laboratory Manual. Cold Spring Harbor (N.Y.) Press). These anchors can serve for attaching the proteins to a solid carrier, for example a polymer matrix, which can for example be used as packing in a chromatography column, or can be used on a microtiter plate or on some other carrier.

At the same time these anchors can also be used for recognition of the proteins. For recognition of the proteins, it is moreover also possible to use usual markers, such as fluorescent dyes, enzyme markers, which form a detectable reaction product after reaction with a substrate, or radioactive markers, alone or in combination with the anchors for derivatization of the proteins.

For the expression of mutants according to the invention, reference may be made to the description of expression of the wild-type enzyme EbN1 and the expression systems usable for this in WO2005/108590 and WO2006/094945, to which reference is hereby expressly made.

6. Enzyme Immobilization

The enzymes according to the invention can be used free or immobilized in the method described herein. An immobilized enzyme is an enzyme that is fixed to an inert carrier. Suitable carrier materials and the enzymes immobilized thereon are known from EP-A-1149849, EP-A-1 069 183 and DE-OS 100193773 and from the references cited therein. Reference is made in this respect to the disclosure of these documents in their entirety. Suitable carrier materials include for example clays, clay minerals, such as kaolinite, diatomaceous earth, perlite, silica, aluminum oxide, sodium carbonate, calcium carbonate, cellulose powder, anion exchanger materials, synthetic polymers, such as polystyrene, acrylic resins, phenol formaldehyde resins, polyurethanes and polyolefins, such as polyethylene and polypropylene. For making the supported enzymes, the carrier materials are usually employed in a finely-divided, particulate form, porous forms being preferred. The particle size of the carrier material is usually not more than 5 mm, in particular not more than 2 mm (particle-size distribution curve). Similarly, when using dehydrogenase as whole-cell catalyst, a free or immobilized form can be selected. Carrier materials are e.g. Ca-alginate, and carrageenan. Enzymes as well as cells can also be crosslinked directly with glutaraldehyde (cross-linking to CLEAs). Corresponding and other immobilization techniques are described for example in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim. Further information on biotransformations and bioreactors for carrying out methods according to the invention are also given for example in Rehm et al. (Ed.) Biotechnology, 2nd Edn, Vol 3, Chapter 17, VCH, Weinheim.

7. Enzymatic Cyclization of Terpenes 7.1 General Description

In particular, the method of cyclization according to the invention is carried out in the presence of an enzyme, wherein the enzyme is encoded by a nucleic acid sequence according to SEQ ID NO: 1 or a functional equivalent thereof, wherein the nucleic acid sequence is a constituent of a gene construct or vector. Said gene constructs or vectors are described in detail in international application PCT/EP2010/057696 on pages 16 to 20, to which reference is expressly made here. Said functional equivalents, in particular those with citronellal-isopulegol cyclase activity, comprise in particular an F486 or F486-analog mutation, as defined herein.

The host cell, which contains a gene construct or a vector, in which the nucleic acid sequence is contained that codes for the enzyme with the desired activity, is also designated as transgenic organism. The production of said transgenic organisms is known in principle and is discussed for example in international application PCT/EP2010/057696 on page 20, to which reference is expressly made here.

Cells from the group comprising bacteria, cyanobacteria, fungi and yeasts are preferably selected as transgenic organisms. The cell is preferably selected from fungi of the genus *Pichia* or bacteria of the genera *Escherichia, Corynebacterium, Ralstonia, Clostridium, Pseudomonas, Bacillus, Zymomonas, Rhodobacter, Streptomyces, Burkholderia, Lactobacillus* or *Lactococcus*. Especially preferably, the cell is selected from bacteria of the species *Escherichia coli, Pseudomonas putida, Burkholderia glumae, Streptomyces lividans, Streptomyces coelicolor* or *Zymomonas mobilis*.

A method according to the invention is preferred, characterized in that the enzyme with the activity of a citronellal-isopulegol cyclase is encoded by a gene that was isolated from a microorganism, selected from *Zymomonas mobilis, Methylococcus capsulatus, Rhodopseudomonas palustris, Bradyrhizobium japonicum, Frankia* spec, *Streptomyces coelicolor* and *Acetobacter pasteurianus*. The relevant genes isolated from *Zymomonas mobilis, Streptomyces coelicolor, Bradyrhizobium japonicum* and *Acetobacter pasteurianus* should be mentioned in particular.

A method according to the invention is further preferred, characterized in that the enzyme with cyclase activity was generated by a microorganism that overproduces the enzyme and that was selected from the group of microorganisms comprising the genera *Escherichia, Corynebacterium, Ralstonia, Clostridium, Pseudomonas, Bacillus, Zymomonas, Rhodobacter, Streptomyces, Burkholderia, Lactobacillus* and *Lactococcus*.

In particular, a method according to the invention should be mentioned that is characterized in that the enzyme with cyclase activity was produced by transgenic microorganisms of the species *Escherichia coli, Pseudomonas putida, Burkholderia glumae, Corynebacterium glutamicum, Saccharomyces cerevisiae, Pichia pastoris, Streptomyces lividans, Streptomyces coelicolor, Bacillus subtilis* or *Zymomonas mobilis*, which overproduce the enzyme with cyclase activity.

Further embodiments for carrying out the biocatalytic cyclization method according to the invention, such as, for example, the method for production of isopulegol:

The method according to the invention is characterized in that the enzyme is in at least one of the following forms:

a) free, optionally purified or partially purified polypeptide;
b) immobilized polypeptide;
c) polypeptide isolated from cells according to a) or b);
d) whole cell, optionally dormant or growing cells, comprising at least one such polypeptide;
e) lysate or homogenizate of the cells according to d).

Another embodiment of the method according to the invention is characterized in that the cells are microorganisms, preferably transgenic microorganisms expressing at least one heterologous nucleic acid molecule coding for a polypeptide with the cyclase activity.

A preferred embodiment of the method according to the invention comprises at least the following steps a), b) and d):

a) isolating or recombinantly producing a microorganism producing an enzyme with cyclase activity from a natural source or,
b) multiplying this microorganism,
c) optionally isolating the enzyme with cyclase activity from the microorganism or preparing a protein fraction comprising said enzyme, and
d) transferring the microorganism according to stage b) or the enzyme according to stage c) to a medium that contains substrate, e.g. citronellal of general formula (I).

In the method according to the invention, substrate, such as, for example, citronellal is contacted with the enzyme, that has the activity of a citronellal-isopulegol cyclase, in a medium and/or is incubated so that conversion of the substrate, such as, for example, of citronellal, to isopulegol, takes place in the presence of the enzyme. Preferably the medium is an aqueous reaction medium.

The pH of the aqueous reaction medium in which the method according to the invention is preferably carried out is advantageously maintained between pH 4 and 12, preferably between pH 4.5 and 9, especially preferably between pH 5 and 8.

The aqueous reaction media are preferably buffered solutions, which as a rule have a pH of preferably from 5 to 8. The buffer used can be a citrate, phosphate, TRIS (Tris (hydroxymethyl)-aminomethane) or MES buffer (2-(N-morpholino)ethanesulfonic acid). Moreover, the reaction medium can contain other additives, for example detergents (for example taurodeoxycholate).

The substrate, such as, for example, citronellal, is used preferably in a concentration of 2-200 mM, especially preferably 5-25 mM in the enzymatic reaction and can be supplied continuously or discontinuously.

As a rule the enzymatic cyclization takes place at a reaction temperature below the deactivation temperature of the enzyme used and above −10° C. Preferably the method according to the invention is carried out at a temperature between 0° C. and 95° C., especially preferably at a temperature between 15° C. and 60° C., in particular between 20 and 40° C., e.g. at about 25 to 30° C.

A method according to the invention in which the reaction of citronellal to isopulegol takes place at a temperature in the range from 20 to 40° C. and/or a pH in the range from 4 to 8 is especially preferred.

As well as these single-phase aqueous systems, in another variant of the invention, two-phase systems are also used. Then, as well as an aqueous phase, organic, non-water-miscible reaction media are used as the second phase. As a result, the reaction products accumulate in the organic phase. After the reaction, the product, such as, for example, isopulegol, in the organic phase can easily be separated from the aqueous phase that comprises the biocatalyst.

A method according to the invention is preferred wherein the production of isopulegol takes place in single-phase aqueous systems or in two-phase systems.

The reaction product isopulegol can be extracted with organic solvents and optionally can be distilled for purification.

Suitable organic solvents are for example aliphatic hydrocarbons, preferably with 5 to 8 carbon atoms, such as pentane, cyclopentane, hexane, cyclohexane, heptane, octane or cyclooctane, halogenated aliphatic hydrocarbons, preferably with one or two carbon atoms, such as dichloromethane, chloroform, carbon tetrachloride, dichloroethane or tetrachloroethane, aromatic hydrocarbons, such as benzene, toluene, the xylenes, chlorobenzene or dichlorobenzene, aliphatic acyclic and cyclic ethers or alcohols, preferably with 4 to 8 carbon atoms, such as ethanol, isopropanol, diethyl ether, methyl-tert-butyl ether, ethyl-tert-butyl ether, dipropyl ether, diisopropyl ether, dibutyl ether, tetrahydrofuran or esters such as ethyl acetate or n-butyl acetate or ketones such as methyl isobutyl ketone or dioxane or mixtures thereof. Especially preferably, the aforementioned heptane, methyl-tert-butyl ether, diisopropyl ether, tetrahydrofuran, and ethyl acetate are used.

The cyclases used according to the invention can be used in the method according to the invention as free or immobilized enzyme, as already described above.

For the method according to the invention it is possible to use dormant or growing, free or immobilized cells, which contain nucleic acids, nucleic acid constructs or vectors coding for the cyclase. Lysed cells, such as cell lysates or cell homogenates can also be used. Lysed cells are for example cells that have been permeabilized by a treatment for example with solvents, or cells that have been disrupted by an enzyme treatment, by a mechanical treatment (e.g. French press or ultrasound) or by some other method. The resultant raw extracts are advantageously suitable for the method according to the invention. Purified or partially purified enzymes can also be used for the method.

Where free organisms or enzymes are used for the method according to the invention, they are usefully isolated, via a filtration or centrifugation, for example, prior to the extraction.

The method according to the invention can be operated batchwise, semibatchwise or continuously.

7.2. Enzymatic Cyclization of Citronellal

The citronellal of formula (II) used in accordance with the invention, and converted by means of an enzyme having citronellal-isopulegol cyclase activity, is available commercially both as (+)-R-citronellal of the formula (R-II) and as (−)-S-citronellal of the formula (S-II), and as a racemate of the formula (II).

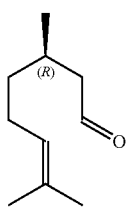

(R-II)

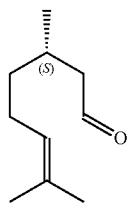

(S-II)

The isopulegol formed in accordance with the invention, of formula (I)

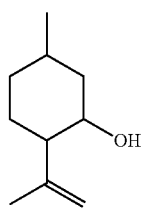

(I)

has a stereocenter in each of positions 1, 3 and 6, and so in principle there are 4 different diastereomers each with 2 enantiomers conceivable, in other words a total of 8 stereomers, if the starting point is the racemate of the citronellal of formula (I).

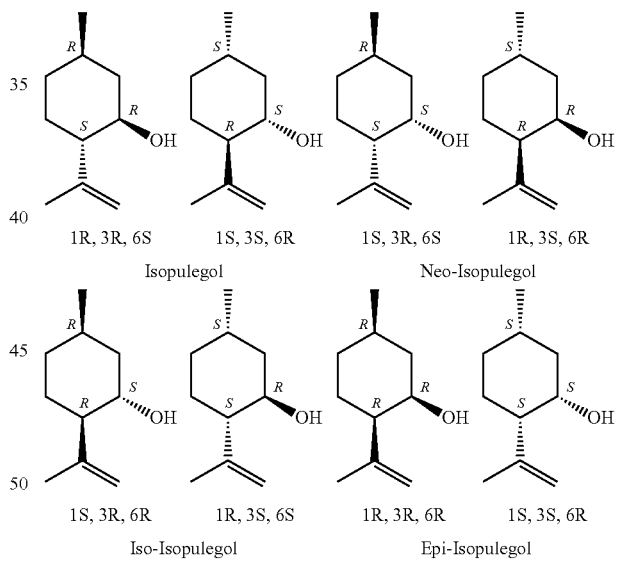

Suitable enzymes having the activity of a citronellal-isopulegol cyclase are intramolecular transferases from the subclass of the isomerases; that is, proteins having the enzyme code EC 5.4 (enzyme code in accordance with Eur. J. Biochem. 1999, 264, 610-650). Preferably they are representatives having the enzyme code 5.4.99.17. Also suitable in particular as enzymes having the activity of citronellal-isopulegol cyclase are those cyclases which also bring about the cyclization of homofarnesol to ambroxan or of squalene to hopene, which are described exhaustively in international application PCT/EP2010/057696, hereby incorporated by reference; the enzymes and mutants described here are also suitable.

One particularly suitable embodiment of the method according to the invention is that wherein the enzyme used in the method according to the invention and having the activity of a citronellal-isopulegol cyclase possesses a polypeptide sequence which either
a) is SEQ ID NO: 2, or
b) in which up to 25% of the amino acid residues are altered relative to SEQ ID NO: 2 by deletion, insertion, substitution or a combination thereof, and which still has at least 50% of the enzymatic activity of SEQ ID NO: 2.

Suitable enzymes with citronellal-isopulegol cyclase activity and comprising an amino sequence according to SEQ ID NO: 2, and also "functional equivalents" or analogs of the specifically disclosed enzymes (E) having citronellal-isopulegol cyclase activity, are described, as already indicated above, exhaustively in the international application PCT/EP2010/057696, hereby incorporated by reference.

In one particularly preferred embodiment of the method, the enzyme having citronellal-isopulegol cyclase activity is selected from enzymes which comprise an amino acid sequence according to SEQ ID NO: 2 or a sequence derived therefrom in which up to 25%, preferably up to 20%, more preferably up to 15%, in particular up to 10, 9, 8, 7, 6, 5, 4, 3, 2, 1% of the amino acid residues have been altered by a deletion, a substitution, an insertion or a combination of deletion, substitution and insertion, the polypeptide sequences altered relative to SEQ ID NO: 2 still possessing at least 50%, preferably 65%, more preferably 80%, more particularly more than 90% of the enzymatic activity of SEQ ID NO: 2. In this context, enzymatic activity of SEQ ID NO: 2 refers to the capacity to effect biocatalytic cyclization of citronellal of general formula (II) to the corresponding isopulegol of formula (I).

The method according to the invention is carried out preferably in the presence of an enzyme, the enzyme being encoded by a nucleic acid sequence according to SEQ ID NO: 1 or a functional equivalent thereof.

Functional equivalents here describe in principle nucleic acid sequences which under standard conditions undergo hybridization with a nucleic acid sequence or parts of a nucleic acid sequence and are capable of bringing about the expression of a protein having the same properties as those of the enzyme having citronellal-isopulegol cyclase activity in a cell or in an organism.

A functional equivalent is additionally understood to refer to nucleic acid sequences which are homologous or identical to a defined percentage with a particular nucleic acid sequence ("original nucleic acid sequence") and have the same activity as the original nucleic acid sequences, and also, in particular, natural or artificial mutations of these nucleic acid sequences.

The nucleic acid sequences which can be used for encoding the enzymes having citronellal-isopulegol cyclase activity that can be used in the method according to the invention are likewise described exhaustively in international application PCT/EP2010/057696, hereby incorporated by reference.

With particular preference the method according to the invention is carried out in the presence of an enzyme, the enzyme being encoded by a nucleic acid sequence according to SEQ ID NO: 1 or a functional equivalent thereof, the nucleic acid sequence being part of a gene construct or vector. Such gene constructs or vectors are described exhaustively in international application PCT/EP2010/057696 on pages 16 to 20, hereby incorporated by reference.

With very particular preference the method according to the invention is carried out in the presence of an enzyme, where the enzyme is encoded by a nucleic acid sequence according to SEQ ID NO: 1 or a functional equivalent thereof, the nucleic acid sequence being part of a gene construct or vector which are present in a host cell.

The host cell which comprises a gene construct or a vector in which the nucleic acid sequence is present that encodes the enzyme having the citronellal-isopulegol cyclase activity is also referred to as a transgenic organism. The production of such transgenic organisms is known in principle and is discussed, for example, in international application PCT/EP2010/057696 on page 20, hereby incorporated by reference.

Transgenic organisms selected are preferably cells from the group consisting of bacteria, cyanobacteria, fungi and yeasts. The cell is preferably selected from fungi of the genus *Pichia* or bacteria of the genera *Escherichia, Corynebacterium, Ralstonia, Clostridium, Pseudomonas, Bacillus, Zymomonas, Rhodobacter, Streptomyces, Burkholderia, Lactobacillus* or *Lactococcus*. With particular preference the cell is selected from bacteria of the species *Escherichia coli, Pseudomonas putida, Burkholderia glumae, Streptomyces lividans, Streptomyces coelicolor* or *Zymomonas mobilis*.

A preferred method according to the invention is that wherein the enzyme having the activity of a citronellal-isopulegol cyclase is encoded by a gene which has been isolated from a microorganism selected from the group of microorganisms consisting of *Zymomonas mobilis, Methylococcus capsulatus, Rhodopseudomonas palustris, Bradyrhizobium japonicum, Frankia* spec. and *Streptomyces coelicolor*. With particular preference the gene in question has been isolated from *Zymomonas mobilis*.

Preferred furthermore is a method according to the invention wherein the enzyme having the activity of a citronellal-isopulegol cyclase has been produced by a microorganism which overproduces the enzyme having the activity of a citronellal-isopulegol cyclase and which has been selected from the group of microorganisms consisting of the genera *Escherichia, Corynebacterium, Ralstonia, Clostridium, Pseudomonas, Bacillus, Zymomonas, Rhodobacter, Streptomyces, Burkholderia, Lactobacillus* and *Lactococcus*.

A particularly preferred method according to the invention is that wherein the enzyme having the activity of a citronellal-isopulegol cyclase has been produced by transgenic microorganisms of the species *Escherichia coli, Pseudomonas putida, Burkholderia glumae, Corynebacterium glutamicum, Saccharomyces cerevisiae, Pichia pastoris, Streptomyces lividans, Streptomyces coelicolor, Bacillus subtilis* or *Zymomonas mobilis* which overproduce the enzyme having the activity of a citronellal-isopulegol cyclase.

The above-described further embodiments for carrying out the biocatalytic method according to the invention for cyclizing terpenes apply correspondingly in respect of the production of isopulegol.

A further subject of the present invention is also the use of an enzyme having the activity of a citronellal-isopulegol cyclase for the biocatalytic conversion of citronellal to isopulegol.

Preference is given to the use of an enzyme having the activity of a citronellal-isopulegol cyclase for the biocatalytic conversion of citronellal to isopulegol, wherein the enzyme possesses a polypeptide sequence which either
a) is SEQ ID NO: 2, or
b) in which up to 25% of the amino acid residues are altered relative to SEQ ID NO: 2 by deletion, insertion, substitution or a combination thereof, and which still has at least 50% of the enzymatic activity of SEQ ID NO: 2.

Also preferred is the use of an enzyme having the activity of a citronellal-isopulegol cyclase for the biocatalytic conversion of citronellal to isopulegol, wherein the enzyme is encoded by a nucleic acid sequence according to SEQ ID NO: 1 or a functional equivalent thereof.

A further subject of the present invention is also the use of a gene construct or vector comprising a nucleic acid sequence according to SEQ ID NO: 1 or a functional equivalent thereof which encode a polypeptide having the activity of a citronellal-isopulegol cyclase which serves the biocatalytic conversion of citronellal to isopulegol in a method of production of isopulegol by cyclization of citronellal.

Likewise a further subject of the present invention is the use, as well, of a host cell which comprises a gene construct or a vector comprising a nucleic acid sequence according to SEQ ID NO: 1 or a functional equivalent thereof for producing an enzyme having the activity of a citronellal-isopulegol cyclase for the biocatalytic conversion of citronellal to isopulegol.

The method described above opens up for the first time the possibility of cyclizing citronellal to isopulegol by means of an enzyme.

8. Methods of Production of Menthol

The isopulegol prepared inventively can be converted into menthol by catalytic hydrogenation in a conventional way. Suitable for this purpose, as well as conventional hydrogenation processes, is, in particular, a catalytic method, as described in WO 2009/013192.

The method according to the invention is implemented in particular using catalysts comprising
   45% to 55% by weight of oxygen-containing compounds of nickel, calculated as NiO,
   25% to 35% by weight of oxygen-containing compounds of zirconium, calculated as $ZrO_2$,
   5% to 20% by weight of oxygen-containing compounds of copper, calculated as CuO,
   1% to 3% by weight of oxygen-containing compounds of molybdenum, calculated as $MoO_3$, and
   0% to 5% by weight of further components,
the figures in % by weight adding up to 100% by weight and relating to the dry, unreduced catalyst.

One particularly preferred catalyst is composed of 49% to 53% by weight of NiO, 15% to 19% by weight of CuO, 28% to 32% by weight of $ZrO_2$ and 1% to 2% by weight of $MoO_3$ and also, optionally, 0% to 3% by weight of further components such as graphite, for example, the respectively selected weight fractions of the individual components being based on the dry, unreduced catalyst and adding up to 100% by weight. Catalysts of this kind are known and can be produced for example as described in EP 0 696 572 or in WO 2009/013192.

In general the catalysts are used preferably in the form of unsupported catalyst. The term "unsupported catalyst" refers to a catalyst which in contrast to a supported catalyst is composed only of catalytically active material. Unsupported catalysts can be used by introducing the catalytically active material, ground to a powder, into the reaction vessel, or by disposing the catalytically active material in the reactor after grinding, mixing with shaping aids, shaping and heat-treating in the form of shaped catalyst bodies—for example, as spheres, cylinders, tablets, rings, coils, strands and the like.

In the context of one preferred embodiment of the hydrogenation method according to the invention, the selected heterogeneous catalyst is employed in the form of a fixed-bed catalyst.

To implement the method according to the invention, the isopulegol starting material as described above is contacted with hydrogen and with the selected catalyst. The hydrogen here may be used in undiluted form, typically in a purity of about 99.9% by volume, or in diluted form, i.e. in the form of mixtures with inert gases such as nitrogen or argon, for example. It is preferred to use hydrogen in undiluted form. The reaction can be carried out successfully without adding solvent or in the presence of organic solvents which are inert under the reaction conditions, such as, for example, methanol, ethanol, isopropanol, hexane, heptane, cyclohexane and the like. It is preferred to carry out the reaction without adding solvent.

The hydrogenation of isopulegol in accordance with the invention can be carried out under a hydrogen pressure (absolute) in the range from 1 to 200 bar, such as from 2 or 3 to 200 bar, in particular from 4 or 5 to 150 bar, such as from 5 to 100 bar, or in the range from 5 to 50 bar. As a reaction temperature for implementing the hydrogenation according to the invention, a temperature is selected, advantageously, that is in the range from 20 to 150° C., such as from 40 to 130° C., or from 60 to 110° C. and more particularly from 70 to 100° C.

The practical approach to the implementation is generally to supply the isopulegol for conversion to the catalyst, which is typically located in a fixed bed reactor heated, in particular, from the outside, such as a tube reactor, autoclave or tube-bundle reactor, for example, at the desired reaction temperature and under the desired pressure. The velocity over the catalyst in this case is generally 0.1 to 1.0, such as 0.1 to 0.6 or 0.2 to 0.4, kg of isopulegol per kg of catalyst per hour. In this context it may be useful to heat the isopulegol that is to be used, even before it is supplied to the reaction vessel or to the reactor, this heating being preferably to reaction temperature.

The reactor can be operated either in liquid phase mode or in trickle mode—that is, the starting materials may be passed through the reactor either from bottom to top or from top to bottom. The hydrogenation method of the invention can be carried out either batchwise or continuously. In both cases, unreacted starting material can be circulated together with the hydrogen.

The hydrogenation according to the invention may also be carried out in stages in a cascade of two or more reactors, i.e. 2 to in general 4, such as 2 or 3, for example, reactors connected in series, preferably fixed bed reactors. In this case, in the first reactor, typically referred to as the main reactor, the main conversion of the reaction is achieved under the reaction conditions described above, and the crude product obtained is passed to a second reactor, typically referred to as secondary reactor, in which the as yet unreacted starting material is at least largely converted inventively into L-menthol. The reaction conditions here may be selected, independently of one another, preferably in the ranges stated above.

The method of the invention can be carried out batchwise, semibatchwise or continuously. It is preferred to carry out the method continuously, more particularly entirely continuously, in which case the starting materials are introduced continuously into the reactor and the resulting reaction mixture or reaction product is discharged continuously from the reactor. It has further proven advantageous, in view of the position of the melting point of the reaction product according to the invention, namely menthol, especially L-menthol, to provide for heating of the transport lines used.

The method of the invention allows menthol to be produced by catalytic hydrogenation of isopulegol, with typically only a minor degree of formation of unwanted diastereomers of menthol. Accordingly, when using isopulegol with a corresponding purity, the method of the invention yields menthol of the formula (III) in a chemical purity of 97% by weight or more, preferably of 98% to 100% by weight, more preferably of 98.5% to 99.9% by weight, very preferably at least 99% to 99.9% by weight. The term "chemical purity" here also encompasses the diastereomeric purity of the resulting menthol in relation to the diastereomers neoisomenthol of formula (IIIa), neomenthol of formula (IIIb) and isomenthol of formula (IIIc). Accordingly, in the context, the method according to the invention preferably yields menthol having a diastereomeric purity of 97% by weight or more, preferably of 98% to 100% by weight, more preferably of 98.5% to 99.9% by weight and very preferably of at least 99% to 99.9% by weight.

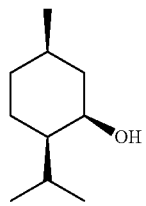

(IIIa)

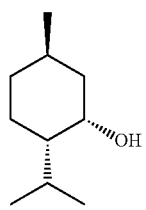

(IIIb)

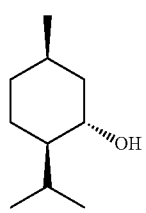

(IIIc)

Where isopulegol is used in optically active form— preferably, in accordance with the invention, mixtures comprising predominantly the L-isopulegol enantiomer—the method product according to the invention that is obtained is generally menthol in optically active form, preferably in the form of (−)- or L-menthol. The hydrogenation according to the invention proceeds generally largely without notable racemization of the material used. Accordingly, according to the enantiomeric excess of the optically active isopulegol used, optically active menthol, preferably L-menthol when using L-isopulegol, is obtained as the product, with an enatiomeric excess (ee) of 80% ee or more, preferably of 85% or 90% ee or more, more preferably of 95% to 100% ee, more preferably of 96% to 99.9% ee, very preferably of 97% to 99.8% ee, even more preferably of 98% to 99.7% ee, and with more particular preference of 98.5% to 99.6% ee.

The menthol obtained according to the invention is notable, furthermore, for a particularly low level of the unwanted by-products menthone of formula (IIId) and isomenthone of formula (IIIe) and neoisomenthol of formula (IIIa).

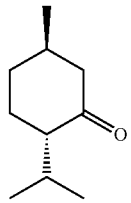

(IIId)

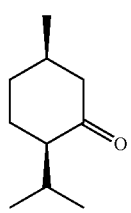

(IIIe)

These by-products are obtained generally, in the context of the method according to the invention, only in a proportion, relative to the amount of menthol obtained, of up to 0.5% by weight, preferably 0.4% by weight, more preferably 0.3% by weight, more particularly 0.2% by weight, and very preferably 0.1% to 0% by weight.

9. Examples of Substrates which can be Used for Enzymatic or Biocatalytic Conversions According to the Invention The enzymes and microorganisms described herein are especially suitable for converting compounds of the general formula IV above. Non-limiting examples thereof are summarized in table A below, which gives the structural formula and the chemical name.

TABLE A

| Further substrates | |
|---|---|
| Formula | Name |
| 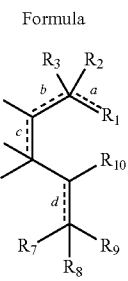<br>(IV) | |
| 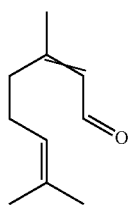 | Citral |

TABLE A-continued

Further substrates

Formula (IV)

| Name | Structure description |
|---|---|
| Neral | (3,7-dimethyl-2,6-octadienal, Z) |
| Nerol | (Z)-3,7-dimethyl-2,6-octadien-1-ol |
| Nerylacetone | |
| Geranial | (E)-3,7-dimethyl-2,6-octadienal |
| Geraniol | (E)-3,7-dimethyl-2,6-octadien-1-ol |
| Geranylic acid | |
| cis-Geranylic acid | |
| Geranylacetone | |
| Farnesol | |
| Farnesylacetone | |
| Homofarnesylic acid | |

TABLE A-continued

Further substrates

Formula (IV) — Name

| Structure | Name |
|---|---|
| (structure shown) | Homofarnesol |
| (structure shown) | Trimethyltri-decatetraene |
| (structure shown) | Melonal |
| (structure shown) | Nonadienal |
| (structure shown) | Citronellol |
| (structure shown) | β-Citronellene |
| (structure shown) | Citronellic acid |
| (structure shown) | Hydroxycitronellal |
| (structure shown) | Heptanal |
| (structure shown) | Linalool |
| (structure shown) | Farnesene (β) |
| (structure shown) | Myrcene |

TABLE A-continued

Further substrates

| Formula (IV) | Name |
|---|---|
| 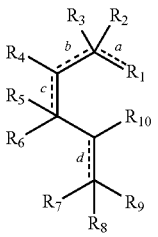 | Myrcenol |
| 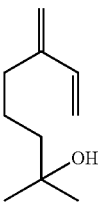 | Dihydromyrcenol |
| 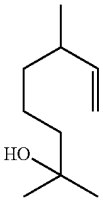 | Lavandulol |
| 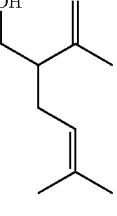 | Nerolidol |
| 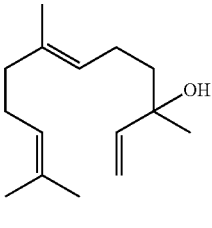 [SMILES: C=CC(C)(O)CC/C=C(\C)CCC=C(C)C] | (E)-β-Ocimene (4 isomers present) |
| 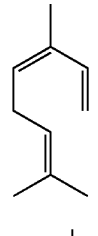 | Tagetone |
| 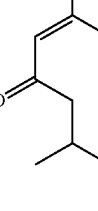 | Solanone |
| 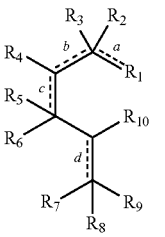 | 2,6,10-Trimethyl-9-undecanal |

The reaction products produced in the conversion of these substrates can be detected and quantified in a conventional way using standard analytical methods, such as chromatography, HPLC, gas chromatography, mass spectrometry, GC/MS or MALDI-TOF, and combinations thereof.

If nonimmobilized organisms or enzymes are used for the method according to the invention, preferably these are separated prior to extraction, for example by filtration or centrifugation.

The method according to the invention can be operated batchwise, semi-batchwise or continuously.

EXPERIMENTAL SECTION

In the absence of special information in the examples below, the general information below is taken to apply.

A. General Information

All materials and microorganisms used are commercially available products.

Unless stated otherwise, the cloning and expression of recombinant proteins is carried out by standard methods, as described for example in Sambrook, J., Fritsch, E. F. and Maniatis, T., Molecular Cloning: A Laboratory Manual, 2nd edition, Cold Spring Harbor Laboratory, Cold Spring Harbor Laboratory Press, Cold Spring Harbor, N.Y., 1989.

a) Bacterial Strains, Plasmids and Growing Conditions

All experiments were carried out with *E. coli*. The SHC proteins were expressed in *E. coli* BL21 (DE3) pLysS or *E. coli* Rosetta pLysRAR62, comprising pET16b constructs with the respective she gene, by growing in Luria-Bertani medium, supplemented with ampicillin (100 µg/ml), chloramphenicol (34 µg/ml), and 0.5 mM isopropylthio-β-D-galactoside at $OD_{600}$ of 0.4 and additional growth for 4 hours at 30° C.

b) Vector Constructs

The respective squalene-hopene cyclase gene (e.g. *Zymomonas mobilis* ZMO1548 [NC_006526.2, region: 1578816 . . . 1580993]) was PCR-amplified from chromosomal DNA, using corresponding primer pairs (e.g. ZMO1548-fwd (5'-gcgctgtttcatatgggtattgaca-3) (SEQ. ID. NO: 327) and ZMO1548-rev (5'-gcgcttaccctggatcctcgaaaat-3) (SEQ. ID. NO: 328)). The restriction enzyme digested (e.g. with NdeI/BamHI) PCR product was cloned into pET16b, (obtaining e.g.) pET1584. The constructs were verified by DNA sequencing and transformed into *E. coli* XL1-blue.

The she-gene from other microorganisms (e.g. from *A. acidocaldarius*) was cloned similarly.

All plasmids were transformed individually into *E. coli* BL21 (DE3) pLysS or *E. coli* Rosetta pLys-RAR62.

c) Cyclization Assay with Various Substrates (Standard Conditions)

Recombinant *E. coli* cells were suspended in 20 mM Tris-HCl pH 8.0 (3 ml per g moist cells).

The cyclization mixture contained 250 µl of cell suspension, 50 µl of 1 M citrate buffer (pH 4.5), 20 mM (final concentration) of substrate and water to 500 µl. In the cyclization of squalene, 1% (v/v) Triton-X100 was added. For the homofarnesol cyclization, *E. coli* cells (6 g moist cells) were suspended in solubilization buffer (50 mM phosphate, 10 mM $MgCl_2$ (pH 6.5; total volume: 25 ml). The cells were lysed at 1500 bar using a Manton-Gaulin homogenizer. Insoluble cellular debris was centrifuged off (15 min at 4° C. and 7150*g). The cyclization mixture contained 1 ml raw cell extract and 20 mM homofarnesol in 1.25 ml buffer (50 mM potassium phosphate, 45 mM $MgCl_2$ (pH 6.5). The reaction mixture was stirred at 30° C. with a magnetic stirrer. The reaction was stopped by extraction with heptane. The organic phase was analyzed by gas chromatography. Controls were carried out with *E. coli* cells bearing an empty vector and with heat-inactivated SHC-expressing cells. Formation of cyclization products was never observed with the controls (data not shown).

d) Gas Chromatography

Terpenoids were analyzed qualitatively and quantitatively by gas chromatography using an Agilent 7890A gas chromatograph, equipped with a DB-5 column (20 m×0.1 mm×0.1 µm) and an ionization detector. 3 µl of the solvent extract was applied on the column (split ratio 1:5, helium flow rate 0.25 or 0.5 ml/min, injector temperature 250° C.).

To separate linear and cyclic monoterpenoids, the initial furnace temperature (60° C.) was raised to 130° C. at 40° C./min, at 2° C./min to 150° C. and then at 40° C./min to 200° C. The retention times of the terpenoids were as follows: (R,S)-citronellal (7.55 min), isopulegol (7.70 min), neo-isopulegol (7.90 min), iso-isopulegol (8.10 min), neoiso-isopulegol (8.25 min), 1-decanol (9.91 min).

For the detection of triterpenes, the injector temperature was set at 300° C. The furnace temperature was initially 60° C., and was increased at 40° C./min to 220° C. and then at 6° C./min to 310° C. and held constant there for 10 min. Squalene and hopene eluted after 19.2 min and 26.9 min respectively.

Homofarnesol and ambroxan were analyzed on a 10 m Optima 1 column (Macherey & Nagel, Düren, Germany). The initial furnace temperature (100° C.) was increased at 5° C./min to 200° C. and held at this temperature for 5 min. Then it was increased at 30° C./min to 320° C. An analysis took 40 min. The retention times were as follows: homofarnesol (10.8 min), ambroxan (9.9 min).

As an alternative, a Shimadzu GC-MS QP 2010 system with an FS Supreme 5 column (30 m×0.25 mm×0.25 µm) was used for coupled GC/MS analysis (split ratio 1:20; 3 min 120° C., increase to 135° C. at 2° C./min and further increase to 365° C. at 10° C./min, followed by cooling to 300° C. at 70° C./min). The GC-MS data were analyzed using LabSolutions GCsolutions Postrun software. It should be noted that the substrates citronellal racemate, (R)-citronellal and (S)-citronellal always contain small amounts of isopulegol and neo-isopulegol as impurities. The GC surface values for these linear terpenoids were established as 100%. The surface values for the isopulegol isomers in the product were corrected by the amount of isopulegol isomer that was already present in the substrate. The standard deviation was calculated on the basis of 24 individual tests using two separately grown *E. coli* cultures.

B. Examples

Example 1: Production of Mutants of the F486X Type of the Squalene-Hopene Cyclases by Rational Protein Design Using Quick-Change Mutagenesis The mutants of various squalene-hopene cyclases were incorporated by means of "quick-change" mutagenesis into the corresponding gene. The procedure based on the manufacturers information (Agilent Technologies, Waldbronn) was largely followed. First, a PCR was carried out:

| | |
|---|---|
| PCR charge: | 1.8 µl DMSO |
| | 2 µl dNTPs (each 2.5 mM) |
| | 1.5 µl forward primer (10 pmol/µl) |
| | 1.5 µl reverse primer (10 pmol/µl) |
| | 1 µl templates (1 µg/µL; recombinant plasmid bearing SHC gene, for example pETZmSHC_1) |
| | 0.2 µl Prime-Star Polymerase (Takara, 2.5 Units/µl) |
| | 6 µl 5x buffer |
| | 16 µl $H_2O$ |
| PCR program: | (1) 95° C. 3 minutes |
| | (2) 95° C. 45 seconds |
| | (3) 53° C. 1 minute |
| | (4) 68° C. 17 minutes |
| | 5x repetition of steps (2), (3) and (4) |

After the PCR, 10 µl of the charge was digested with the restriction enzyme DpnI for at least 1 hour at 37° C. Then transformation into *E. coli* XL1-blue cells was carried out. After DNA sequencing, transformation into the expression strain e.g. *E. coli* Rosetta pLysRAR62 took place. The gene can also be modified similarly in other expression plasmids.

The following primers were used for the quick-change PCR. The respective exchange is shown printed in bold in the primer names. The genes that are modified by the respective primers are indicated with italics in the primer names; there is the following correspondence:

ZmSHC_1 SEQ ID NO: 2;

ZmSHC_2 SEQ ID NO: 6;

Ap SEQ ID NO: 4;

Bj SEQ ID NO: 5 and

Sc SEQ ID NO: 3.

| Primer name | Sequence | SEQ ID NO |
|---|---|---|
| ZmSHC_1F486Ilefor | GTTATTATCCTTATCGATGGCTCCCCAACCG | 329 |
| ZmSHC_1F486Ilerev | GGTTGGGGAGCCATCGATAAGGATAATAACAG | 330 |
| ZmSHC_1F486Metfor | GTTATTATCCTTATCCATGGCTCCCCAACCG | 331 |
| ZmSHC_1F486Metrev | GGTTGGGGAGCCATGGATAAGGATAATAACAG | 332 |
| ZmSHC_1F486Thrfor | GTTATTATCCTTATCGGTGGCTCCCCAACCG | 333 |
| ZmSHC_1F486Thrrev | GGTTGGGGAGCCACCGATAAGGATAATAACAG | 334 |
| ZmSHC_1F486Glnfor | GTTATTATCCTTATCCTGGGCTCCCCAACCG | 335 |
| ZmSHC_1F486Glnrev | GGTTGGGGAGCCCAGGATAAGGATAATAACAG | 336 |
| ZmSHC_1F486Asnfor | GTTATTATCCTTATCGTTGGCTCCCCAACCG | 337 |
| ZmSHC_1F486Asnrev | GGTTGGGGAGCCAACGATAAGGATAATAACAG | 338 |
| ZmSHC_1F486Lysfor | GTTATTATCCTTATCTTTGGCTCCCCAACCG | 339 |
| ZmSHC_1F486Lysrev | GGTTGGGGAGCCAAAGATAAGGATAATAACAG | 340 |
| ZmSHC_1F486Aspfor | GTTATTATCCTTATCATCGGCTCCCCAACCG | 341 |
| ZmSHC_1F486Asprev | GGTTGGGGAGCCGATGATAAGGATAATAACAG | 342 |
| ZmSHC_1F486Glufor | GTTATTATCCTTATCTTCGGCTCCCCAACCG | 343 |
| ZmSHC_1F486Glurev | GGTTGGGGAGCCGAAGATAAGGATAATAACAG | 344 |
| ZmSHC_1F486Trpfor | GTTATTATCCTTATCCCAGGCTCCCCAACCG | 345 |
| ZmSHC_1F486Trprev | GGTTGGGGAGCCTGGGATAAGGATAATAACAG | 346 |
| ZmSHC_1F486Argfor | GTTATTATCCTTATCACGGGCTCCCCAACCG | 347 |
| ZmSHC_1F486Argrev | GGTTGGGGAGCCCGTGATAAGGATAATAACAG | 348 |
| ZmSHC_1F486Cysfor | GTTATTATCCTTATCGCAGGCTCCCCAACCG | 349 |
| ZmSHC_1F486Cysrev | GGTTGGGGAGCCTGCGATAAGGATAATAACAG | 350 |
| ZmSHC_1F486Gfor | GTTATTATCCTTATCACCGGCTCCCCAACCG | 351 |
| ZmSHC_1F486Grev | GGTTGGGGAGCCGGTGATAAGGATAATAACAG | 352 |
| ZmSHC_1F486Sfor | GTTATTATCCTTATCGCTGGCTCCCCAACCG | 353 |
| ZmSHC_1F486Srev | GGTTGGGGAGCCAGCGATAAGGATAATAACAG | 354 |
| ZmSHC_1F486Pfor | GTTATTATCCTTATCCGGGGCTCCCCAACCG | 355 |
| ZmSHC_1F486Prev | GGTTGGGGAGCCCCGGATAAGGATAATAACAG | 356 |
| ZmSHC_1F486Hfor | GTTATTATCCTTATCATGGGCTCCCCAACCG | 357 |
| ZmSHC_1F486Hrev | GGTTGGGGAGCCCATGATAAGGATAATAACAG | 358 |
| ZmSHC_1F486Lfor | GTTATTATCCTTATCCAGGGCTCCCCAACCG | 359 |
| ZmSHC_1F486Lrev | GGTTGGGGAGCCCTGGATAAGGATAATAACAG | 360 |
| ZmSHC_1F486Vfor | GTTATTATCCTTATCAACGGCTCCCCAACCG | 361 |
| ZmSHC_1F486Vrev | GGTTGGGGAGCCGTTGATAAGGATAATAACAG | 362 |
| ZmSHC_1F486Afor | GTTATTATCCTTATCCGCGGCTCCCCAACCG | 363 |
| ZmSHC_1F486Arev | GGTTGGGGAGCCGCGGATAAGGATAATAACAG | 364 |
| ZmSHC_1F486Yfor | GTTATTATCCTTATCATAGGCTCCCCAACCG | 365 |
| ZmSHC_1F486Yrev | GGTTGGGGAGCCTATGATAAGGATAATAACAG | 366 |
| ZmSHC_1Y702Cfor | GCCGATAAAAATCGCAACGCAGCATAAACG | 367 |
| ZmSHC_1Y702Crev | CGTTTATGCTGCGTTGCGATTTTTATCGGC | 368 |

-continued

| Primer name | Sequence | SEQ ID NO |
|---|---|---|
| ZmSHC_1Y702Ffor | GCCGATAAAAATCTTTACGCAGCATAAACG | 369 |
| ZmSHC_1Y702Frev | CGTTTATGCTGCGTAAAGATTTTTATCGGC | 370 |
| ZmSHC_1Y702Afor | GCCGATAAAAATCCGCACGCAGCATAAACG | 371 |
| ZmSHC_1Y702Arev | CGTTTATGCTGCGTGCGGATTTTTATCGGC | 372 |
| ZmSHC_1Y702Sfor | GCCGATAAAAATCGCTACGCAGCATAAACG | 373 |
| ZmSHC_1Y702Srev | CGTTTATGCTGCGTAGCGATTTTTATCGGC | 374 |
| ZmSHC_1Y561Afor | GAACCGCACCGGTGCCATAGATCGCATTAACG | 375 |
| ZmSHC_1Y561Arev | GGTTTGGTCGTTGGGGCGTTAATGCGATCTATGG | 376 |
| ZmSHC_1Y705Afor | CCATAATCGGGAAGAATTGCCGCGCAAAATC | 377 |
| ZmSHC_1Y705Arev | CTGCGTTATGATTTTGCGCGGCAATTCTTC | 378 |
| ZmSHC_2F486Cfor | GGCGGTTGGGGCGCTTGCGATGCCAATAACAG | 379 |
| ZmSHC_2F486Crev | CTGTTATTGGCATCGCAAGCGCCCCAACCGCC | 380 |
| ApF486Crev | CATTATCTTTATCGCATGCACCCCAACCACC | 381 |
| ApF486Cfor | GGTGGTTGGGGTGCATGCGATAAAGATAATG | 382 |
| BjF486Cfor | CGGCTGGGGCGCGTGCGATAAAGATAAC | 383 |
| BjF486Crev | GTTATCTTTATCGCACGCGCCCCAGCCG | 384 |
| ScF486Cfor | CGGCGCCTGGGGCGCCTGCGACGTCGACAAC | 385 |
| ScF486Crev | GTTGTCGACGTCGCAGGCGCCCCAGGCGCCG | 386 |

Example 2: Activity Tests with Mutants of Squalene-Hopene Cyclase-1 (SHC-1) from *Zymomonas mobilis*

The influence of various single mutations, produced according to example 1, in the sequence position corresponding to F486, on the cyclase activity was determined for various substrates.

a) Citronellal

After the general detection of a slight cyclization activity of the squalene-hopene cyclase-1 from *Zymomonas mobilis* (SEQ ID NO:2) with respect to citronellal, the turnover rate was greatly improved by rational protein design. Exchange of the phenylalanine residue F486 for alanine led in preliminary tests (cf. FIG. 2) to a greatly increased production of isopulegol (2) starting from citronellal (1).

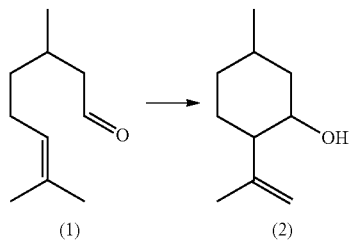

The increased activity of the SHC_1-F486A mutant was then investigated in more detail. In addition to a far better conversion of the citronellal substrate, it was also found that this prefers the R(+) isomer as substrate and compared with the WT it is also converted in a much shorter time (cf. FIG. 2). Whereas with the WT enzyme the reaction with R(+)-citronellal is not measurable until after quite long incubation, the F486A mutant shows high conversions, in particular at the start of the reaction. This effect is not observed with S(−)-citronellal as substrate. It is notable that the F486A mutant only forms isopulegol I and II, whatever the stereoconfiguration of the substrate. The WT, in contrast, is dependent on the stereoconfiguration of the substrate and forms, as well as isopulegol I, mainly isopulegol II from R(+)-citronellal and almost exclusively isopulegol III from S(−)-citronellal.

Figure 3:
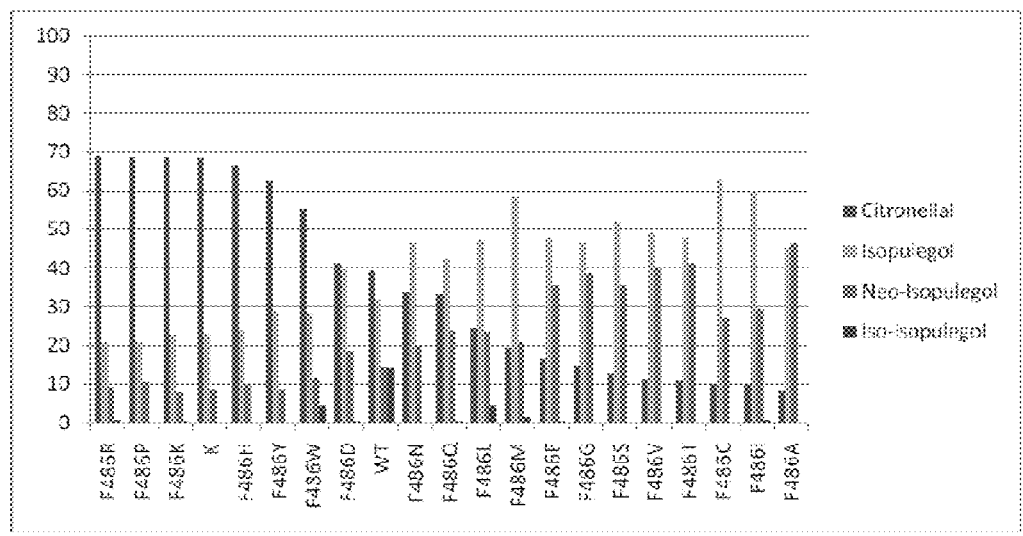
FIG. 3 shows the turnover of the various mutants of Zm-SHC-1 compared with the wild type (wt) and the control without enzyme (K) with 10 mM citronellal racemate as substrate. The percentage distribution of substrate and isopulegol product isomers after incubation overnight at 30° C. is shown in each case.

Based on these results, in further experiments the importance of the amino acid residues at position 486 was investigated more closely. For this, by means of mutagenesis, the phenylalanine residue was exchanged against each further amino acid and the activity of the various muteins was tested with citronellal as substrate (for sequences see FIGS. 1a and b). It was found that some amino acids at this position not only improve the conversion of citronellal by the enzyme, but additionally lead to higher product specificity in the reaction, so that fewer isomers of isopulegol are produced (see FIG. 3).

Exchange for arginine, proline and lysine leads to a loss in activity with respect to citronellal. The amounts of product determined also occur, in the same distribution, as contamination in the negative control ('K' see FIG. 3). The highest activity was observed after exchange for valine, threonine, cysteine, isoleucine and alanine. Overall, the altered product spectrum of some muteins is notable. Not all show the formation of three isopulegol peaks as the wild type as well as the quantitative distribution differs.

There are altogether $2^3$ isopulegol isomers:

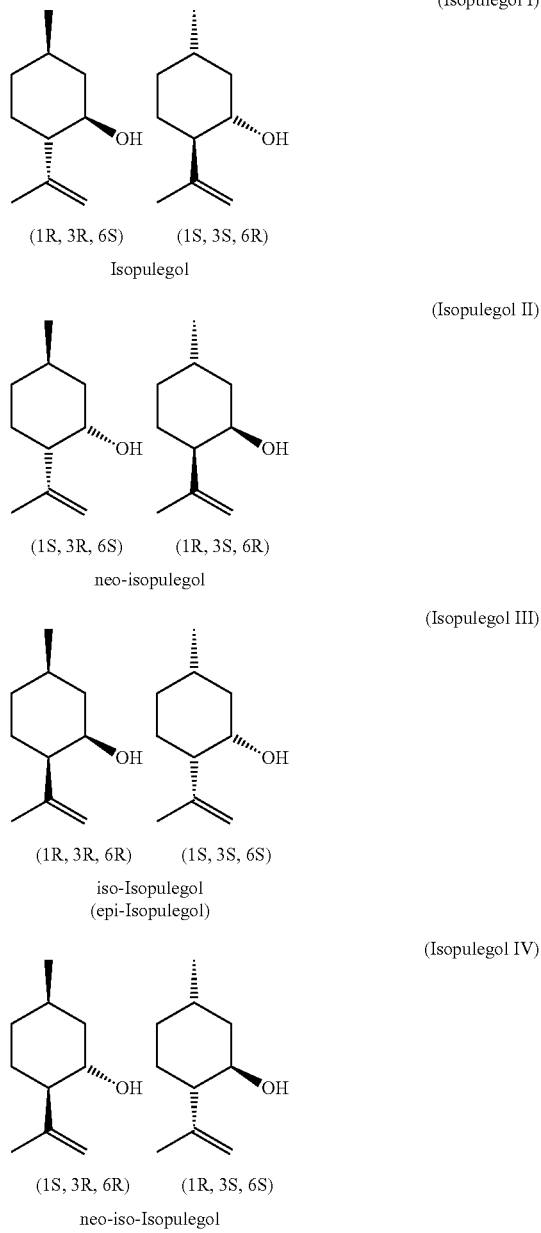

(Isopulegol I)

(1R, 3R, 6S)   (1S, 3S, 6R)
Isopulegol (Isopulegol II)

(1S, 3R, 6S)   (1R, 3S, 6R)
neo-isopulegol (Isopulegol III)

(1R, 3R, 6R)   (1S, 3S, 6S)
iso-Isopulegol
(epi-Isopulegol)

(Isopulegol IV)

(1S, 3R, 6R)   (1R, 3S, 6S)
neo-iso-Isopulegol

Until now, the main product (isopulegol I) has been assigned to the enantiomeric pair (1R,3R,6S)-isopulegol or (1S,3S,6R)-isopulegol.

The highest yield of isopulegol with the least by-products (consisting of further isomers) accompanied by high enzyme activity is displayed by the Zm-SHC-1 F486C mutant.

b) Squalene

Figure 4:
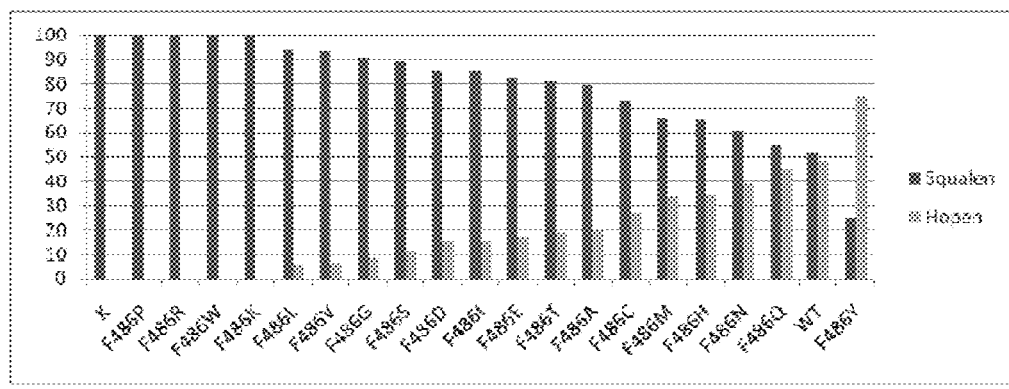
FIG. 4 shows the turnover of the various Zm-SHC-1 mutants compared with the wild type (wt) and the control without enzyme (K) with 25 mM squalene as substrate in the presence of 1% Triton. The percentage distribution of squalene and hopene after incubation for 70 h at 30° C. is shown in each case.

Clear changes in activity after mutation at position F486 are also seen with squalene as substrate. Interestingly, in this case the exchange of phenylalanine for tyrosine produces almost a doubling of the conversion (see FIG. 4).

Example 3: Activity Tests with Mutants of Other Squalene-Hopene Cyclases

The influence of various single mutations, produced according to example 1, in the sequence position corresponding to F486 on the cyclase activity of various other SHCs was determined for various citronellal substrates (in each case 20 mM overnight incubation):

The mutants are as follows:
Ap-SHC: F481C,
Bj-SHC: F447C,
Sc-SHC: F449C,
Zm SHC-2: F438C The phenylalanine residues are located in positions that are analogous to the F486 of Zm-SHC-1 (SEQ ID NO:2).

Figure 5:
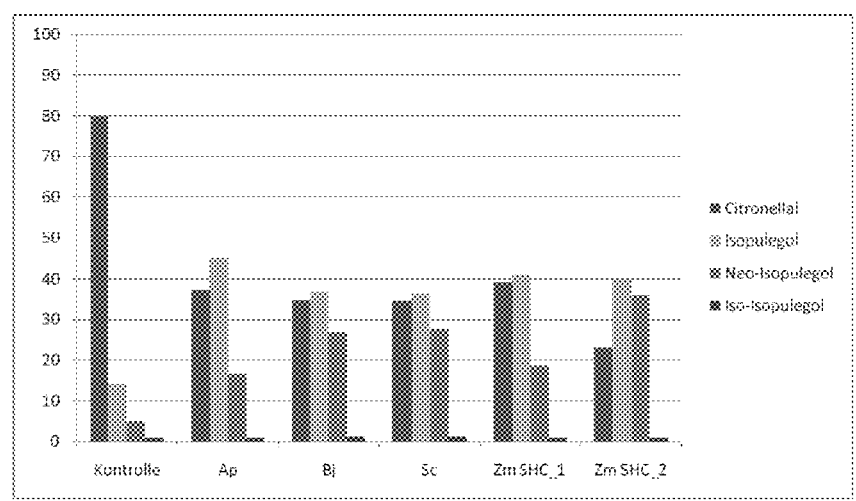
FIGS. 5 to 7 show the reaction of in each case 20 mM substrate after incubation overnight with the mutants Ap-SHC: F481C, Bj-SHC: F447C, Sc-SHC: F449C, Zm SHC-2: F438C and Zm SHC-1 compared with the control; the substrates were citronellal racemate in FIG. 5, R(+)-citronellal in FIG. 6 and S(−)-citronellal in FIG. 7.
Figure 6:
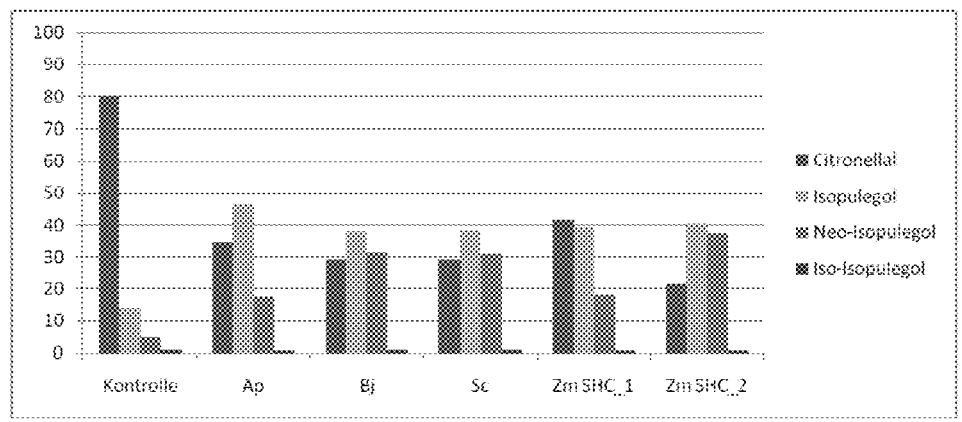
Figure 7:
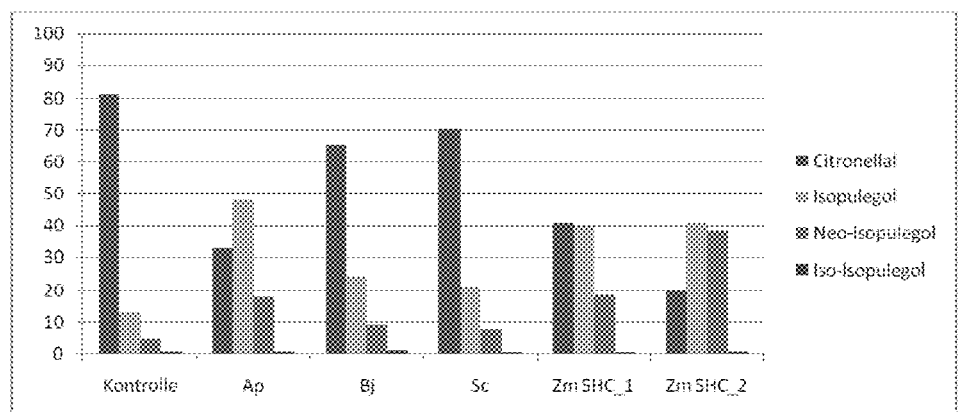

The results can be seen in FIG. 5 (citronellal racemate as substrate), FIG. 6 (R(+)-citronellal as substrate), and FIG. 7 (S(−)-citronellal as substrate). The control was a charge without active biocatalyst.

It can be seen that the wild-type enzymes, through mutation at the stated position corresponding to F486 (of Zm SHC-1), can now cyclize citronellal to isopulegol and moreover convert the R(+) form with increased selectivity compared with the S(−) form.

Example 4: Conversion of Compounds of Formula IV

These substances were converted under conditions corresponding to those employed for the conversion of citronellal as described above.

Example 5: Isolation and Characterization of the Squalene-Hopene Cyclase from *Zymomonas mobilis* (Zm-SHC)

International application PCT/EP2010/057696, hereby incorporated by reference, describes how, using specific oligonucleotides, the Zm-SHC gene from the genomic DNA of *Zymomonas mobilis* was amplified and expressed in *Escherichia coli*.

a) Material and Methods:

Addressed below are only materials and methods not mentioned in this form in international application PCT/EP2010/057696.

b) Strains, Plasmids and Culture Conditions:

The *E. coli* strain DH5a, the *E. coli* strain BL21 (DE3) pLysS (Novagen) and the *E. coli* Rosetta strain were used. The plasmid pET16b (Novagen) was used for cloning. For the overexpression of the SHC, moreover, the plasmid pLysRAR62 was additionally transformed for the adaptation of the codon usage to *E. coli*. Furthermore, the plasmid pDHE+ZmSHC-1 from *E. coli* Lu15568 was used (international application PCT/EP2010/057696). The strains were grown using LB medium at 30° C.

c) Chemicals:

Squalene, (+/−)-citronellal, (+)-R-citronellal and (−)-S-citronellal were purchased from Sigma (Sigma-Aldrich Chemie GmbH, Munich). Restriction enzymes, T4 ligase, and DNA polymerase came from New England Biolabs (New England Biolabs GmbH, Frankfurt).

d) Isolation of DNA and transformation:

Plasmids were isolated from *E. coli* using the Qiaprep Spin Miniprep Kits from Qiagen (Qiagen, GmbH, Hilden). For gel extractions or PCR purifications, the Qiaquick Gel Extraction Kit from Qiagen was used. All of the *E. coli* strains used were transformed using the CaCl$_2$ method.

e) PCR and Sequencing:

The DNA from *Zymomonas mobilis* subspec. *mobilis* CP4 was provided by Prof. Sprenger (Institute of Microbiology, University of Stuttgart). The PCR was carried out using Prime Star Polymerase. The following primers were used for synthesizing the squalene-hopene cyclase gene from *Zymomonas mobilis*:

```
SHC_1:
SHC-for
                                          (SEQ ID NO: 387)
TATGCATATGGGTATTGACAGAAT SHC-rev
                                          (SEQ ID NO: 388)
CCGGATCCTCAATTATTCAAATCAATC
```

The correctness of the cloned genes was verified by means of sequencing by the company GATC Biotech. Sequence analyses were carried out using the program Clone Manager 7.0. After restriction of the corresponding amplificates, they were cloned in-frame into the pET16b vector using N-terminally encoded His-tag. The plasmids were subsequently transformed first in *E. coli* DH5a and thereafter in *E. coli* BL21 (DE3)pLysS and *E. coli* Rosetta. For better expression, the plasmid pLysRAR62 was transformed into the *E. coli* Rosetta strains in addition to the pET16b constructs. Corresponding clonings with empty vectors were carried out in parallel. In addition, the plasmid pDHE+ZmSHC_1 (corresponding to SHC_1 with codon usage adapted to *E. coli*) was transformed in *E. coli* BL21 (DE3) pLysS.

f) Expression and Cell Digestion:

The corresponding *E. coli* B121 (DE3) pLysS and *E. coli* Rosetta transformants were cultured in LB medium with ampicillin and chloramphenicol (100 µg/ml and 32 µg/ml, respectively) at 30° C. The synthesis of the squalene-hopene cyclases was induced by addition of 0.5-1 mM IPTG or 0.1% rhamnose (when using the pDHE derivatives) with an $OD_{600}$ of 0.4-0.6. The cells were allowed to grow further for 4-6 hours, and subsequently harvested. This was done by centrifuging off the cells and taking them up in 5 ml/g wet weight of 25 mM Tris/HCl with 40% glycerol. If the cells were not used further immediately, they were stored at −20° C. For digestion of the cells, they were each subjected 2× to a French Press and used, either directly or following removal of the cell debris by centrifugation, for the activity assays. Alternatively, cell digestion took place using ultrasound. Following centrifugation, the SHC proteins were subsequently dissolved with solubilization buffer (50 mM Tris/HCl pH 8, 10 mM $MgCl_2$, 1% Triton X-100) to remove the cell debris, and hence partially enriched.

g) Activity Assays:

Each batch for determining the activity of the squalene-hopene cyclases had a final volume of 1 ml. This was made up of 600 µl of cells digested by French Press (alternatively 800 µl after solubilization from the cell membrane), 100 mM Na citrate buffer with different pH levels (pH 4.0 to pH 8.0 were used for testing) and 10 mM substrate solution [(+/−) citronellal, (+)-R-citronellal and (−)-S-citronellal]. In addition to the substrate and $H_2O$, the substrate solution also comprised Triton X-100, which was present in each of the activity batches at a concentration of 0.2%.

The batches were incubated with shaking for 6 hours to 24 hours at temperatures of 22° C., 30° C. and 37° C. The substrate and possible products were extracted with one volume of chloroform or hexane/propanol in a ratio of 2:3. The extract was used directly for analysis by gas chromatography.

h) GC Measurements:

The gas-chromatographic measurements took place on an Agilent 7890A gas chromatograph with flame ionization detector. The column used was a DB-5 (Agilent Technologies) with a length of 20 m, a diameter of 0.1 mm and 0.25 µM coating. Substances were identified by comparison of the retention times with available standard solutions.

For verification, the samples were analyzed in parallel on a Shimadzu Gas chromatograph with mass spectrometer. Using the column FS Supreme with a length of 30 m, an internal diameter of 0.25 mm and a coating of 0.25 µm, the retention times were again compared with standard solutions, and the respective mass spectra of the substances present were analyzed.

With the aid of a standard, the diastereomer identified below as isopulegol I was assigned to (1R,3R,6S) or (1S, 3S,6R) isopulegol, whereas no assignment was possible for the isomers identified as isopulegol II and isopulegol III.

i) Results of the Activity Assays:

1. Test 1a: (comparative) (controls i.e. results with boiled-off protein, with empty vector and without protein)

|  | pH 4.0 | pH 4.5 | pH 5.0 | pH 5.5 | pH 6.0 | pH 6.5 | pH 7.0 |
|---|---|---|---|---|---|---|---|
| Citronellal | 85.4 | 85.4 | 86.0 | 85.6 | 84.4 | 84.7 | 85.1 |
| Isopulegol I | 10.8 | 10.8 | 10.4 | 10.8 | 11.7 | 11.5 | 11.2 |
| Isopulegol II | 3.8 | 3.8 | 3.6 | 3.6 | 3.9 | 3.8 | 3.7 |
| Isopulegol III | 0 | 0 | 0 | 0 | 0 | 0 | 0 |

In the information below concerning the substrate rac-citronellal, take place with the amounts of isopulegol found in the controls having already been deducted.

2. Test 1 b: Comparison of the two overexpressed SHC_1 proteins (from pDHE and pET16b vector and influence of the His-tag on activity at pH 4.5)

|  | pDHE | pET16b |
|---|---|---|
| Citronellal | 95.2 | 95.2 |
| Isopulegol I | 0.7 | 0.8 |
| Isopulegol II | 1.7 | 1.6 |
| Isopulegol III | 2.4 | 2.4 |

3. Test 1c: pH dependence

|  | pH 4.0 | pH 4.5 | pH 5.0 | pH 5.5 | pH 6.0 | pH 6.5 | pH 7.0 |
|---|---|---|---|---|---|---|---|
| Citronellal | 95.9 | 94.9 | 94.7 | 94.4 | 95.1 | 98.7 | 98.8 |
| Isopulegol I | 0.4 | 0.8 | 0.8 | 1.0 | 1.1 | 0.8 | 0.5 |
| Isopulegol II | 1.1 | 2.4 | 2.1 | 2.1 | 1.6 | 0.5 | 0.7 |
| Isopulegol III | 2.6 | 1.9 | 2.4 | 2.5 | 2.2 | 0 | 0 |

4. Test 1d: Influence of salts at pH 4.5

|  | none | $BaCl_2$ | $CaCl_2$ | $MgCl_2$ |
|---|---|---|---|---|
| Citronellal | 94.9 | 95.2 | 94.9 | 95.0 |
| Isopulegol I | 0.7 | 0.8 | 1.0 | 0.9 |
| Isopulegol II | 2.5 | 2.4 | 2.4 | 2.5 |
| Isopulegol III | 1.9 | 1.6 | 1.7 | 1.6 |

5. Test 1e: Influence of temperature at pH 4.5

|  | 22° C. | 30° C. | 37° C. |
|---|---|---|---|
| Citronellal | 95.3 | 94.9 | 95.4 |
| Isopulegol I | 0.8 | 1.0 | 0.8 |
| Isopulegol II | 1.8 | 2.2 | 1.6 |
| Isopulegol III | 2.1 | 1.9 | 2.2 |

6. Test 2: S(−)-Citronellal as substrate

|  | pH 4.0 | CTRL | pH 4.5 | CTRL | pH 5.0 | CTRL | pH 5.5 | CTRL |
|---|---|---|---|---|---|---|---|---|
| Citronellal | 90.8 | 95.5 | 90.8 | 95.7 | 91.7 | 96.2 | 92.4 | 96.2 |
| Isopulegol I | 4.9 | 4.5 | 4.7 | 4.3 | 4.4 | 3.8 | 4.1 | 3.8 |
| Isopulegol II | 0 | 0 | 0 | 0 | 0 | 0 | 0 | 0 |
| Isopulegol III | 4.3 | 0 | 4.5 | 0 | 3.9 | 0 | 3.5 | 0 |

|  | pH 6.0 | CTRL | pH 6.5 | CTRL | pH 7.0 | CTRL |
|---|---|---|---|---|---|---|
| Citronellal | 94.1 | 96.6 | 96.4 | 96.5 | 96.5 | 96.4 |
| Isopulegol I | 3.8 | 3.4 | 3.6 | 3.5 | 3.5 | 3.6 |
| Isopulegol II | 0 | 0 | 0 | 0 | 0 | 0 |
| Isopulegol III | 2.1 | 0 | 0 | 0 | 0 | 0 |

7. Test 3: R-(+)-Citronellal as substrate

|  | pH 4.0 | CTRL | pH 4.5 | CTRL | pH 5.0 | CTRL | pH 5.5 | CTRL |
|---|---|---|---|---|---|---|---|---|
| Citronellal | 80.0 | 84.2 | 78.4 | 83.8 | 81.1 | 85.6 | 81.7 | 86.8 |
| Isopulegol I | 15.9 | 15.8 | 16.0 | 16.2 | 14.1 | 14.4 | 13.5 | 13.2 |
| Isopulegol II | 4.1 | 0 | 5.6 | 0 | 4.8 | 0 | 4.8 | 0 |
| Isopulegol III | 4.3 | 0 | 4.5 | 0 | 3.9 | 0 | 3.5 | 0 |

|  | pH 6.0 | CTRL | pH 6.5 | CTRL | pH 7.0 | CTRL |
|---|---|---|---|---|---|---|
| Citronellal | 81 | 85.5 | 80.8 | 85.8 | 81.4 | 86.2 |
| Isopulegol I | 14.3 | 14.5 | 14.5 | 14.2 | 14.0 | 13.8 |
| Isopulegol II | 4.7 | 0 | 4.7 | 0 | 4.6 | 0 |
| Isopulegol III | 2.1 | 0 | 0 | 0 | 0 | 0 | j) Summary of the Results:

The squalene-hopene cyclase from *Zymomonas mobilis* was prepared recombinantly in *E. coli*. The enzyme is able to convert citronellal to isopulegol.

Here, the two overproduced Zm-SHC-1 proteins, once without and once with N-terminally appended His-tag, showed no differences in their activity under the conditions tested (cf. Test 1b).

This reaction was verified after 12 hours with the techniques described. The dependence of the reaction on the pH level was low. In a pH range from pH 4 to pH 6, conversion rates totaling about 5% were measured for different isopulegol isomers after 20-hour incubation.

Here it was not critical whether the batches were incubated at RT, 30° C. or 37° C. The conversion was also not increased by addition of divalent ions, such as MgCl$_2$, for example (cf. Test 1d). What was critical, however, was that the cell extracts, in the case of measurements above a pH of pH 5, either were dialyzed before the substrate was added, or EDTA was added to the batches, in order to suppress reduction of the citronellal substrate to citronellol by enzymes of the host. No effect of this treatment on the activity of the Zm-SHC-1 was found. Where this treatment was not carried out, the substrate was reduced almost completely to citronellol within 20 hours, and there was no longer any measurable cyclization to isopulegol. Zm-SHC-1 is therefore able to cyclize citronellal, but not citronellol, to isopulegol. It is very likely that unspecific dehydrogenases are responsible for the reduction reaction.

In order to rule out a chemical reaction being responsible for the cyclization, boiled-off cell extracts were used. In these controls and in controls with cell extracts from cultivation with empty vectors, however, no corresponding conversion was found (cf. Test 1a).

With (+/−)-citronellal as the substrate it was possible, following the reaction, to detect various isomers of isopulegol, which have not yet been precisely identified (cf. Tests 2 and 3). In order to verify whether these isomers originated from the different isomers of the starting substrate or if only one isomer was accepted as the substrate and was differently converted, the same studies were carried out with (+)-R-citronellal and (−)-S-citronellal. Here it was found that, depending on the substrate, different isopulegol isomers are formed. Interestingly, the conversion of (+)-R-citronellal took place from a pH of 4 to a pH of 7 without substantial differences, at a rate of about 5%. The enantiomer, in contrast, was converted with conversion rates of approximately 4.5% only up to a pH level of pH 6. Here as well, the conversion rate showed virtually no fluctuation in terms of the individual pH levels between pH 4 and pH 6.

Sequences:
SEQ ID NO: 1-326 nucleic acid/amino acid sequences of various SHC genes
SEQ ID NO: 327-388 PCR primers
The disclosure of the publications cited herein is expressly referred to.
There follows a listing of SHC enzyme sequences which can be used in accordance with the invention:

Enzyme Sequences

>seq_ID 4
MNMASRFSLKKILRSGSDTQGTNVNTLIQSGTSDIVRQKPAPQEPADLSALKAMGNSLTHTLSS
ACEWLMKQQKPDGHWVGSVGSNASMEAEWCLALWFLGLEDHPLRPRLGKALLEMQRPDGS
WGTYYGAGSGDINATVESYAALRSLGYAEDDPAVSKAAAWIISKGGLKNVRVFTRYWLALIGE
WPWEKTPNLPPEIIWFPDNFVFSIYNFAQWARATMMPLAILSARRPSRPLRPQDRLDALFPGG
RANFDYELPTKEGRDVIADFFRLADKGLHWLQSSFLKRAPSREAAIKYVLEWIIWHQDADGGW
GGIQPPWVYGLMALHGEGYQFHHPVMAKALDDALNDPGWRHDKGDASWIQATNSPVWDTML
SLMALHDANAEERFTPEMDKALDWLLSRQVRVKGDWSVKLPNTEPGGWAFEYANDRYPDTD
DTAVALIAIASCRNRPEWQAKGVEEAIGRGVRWLVAMQSSCGGWGAFDKDNNKSILAKIPFCD
FGEALDPPSVDVTAHVLEAFGLLGLPRDLPCIQRGLAYIRKEQDPTGPWFGRWGVNYLYGTGA
VLPALAALGEDMTQPYISKACDWLINCQQENGGWGESCASYMEVSSIGHGATTPSQTAWALM
GLIAANRPQDYEAIAKGCRYLIDLQEEDGSWNEEEFTGTGFPGYGVGQTIKLDDPAISKRLMQG
AELSRAFMLRYDLYRQLFPIIALSRASRLIKLGN >seq_ID 2
MGIDRMNSLSRLLMKKIFGAEKTSYKPASDTIIGTDTLKRPNRRPEPTAKVDKTIFKTMGNSLNN
TLVSACDWLIGQQKPDGHWVGAVESNASMEAEWCLALWFLGLEDHPLRPRLGNALLEMQRE
DGSWGVYFGAGNGDINATVEAYAALRSLGYSADNPVLKKAAAWIAEKGGLKNIRVFTRYWLALI
GEWPWEKTPNLPPEIIWFPDNFVFSIYNFAQWARATMVPIAILSARRPSRPLRPQDRLDELFPE
GRARFDYELPKKEGIDLWSQFFRTTDRGLHWVQSNLLKRNSLREAAIRHVLEWIIRHQDADGG
WGGIQPPWVYGLMALHGEGYQLYHPVMAKALSALDDPGWRHDRGESSWIQATNSPVWDTM
LALMALKDAKAEDRFTPEMDKAADWLLARQVKVKGDWSIKLPDVEPGGWAFEYANDRYPDTD
DTAVALIALSSYRDKEEWQKKGVEDAITRGVNWLIAMQSECGGWGAFDKDNNRSILSKIPFCD
FGESIDPPSVDVTAHVLEAFGTLGLSRDMPVIQKAIDYVRSEQEAEGAWFGRWGVNYIYGTGA
VLPALAAIGEDMTQPYITKACDWLVAHQQEDGGWGESCSSYMEIDSIGKGPTTPSQTAWALM
GLIAANRPEDYEAIAKGCHYLIDRQEQDGSWKEEEFTGTGFPGYGVGQTIKLDDPALSKRLLQG
AELSRAFMLRYDFYRQFFPIMALSRAERLIDLNN >seq_ID 5
MTVTSSASARATRDPGNYQTALQSTVRAAADWLIANQKPDGHWVGRAESNACMEAQWCLAL
WFMGLEDHPLRKRLGQSLLDSQRPDGAWQVYFGAPNGDINATVEAYAALRSLGFRDDEPAVR
RAREWIEAKGGLRNIRVFTRYWLALIGEWPWEKTPNIPPEVIWFPLWFPFSIYNFAQWARATLM
PIAVLSARRPSRPLPPENRLDALFPHGRKAFDYELPVKAGAGGWDRFFRGADKVLHKLQNLGN
RLNLGLFRPAATSRVLEWMIRHQDFDGAWGGIQPPWIYGLMALYAEGYPLNHPVLAKGLDALN
DPGWRVDVGDATYIQATNSPVWDTILTLLAFDDAGVLGDYPEAVDKAVDWVLQRQVRVPGDW
SMKLPHVKPGGWAFEYANNYYPDTDDTAVALIALAPLRHDPKWKAKGIDEAIQLGVDWLIGMQ
SQGGGWGAFDKDNNQKILTKIPFCDYGEALDPPSVDVTAHIIEAFGKLGISRNHPSMVQALDYI
RREQEPSGPWFGRWGVNYVYGTGAVLPALAAIGEDMTQPYIGRACDWLVAHQQADGGWGE
SCASYMDVSAVGRGTTTASQTAWALMALLAANRPQDKDAIERGCMWLVERQSAGTWDEPEF
TGTGFPGYGVGQTIKLNDPALSQRLMQGPELSRAFMLRYGMYRHYFPLMALGRALRPQSHS >seq_ID 78
MTLTSSASARAPRDPGNYQTALQSTVRAAADWLIANQKPDGHWVGRAESNACMEAQWCLAL
WFMGLEDHPLRKRLGQSLLDTQRPDGAWQVYFNAPNGDINATVEAYAALRSLGYPDSEPAVR
RAREWIEAKGGLRNIRVFTRYWLALIGEWPWEKTPNIPPEVIWFPLWFPFSIYNFAQWARATLM
PIALLSARRPSRPLPPENRLDTLFPRGRDAFDYELPVKANAGGWDKFFRGADKVLHALQNFGN
RLNLGLFRPAATSRVLEWMIRHQDFDGAWGGIQPPWIYGLMALYAEGYPLNHPVLAKGLDALN
DPGWRVDVGEATYIQATNSPVVVDTILTLLAFDDAGVLGDYPDAVDKAVNWVLARQVRVPGDW
SMKLPHVKPGGWAFEYANNHYPDTDDTAVALIALAPLRHDPKWKAKGIDEAIQLGVDWLIGMQ
SQGGGWGAFDKDNNQQILTKIPFCDYGEALDPPSVDVTAHIVEAFGKLGISRNHPSMVQALDYI
RKEQEPSGPWFGRWGVNYVYGTGAVLPALAAIGEDMTQPYIGRACDWLVAHQQPDGGWGE
SCASYMDISAVGRGTTTASQTAWALMALLAANRPQDKDAIERGCMWLVERQSAGTWDEPEFT
GTGFPGYGVGQTIKLTDPSLQERLMQGPELSRAFMLRYGMYRHYFPLMALGRALRPQGHG >seq_ID 209
MDSILAPRADAPRNIDGALRESVQQAADWLVANQKPDGHWVGRAETNATMEAQWCLALWFL
GLEDHPLRVRLGRALLDTQRPDGAWHVFYGAPNGDINATVEAYAALRSLGHRDDEEPLRKAR
DWILSKGGLANIRVFTRYWLALIGEWPWEKTPNILPEVIWLPTWFPFSIYNFAQWARATLMPIAV
LSAHRPSRPLAPQDRLDALFPQGRDSFNYDLPARLGAGVWDVIFRKIDTILHRLQDWGARRGP
HGIMRRGAIDHVLQWIIRHQDYDGSWGGIQPPWIYGLMALHTEGYAMTHPVMAKALDDALNEG
WRIDIGDATFIQATNSPVVVDTMLSLLAFDDAGLGERYPEQVERAVRWVLKRQVLVPGDWSVKL
PDVKPGGWAFEYANNFYPDTDDTSVALMALAPFRHDPKWQAEGIEDAIQRGIDWLVAMQCKE
GGWGAFDKDNDKKILAKIPFCDFGEALDPPSADVTAHIIEAFAKVGLDRNHPSIVRALDYLKREQ
EPEGPWFGRWGVNYVYGTGAVLPALAAIGEDMRQPYIARACDWLIARQQANGGWGESCVSY
MDAKQAGEGTATASQTAWALMALIAADRPQDRDAIERGCLYLTETQRDGTWQEVHYTGTGFPP
GYGVGQTIKLNDPLLSKRLMQGPELSRSFMLRYDLYRHYFPMMAIGRVLRQRGDRSGH >seq_ID 193
MNVIRQLNSGVNAAKSLDDGIESAIEWLAENQDKEGFWVGMLESNSCIEAEWILAMHLLGVKD
DPKYDKVVQAILNEQREDGSWAVYYDAPAGDINATVEAYAALRTAGFGAGDERLIKARNWIFS
HGGLKNVRVFTRYVVLALIGEWPWDETPALAPEIIYLPAWCPLNIYDFACWARATLVPLSVLSVR
RPVKPLPAESRLDELFPEGRENADYSLPESEKGLAERFFLVVDWFLKKYNRLPMQFGREKAIR
LCLEWIVRHQDYDGGWGGIQPPLIYSLIALNTEGYGINHPVISKGLDAFNPPWAYEKNGGVYLQ
CSESPVVVDTLFTMLALFESGCSFDDTPMMRPALDWILSKQITSWGDWQVKVRGVRPGGWAF
ERANTAYPDVDDTALALVVLAEARRHVKDSAAVDAALERAEEWILGLQCRNGGWAAFDRDNN
SAIVTKIPFCDFGEVLDPPSVDVTAHVVEALAALGRDHDPVVARALKYIRSEQEPGGSWFGR

| Enzyme Sequences |
|---|
| WGVNHIYGTCAVLPALAAIGEDMRAPYVLRAADWLVRHQNDDGGWGESCASYMDDSQCGQ<br>GSSTASQTGWALMALVAMSSHDYDEAIRRGLDYLLSHQKSGTWDEPQYTGTGFPGYGVGER<br>TNLKEAGATLDQGCELARGFMINYNMYRHYFPLIAMARARRHLGLAANPRHQDSRSSVEVAPE<br>ALRGRACG<br><br>>seq_ID 246<br>MRRLDTFPPEIPTGSRDKPPSGEEHSCSTPAEPLRSRLDEGILRAVDWLVCDQHPDGFWAGM<br>LQSNSCMEAEWVLAMHFLGIDDDPKYDGVIRAILGEQRADGSWGVFHKAPNGDINTTVECYAA<br>LRASGLAPESAPLSSAREWILAGGGLANIRNFTKYWLALIGEWPWEGTPTIPPELIFFPPRMPLN<br>IYHFASWARSTIVPLSILSARRPVRPLPEDRRLDELFPQGRSAFDFRLPRKDGWLSWEGFFHVC<br>DRILRLYARTRRAPFRETAIRVCLEWIIRRQETDGAWSGIQPPWIYALLALHAEGYGLDHPILRA<br>GLRAFDSHWSYERDGGIYLQASESPVWDTVLSLRALADCGEERKASVSIASALEWLLNRQISV<br>PGDWAVRVPSVPCGGWAFQRANSFYPDVDDTAVAIEVLARLRPFTANQSAVDRAIRSARDWV<br>LAMQCSNGGWAAFDRDNDFKLVTKIPFCDFGELLDPPSVDVTAHVIEALAALGWDMTSREIEA<br>AVSFIRREQEAEGSWFGRWGVNHIYGTATVLPALRAIGEDMSSAYVLRAADWLASRQNADGG<br>WGETPASYMDDSLRGVGESTASQTAWAIMGLVAVGSGAHDDTVRRGIDFLLFAQHGGTWEE<br>PQYTGTGFPGYSVGERIRLRDMGASLKQGTELQRAFMINYNLRYHFPLMALGRARYHLQLRR<br>SAREGGNGETTPNGSAL<br><br>>seq_ID 151<br>MKISKNPISHALTSFNDAARETADNSAARKSGKIHHLPATIWKKKESTVSSPLDIAIERTQEFFFR<br>EQLPAGYVWVAELESNATITAEYIMLFHFMGLVNREKERKMANYLLRQQTTEGYWTIWHGGPG<br>DLSTTIEAYFALKLAGYPADHPSMSKARAFILEHGGILKARVFTKIFLALFGEFSWLGVPSMPIEM<br>MLLPAGFTFNMYEFSSWSRATIIPLSIVMAERPVRKLPPWARVQELYVRPPRPTDYTFTKEDGIL<br>TWKNIFIGIDHVLKVYEASPIRPGRKKAMAIAEKWVLEHQEPTGDWGGIQPAMLNSVLALHVLG<br>YANDHPAVAKGLQALANFCIEGEDELVLQSCVSPVVVDTALGLMAMVDSGVPTDHPSLSKAAQ<br>WLLDREVRRPGDWKIKCPDLEPGGWAFEFMNDWYPDVDDSGIVMMAIKNVKVKDQRAKEDTI<br>TRGIAWCLGMQSKNGGWGAFDKDNTKHILNKIPFADLEALIDPPTADLTGRMLELMGTYGYPK<br>DHPAAVRALKFIRETQEPDGPVWVGRWGVNYIYGTWSVMSGLAAFGEDMSQPWIRKAVDWLV<br>EHQNEDGGWGECCESYADPRLAGVGPSTASQTGWALLTLLAAGEVASSSVVRGVQYLLDTQ<br>KPDGTWDEDAFTGTGFPKFFMIKYHIYRNCFPLMALGRYRTLAGKGL<br><br>>seq_ID 142<br>MKSRKYPISHALTSFNHTTVAPVEAPAPISVKSPAKVHRLPSSIWKKMEGSAGNPLDKAVELTR<br>DFFFREQLPDGYVVWAELESNVTITAEYIMLFHFLGMVDKDKERKMANYLLRQQTEEGYWTVW<br>HNGPGDLSTTIEAYFALKLAGYHADHIALRKARDFILANGGILKSRVFTKTFLAMFGEFSWLGVP<br>SMPIELMLLPDWAYLNVYEFSSWARATIIPMSVLMANRPVYKLPPHARVQELYVRPPRPTDYTF<br>TKEDGIFSLKNFFIGVDHLLKIYESSPIRPFKKRATEKVEQWILEHQEKTGDWGGIQPAMLNAILA<br>LHCLGYANDHPAVAKGLEALANFTIEDSDSLVLQSCISPVVVDTALVLQAMQEASVPLDHPSLIK<br>ASQWLLDREVRIKGDWKIKSPDLEPGGWAFEFQNDWYPDVDDSTAVMIAIKDIKVKNTKARQD<br>AIRRGIDWCLGMQSENGGWAAFDKDNTKHMLNKIPFADLEALIDPPTADLTGRMLELMGNFGY<br>TKDHPQAVSALEFLKNEQEPEGPWFGRWGVNYIYGTWYVLIGLEAIGEDMNSPYIKKSVNWIK<br>SRQNLDGGWGEVCDSYWDRTLMGCGPSTASQTSWALMALMAAGEVGCQAVERGIQYLLAT<br>QNSDGTWDEEAFTGTGFPKYFMIKYHIYRNCFPLTALGRYRRLTAGTHAQ<br><br>>seq_ID 152<br>MNSCKHPISHALTSFNGETADAAKKQPVKPGAKIHHLPASIWKKKEGESKSPLDIAIENSRDFFF<br>REQLPDGYVVWAELESNCTITAEYLMLYHFMGIVDQERERKMATYLLSKQTAEGFWTIYFGGPG<br>DLSTTVEAYFALKLAGYPADHPAMAKARAFILDNGGIIKCRVFTKIFLALFGEFAWFGVPSMPIEL<br>ILLPNWAYFNMYELSSWSRATIIPLSIVMTERPVRKLPPSSRVQELYVRPPRPIDYTFSKEDGIIT<br>WKNFFIGVDHILKVYESNPIRPFKKRALATAENWVLDHQESTGDWGGIQPAMLNSVLALHCLG<br>YANDHPAVAKGLEALANFCIETEDSLVLQSCISPIWDTALALKALVDSDVPTDHPALVKAAQWLL<br>DKEVRKPGDWKIKCPELESGGWAFEFLNDWYPDVDDSGFVMMALKDVAVKDRKSMDGAIKR<br>GINWCLGMQSKNGGWGAFDKDNTKYLLNKIPFADLEALIDPPTADLTGRMLELMGTFGYSKDY<br>PAAVRALEFIKKNQEPEGSVWVGRWGVNYIYGTWSVLGGLAAIGEDLNQPYIRKAVNWLKSRQ<br>NMDGGWGETCESYHDTSLAGIGESTPSQTGWALLSLMSAGEANSSTVARGIQYLIANQKSDG<br>TWDEEQYTGTGFPKFFMIKYHIYRNCFPLTALGTYRKLTGGMA<br><br>>seq_ID 146<br>MTSPFKHPISNALTSFNGNFAEPEQCVEQQTGAKVHHLPASIWKRKMGKAKSPLDVAIEGSRD<br>FFFEQLPKGYVWVAELESNVTITAEYIMLFHFLGLVDRERQRKMSNYLLSKQTEEGFWPIYYG<br>GPGDLSTTIEAYFALKLSGYPADHPALAKARAFILEQGGVVKSRVFTKIFLALFGEFEWQGVPS<br>MPVELNLLPDWAYINIYEFSSWARATIVPLSVVMHSRPVRRVPPSARVQELFVRQPTAADYSFA<br>KNDGIFTWENFFLGLDRVLKVYEKSPLRPFKNMALAKAEEWVLEHQEPTGDWGGIQPAMLNA<br>VLALNVLGYQNDHPAVEQGLRALANFCIETEDQLVLQSCVSPVVVDTALALKALLDAGVPPDHP<br>SLVKGAQWLLDKEVTRPGDWRVKSPALEPGGWAFEFLNDWYPDVDDSGFVMIALKGIQVKDR<br>KSMDAAIKRGINWCLGMQSKNGGWGAFDKDNTRHVLNKIPFADLEALIDPPTADLTGRMLELM<br>GTFNYPITLPAAQRAIEFLKKNQEPEGPVWVGRWGVNYLYGTWSVLCGLAAIGEDMDQPYIRKA<br>VNWIKSRQNIDGGWGETCQSYHDRTLAGVGESTPSQTGWALLGLLAAGEMHSATVVRGVQY<br>LISTQNSDGTWDEQQYTGTGFPKYFMIKYHIYRNCFPLMALGTYRTLTRTQP<br><br>>seq_ID 147<br>MSPCKHPISHALTSFNGETADSVPVQTPKTGAKIHHLPPSIWKKKEGELKSPLDIAIENSRDFFF<br>REQLPDGYVVWAELESNCTITAEYVMLYHFMDLVDRERERKMANYLLSKQTEEGFWTIYYGGP<br>GDLSTTVEAYFALKLAGYPADHPAMVKARAFILDNGGIIKTRVFTKIFLALFGEFAWFGVPSMPIE<br>LILLPNWAYFNMYELSSWSRATIIPLSIVMTQRPVRKLPPASRVQELYVRPPSPIDYTFTKEDGIF<br>TWKNFFIGVDHILKVYESNPIRPFKKKAMLAAENWVLEHQEATGDWGGIQPAMLNSVLALHCL |

| Enzyme Sequences |
|---|

GYANNHPAVAKGLEALENFCIESEDSLVLQSCISPVVVDTALALKALVDSDVPNDHPALVKAAQ
WLLDKEIRKAGDWKVKSPELEPGGWAFEFLNDWYPDVDDSGFVMMALKDVAVKDRKSMDTAI
KRGISWCLGMQSKNGGWGAFDKDNTKYLLNKIPFADLEALIDPPTVDLTGRMMELMGTFGYAK
DYPPAVRALDFIKRNQEPDGSVWVGRWGVNYIYGTWSVLCGLSAMGEDLNQPYIRKAINWLKS
RQNIDGGWGETCESYHDSSLAGIGASTASQTGWALLALMAVGEENASAVARGVQYLLATQKS
DGTWDEDLYTGTGFPKFFMIKYHIYRNCFPLTALGTYRRKTGGRAEMQVSEHNK

>seq_ID 144
MKISKHPISHALTSFNETAKETKEEPQKKRGGKVHHLPASIWKKRDVETTSPLDQAIKRSQEFFL
REQLPAGYVWVAELESNVTITAEYVILFHFMGLVNRDKDRKMATYLLSKQTEEGCWCIWHGGP
GDLSTTIEAYFALKLAGYPADHPAMQKARTFILGKGGILKARVFTKIFLALFGEFSWLGVPSMPIE
MMLLPNGFTFNLYEFSSWSRATIIPLSIVMAERPVRKLPPWARVQELYVRPPRPMDYTFTKEDG
ILTWKNIFIGIDHILKVYEASPIRPGMKKAMAIAEQWVLDHQEPTGDWGGIQPAMLNSVLALHCL
GYANDHPAVAKGLQALANFCIESDDEIVLQSCISPVVVDTALALMAMVDSEVPTDHPALVKAAQ
WLLDREVRKVGDWKIKAPNLEPGGWAFEFQNDWYPDVDDSGIVMMAIKDVKVKDSKAKAEAI
QRGIAWCIGMQSKNGGWGAFDKDNTKHILNKIPFADLEALIDPPTADLTGRMLELMGTFGYPK
DHPAAVRALQFVKENQEPDGPVWVGRWGVNYIYGTWSVLCGLKAYGEDMGQPYVRKAVEWL
AAHQNPDGGWGECCESYCDQKLAGTGPSTASQTGWALLSMLAAGDVDHPAVARGIRYLIETQ
QPDGTWDEDQFTGTGFPKYFMIKYHIYRNCFPLMAMGRYRALKGHKG >seq_ID 15
MAEQLVEAPAYARTLDRAVEYLLSCQKDEGYVWVGPLLSNVTMEAEYVLLCHILDRVDRDRME
KIRRYLLHEQREDGTWALYPGGPPDLDTTIEAYVALKYIGMSRDEEPMQKALRFIQSQGGIESS
RVFTRMWLALVGEYPWEKVPMVPPEIMFLGKRMPLNIYEFGSWARATVVAISIVMSRQPVFPL
PERARVPELYDTDVPPRRRGAKGGGGRIFDALDRALHGYQKLSVHPFRRAAEIRALDWLLERQ
AGDGSWGGIQPPWFYTLIALKILDMTQHPAFIKGWEGLELYGVDLDYGGWMFQASISPVVVDT
GLAVLALRAAGLPADHDRLVKAGEWLLDRQITVPGDWAVKRPNLKPGGFAFQFDNVYYPDVD
DTAVNNWALNSLRLPDERRRRDVMTKGFRWIVGMQSSNGGWGAYDVDNTSDLPNHIPFCD
GEVTDPPSEDVTAHVLECFGSFGYDDAWKVIRRAVEYLKREQRPDGSWFGRWGVNYLYGTG
AVVPALKAVGIDVREPPIQKALDWVEQHQNPDGGWGEDCRSYEDPAYAGKGASTPSQTAWA
LMALIAGGRAESDSVRRGVQYLVETQRPDGGWDEPYYTGTGFPGDFYLGYTMYRHVFPTLAL
GRYKQAIERR >seq_ID 16
MAEQLVEAPAYARTLDRAVEYLLSCQKDEGYVWVGPLLSNVTMEAEYVLLCHILDRVDRDRME
KIRRYLLHEQREDGTWALYPGGPPDLDTTIEAYVALKYIGMSRDEEPMQKALRFIQSQGGIESS
RVFTRMWLALVGEYPWEKVPMVPPEIMFLGKRMPLNIYEFGSWARATVVALSIVMSRQPVFPL
PERARVPELYETDVPPRRRGAKGGGGWIFDALDRALHGYQKLSVHPFRRAAEIRALDWLLER
QAGDGSWGGIQPPWFYALIALKILDMTQHPAFIKGWEGLELYGVELDYGGWMFQASISPVVVD
TGLAVLALRAAGLPADHDRLVKAGEWLLDRQITVPGDWAVKRPNLKPGGFAFQFDNVYYPDV
DDTAVVVVVALNTLRLPDERRRRDAMTKGFRWIVGMQSSNGGWGAYDVDNTSDLPNHIPFCD
FGEVTDPPSEDVTAHVLECFGSFGYDDAWKVIRRAVEYLKREQKPDGSWFGRWGVNYLYGT
GAVVSALKAVGIDTREPYIQKALDWVEQHQNPDGGWGEDCRSYEDPAYAGKGASTPSQTAW
ALMALIAGGRAESEAARRGVQYLVETQRPDGGWDEPYYTGTGFPGDFYLGYTMYRHVFPTLA
LGRYKQAIERR >seq_ID 141
MTSPFKHPISNALTSFNGNVAEPEQSVEQQSGAKVHHLPASIWKRKMGRAKSPLDVAIEGSRD
FFFQEQLPKGYVWVAELESNVTITAEYIMLFHFLGLVDPERQRKMSTYLLSKQTEEGFWTIYYG
GPGDLSTTIEAYFALKLSGYPEDHPALAKARAFILEQGGVVKSRVFTKIFLALFGEFDWQGIPSM
PVELNLLPDWAYINIYEFSSWARATIVPLSVVMHSRPVRRVPPSARVQELFVRQPTAADYSFAK
NDGLFTWEKFFLGLDRVLKVYEKSPLRPFKKTALAKAEEWVLEHQEPTGDWGGIQPAMLNAIL
ALNVLGYRNDHPAVEQGLRALANFCIETEDQLVLQSCVSPVVVDTALALKALLDAGVPPDHPSL
VKGAQWLLDKEVTRAGDWRVKSPNLEAGGWAFEFLNDWYPDVDDSGFVMIALKGIQVKDHK
AMDAAIKRGINWCLGMQSKNGGWGAFDKDNTKHVLNKIPFADLEALIDPPTADLTGRMLELMG
TFDYPVTFPAAQRAIEFLKKNQEPEGPWWGRWGVNYLYGTWSVLCGLAAIGEDMDQPYIRKA
VNWIKSRQNIDGGWGETCQSYHDRTLAGVGESTPSQTGWALLSLLAAGEMHSATVVRGVQYL
ISTQNSDGTWDEQQYTGTGFPKYFMIKYHIYRNCFPLMALGTYRTLTRTQP >seq_ID 195
MNPAKYKISSSLTSLNAEPVEQAPLPAKRTGSKVHRLPPSIWKKMVAEAKSPLDKGIERTRDFF
LREQLPDGYVVWAELESNVTISAEYVMLFHFLGMVDRERERKLANYILAKQTSEGFWSLWHNG
PGDLSTTIEAYFALKLAGYSADHPAMAKARAFVLANGGIIKARVFTKIFLALFGEFAWFGVPSMPI
ELMLLPDWAYFNMYEFSSWSRATIIPLSVVMSERPVRKLPPRAQVQELFVRPPRPTDYTITRED
GLFTWKNFFIGADHLIKVYESSPIRPFKKRAVALAENWILEHQESGDWGGIQPAMLNSILALHC
LGYANDHPAVAKGLDALANFCIEDDDCIVLQSCVSPVVVDTALALVALQEADVPADHPALVKAA
QWLLNLEVRRKGDWQVKCPELEPGGWAFEFLNDWYPDVDDSGFVMLSIKNIKVRDRKHREE
AIKRGIAWCLGMQSENGGWGAFDRNNTKYLLNKIPFADLEALIDPPTADLTGRMLELMGNFDY
PKSHPAAERALAFLKKEQESEGPWWGRWGVNYLYGTWSVLCGLEAIGEDMNQPYIRKAVNWI
KSRQNNDGGWGEVCESYFDRSLMGSGPSTASQTGWALLALMAAGEANSRAAAQGVKYLLET
QNEDGTWDEDAFTGTGFPKFFMIKYHIYRNCFPLTALGRYRRLTAAKG >seq_ID 3
MTATTDGSTGASLRPLAASASDTDITIPAAAAGVPEAAARATRRATDFLLAKQDAEGVWVKGDL
ETNVTMDAEDLLLRQFLGIQDEETTRAAALFIRGEQREDGTWATFYGGPGELSTTIEAYVALRL
AGDSPEAPHMARAAEWIRSRGGIASARVFTRIWLALFGVWVKWDDLPELPPELIYFPTWVPLNI
YDFGCWARQTIVPLTIVSAKRPVRPAPFPLDELHTDPARPNPPRPLAPVASWDGAFQRIDKALH

| Enzyme Sequences |
|---|
| AYRKVAPRRLRRAAMNSAARWIIERQENDGCWGGIQPPAVYSVIALYLLGYDLEHPVMRAGLE<br>SLDRFAVVREDGARMIEACQSPVVVDTCLATIALADAGVPEDHPQLVKASDWMLGEQIVRPGD<br>WSVKRPGLPPGGWAFEFHNDNYPDIDDTAEVVLALRRVRHHDPERVEKAIGRGVRWNLGMQ<br>SKNGAWGAFDVDNTSAFPNRLPFCDFGEVIDPPSADVTAHVVEMLAVEGLAHDPRTRRGIQW<br>LLDAQETDGSWFGRWGVNYVYGTGSVIPALTAAGLPTSHPAIRRAVRWLESVQNEDGGWGE<br>DLRSYRYVREWSGRGASTASQTGWALMALLAAGERDSKAVERGVAWLAATQREDGSWDEP<br>YFTGTGFPWDFSINYNLYRQVFPLTALGRYVHGEPFAKKPRAADAPAEAAPAEVKGS<br><br>>seq_ID 18<br>MTKQLLDTPMVQATLEAGVAHLLRRQAPDGYVWVAPLLSNVCMEAEYVLLCHCLGKKNPEREA<br>QIRKYIISQRREDGTWSIYPGGPSDLNATVEAYVALKYLGEPASDPQMVQAKEFIQNEGGIEST<br>RVFTRLWLAMVGQYPWDKLPVIPPEIMHLPKSVPLNIYDFASWARATIVTLSYRHESPTCDATS<br>GLCKGSGIVRGEGPPKRRSAKGGDSGFFVALDKFLKAYNKWPIQPGRKSGEQKALEWILAHQ<br>EADGCWGGIQPPWFYALLALKCLNMTDHPAFVKGFEGLEAYGVHTSDGGWMFQASISPIWDT<br>GLTVLALRSAGLPPDHPALIKAGEWLVSKQILKDGDWKVRRRKAKPGGWAFEFHCENYPDVD<br>DTAMVVLALNGIQLPDEGKRRDALTRGFRWLREMQSSNGGWGAYDVDNTRQLTKSDSIFATS<br>GEVIDPPSEDVTAHVLECFGSFGYDEAWKVIRKAVEYLKAQQRPDGSWFGRWGVNYVYGIGA<br>WPGLKAVGVDMREPWVQKSLDWLVEHQNEDGGWGEDCRSYDDPRLAGQGVSTPSQTAW<br>ALMALIAGGRVESDAVLRGVTYLHDTQRADGGWDEEVYTGTGFPGDFYLAYTMYRDILPVVVA<br>LGRYQEAMQRIRG<br><br>>seq_ID 245<br>MNPIRGKRGSAADFLEEEYQWENLADHGESGRTPGGGHPAALKEYEAGSATEHTGHHCVHH<br>LGVRNSWLRKIEKAIDNACGQLFKTQYEDGYWWSELESNVTITSEYIMLLYLLEVSRPEQQKSM<br>VKYLLNQQRPDGSWGLYYGDGGNLSTTIEAYFALKLAGEHCESEPMRRAREFILSKGGIESAR<br>VPFTKIWLALFSQYDWDKVPSMPVELVLLPSSLYFNIYEFSSWARGTVVPLSIVMSIRPRCPLPAK<br>CSIKELYVPGSKHKNFASCTHKLFFLFDRIAKAFERRPVPSLRNKAVQAAETWVLDHQEDSGD<br>WGGIQPPMVYSVLALYYLGYPLDHEVIVKGIKALDAFCMEDEEGTRMQSCVSPVVVDTALTVLS<br>MLDAGVAAEHPGLEKAGRWLLENQVLTGGDWQIKNDSLPGGWAFEFYNTRYPDVDDSAVVL<br>STLNRFNAERVEGLEFAKCRGMEWCLSMQSSNGGWAAFDKDNTLEILNRIPPADQEAMVDYP<br>TADVTGRVLEAMGYLGYDGSHPRARKAIQFLKKRQERDGCWWGRWGVNYIYGTWSVLKGLI<br>SIGEDPRAAYIRAAVRWVKDHQNSDGGWGETCESYENPELRGQGPSTPSQTAWALMSLIACG<br>EMKSQEASRGIQYLLRTQKRDGTWEELHFTGTGFPKHFYIRYHNYRNCFPLMALGQYLRALER<br><br>>seq_ID 221<br>MTATTDGSTGALPPRAASASEPHDTIPQAAGSVGIQDAAARATQRATDFLLSRQDAEGWWKG<br>DLETNVTMDAEDLLLRQFLGIQDEKTTRAAGLFIRGEQRADGTWATFYGGPGDLSATIEAYVAL<br>RLAGDGPDEPHMAKASAWIRERGGIASARVFTRIWLALFGWWKWDDLPELPPELIYFPKWMP<br>LNIYDFGCWARQTIVPLIVVSAKRPVRPAPFPLDELHADANDPNPAKPLAPMVSWDGLFQRLD<br>VALHTYRKVAPRRLRKAAMNTAARWIIERQENDGCWGGIQPPAVYSVIALYLLGYDLEHPVMR<br>EGLASLDRFAVWRDDGARMIEACQSPVVVDTCLATIALADAGVPADHPQLVRAADWMLGEEIV<br>RPGDWAVKRPQLPPGGWAFEFHNDNYPDIDDTAEVVLALRRVKHHDPERLDNAIRRGVRWNL<br>GMQSKDGGWGAFDVDNTSPFPNRLPFCDFGEVIDPPSADVTAHVVEMLAFEGLSHDPRTRR<br>CIQWLLSAQEANGSWFGRWGVNYVYGTGSVVPALVAAGLPASHPAIRRAVTWLETVQNDDG<br>GWGEDLRSYPEAAEWSGKGASTASQTGWALLALLAAGERESKAVERGIEWLAQTQRPDGSW<br>DEPYFTGTGFPWDFSINYHLYRQVFPLTALGRYVNGEPLVEVKGG<br><br>>seq_ID 160<br>MKGKEPTREELLSFSSGIQMDSSAENTTPVSTEELQEKVRLAAESLISRQVEEGYWVEPLEAD<br>VTITSEYILLQYLLGRERDEFFRRAAPFILESQGEDGGWPLYHGGPAEISATVKAYLALKLLGYD<br>ADHPAMQRARALVLERGGAINVNVFTRITLALFGQYDWKGVPALPPEMILLPRWFPLSIYTVSY<br>WSRTVIVPLLFIYHYKPLLELPPEKGVQELFITPMSEVRVHYAWDKHWVSWKNLFFVLDRILQA<br>WNRHPPSFLRRKALKKAMEWMIPRLKGEGGLGAIYPAMANSVLALRLEGYAMDHPLVRRAIQS<br>IDDLVFDLGEQQSVQPCHSPIWDTALALGALYEAGLDEGSPFVSRALDWFCRKEVRTVGDWS<br>VRVPGVEAGGWAFQFENDYYPDIDDTSVVLMDFAKWVPEMGAYRDVFRRAIEWTLSMQGTD<br>GGWGAFDKDNDFLFLNNIPFADHGALLDPSTSDVTGRVTELLGILGYDARTPVVRRALRFLRKE<br>QEEENGSWYGRWGVNYIYGTWSNSALKAVGEDMSAPYVQKAMQFLFSRQNPDGGWGESCY<br>SYFRKDTAGEGVSTSSQTAWALIALIHGGHVRHPAVSKGIDFLLSRQQADGKWLEQEYTGTGF<br>PKVFYLRYNMYRDYFSLWALSLYRNVLLDGQSRVERLARRWKGNPYPVRSRFLA<br><br>>seq_ID 161<br>MEGKDPTREELLSFTSGIQMDSRVGNTNPVSTEELQEKVRLAAESLISRQEEGYWVEPLEAD<br>ITITSEYVLLQYLLGRERDEFFRRAAPFILESQGEDGGWPLYNGGPAEISATVKAYLALKLLGYD<br>ADHPAMQRARALVLERGGAINVNVFTRITLALFGQYDWKGVPALPPEMILLPRWFPLSIYTVSY<br>WSRTVIVPLLFIYHYKPLLELPPEKGVQELFITPMSEVRVHYAWDKHWVSWKNLFFVLDRILQA<br>WNRHPPSFLRRKALKKAMEWMIPRLKGEGGLGAIYPAMANSVLALRLEGYEMDHPLVRRAIQS<br>IDDLVFDLGEQQSVQPCHSPIWDTALALGALYEAGLDEGSPFVSRALDWFCRKEVRTVGDWS<br>VRVPGVEAGGWAFQFENDYYPDIDDTSVVLMDFAKWVPEMGAYRDVFRRAIEWTLSMQGTD<br>GGWGAFDKDNDFLFLNNIPFADHGALLDPSTSDVTGRVTELLGILGYDARTPVVRRALRFLRKE<br>QEEENGSWYGRWGVNYIYGTWSNSALKAVGEDMSAPYVQRAMQFLFSRQNPDGGWGESCY<br>SYFRKDTAGEGVSTASQTAWALIALIHGGHVRHPAVSKGIDFLLSRQQADGKWLEQEYTGTGF<br>PKVFYLRYNMYRDYFSLWALSLYRNVLLDGQSRVERLSRRWKGTPYPVRSRFLA<br><br>>seq_ID 240<br>MHEGEAMTATTDGSTGALPPRAAAASETHLDTPVAAGIQEAAVRAVQRATEHLLARQDAEGW<br>WKGDLETNVTMDAEDLLLRQFLGIRDESTTRAAAKFIRGEQREDGTWAGFYGGPGELSTTVEA<br>YVALRLDGDAPDAPHMAKASAWIRAQGGIAAARVFTRIWLALFGVWVKWEDLPELPPELIYFPK |

Enzyme Sequences

WAPLNIYDFGCWARQTIVPLTIVSAKRPVRPAPFPLDELHADPADPNPAKPLAPVASWDGAFQ
RLDKAMHQLRKVAPRRLRRAAMNSAARWIIERQENDGCWGGIQPPAVYSVIALHLLGYDLQHP
VMRAGLESLDRFAIWREDGSRMIEACQSPVVVDTCLATIALVDAGVPADHPQLVKAADWMLGE
EIVRPGDWSVKRPQLPPGGWAFEFHNDNYPDIDDTAEVVLALRRVRHHDPDRVENAIGRGVR
WNLGMQSKNGAWGAFDVDNTSPFPNRLPFCDFGEVIDPPSADVTAHVVEMLAVEGLSHDPRT
RRGIEWLLAEQEPDGSWFGRWGVNYIYGTGSVVPALTAAGLPASHPAIRRAVAWLEKVQNDD
GGWGEDLRSYKYVKEWSGRGASTASQTAWALMALLAAGERDSKAVERGVEWLASTQRADG
SWDEPYFTGTGFPWDFSINYHLYRQVFPLTALGRYVHGEPFSRTEAL

>seq_ID 231
MTATTDGSSGPVRAGAATAGDTTTTTAARTTAPGTDVREAAGRAAERAVEHLLARQDAQGW
WKGDLETNVTMDAEDLLLRQFLGIQDAATVEASARFIRGQQRDDGTWATFYGGPGELSTTIEA
YVALRLAGDRPDDPHMQRAASWVRSRGGIAAARVFTRIWLALFGVWKWDDLPELPPELILLPK
WVPLNIYDFGCWARQTIVPLTVNSAKRPVRPAPFALDELHTDPAMPNPQKRFAPAASWDGFF
QRADKALHLYKVAPRRLRRAAMNAAARWIIERQENDGCWGGIQPPAVYSVIALHLLGYDLEH
PVMRAGLESLDRFAVHREEEGLPVRMIEACQSPVVVDTCLATIALADAGLRPADHPALVKAADWM
LSEQIVRPGDWAVRRPGLGPGGWAFEFHNDNYPDIDDTAEVILALRRVKHPDPERVEAAVARG
TRWNLGMQSLNGAWGAFDADNTSPFPNRLPFCDFGEVIDPPSADVTAHVVEMLAHEGMAED
PRTRRGVRWLLREQEANGAWFGRWGVNYVYGTGAVVPALIAAGLPASHPSVRRAVTWLESV
QNEDGGWGEDLRSYREEQSIGRGASTASQTGWALLALLSAGERDGRAVERGVAWLARTQRP
DGSWDEPYFTGTGFPWDFSINYHLYRQVFPLTALGRFLHGEKPVGRAAAREGG >seq_ID 227
MTATTDGSTGAANPSEATAHDPTDTTTAADDLTVAARRAAERSVEHLLGRQDEQGVWVKGDL
ATNVTMDAEDLLLRQFLSIQDPETTRAAALFIRGEQLGDGTWNTFYGGPGDLSATIEAYVALRL
AGDRPDEPHMARAAGWIRDQGGIAAARVFTRIWLALFGVWVKWDDLPELPPELMFFPKWVPL
NIYDFGCWARQTIVPLTIVSAKRPVRPAPFALDELHTDPDHPNPPRKLAPPTSWDGLFQRLDKG
LHLYHKVAPRPLRRVAMNLAARWIIERQENDGCWGGIQPPAVYSVIALHLLGYDLDHPVMKAG
LASLDRFAVRREDGARMIEACQSPVVVDTCLATIALADAGLRPDHPALVKAADWMLAEEITRPG
DWSVRKPELAPGGWAFEFHNDNYPDIDDTAEVVLALRRVRHPDPARLQAAIDRGVRWNLGM
QSRNGAWGAFDADNTSPFPNRLPFCDFGEVIDPPSADVTGHVVEMLAVEGLASHPRTREGIE
WLLAEQEACGAWFGRWGVNYVYGTGSVVPALITAGLPAGHPAIRRAVAWLESVQNDDGGWG
EDLRSYQEEKWIGHGESTASQTAWALLALLAAGRRDTRPVARGVTWLTEAQQADGSWDEPY
FTGTGFPWDFSINYHLYRQVFPLTALGRYVHGDPFADRAMAAEGA >seq_ID 121
MQTQNRVTSTQKVELSNLTKAIIASQNYIMSRQYPEGYWWGELESNITLTAETILLHKIWKTDKT
RPFHKVETYLRRQQNEQGGWELFYGDGGELSTSVEAYMALRLLGVTPEDPALIRAKDFILSQG
GISKTRIFTKFHLALIGCYDWKGIPSIPPWIMLFPDNFPFTIYEMSSWARESTVPLLIVFDKKPIFEI
EPAFNLDELYAEGVENVKYALPRNHNWSDIFLGLDKLFKWTEKNNLVPFHKKSLQAAERWMLN
HQQESGDWGGIMPPMVNSLIAFKVLNYDVADPSVQRGFEAIDRFSIEEEDTYRVQACVSPVVVD
TAWVIRALVDSGLKPDHPSLVKAGEWLLDKQILEYGDWAIKNKQGKPGGWAFEFINRFYPDLD
DSAVVVMALNGIKLPDENCKKAAINRCLEWMATMQCKPGGWAAFDVDNDQAWINEIPYGDLK
AMIDPNTADVTARVLEMVGSCGLKMDENRVQKALFYLEKEQESDGSWFGRWGVNYIYGTSGV
LSALAVIAPNTHKPQMEKAVNWLISCQNEDGGWGETCWSYNDPSLKGTGVSTASQTAWALIG
LLDAGEALETLATDAIKRGINYLLDTQTPDGTWEEAEFTGTGFPCHFYIRYHLYRHYFPLIALGR
YWKIGLKNLKG >seq_ID 120
MQTQNRVTSTQKVELSNLTQAIIASQNYILSRQYPEGYWWGELESNITLTAETVLLHKIWKTDKT
RPFHKVETYLRRQQNEQGGWELFYGDGGELSTSVEAYMALRLLGVTPEDPALIRAKDFILSKG
GISKTRIFTKFHLALIGCYDWKGIPSIPPWIMLFPDNFPFTIYEMSSWARESTVPLLIVFDKKPIFEI
EPAFNLDELYAEGVENVKYALPRNHNWSDIFLGLDKLFKWTEKNNLVPFHKKSLQAAEKWMLN
HQQESGDWGGIMPPMVNSLIAFKVLNYDVADPSVQRGFEAIDRFSIEEEDTYRVQACVSPVVVD
TAWVIRALVDSGLKPDHPSLVKAGEWLLDKQILEYGDWAIKNKQGKPGGWAFEFINRFYPDLD
DSAVVVMALNGIKLPDENRKKAAINRCLEWMATMQCKPGGWAAFDVDNDQAWINEIPYGDLK
AMIDPNTADVTARVLEMVGSCGLKMDENRVQKALFYLEKEQESDGSWFGRWGVNYIYGTSGV
LSALAVIAPNTHKPQMEKAVNWLISCQNEDGGWGETCWSYNDSSLKGTGISTASQTAWAIIGL
LDAGEALETLATDAIKRGIDYLLATQTPDGTWEEAEFTGTGFPCHFYIRYHLYRHYFPLIALGRY
WKIGLKTPSVIPLN >seq_ID 132
MFQGSDRPPVTLVMNDMRGPDMNVSDTVSVTRESIPTQTSAGDATARDLTAAVGSELTRALR
LATDHLLALQDGTGWWKFDLETNTSMDAEDLLLREYLGIRTTEVTAASARFIRSRQSDDGSWP
QYFGGPGELSTTVESYIALRLAGDDASAPHMLSAATWVRDHGGVPATRVFTRIWLALFGVWVR
WEDLPALPPEIMLLPRRAPLNIYSFGSWARQTLVSLTVVSALRPVRPAPFDLDELYPDGPASAW
SGAGPSNVLERISTRFTAKEIFLGIDRLLHVYHRRPVRSMRNHALRAAERWIIARQEADGCFGGI
QPPAVYSIIALRLLGYELDHPVLKAALRALDDYSVTLPDGSRMVEASQSPVVVDTALAVNALADA
GATAAIAPDHPALVRAAGWLLGQEVRHRRGDWAVNHPDVPASGWAFEFENDTYPDTDDTAE
VLLALRRVRHPARDELDAAERRVAWLFGLQSDGGWGAYDADNTSTIPYQIPFADFGALTDP
PSADVTAHVVELLAEAGLGDDRTRRGVDWLLDHQEADGSWFGRWGVNYVYGTGSVMPAL
RAAGLEPSHPAMRAGADWLLTHQNADGGWGEDLRSYTDPEWSGRGESTASQTAWAMLALL
TVGDQPEVSGALARGARWLADHQRPDGSWDEDQFTGTGFPGDFYINYHGYRLLWPIMALGR
YLRG

Enzyme Sequences

>seq_ID 118
MLTYKEYRRSVTEIAMQTRDRQTQKPALSLNDAITASQNYLLSLQYPQGYVVWAELESNITLTAE
TVLLHKIWGTDKTRPLHKVEAYLRQQQREQGGWELFYGDGGEISTSVEAYMALRLLGVPQDD
PALIRAKDFILSKGGISKTRIFTKFHLALIGCYSWKGIPSIPPWIMLFPNSFPFTIYEMASWAREST
VPLIIVFNDKPVFAVDPIFNLDELYAEGIENVKYELPKNNNWGDIFLGLDKVFKFAEQVDLVPFRK
KGLQAAERWMLNHQQETGDWGGIMPPMVNSLLAFRVLNYDVNDPSVQRGFEAIDRFSIEENE
TYRVQACVSPVWDTAWCVRALTNSGLPKDHFSLVKAGKWLLEKQCLEYGDWAVKNKTGKPG
GWAFEFTNRFYPDIDDSAVVVMALNGIKLPDEARKQAAINRCVKWIETMQCKEGGWAAFDVD
NDQAWLNEVPYGDLKAMIDPNTADVTARVVEMVGSCDLEISSKRLNKALNYLYKEQEKDGSW
FGRWGVNYIYGTSGVLSALAVINPEKHQPQIEQGINWLLSCQNKDGGWGETCWSYNDSNLKG
KGISTASQTAWALIGLLDAGEALNHFETDSIQRGISYLLNTQTEEGTWEESEFTGTGFPCHFYIR
YHFYRHYFPLIALGRYQNLSSEFGIRNSEL >seq_ID 230
MTATTDGSSGPLRGGAATAGETTSTSAARTTEPGTDLREAAARAAERAVEHLLARQDAEGWW
KGDLETNVTMDAEDLLLRQFLGIQDPATVGASARFIRGQQRDDGTWATFYGGPGELSTTVEAY
VALRLAGDRPDDPHMQRAASWVRSRGGIAASRVFTRIWLALFGVWVKWEDLPELPPELIFLPK
WFPLNIYDFGCWARQTIVPLTWSAKRPVRPAPFALDELHTDPALPNPGKRLAPAASWDGFFQ
RADKALHAYHKVAPRRLRRAAMNAAARWIIERQENDGCWGGIQPPAVYSVIALHLLGYDLEHP
VMRAGLESLDRFAVHHEEEGLPVRMIEACQSPVWDTCLATIALADAGLPADHPALVKAADWML
SEQIVRPGDWSVRRPGLGPGGWAFEFHNDNYPDIDDTAEVVLALRRVKHPDPERVDAAVARG
TRWNLGMQSRDGAWGAFDADNTSPFPNRLPFCDFGEVIDPPSADVTAHVVEILAHEGMAHDP
RTRRGVRWLLAHQEANGAWFGRWGVNYVYGTGAVVPALTAAGLPGSHPAIRRAVAWLESVQ
NEDGGWGEDLRSYREEKSIGRGVSTASQTGWALLALLAAGERESKAVERGVAHLAQTQAPD
GSWDEPYFTGTGFPWDFSINYHLYRQVFPLTALGRYVHGEKLPGRAGAREGR >seq_ID 234
MHEGEAMTATTDGSTGAATPPATTASAPLHLSPEARETHEATARATRRAVDFLLARQSDEGW
WKGDLATNVTMDAEDLLLRQFLGIRDEATTRAAALFIRGEQQEDGTWNTFYGGPGDLSATIEG
YVALRLAGDSPEAPHMRKASAFVRAQGGVARARVFTRIWLALFGVWVKWEDLPEMPPELMFF
PKWAPLNIYDFGCWARQTIVPLTVVCAQRPVRPAPFALEELHTDPADPDPAQPAPPVVSWDNV
FHKLDKLLHGYRRIAPRRVREAAMRAAATWIVERQENDGCWGGIQPPAVYSIMALNLLGYDLD
HPVLRAGLASLDRFAVWREDGARMIEACQSPVVVDTCLATVALADAGVPADHPQMIKAADWML
AEQIVRPGDWVVRRPDLPPGGWAFEFHNDNYPDIDDTAEVVLALRRVAHPDATRVDKAVRRA
VDWNVGMQSKNGAWGAFDADNTSPFPNRLPFSDFGEVIDPPSADVTAHVVEMLAEEGLAHH
PRTRRGIEWLLKNQEGNGSWFGRWGVNYVYGTGAVVPALVAAGLPASHPAIRRSVSWLGQV
QNEDGGWGEDLRSYQDSAWHGRGHSTASQTAWALLALLAAGERETEQVRRGIAYLVETQTE
DGTWDEPWFTGTGFPWDFTINYHLYRQVFPVTALGRYLNGTGPGEN >seq_ID 123
MQTRDRQTHKPALSLNDAITASQNYLLSLQYPQGYVVWVAELESNITLTAETVLLHKIWGTDKTRP
LHKVEAYLRQQQREHGGWELFYGDGGEISTSVEAYMALRLLGVPSNDPALIRAKNFIISQGGIS
KTRIFTKFHLALIGCYSWKGIPSIPPWIMLFPNSFPFTIYEMASWARESTVPLIIVFNDKPVFAIDPI
FNLDELYAEGIENVKYELPKNNNWGDLFLGLDKVFKLAEQVDLVPFRKQGLQAAERWMLDHQ
QETGDWGGIMPPMVNSLLAFRVLNYDVADPSVQRGFEAIDRFSIEENDTYRVQACVSPVWDT
AWCIRALTDSGLPKDHFSLVKAGKWLLEKQVLEYGDWAVKNKTGKPGGWAFEFTNRFYPDID
DSATVVMALNGIKLPDEALKQAAINRCLKWIETMQCKAGGWAAFDVDNDQAWLNEIPYGDLKA
MIDPNTADVTARVVEMVGSCDLEMSSDRLNKALDYLYEEQEKDGSWFGRWGVNYIYGTSGVL
SALAVINPKQHKSQIEQGMNWLLSCQNEDGGWGETCWSYNDLSLKGKGVSTPSQTAWALIGL
LDAGEVLNHFETDSIERGINYLLNTQTEEGTWEESEFTGTGFPCHFYIRYHFYRHYFPLIALGRY
QQMLGS >seq_ID 10
MTQASVREDAKAALDRAVDYLLSLQDEKGFWKGELETNVTIEAEDLLLREFLGIRTPDITAETAR
WIRAKQRSDGTWATFYDGPPDLSTSVEAYVALKLAGDDPAAPHMEKAAAYIRGAGGVERTRV
FTRLWLALFGLWPWDDLPTLPPEMIFLPSWFPLNIYDWGCWARQTVNPLTIVSALRPVRPIPLSI
DEIRTGAPPPPRDPAWTIRGFFQRLDDLLRGYRRVADHGPARLFRRLAMRRAAEWIIARQEAD
GSWGGIQPPWVYSLIALHLLGYPLDHPVLRRGLDGLNGFTIREETADGAVRRLEACQSPVVVDT
ALAVTALRDAGLPADHPRVQAAARWLVGEEVRVAGDWAVRRPGLPPGGWAFEFANDNYPDT
DDTAEVVLALRRVRLEDADQQALEAAVRRATTWVIGMQSTDGGWGAFDADNTRELVLRLPFC
DFGAVIDPPSADVTAHIVEMLAALGMRDHPATVAGVRWLLAHQEPDGSWFGRWGANHIYGTG
AVVPALIAAGVSPDTPPIRRAIRWLEEHQNPDGGWGEDLRSYTDPALWVGRGVSTASQTAWA
LLALLAAGEEASPAVDRGVRWLVTTQQPDGGWDEPHYTGTGFPGDFYINYHLYRLVFPISALG
RYVNR >seq_ID 233
MRRRRSPRGPGAGPEADYGPARASAPDRLRGDAARGDAARRVQDATARAIRNLLGRQDPAG
WWKGDLETNVTMDAEDLLLRQFLGIRDEAVTQAAALFIRREQREDGTWATFHGGPPELSATIE
AYVALRLAGDAPDAPHMATASAWIRAHGGLAAARVFTRIWLALFGVWVDWENLPELPPELVLLP
PWVPLNIYDFGCWARQTIVPLTWSAMRPVRPAPFALDELHTDARVPVPPRRMAPPTTWNGA
FQWMDRALHVYRRFAPRRLREAAMASAGRWIIERQENDGCWGGIQPPAVYSVIALHLLGYDL
GHPVMRAGLESLDRFAVWREDGSRMIEACQSPVVVDTCLAAIALADAGVRPDHPALVKAADW
MLGEEIVRTGDWAVRRPGLAPGGWAFEFHNDTYPDIDDTAEVVLALRRIRHPDPARVEAAIAR
GVSWNLGMQSRGGAWGAFDADNTSPFPNRLPFCDFGEVIDPPSADVTAHVVEMLAAEGRAA

| Enzyme Sequences |
| --- |
| DPRTRRGIAWLLAEQEPEGPWFGRWGTNYVYGTGSVVPALTAAGLSPGHPAIRRAVLWLESV<br>QNPDGGWGEDQRSYQDRAWAGKGESTPSQTAWALMALLSAGERDAKTVERGIAYLVETQLA<br>DGGWDEPHFTGTGFPWDFSINYHLYRHVFPLTALGRYLYGEPFGHDGRHIGAHLGDRTGVPA<br>EGV<br><br>>seq_ID 116<br>MQTQDRLTQKQPLSLKDAITASQNYLLSLQYPQGYVVWAELESNITLTAETVLLHKIWGTDKTRP<br>LHKVEAYLRQQQREHGGWELFYGDGGEISTSVEAYMALRLLGVPQDDPALIRAKDFIISKGGIS<br>KTRIFTKFHLALIGCYDWKGIPSIPPWIMLFPDSFPFTIYEMASWARESTVPLIIVFNDKPVFSVDP<br>VFNLDELYAEGVENVKYELPKNNNWGDIFLGIDQVFKFAEQVDLVPFRKEGLKAAEKWILNHQ<br>QETGDWGGIMPPMLNSLLAFRTLNYDVNDPSVKLGFEAIDRFSIEEDDTYRLQACVSPIWDTA<br>WCVRALTDSGLEKDHFSLVKAGKWLLDKQVMEYGDWAVKNKAGKPGGWAFEFTNRFYPDLD<br>DSATVVMALNGIKLPDEARKQAAINRCLQWIETMQCKEGGWAAFDLNNDQAWLNEVPYGDLK<br>AMIDPNTADVTARVVEMLGSCDLEIESDRLNKSLNYLYKEQEKDGSWFGRWGVNYIYGTSGVL<br>SALAVINPEKHKTQMEQGINWLLSCQNKDGGWGETCRSYNDPSLKGKGVSTPSQTAWSLIGL<br>LDAGEALNKFETDAIERGVNYLLDTQTEEGTWEESEFTGTGFPCHFYIRYHFYRHYFPLIALGR<br>YQNLSSEFGVRS<br><br>>seq_ID 124<br>MQIRATVDTAKLEKAIAASQEHLLSTQYPEGYWWAELESNVTMTAEVVLLHKIWKTDGTRPMH<br>KAEKYLRSEQREHGGWELFYGDGGDLSTSVETYTALRLLGVPASDPALLKAKDFILRRGGISKT<br>RIFTKLHLALIGCYDWRGLPSLPPWVMLLPENFPFTIYELSSWARGSTVPLLIVMDRKPVFSVNP<br>QINVDELYAEGRDRVKFELPRKGDWTDLFIELDGLFKFTEQNNLVPFREEGLRAAERWVLERQ<br>EATGDWGGIIPAMLNSLLALRALGYHPADPVVRRGMAAVDRFAIETADTYRVQPCVSPVVVDTA<br>LVMRGLIDSGLPADHPAIVKAGEWLLEKQILAYGDWAVKNKTGQPGAWAFEFENRFYPDVDDS<br>AVVVMALQAAQLPDEDLKQQAIERCVKWIATMQCKPGGWAAFDVDNDQDWLNQIPYGDLKA<br>MIDPNTADVTARVLEMIGRSGVTTGEASVERALAYLRREQEVEGCWFGRWGVNYIYGTSGVL<br>AALALIAPKSDHAMIQRGADWLVRCQNADGGWGETCRSYNDPHLKGQGPSTASQTAWALIGL<br>LAAGEATGEFAWGAIDRGINYLLATQQQDGRWDEDWFTGTGFPGHFYLKYHLYQQHFPLTAL<br>GRYSSLTGLKQELKIPLQLKSKPEVVMIEDSDLLSDEDAT<br><br>>seq_ID 119<br>MQIQDRNSSPQVTEVLNQVKDAIAASQDYLMSIQYPEGYVWVAELESNVTITAEVVLLHKIWGTD<br>KTRPLHKVETYLRRQQREHGGWELFYGDGGDLSTSVEAYMALRLLGVSIDDPALIRGREFILKR<br>GGISKSRIFTKLHLALIGCYDWRGIPSIPPWIMLLPENFPFTIYEMSSWARSSTVPLLIVFDKKPVY<br>CCDPTINLDELYSEGIENVKYDLPKTGDWTDIFVVVLDGVFKFAQDYNLVPLRQESLQAAERWV<br>LERQEDSGDWGGIIPAMLNSLLALRALNYEAVDPIVHRGLQSVDNFAIETEDTYHVQPCISPVVV<br>DTAWAIRALVESGLKADDPRLVKGAQWLLDKQILDYGDWAVKNKQGTPGGWAFEFDNRWYP<br>DLDDSAVVVMALDQVKMPNEDLKNGAIRRCVRWMATMQCKDGGWGAFDLDNDQNWLNFLP<br>YADLKAMIDPNTSDVTARVLEMLGTCGLIMDSNRVQKAIAYLEKEQEPDGSWFGRWGVNYIYG<br>TSGVLSALAVIAPETHQKELKKGAAWLVGCQNADGGWGETCFSYNDSSLKGKGDSTASQTA<br>WGLIGLLAAGEATGEFFKTAIERGVNYLLKTQREDGTWDENYFTGTGFPCHFYLKYHLYLQYFP<br>LIALSRYQRLLT<br><br>>seq_ID 9<br>MSVSERAQPGGNPIPGSTSQSAVKFGRIDAALEDVKRAIAGAKDRVFAQQSKDGWWCGELEA<br>DSMLEADYIFAHTLLGTGDAGKMKRALTEMLRYQNEDGSWSIYPGGPGNISLTVKCYFSAKLM<br>GMTADNPILVKAREWILAHGGVVECNTFTKIYLCFLGQYEYDAVPAIPPEIVLFPNWFYFNIYEIS<br>SWSRAILVPLSIAYAKKPFKKIPPEQGIDELFVGGREKANLHLRWDSKNLLSWRNFFLALDRVTH<br>WFERVHIRPLRSIALKKAEKWMLARFEMSDGLGAIYPAMLNAIIALRCLGYSLDDPQVLRAMDE<br>FEKLGIDEPEGTAEYAEPTFRMQPCVSPVWDTAQAVFALGEAGVPRNDPRMQKAADWLLSKE<br>VRHKGDWAMKVRNAQPGGWYFEFNNEFYPDVDDSAQVLLALNKVDNPRERYQYDVCQRAID<br>WIFAMQCRNGGWASFDKDNTKMIFQYVPFADHNAMLDPPTVDITGRILEMLATYGYTRKDRRV<br>EKAIKFIYDEQEPDGSWFGRWGVNYLYGTFLVLRGLEAIGVVVNHEPQIQQAAEWIRSVQNADG<br>GWGETCGSYDDPNTRGVGPSTPSQTAWAILGLLSAGDDRSDSVAKGIKWLLAHQKPDGGWD<br>ESTGSGSKHQALYTGTGFPRVFYLAYHQYRDYFPLLALTNYEKAMERGE<br><br>>seq_ID 217<br>MTEEVLQRTAAPAEVLAAAREHLLSLQHERGVWVKGELETNVTMDVEDLLLRRFLGILTTAETE<br>QAARWIRSRQRADGTWAQFHGGPGDLSTTVEAYVGLKLAGDDVDSEHMAAARAWILERGGIE<br>ETRVFTRIWLALFGEWSWDDLPAMPPELVLLPPWVPLNLADWGCWARQTIVPLTVVCTLRPR<br>RDLGVGLAELRSGRRRRKVPSPSWAGAFQVLDGALHGYQRHPLRGLREHAMRRAAEWIVAR<br>QEADGSWGGIQPPWVYSLLALHLLGYPLDHPVLRQGLAGLERFLIREETPEGTVRRLEACQSP<br>VVVDTVLSMQALRDAGLAADHPALRRAADFVLAEEIRVKGDWSVRRPDLAPGGWAFEFDNDG<br>YPDIDDTAEVVLALNRVDHERPGAVNAAIDRGVRWMSGMQSADGGWGAFDADNTRELVNEL<br>PPFCDFGAVIDPPSADVTAHVVEALCVLGRGDGEAVRRGVRWLLDHQELDGSWFGRWGANHV<br>YGTGAAVPALVRAGLRRDHLALRRAVRWLEVHQNDDGGWGEDLRSYDDPVMGRGRSTAS<br>QTAWALLALLAVDLHDTDAVRRGVGFLAETQRPDGTWDEPQFTGTGFPGDFYINYHLYRLVFP<br>VTALGRYEQARREQSGGSG<br><br>>seq_ID 249<br>MIEKNKVKQSILASQKHLLSLQETEGYWWGQLESNVTITAEIILLHKIWQTDKKIPLNKAKNYLIS<br>QQREHGGWELFYGDGGDLSTSIEAYMALRLLGVSRTDPIMIEAQNFIIKKGGISCSRIFTKLHLAL<br>IGCYSWQGIPSIPSSIMLLPEDFPFTIYEMSSWARSSTVPLLIVFDKKPIFSVNPTINLDELYAEGI<br>NNASFELPRKYDLTDLFLGLDKAFKFAENLNLMPLQQEGLKAAEKWILERQEVTGDWGGIIPAM<br>LNSMLALKCLEYDVADPVVVRGLEAIDRFAIENEDSYRVQACVSPVVVDTAWVIRSLVDSGISPS<br>HPAMVKAGQWLLQQQILDYGDWVFKNKFGKPGGWAFEFMNRFYPDIDDTAVVVMALDVVEL |

Enzyme Sequences

PDEDLKGKAIARGMEWIASMQCEAGGWAAFDVDNNQDWLNATPYGDLKAMIDPNTADVTGR
VLEMVGCCGLAMDSWRVKRGIDFLVREQEEEGCWFGRWGVNYIYGTSGVILALAVMARESHR
GYIERGASWLVGCQNSDGGWGESCWSYNDPSLKGKGKSTASQTAWALIGLLAAGEGTGNFA
RDAIDGGVGFLVSTQNDDGSWLEDEFTGTGFPGHFYIKYHFYSQYFPLMALGRYESLLSG

>seq_ID 222
MAVRDRVNPKTLEAAIAASQSYLLTQQDETGYVWVAELESNVSITSEVVLLHKIWGTDRSRPLE
KVETYLRSQQRDHGGWELYFDDGGEISVSVEAYMALKLLGVPMEDPAMVRARQFILEHGGISR
TRVFTKLHLALIGCYEWRGIPSLPPWVMLLPEQFPFTIYEMSSWARGSTVPLLIVMDREPVYAV
EAGFNLDELYVEGRHRAQFDLPLSNEWTDAFIYLDGLFKFAESTNLVPFREEGIRAAERWILER
QEATGDWGGIIPAMLNSLLGLKALDYDVHDPIIERGMAALDAFALETEDQYWIQPCISPVWDTA
LVVRGLAESGLAPDHPALVKAGEWLLNKQILDYGDWSVKNPGGLPGGWAFEFDNRFYPDVDD
TAVVVMALNEVQLPDEQAKDAAIARAVNWIATMQCRPGGWAAFDINNDQDWLNALPYGDLKA
MIDPNTADVTARVLEMIGRCHQTTGKNSVDRALRYLRTEQEPEGCWFGRWGVNYIYGTSGVL
AALALIDPQGWQSQIQQAAAWLVSCQNTDGGWGETCASYDNPKLKGQGPSTASQTAWAIMG
LLSAGEATSVYAEAAIERGVNYLTTTQKMDGTWDEDYFTGTGFPGHFYLKYHLYQQHFPLTAL
GRYQAMLQQKS >seq_ID 186
MRTQDRVQVNSIAEAIAASQKYLLSLQNPAGYVVWAELESNVTITAEVVLLHKIWGTDKTRPLHK
VEAYLRSQQKQHGGWELFYGDGGELSTSVEAYMALKLLGVPATDPAMIQARDFILQRGGISKT
RIFTKFHLALIGCYNWRGLPSLPAWVMLLPNQFPVNIYEMSSWARSSTVPLLIVFDQKPVYQVN
PTITLDELYAEGVENVRYELPRSGDWTDLFLTLDEGFKLAESFNFIPFREEGIKAAEKWIIERQEA
TGDWGGIIPAMLNSMLALRSLGYDTNDPIVERGLQALDNFAIETVDCYRVQPCVSPVVVDTAWVI
RALIDSGIAPDHPAIVKAGEWLLQKQILDYGDWNVKNRQGKPGAWAFEFENRFYPDVDDTAVV
VMALHAAKLPNEQLKQKACDRALQWVASMQCKPGGWAAFDLDNDQDWLNSVPYGDLKAMID
PNTADVTARVIEMLGACNLSIDSHNLERALTYLLNEQEAEGCWFGRWGVNYIYGTSGVLSALAL
INPQKYQRHIQQGATWLVGCQNPDGGWGETCFSYNDPSLKGQGDSTPSQTAWALIGLIAAGE
ATGNFAHDAIERGINHLVSTQQPDGSWFEAYFTGTGFPCHFYLKYHYYQQYFPLIALGRYQAIK
SL >seq_ID 153
MQVQPRIEKKHLDSAIEASQAYLLARQYSPGYVVWAELESNVSMTAEVVLLHKIWRTDTGRPLA
KATAHLLAEQRAHGGWELFYGDGGDLNTSIEAYMALKLLGLTADHPALARARAFILAKGGISRA
RIFTKIHLALIGCYDWRGVPSIPPWVMLLPEAFPVNIYEMSSWARGSTVPLLIVFDRKPVFAVEP
AITLDELFVEGRAQARFDLPRSSSDWWANLFVDLDWGFKLAESLGAVPLREEGLKAAERWVLE
RQEATGDWGGIIPAMLNSLLALRCLDYDPHDPVVERGMAAVDRFAIETESTYRLQPCVSPVVVD
TALTMRALVDSGLPPDHPALAAAGTWLLKKQILDYGDWAVKNRTGPPGGWAFEFDNRFYPDV
DDTAVVVMALDAVRLADETAKGQAIARAVCWVASMQCRGGGWAAFDIDNDAHWLNSLPYAD
LKAMIDPNTADVTARVLEMYGRCRLIPAAAGAQRALDYLRRTQEPEGCWFGRWGVNYLYGTS
GVLSALAAFAPAERTAIERAAAWLRGCQNTDGGWGETCGSYVDRTLMGQGPSTASQTAWAL
LGLIDASRVARFSDSSALERGLAYLVETQKADGSWDEPYFTGTGFPGHFYLKYHLYQQHFPLS
ALGRYRRLLS >seq_ID 122
MQIQARNISTKVTEVFSKVKEAIAASQQYLLSIQYPEGYVWVAELESNVTITAEAVLLHKIWGTDT
TRPLHKVETYLRRQQREHGGWELFYGDGGDLSTSVEAYMALRLLGVSASDPALVRAKAFILSR
GGISKSRIFTKMHLALIGCYDWRGVPSIPPWIMLLPENFPFTIYEMSSWARGSTVPLLIVFDKKP
VYQCGITLDELYSEGINHVRYDLPRNGDWTDVFVWLDGVFKFAETNNLIPFRNESLKAAERWV
LERQEDTGDWGGIIPAMLNSLLALRALDYEVNDPIVHRGFKSVDNFAIETEETYHVQPCISPVVV
DTAWVLRALVESGLKPDEPVLVKGAQWLLDKQILDYGDWAVKNKEGTPGGWAFEFDNRWYP
DLDDSAVVVMALEQVKMPDEQLKYGAMRRCVRWMATMQCKAGGWGAFDVNNDQNWLNYL
PYADLKAMIDPNTADVTARVLEMLGTCELSMDHDRVKRAIAYLEQEQEADGSWFGRWGVNYI
YGTSGALSALAAIAPVTHQAQIEKGAAWLVGCQNPDGGWGETCFSYNNPALRGKGDSTASQT
AWGLIGLLAAGEATGKFAKTALERGVNYLLATQRPDGTWDESYFTGTGFPCHFYLKYHLYLQY
FPLIALSRYQRLLGFN >seq_ID 129
MSLTSDPSPAAPTAEKSPKRPTIPVPATADAYGISRSSPPLPAATGRPQAAGPASAGVATARAR
DHLLALQSEEGVWVKGDLETNVTMDAEDLFMKQFLGIRGDDETEQTARWIRSQQLADGGWPT
FYGGPADLSTTIEAYIALRLAGDAVDAPHMARAAELVRAQGGVAASRVFTRIWLAALGQWSWD
DVPVIPPELIFLPSWIPLNVYDFACWARQTIVALTIVGSLRPSHDLGFSIDELKVPAAARKPAALR
SWEGAFERLDKLLHRYEKRPIKLLRTLALRRATEWVVARQEADGCWGGIQPPWVYSVMALHL
MGYPLNHPVIATAFRGMERYVIRRDTPQGPIRQIEACQSPVVVDTALAVVALADAGVPGDHPAM
VKAGRWLVDEEVRVAGDWAVRRPELAPGGWAFEFDNDFYPDVDDTAEVVLALRRLLGAGHV
APPASRQGRAEAPPVNTVEDADPRLAAAMRAAAARGVDWSVGMRSSNGAWGAFDADNVRT
LTTKIPFCDFGEVVDPPSADVTAHIVEMLADLGRSDHPITQRAVQWLLDNQEPGGSWFGRWG
VNHLYGTGAVVPALIGAGVPTDHPAITAAVRWLLEHQSPEGGWGEDLRSYTDPAWIGRGELTA
SQTAWALLALLAVDPHSLAVKRGVRWLCETQRPDGTWDEPYFTGTGFPGDFSLNYHLYRLVF
PLTALGRYVSLTGVATP >seq_ID 164
MHSGRVFLEKENREENRATFHSSPLILVEESLNLPKKVEETIKKAQRYLLSIQKEDGHWVGELF
VDVTLACDCIHLMHWRGKIDYKKQLRLVKHIVDRQLPDGGWNIYPGGPSEVNATVKAYFALKLA
GFSPDDPLMAKARSTILRLGGIPKCMTYTKLGLALLGVYPWDRLPVIPPEIILFPNWFPFNIYEISA
WSRAMLVPLSVIHHFKPTRNLPEKYQLHELFPYGTEHGKFSWLKKGARYLSKQGLFLACDKFL
QYWDKTSLKPFRKMALKKAEKWLLERISAGSDGLGAIFPAMHYAIMALIAMGYTEDNPILKKAIA

| Enzyme Sequences |
| --- |
| DFEGLEVDDKKNDDLRIQPCLSPVVVDTAVGLVALAESGVARNAKELKRAAYWLLDREIKIKGD<br>WHVRNPHPEPSGWAFEYNNVYYPDVDDTLMVLLALRLIDIEDKIRKEEVMQRALRWVISFQCK<br>NGGWAAFDKDVYKKWLEDIPFADHNAILDPPCSDITARALELFGKMGIKKTERFVQKAIAYLKET<br>QENDGSWMGRWGVNYIYGTWQALRGLQAIGENMNQEWILRARDWLESCQNEDGGWETP<br>ASYDNPQLKGKGPSTASQTAWAVSGIMACGDIFRPSVSRGIKYLCDRQLSDGSWAEEFLTGT<br>GFPGVFYLKYDMYRNAWPLLVIGEYHRQYLKAKEQVSYWVDGTIGRKVKKERLPEI<br><br>>seq_ID 20<br>MRTQDRVQVNSIAEAIAASQKYLLSLQNPTGYWWAELESNVTITAEVVLLHKIWGTDKTRPLHKI<br>EAYLRSQQKQHGGWELFYGDGGELSTSVEAYMALKLLGVPATDPAMIQARDFILQRGGISKTR<br>IFTKFHLALIGCYNWRGLPSLPAWVMLLPNQFPVNIYEMSSWARSSTVPLLIVFDQKPVYQVNP<br>AITLDELYAEGVENVRYELPRSGDWTDLFLTLDEGFKLAESFNFIPFREEGIKAAEKWIIERQEAT<br>GDWGGIIPAMLNSMLALRVLGYATNDPIVERGLQAIDNFAIETADCYRVQPCVSPVVVDTAWVIR<br>ALIDSGMAPDHPAIVKAGEWLLQKQIFDYGDWNVKNRQGQPGAWAFEFDNRFYPDVDDTAVV<br>VMALHAAKLPHEQLKQKACDRALQWVASMQCKPGGWAAFDIDNDQDWLNAVPYGDLKAMID<br>PNTADVTARVIEMLGACNLSIDSHDLERALTYLLNEQEAEGCWFGRWGVNYIYGTSGVLCALAL<br>INPQKYQRHIQQGATWLVGCQNPDGGWGETCFSYNDPSLKGQGDSTPSQTAWALIGLIAAGE<br>ATGNFAHDVIERGINHLVSTQQPDGSWFEAYFTGTGFPCHFYLKYHYYQQYFPLIALGRYQAIN<br>PL<br><br>>seq_ID 185<br>MQTQDRVKVNQVAEAIAASQQYLLSIQNPAGYVWVAELESNVTITAETVLLHKIWGTDQTRPLH<br>KVEAYLRQEQRQHGGWELFYGDGGELSTSVEAYMALRLLGVPATDPAMIRAQAFILRGGISK<br>TRIFTKLHLALIGCYNWRGIPSLPPWIMLLPKAFPVNIYEMSSWARSSTVPLLVVCDRKPVFITDP<br>TINLDELYAEGIDRVRWELPQSGDWTDLFLTLDQGFKWAESLNLVPFREEGIKAAEKWILERQE<br>ATGDWGGIIPAMLNSMLALRCLDYDRSDPIVERGLQAIDNFAIETDNSYRVQPCVSPVVVDTAW<br>VMRALVESGFVPDHPAVVKAGEWLLQKQILDYGDWAVKNRQGKPGAWAFEFENRFYPDVDD<br>SAVVVMALHLAKLPNEKIKQAAIARAVNWIASMQCKPGGWAAFDLDNDQDWLNSIPYGDLKAM<br>IDPNTADVTARVVEMLGACDLSIDSDNLERSLTYLLREQETEGCWFGRWGVNYIYGTSGVLSA<br>LALIDPQRHKLSIERGAAWLLGCQNLDGGWGETCRSYDDPSLKGKGDSTASQTAWALIGLLAA<br>GEATGKLAVKAIEQGIGYLMATQQPDGTWFEANFTGTGFPCYFYLKYHLYQQYFPLIALGRYQ<br>AAIKES<br><br>>seq_ID 244<br>MVIAASPSVPCPSTEQVRQAIAASRDFLLSEQYADGYVWVSELESNVTITAEVVILHKIWGTAAQ<br>RPLEKAKNYLLQQQRDHGGWELYYGDGGELSTSVEAYTALRILGVPATDPALVKAKNFIVGRG<br>GISKSRIFTKMHLALIGCYDWRGTPSIPPWVMLLPNNFFFNIYEMSSWARSSTVPLMIVCDQKP<br>VYDIAQGLRVDELYAEGMENVQYKLPESGTIWDIFIGLDSLFKLQEQAKVVPFREQGLALAEKWI<br>LERQEVSGDWGGIIPAMLNSLLALKVLGYDVNDLYVQRGLAAIDNFAVETEDSYAIQACVSPVVV<br>DTAWVVRALAEADLGKDHPALVKAGQWLLDKQILTYGDWQIKNPHGEPGAWAFEFDNNFYPD<br>IDDTCVVMMALQGITLPDEERKQGAINKALQWIATMQCKTGGWAAFDIDNDQDWLNQLPYGDL<br>KAMIDPSTADITARVVEMLGACGLTMDSPRVERGLTYLLQEQEQDGSWFGRWGVNYLYGTSG<br>ALSALAIYDAQRFAPQIKTAIAWLLSCQNADGGWGETCESYKNKQLKGQGNSTASQTAWALIG<br>LLDALKYLPSLGQDAKLTTAIEGGVAFLVQGQTPKGTWEEAEYTGTGFPCHFYIRYHYYRQYFP<br>LIALARYSHLQAS<br><br>>seq_ID 109<br>MDDRHIQSEITFGKIDGIRERIQQAMDAAKRYLFSKQDPEGFWCGELEADTTLQSDYIVMHTLL<br>GTGDPVKMQKAGKQILQHQNPDGGWNIYPDGPSNISAAVKAYFSLKLIGHKPDEPEMTKARE<br>WILAHGGVTACNTFSKMYLCFFGQYDYDTVPAIPPEIVLFPNWFWFNLYEISSWSRGILVPLAIC<br>YAKKPFKKIPDEANIDELFVEGRHANLHLTWDKKPFSWRNFFLVLNNMVHFFERVHVRPLRKLA<br>MKRAEKWMLERLEMSDGLGGIYPAILNSIIALRALGYSTDDPQVIRAMDEFEKLGIEEDDTFRM<br>QPCMSPVVVDTAYALYALGEAGVPGSDPRMQKAAEWMLKKQVTHKGDWAVKVRNVQPGGW<br>YFEFNNEFYPDVDDTAQVILSLNHVRTSNERYQDDTVKRALDWQLAMQCKNGGWASFDKDN<br>NKMVFQYIPFADHNAMLDPATVDITGRVLEALSHHGYSLKDKVVQRAVKFIQSEQEPDGSWFG<br>RWGVNYIYGTMLCLRGLAAVGVDHHEPMVQQAAEWLRMVQNPDGGWGESVGSYDDPKLRG<br>QGPSTASQTAWAVMGLLAANDLRSDSVTRGIAWLLENQKPNGSVWVEKWITGTGFPRVFYLKY<br>TMYAEYFPLIAFAEYLRRLNTPLDEKVKLGPQA<br><br>>seq_ID 174<br>MQIQDKITEIAAKTAKAIELSQNYLLSTQYSEGYVWVAELESNVTITSEAILLHKIWKTDKKRPLDK<br>AATYLRQQQCPNGAWELFYGDGGDLSTTVEAYMGLRLLGIPANDPALEKAREFILAKGGISKTR<br>IFTKMHLALIGCYDWQGVPSIPAWIMLLPENFPPFTIYEMSSWARGSTVPLLIVFDKKPVYKMGFN<br>LDELYTEGVNNVKYELPKNNNWSDVFLWLDGLFKWAEKTDLVPFRQESLKAAEKWVIERQED<br>TGDWGGIIPAMLNSLLALKALDYDVYDPIVARGLKAVDNFAIETDNTYCVQPCVSPVVVDTAWVI<br>RSLIESGLNPAHPAMIKAGQWLIDQQILDYGDWAIKNKIGTLGDWFDNRWYPDLDDSAVV<br>VMALELIKMPDENIKTSVMKRAVNWMATMQCKAGGWGAFDIDNDQNWLNSLPYADLKAMIDP<br>NTADVTARVLEMLGTCDVKMGENRVKKALDYLEKEQEADGSWFGRWGVNYIYGTSGALSALA<br>FLEPNQYRQQLQKGANWLSSCQNVDGGWGETCFSYNNPKFKGQGNSTASQTAWALIGLLAV<br>GKVTGNYQREVIEKGVNYLLVTQKENGTWDEDYFTGTGFPCHFYLKYHFYQQYFPLLALGRYR<br>ALI<br><br>>seq_ID 130<br>MSLTSDPSPAAPKAAKSSKRVNIPAPATPDAYGISRSSPPLSGGGVSGGGVSGGGAATADGTP<br>PTTQTSVDPDLAAAMTAANQARDHLLGLQSEEGVWVKGDLETNVTIDAEHLFMKQFLGIRTEEE<br>TEPIARWVRSQQLADGGWATYYGGPAELSTTVEAYIALRLAGDEPDAPHMAAAAALIRSQGGV<br>AAARVFTRIWLATFGEWSWDDVPVLPPELIFLPSWFPLNVYDFGCWARQTIVALTIVGSLRPVR |

Enzyme Sequences

```
DLGFSIDEIKVAAPVTPPKPAPLHSWEGAFERLDAILHRYERRPIKVLRTLALRRATEWVVARQE
ADGCWGGIQPPWIYSVMALHLMGYPLNHPVIATAFRGMERYIIRRETPEGPTAQIEACQSPVVV
DTALAVVALSDAGVPADHPAMVRAGRWLVDEEVRVAGDWAVRRPALAPGGWAFEFDNDFYP
DTDDTAEVVLALRRLLGGSHVTPGGTVTPSGSVTPGGTAELSPAARDRASRGLAAVDPQLAG
AMRAAAARGVDWSVGMRSSDGAWGAFDADNVRTLTAKIPFCDFGEVVDPPSADVTAHIVEML
ADLGRSDHPITRRAVQWLLDNQEPGGSWFGRWGINHVYGTGAVVPALIAAGVPADHPAITAAV
RWLLEHQSPDGGWGEDPRSYDDPAWIGRGELTASQTAWALLALLAVDPHSKAVKRGVRWLC
ETQRPDGTWDEPQFTGTGFPGDFYLNYHLYRLVFPLTALGRYVTLTGVATP

>seq_ID 248
MPTSLATAIDPKQLQQAIRASQDFLFSQQYAEGYVWVAELESNVTMTAEVILLHKIWGTEQRLPL
AKAEQYLRNHQRDHGGWELFYGDGGDLSTSVEAYMGLRLLGVPETDPALVKARQFILARGGI
SKTRIFTKLHLALIGCYDWRGIPSLPPWIMLLPEGSPFTIYEMSSWARSSTVPLLIVMDRKPVYG
MDPPITLDELYSEGRANVVVVELPRQGDWRDVFIGLDRVFKLFETLNIHPLREQGLKAAEEWVL
ERQEASGDWGGIIPAMLNSLLALRALDYAVDDPIVQRGMAAVDRFAIETETEYRVQPCVSPVVV
DTALVMRAMVDSGVAPDHPALVKAGEWLLSKQILDYGDWHIKNKKGRPGGWAFEFENRFYPD
VDDTAVVVMALHAVTLPNENLKRRAIERAVAWIASMQCRPGGWAAFDVDNDQDWLNGIPYGD
LKAMIDPNTADVTARVLEMVGRCQLAFDRVALDRALAYLRNEQEPEGCWFGRWGVNYLYGTS
GVLTALSLVAPRYDRWRIRRAAEWLMQCQNADGGWGETCWSYHDPSLKGKGDSTASQTAW
AIIGLLAAGDATGDYATEAIERGIAYLLETQRPDGTWHEDYFTGTGFPCHFYLKYHYYQQHFPLT
ALGRYARWRNLLAT >seq_ID 150
MAKGILNKFAVIAGTKKAGPPAGEERTVIAPIKEISGKAVHCSQAVKKAEEYLLALQNPEGYWVF
ELEADVTIPSEYIMLQRFLGREISPELGKRLENYLLDRQLPDGGWPLYAEDGFANISATVKAYLA
LKVLGHSPQAPHMIRARLMVLSLGGAARCNVFTRILLALFGQIPWHTPPAMPVEIVLLPQWFFF
HLSKVSYWRSRTVIVPLLLLYAKQPVCRLRPEEGIPELFSTPPDKLRHLDGFQPGYWRKNAFIIFD
RLLKRFNRFIPSALHRKAIAEAEQWTRSHMQGSGGIGAIFPAMAYAVMALRVLGCGEGDPDYIR
GLQAIDDLLQHRTPQEADPPRTDGTCIDSGMSAAFALTPSAHAAADGTGSSSICQPCNSPIWD
TCLSLSALMEAGMPASHPAATQAVEWLLSQQILSPGDWSLKVPDLEGGGWAFQFENTLYPDL
DDTSKVIMSLLRAGALENERYRDRIARGVNWVLGMQSSDGGWAAFDIDNNYHYLNDIPFADHG
ALLDPSTSDLTGRCIELLSMVGFDRTFPPIARGIGFLRSEQEENGAWFGRWGVNYIYGTWSVLS
GLRQAGEDMQQPYIRKAVGWLASCQNHDGGWGETCYSYDDPSLAGKGASTPSQTAWSLLG
LMAAGEVNSLAVRRGVRYLLDHQNQWGTWEEKHFTGTGFPRVFYLRYHGYRHFFPLWALGV
YSRLSSGQKACQDERRHASPGDLHLPWLERIKKR >seq_ID 128
MPDLELRDVDRADGRHHAPNLGRTDTLSPSAPTGEPAPASTPAAVATPTPTPTTAPAPAPAPE
NALRETVQRAAEHLLRLQDPRGVWVKFDLETNPTMDAEDLLLREYLGIRTVEQTEATAKHIRSR
RLDDGSWPTYFGGPGELSTTVECYIALRLAGDSPDDEPLRRSAAWIRERGGIPATRVFTRIWLA
LFGVWVRWEDLPVLPPEIMFLPPRAPLSIYSFASWARQTIVTIVSAARPQCPAPFDLAELDPD
EVPAAQSHGAAQSPDTRSPAGGRTLRGAMRRLGGDRPNTAKVFFRGLDAALHRYHRHPIGPL
RRHALRTAERWIIARQEADGCFGGIQPPAVYSIIALRLLGYDLDHPVLAAALRSLDAYTLHREDG
SRMIEASQSPIWDTALAVLALADAGIDAPADVDVAPALPTQRVATGAPAPSAPVPTALERAADW
LLGQEIQHRRGDWAITHPGVAPGGWAFEFDNTDYPDTDDTAEVVLALHRLNRLRRLRHPTNTR
IDAALERSTAWLFALQSRDGGWGAYDSDNASTLVYQIPFADFGALTDPSSADVTAHVVELLCE
TGRIRDPRTLRGVDWLLRNQEADGSWYGRWGVNYVYGTGSVLPALQAAGLPPTHPAMVAGA
RWLLSRQNSDGGWGEDIRSYGDPAWSGRGLSTPSQTAWAMLGLLATDHGGVHADALAAAA
RWLTEQQRPDGGWDEEMFTGTGFPGFFYLNYHGYRLVVVPVMALGRYLHSRQHPSD >seq_ID 131
MSLTSDQSSAAPTAAAQSPKIPNPSVARPSADAGSFETAGAVRTDSVSIDSVSTGTPVDPVVG
AMRRGRDHLLSLQAEEGVWVKGELETNVTMDAEDLMLRQFLGILTPSTATETGRWIRSQQLSD
GGWATFYGGPSDLSTTIEAYVALRLAGDDPDAPHMRSAAEWVRSAGGIAASRVFTRIWLALFG
EWSWDDVPVLPAEMTFLPPWFPLNIYDFACWARQTVVALTIVGSLRPVRSFGFTLDELRVQAP
KATKAPLRSWAGAFERLDSVLHRYEKRPFQPLRRLALRRAAEWVIARQEADGCWGGIQPPMV
YSIMALHLMGYPLNHPVISMAFRALDRFTIREETPEGTVRRIEACQSPVVVDTALAVVALADAGL
GGDHPAMVRAGRWLADEEVRVAGDWAVRRPTLAPGGWAFEFDNDFYPDVDDTAEVVIAIRR
LLGDGHGPVDHSDGSGPGSAAATAASAAAEAAVAAAGTIAAADPELAARLRAAAERGVDWSV
GMRSSNGAWAAFDADNVRTLVRKIPFCDFGEVVDPPSADVTAHMVEMLALLGRSDHPITQRG
VRWLLDNQEAGGSWFGRWGVNHVYGTGAVVPALISAGVDAEHPAIVSSMHWLVEHQTPEGG
WGEDLRSYRDDEWIGRGEPTASQTAWALLALLAAEPASGTAEWEAVERGVRWLCDTQRPDG
TWDEPQFTGTGFPWDFSINYHLYRLVFPVTALGRYVTLTGRSTS >seq_ID 242
MSISALQTDRLSQTLTQSVVAAQQHLLSIQNPEGYVVWANLESNASITAEVVLLHKIWGTLDSQP
LAKLENYLRAQQKTHGGWELYWNDGGELSTSVEAYMGLRLLGVPASDPALVKAKQFILHRGG
VSKTRIFTKFHLALIGCYRWQGLPSLPAWVMQLESPFPFSIYELSSWARGSTVPLLIVFDKKPVY
PLQPSPTLDELFTESAENVRWELEEKGDWSDAFLWLDKAFKLAESVDLVPFREESIRKAEKVV
LERQEPSGDWGGIIPAMLNSMLALRALGYSVSDPVVRRGFQAIDNFMVESETECWAQPCISPV
WDTGLAVRSLTDSGLSPNHPALVKAGEWLLLDKQILSYGDWSVKNPQGQPGGWAFEFENSFY
PDVDDTAVVAMALQDITLPNEPLKRRAIARAVRWIATMQCKTGGWAAFDINNDQDWLNDIPYG
DLRAMIDPSTADITGRVLEMHGRFAADLDLANSYAADLSPYRLSRGLNYLIKEQELDGSWFGR
WGVNYIYGTGQALSALALIAPERCRIQIERGIAWFVSVQNADGGWGETCESYKDKSLKGKGIST
ASQTAWALLGLLDVSFCLDPAAKIAVDRGIQYLVSTQSEGTWQEESFTGTGFPQHFYLRYRLY
CHYFPLMALGRYQRVINSSAGI
```

| Enzyme Sequences |
|---|

>seq_ID 143
MAKGILNKFAVIAGNKNAGLTAEEECTVVAPIKEVSGKAVHCRQAVKMAEEYLLALQNPEGYW
VFELEADVTIPSEYIMLQRFLGREISPELRMRLENYLLDRQLPDGGWPLYAVDGFANISATVKAY
LALKVLGHSPQAPHMIRARIMVLSLGGAARCNVFTRILLALFGQLPWHTPPAMPVEIVLLPQRFF
FHLSKVSYWSRTVIVPMLLLYAKQPVCRLRPEEGIPELFNTPPDKLRNLDGFQSGRWRKNAFIII
DRLLKRFNRFIPSAIHRKAMAEAEHWTRSRMQGSGGIGAIFPAMAYAVMALRVLGCREDDPDY
VRGMQAIDDLLQHRTPQEADSPRTGGPCIDSGTSAAFAFDPSPHAAADGRGNSSICQPCNSPI
WDTCLSLSALMEAGMPASHPAAKQAVEWLLSQQIFSPGDWSLKAPDLEGGGWAFQFENTLY
PDLDDTSKVIMSLLRAGALENGLYRDRVARGVNWVLGMQSSDGGWAAFDIDNNYHYLNDIPF
ADHGALLDPSTSDLTGRCIELLSMVGFDRTFPPIAQGIGFLRSKQEGSGAWFGRWGVNYIYGT
WSVLSGLRQAGEDMQQPYIRRAVGWLTSCQNHDGGWGETCYSYDDPSLAGQGESTPSQTA
WSLLGLMAAGDVHSLAVRRGVRYLLDHQNQWGTWEEKHFTGTGFPRVFYLRYHGYRHYFPL
WALGVYSRLSSGQKTRQEERRHSSPGDLHLPWLERIGRR >seq_ID 71
MIKNFTALWPIRRVKGVSVTSQDGHSANGASKPDFEVRPHVDLETAIHRSQSFLLKEQKPEGY
WVGELIVDSTLVSDTIAYHHWNGKVDMEWQRKAVNHIFSMQLPDGGWNIYYGGPAEINATVKA
YLALKLAGVPVMDPRMLRARSVALSMGGVPRMNTFSKLYLALLGLFPWNYVPTIPCEVILIGKW
FHVNFYEMSSWSRSMLVPLAIINHFKPTRKLQNQVKLDELYPEGYHERDLALPPDPEFLTFRNF
FLWLDKLHKFAELWVQAGIHPFRRRALKKCEHWMLERFEGSNGLAAIFPAMLNSLIALKALGYP
GDHPEVKRAEKELKNLEHETADTVRIEPCFSPVWDTAIVAICLHESGIPSDHPALKKSAEWLIDK
EIRFRGDWYFKNPVDVEPSGWVFEFENKWNPDVDDTAMVLLALRKIPTSDVKRRDECFQRGL
KWMMAFQCKDGGWAAFDKDCTKGILEKVPFADHNAMLDPECADITARILELLGYEGVGVDHP
QIKKALQFIQEEQEDDGSWYGRWGVNYIYGTWQVLRGLRALNINMNQPWLLKARDWLESVQH
EDGGWGERCNTYDDPVFKGQGPSTASQTAWAVMGLCTFDDPQRPSLMRGIDYLIKTQNSDG
SWTEHEITGTGFPRVFYLKYDMYRNSWPLLALATYRNLYASSEKTANGHTNGHSVQLPEALKT
PPAFK >seq_ID 126
MNKKSAMKLKKKAKNHVVSLLQPTDALNRVMKRFRSLQSPEGYWVFALEADVTIPSEYIMFNR
FLGRKMDKGLAERLGNYIRAKQMADGGWPLHDNDGPVNISASVKAYMALKMLGDNKDAEHM
VRARQIILAKGGAETANVFTRICLATFGQIPWHCPPAMPIEIVLLPKWFFFHLDKVSYWSRSVIYP
LLIIYAKQPVCRLRPEEAVPELFCKPAEEHIHIDKYRDKGWRKNLFILLDRVLKRTIHLVPKSINKK
ALNYAEKWTREHMAGRGGIGAIFPAMANAVMALSLLGYDESDPDFARGMQSVDDLMVDKFHV
PEKSPWEHTVITGGAELSAAPELDISPDHGTAENLEQAMCQPCNSPIWDTCLTLSAMMEAGEN
QDSKSTQQALNWLWDQQIFFRGDWISKAPKLEGGGWAFQFENTFYPDLDDTAMVLMAMCRA
GVLDQPEHRENFIKGVNWLIGMQSSNGGWAAFDIDNCAEYLNDIPFADHGALLDPPTSDLTAR
VIELLGVLGYDKSFRPIKDGIEFLKKEQEDDGSWFGRWGVNYIYGTWSVLCGLRQAGEDMNSS
YVCKAVEWFENHQNKDGGWGESCLSYNDKNYAGLGDSTASQTAWALLGLMAAGRVHSKAV
SRGVRYLLDTQKDDGSWDESLFTGTGFPRVFYLRYHGYSQYFPMWALGVYQRFSADEDTKQI
MMRRKSPLDLGRKW >seq_ID 114
MIFTDTPTGSTQNRLDVAIRRAQQNLLRLQHNEGYWCGELFVDSTLCSDYVLFMHWADEIDPV
MEEKCVAHIRRRQLEDGGWNIYEGGPSDVNATVKAYFALKLAGHAPTQPWMQEARACILRLG
CIPKMNTYAKLYLALLGQFPWRYLPTVPVEIMFMPRWFFFDIYEVSSWSRAMLMPLAILNHYKP
TKHLPADKQLHELYPIGSEESDLGLGMQKPRFSWPNFFLFCDRLIKIMHSLPWKPWKRAALAR
AEAWMTQRMGEGSDGLAAIFPAMLNSMIALRTLRYSREHPLYVKAKNDFAGLFVDDPQDFRIQ
PCLSPVVVDTAINLVALLESGLDPHDPKIEAAVNWLKEKEVRINGDWYVKNHHVPPSGWAFEFN
NVYYPDTDDTMMVLAALARAGAHEESAPVETKAMFERALKWLLSFQCRDGGWAAFDKDVTQ
GWLEDVPFADHNAILDPTCSDLTGRVLELLGLIDYDRNCTPVRRALKFLRDTQEDDGSWYGRW
GVNYIYGTWQVLRGLRSIGEDMRQQWIVRARDWLESCQNEDGGWGETCASYDDPTLKGKGP
STASQTAWALMGLIAAADPTEPGAFDRKSIRQGVDYLLSTQVADGSWVEPEVTGTGFPRVFYL
RYDMYRNNFPLMALATYRKAREGKLPVRQRE >seq_ID 194
MKKATRSVFSLLDGGKISDSGSRGDSRHAGSRLDSVTKSAAALLASRQNPDGHWVFDLEADV
TIPAEYVMMRCFIGEPLDSDMASRLSAYLLERQLPDGGWPLYAVDGNANISATVKAYFALKLLG
HDKYAPHMVSARRMILAQGGAERSNVFTRITLALFGQVPWHTTPAMPIEIMLLPKWFFFHLSKV
AYWSRTVIVPLLILYNKQPVCRLGYSEGIAELFSTSPDMLVHLDHFRYRAWRKNAFIVLDRLLKR
TMHLVPGRIKRRALEEAERWTRERMKGDGSIGAIYPAMANAVMALKTLGCGDSDPDYLRGLR
AIDRLLIHGKPEAGALPADGAGTLFPVLDGASSAAVDLYPASLSDTAKSHAFSFCQPCNSPVWD
TALSLTALSEAGGGGYSPERAMEWLFNRQIATQGDWTERCPGLECGGWAFQYENALYPDVD
DTAKVLMSLFRAGALERGEYPEKIAKAVRWVLGMQGADGGWAFDVDNNHFYLNDIPPFADHG
ALLDPSTADLTGRCIEMLGMLGHGPDYPPITRGIEFLREEQEPFGGWFGRWGVNYIYGTWSVL
SGLSQAGEDMGRPYVRKAVEWLVSCQNDDGGWGETCASYDDPSLAGSGASTASQTAWALL
GLMAAGEADHAAVRAGIAYLADSFADGWDERHFTGTGFPRVFYLRYHGYSLFFPVVVALGVYA
RHREGGKTVQEQVRERGVNGVFDFVMGGSA >seq_ID 154
MMANATDTIELPPSRAADRIVPMTDIDQAVDAAHAALGRRQQDDGHWVFELEADATIPAEYVLL
EHYLDRIDPALEERIGVYLRRIQGDHGGWPLYHGGKFDVSATVKAYFALKAIGDDIDAPHMARA
RAAILDHGGAERSNVFTRFQLALFGEVPWHATPVMPVELMLLPRKALFSVWNMSYWSRTVIAP
LLVLAALRPRAINPRDVHVPELFVTPPDQVRDWIRGPYRSQLGRLFKYVDIALRPAERLIPDATR
QRAIKAAVDFIEPRLNGEDGLGAIYPAMANTVMMYRALGVPSDPRAATAWEAVRRLLVELDG
EAYCQPCVSPIWDTGLAGHAMIEAASGPEGIRPEDTKKKLAAAAEWLRERQILNVKGDWAINC
PDVPPGGWAFQYNNDYYPDVDDTAVVGMLLHREGDPANDEALERARQWIIGMQSSNGGWG

Enzyme Sequences

AFDIDNNLDFLNHIPFADHGALLDPPTADVTARCISFLAQLGHPEDRPVIERGIAYLRTDQEREG
CWFGRWGTNYIYGTWSVLCAYNAAGVAHDDPSVVRAVDWLRSVQREDGGWGEDCASYEGA
TPGIYTESLPSQTAWAVLGLMAVGLRDDPAVMRGMAYLTRTQKDDGEWDEEPYNAVGFPKVF
YLRYHGYRQFFPLLALSRYRNLASSNSRHVAFGF

>seq_ID 156
MLIYSDILEKEDRVSETLSRQSVEPDEINHAIEGAQAALGGKQKSDGHWVYELEADATIPAEYVL
LEHYLDRIDPEKQAKIGVYLRRIQGHHGGWPLYHDGGFDLSATVKAYFALKAIGDDINAPHMRIA
REAILDHGGAARTNVFTRIQLALFGEVPWDATPVMPVELMLLPRKAFFSVWNMSYWSRAVIAP
LLVLNALRPKAINPRGIHVQELFVKPPSEVKDWIRGPYRSVWGRFFKHLDSALRPVLPLIPRSVH
KKALKAASDFIEPRLSRGGLGAIYPAMANVVMMYRAQGVPDSDPRAKTAWDAIQDLLVDHGDE
IYCQPCVSPVVVDTGLSGLAMIEAASGPAGTKTKETLAALKKSAEWLREHQILDVKGDWAINAPD
LRPGGWAFQYENDYYPDVDDTAVVAMLLHRVDPENSREAISRAREWIIGMQSTNGGWGAFDI
DNDHELLNHIPFSDHGALLDPPTADVSARCISFLAQLGDPDDRPVILKAIEYLRSEQEPEGCWF
GRWGTNYIYGTWSVLCALNIAGVPHDDPMVLRAVNWLESVQRPDGGWGEDCATYEGGTAGT
YKKSLPSQTAWAVLALMAVGRRESEAVKRGVAYLVSQQNEKGEWQEEAYNAVGFPKVFYLR
YHGYKQFFPLTALARYRNLGVSNSGKVEYGF >seq_ID 74
MEGASPTASNRISQYAVDLRAKARAAVASTCDWLLSHQHADGHWCAELEGDSILQSEYILLLA
WLGKERTEIARRCAAHLLKQQEPNGAWTQFPGAPIDVGSSVKAYFALKLTGHDAAADYMVRA
RNAILEAGGADKVNSFTRFYLALLGQIPFELCPAVPPEMVLLPNWSPINIYRISSWSRTIFVPLSIV
WAHRAARDIVEDVSIHELFIRKPEDWPELRCPGLEKPAGLFSWDRFFRTADSGLKLLEKYGLRP
LRKRALRQAQQWMLDRFQQSDGPGAIFPPIVWSAIALRTLGYAEDSPEIQYCLDHLERLVLEDG
ETTKLQPCKSPVVVDTSITLRALAAAGLGLAQEPTCRGVEWLLSKEVRVPGDWTNNVDCEPGG
WFFEYENAFYPDNDDTSMGIMALADQLAAANITLEVHPGETLANTSVVVGGRGIAEQLAGSSA
AMMEQAAAATRRAVAWMVAMQNKDGGWGAFDKNNDAEFLCHVPFADHNAMIDPSTPDLSA
RVIESFGRLGVTIESPGKLGDTVRRAVAYIRANQLSDGSWFGRWGVNYIYGTWQCLVGLRAVG
VPANDPAIEQGKLWLLAHQQACGGWGESCETYEDPSLRGQGSPTASQTAWALLGIIAAGGAN
LAEVVHGVQYLMDTQREDGAWDEIEFTGTGFPRVFYLKYHYYPIYFPLLALAEWNRATARS >seq_ID 326
MFDTISFDFDALDQAISRAHARLSAEQRADGHYVYELEADATIPAEYVLLEHFLDRIDPELEARIG
VPLRGIQGNSPQNPGGWPLFHDGAMDISASVKAYFALKAIGDDPDAPHMRRAREAILARGGAA
RTNVFTRIQLALFGAVPWRACPVMPVEIMLLPDWFPITIWKISYWSRTVIAPLLVLLTERPIARNP
RNVRIDELFVTPPDQVTDYIRGPYRSNWGYLFKAIDSALRPLERHFPPARSRKRAIQAAIDFITPRL
NGEDGLGAIYPAMANTVMMYHTLGYSPDHPDYATAWASVRKLVTDASYRFEGASYVQPCLSP
VVVDTSLAAHALAEAGSPGDAQLAAACDWLIPRQILDVKGDWAYRKPDAPPGGWAFQYNNAH
YPDVDDTAVVGMILDRNGDPAHREAVERARQWILGMQSRSGGWGAFDSDNEFHYLNHIPFAD
HGALLDPPTADVTARCISFLAQLGHAEDRPAIERGVAYLRREQEQDGSWFGRWGTNYIYGTW
SSLCALNAAGVAQDDPMMVRAVEWLLARQRPDGGWGEDCETYAHAKPGEYHESLPSQTAW
ALLGLMAAGQAEHEAVARGIAWLQSVQEDDGSWTEQPYNAVGFPRVFYLRYHGYPRFFPLLA
MARYRNLARGNSRQVQFGF >seq_ID 192
MDKIKMKNINQPKFRVFRGGQKAATPCPGTTNERRGALDRGRLSASLKHSREWLLSLQADAG
NWVFALEADTTIASEYVMLQRFLGRPLAPELQQRLANYLLSRQLPDGGWPLYAEDGFANISTT
VKAYLALKLLGYPTHCDPLVRARQIVLALGGAEKCNVFTRIALALFGQIPWRTTPAMPVEIMLLP
RWFYFHLSKISYWARTVNPLLILYAKRPVCRLEPWEGIPELFVTPPDKLGYLDVCKPGQWRKN
VFIWVDRLTRKMVRCVPRRLHNLALRAAETWTREHMQGAGGIGAIFPAMANAVMALRTLGCS
PDDADYQRGLKALDDLLIDRCDVPPREDTPVSPCWCTGTSAAPMLDSPAGSHAQGGDQGIC
QPCASPIWDTGLALTALLEGGLDARHPAVDRAVRWLLDQQVDVKGDWAQRVPNLEAGGWAF
QFENALYPDLDDTSKVLMSLIRAGAMDNPGYRQELSRAINWVIGMQNSDGGWGAFDVDNNYL
YLNDIPFADHGALLDPSTADVTGRCIEMLAMAGFGRDFLPIARGVDFLRREQEDFGGWYGRW
GVNYIYGTWSALSGLIHAGEDLQAPYIRQAVGWLESVQNPDGGWGETCYSYDDPALAGRGVS
TASQTAWALLGLMAAGEVDNLAVRRGIQYLVEEQNRAGGWDERHFTGTGFPRVFYLRYHGYS
QYFPLWALGLYERLSSGNPSRQQMVRRAGPAGLHLPVLDRRKKLRRKRKA >seq_ID 72
MKSEEVTIKPAVGLEKDELNAAITRSQSFLLCEQKPEGYWVGELMVDSTIVSDTIAYHHWNGKV
DPEWQRKAVNHILSMQLPEGGWNIYQNGPPEVNATIKAYLALKLAGIPITDPRMLKARQVALTL
GGVPRMNTFSKLYLALLGLWPWKYVPTIPCEVLLLGKWFHVNIWDMSNWSRAMIVPLAIINHYK
PTRPVKVDLSELFLEGFHERDLALPKDPQSFTWRNFFLGLDQLHKFAELWVNAGIHPFRRLALK
KCEQWMLERFEGSDGLAAIFPAMLNSLIALKSLGYPDDHPEVLRAERELKKLEHETKDTVRIEP
CLSPGWDTAIAAMCLRESGVPAEHPRLKKAGDWLVNREVRFKADWHHKNPVDVEPSGWVFQ
FNNKWNPDLDDTAMVLLALRLIPTDHPRRRDEAFQRGLKWLLAFQCRDGGWAAYDKDCTKNI
LEKVPFADHNAMLDPECADITARVLELLGFEGYALDHPQVQEAVEYLREHQETDGSWYGRWG
VNYIYGTWQTLRGLWALKMDMNQPWLLKARDWLESVQLPDGGWGERCNTYDDPVFKGQGP
STASQTAWAVMALCTFGDPKRPSLVRGIQYLIENQNEDGSWTELETTGTGFPRVYYLKYDIYR
NTWPLLAMATYRKMLDPKEVRVK >seq_ID 145
MNKHKGTFSVIEGGKTTQARGSETCAIMDAADLEKVTSVAASQLAGQQQDDGHWVFDLEADV
TIPAEYVMLQRFIGREIDPEISERLAAYMQERQLPDGGWPLYAVDGNVNISASVKAYFALKLLGH
DKNAPHMVRARQLILSLGGAAKCNVFTRITLATFGQIPWHTAPAMPIEIMLLPRWFFFHLNKVAY
WSRTVIVPLLILYATQPICRLQYNEGITELFTTPPDMLVHLDKFRHHAWRKNVFIALDRVLKRTM
HLVPGRIKQHALAEAERWTRARMQGDGGIGAIYPAMANAVMALKTLGCSDDDADYLRGLEAV

| Enzyme Sequences |
|---|
| DNLMVHRNLKTGTIPMDDDSGGIAIDNSSAAPELSPTYLTDTAGNTEFSFCQPCNSPIWDTCMS<br>LSALCESGYAENNSGVTDRAIKWLFSQQIATPGDWSEKCPGLESGGWAFQYENSRYPDVDDT<br>AKVLMSLFRAGALEKPEYREKIERAIRWVQGMQSTDGGWAGIFPDVDNDYFYLNDIPFADHGALL<br>DPSTADLTGRCIEMMGMLGHGPDYPPIARGIAYLKKEQEPFGGWFGRWGVNYIYGTWSVLSG<br>LHQAGENMDAPYVRKAVEWLISCQNSDGGWGETCASYDDPSLAGSGASTASQTSWALMALM<br>AAGEWRHSAVRNGVRYLTESYCNGWNEKQFTGTGFPRVFYLRYHGYSLFFPVWALAVYSRYI<br>NGTATVQEKVREKQFRQCLMV<br><br>>seq_ID 127<br>MLPYNQDFYNEDEALKDDHCEGAGNVSNPPTLDEAIKRSQDFLLSQQYPEGYWWAELEGNPT<br>ITSHTVILYKILGIEDEYPMDKMEKYLRRMQCIHGGWELFYGDGGQLSVTIESYVALRLLNVPPT<br>DPALKKALKFIIDKGGVXKSRMFTKICLALLGCFDWRGIPSLPPWVMLLPGWFLSSIYETACWA<br>RGCVNPLIVVFDKKPVFKVSPEVSFDELYAEGREHACKTLPFCGDWTSHFFIAVDRVFKMMER<br>LGVVPFQQWGIREAEKWLLERQEDTGDFLGVYPPMFYSWCMKTLGYEVTDPVVRRALLSFK<br>KFSIERADECSVQSSLSPVWDTALVVRSLVESGLPPDHPALQRAGEWLLQKQITKHGDWSFKN<br>QSGVAGGWAFQFFNRWYPDLDSAVVVMALDCLKLPNEDVKNGAITRCLKWISSMQCKGGG<br>WAAFDKDNHQHWINSTPFSDLKAMVDPSTTDISARVLEMVGRLKLHGTSFDEAHFLPPESIAR<br>GLVYLRREQENEGCWFGRWGVNYIYGTCGALVALSLVAPMTHEEEIARGARWLVQVQNMHG<br>KKINGPQDGGWGETCFSYNDPALKGQGDVSTASQTAWALQGLLAAGDALGKYEVESIGHGV<br>QYLLSTQRKDGSWHESQFTGGGFPIHFYLRYHFYAQHFTLSSLARYRTRLQASKIKPPIP<br><br>>seq_ID 166<br>MNTEPRFSAPETLRAIAGAGRALGRHQRRDGHWVFELEADATIPAEYVLLEHYMDRITPERQA<br>RIGAYLRRIQGEHGGWPMFHAGEFNISASVKAYCALKAIGDDPQAPHMVRARQAILGHGGAER<br>ANVFTRIQLALFGAIPWRGVPVMPVEIMHLPKWFFFNIWAMSYWARTCVVPLLVLQARKPRAR<br>NPRQVSFDEIFRTEPDEVRDWIRGPYRSRWGVVFKHIDTVLRWTEPLFSKVARESAIFKAVDFV<br>EERLNGEDGLGAIYPAMAYALMMYDVLGYPEDDPRCVTIWKAIDKLLIETDEEVYCQPCVSPV<br>WDTSLSGHAMIEAARTGGIEAQAELDAACDWLVARQVKDVRGDWAETRPDAEPGGWAFQYR<br>NDHYPDVDDTAVVAMLLHRNGRPEHAEAIEKARRWVVGVQSRNGGWGAFDADNDREFLNHI<br>PFSDHGALLDPPTADVTGRCISFLSQLGHEEDRPVIERALAYLRAEQERDGSWYGRWGTNYV<br>YGTWTVLCGLNAAGIPHDDPMVRRAVDWLVSIQRADGGWGEDERSYDVGHYVENAESLPSQ<br>TAWAMLGLMSVGQADHPAVLRGAAYLQRTQGPDGEWQERAYNAVGFPRVFYLKYHGYRLFF<br>PLFALSRLHNLQRGNSREVSFGF<br><br>>seq_ID 21<br>MSGEVRVAGDALAEDAGRAAAAASQYLYRTQQRDHWRAELESNVTVTAEYVLLRQALGLDLE<br>ERRDALVRYLCSRQKADGSFGIASTLPGDVSTTAEAYLALRLLGLDREDERLRAAERFIRGAGG<br>LARVRVFTRINLALFGLFPWEAVPTVPAELIFLPRWAPVNVYRLASWARSTMVPLFVLFHHRPV<br>FALPGGAGSDWLDHLWLGPGDKRVPYRTSVMETVRRHGPGWKAFFNAADAWLRVHDRLRH<br>LPPLGRLRTEALRACEEWILARQEASGDWAGIFPPMLNGVLALHVAGHGLDAAPVRRGLEAIE<br>RFAVSDREGFRIEACQSPVVVDTILALIGLLDSGESPTDPRLVAARRWIEGMQLTNDWGDWKVY<br>DPRGEPGGWAFEYANSWYPDVDDTAAVIVGLLKHDPASRAGETVRRAAAWVASMQNRDGG<br>WAAFDVNNDRLFLNEIPFSDMDSLCDPSSPDVTGRVLEAFGMLDAPHLRAACRRGVAYLRRA<br>QEPEGSWYGRWGVNYVYGTSNVLNGLARQRVPASDPMVARALGWLDSVQNADGGFGEGLE<br>SYADRAAMGRGPSTASQTAWGVMGLLAYRAADDAAVRRGIAWLVERQLADGEAQGSWEEE<br>AFTGTGFPRHFYLRYHLYRHYFPLMALGRFCAQGRG<br><br>>seq_ID 111<br>MSYEWTEPVRPGRRHAVSPVQNFCQSLAPAIQRACDALFSQQAADGFWCGELTADTTLESDY<br>ILLQLWLNQPDDHGWNPPTRPRIDRAGRSILERQLPDGGFNIYAGGPSEVSATIKAYCALKLAG<br>LDPHSPPLRRARERILALGGLQAANSYVKINLSLFGLYPRKHVPSVPPEIVMLPGNVLYEMSSW<br>TRSILVPLSIVQARGSNRRAPNGFNLDELLLPGVKLALPKRKGLAVLFHHLDRMFKVWEKRGSE<br>RIRGAAIREAERWLIARTHYTEGLGAIYPAMMYFIMALDALGYAEDHPDRSEAIRHFESLLIETDD<br>RFLFQPCVSPVVVDTAICAFALGEAGNTDDPRMTLAADWLISKEVRRKGDWSIKRPDTEPSGW<br>APEFEFANEFYPDIDDTAMVLLALMHANGSNPEAQAAAERRAVNWLLAMQSSDGGWAAFDVDN<br>NWAMLNQVPFADHNAMLDPTCPDITGRVLECLCRRGMAGHDAARRGVAYLLQAQEKDGSWY<br>GRWGVNYIYGSFLAMRGLTTSGAPGSQDAVDRAARWLRAIQNPDGGWGESCASYARDGYVA<br>APSSASQTAWALLGLCAAGDRDSAQFRRGVEYLLTLQAPDGKWPEGATTGTGFPNVFYLTYA<br>MYRDYFPLLALSQV<br><br>>seq_ID 157<br>MPKDIPADLASEAISCDMLEQAVLRASMALHRKQQTDGHWVFELEADATIPAEYVLLEHFLDRI<br>DDDLERKIGVYLRRIQGDHGGWPLFHEGAFNLSASVKAYYALKAIGDDPDAPHMRRAREAILAA<br>GGAERSNVFTRIQLALFGQIPWRGVPVMPAELMIAPKWFPINMWKVSYWSRTVIAPLLVLMDR<br>KPKARNPRNVHVRELFLHDPDRIRDWIRGPFRSGWGHFFKYLDSVLRVVEPVALKPMRPRSIR<br>LAVDFVRERLNGEDGLGAIYPAMANSVMMYDVLGYSPDHPEAAIAWESVRKLLVIKEDEAYCQ<br>PCLSPIWDTGLSGHAMAEAEGAVSPGVAAACDWLRNRQITDVVGDWAEIRPGVQPGGWAFQ<br>YNNAHYPDVDDTAVVAMLLHRGDPAHEESIRKAREWIIGLQCRDGGWGAFDADNDKDYLNH<br>IPPFADHGALLDPPTADVTARCISFLAQLGNPEDKPVIDRAMAWLRKEQEADGSWFGRWGTNYI<br>YGTWSVLCAMNVAGMPHDDPAIRRAVNFLVATQREDGGWGEDEETYDPASGAQPGRYKEST<br>PSQTAWALIGLMAAGEAEHEATRRGIAYLQATQKPDGEWDEAAYTAVGFPRVFYLKYHGYRQ<br>FFPLMALSRYKNLRSSNMKKVSFGF<br><br>>seq_ID 205<br>MNQAATITRPQDETLTTSARRPAQPALPDPLDAGIAHVVESLLAQQQSDGHWVYELEADATIPA<br>EYILMVHYLGETPDLVLEGKIANYLRRIQNADGGWPLFHAGASDISASVKGYFALKMAGDNPEA<br>EHMRRARAAIHAMGGAEASNVFTRTLLALYGVMPWQAVPMMVEIMLLPEWFPFHLSKVSYW |

| Enzyme Sequences |
|---|
| ARTVIVPLLVLNSLRPQARNPRKIGIDELFVRPCQATRLPRRAPHQSPLWVGVFRTLDAVVRMA<br>EPLFPRGLRQRAIERAREFTVERLNGEDGLGAIFPAMVNSVLMFDVLGVPESDPNRAIARRSID<br>KLLVIKDDEAYCQPCLSPVVVDTSLAAHALLEVGEPRTIAAAARGLDWLLPLQELELRGDWTVRR<br>PNVRPGGWAFQYANPHYPDVDDTAVVAAAMDRVDKGDRSNRYDEAVSRACEWIVGMQSSN<br>GGWGAFEPENTHLYLNNIPFADHGALLDPPTADVSARCLAMLCQLGQMPANSEPAARALRYLL<br>DEQEADGSWFGRWGTNYIYGTWSALCGLNAAGIGTDAPEMKRAAQWLLSIQNEDGGWGESG<br>DSYKLEYRGYEKAPSTASQTAWAMLGLMAAGAGDHPALVRGVEYLLRTQASHGFWDEPYFT<br>AVGFPRVFYLRYHGYSRFFPLWALARFRNLLRDGNRAISWGL<br><br>>seq_ID 218<br>MKTDGNTTLDTTISMEELERTVKSAYEALAKDQQDDGHWIYELEADVTIPAQFILLEHTLDKIDE<br>ELEQKIANYLRRCQSREHWGWPVYYGGEFNISASVQAYFALKMTGEDINAPHMVRAREAILAH<br>GGPEYANVFTRIQLSLFGEASWLATPFMPVEIMLLPRWMYFSIWNMSYWSRTTVAPLLIVADLK<br>PKAINPRNVHIPELFPTPPDKVKTWIHGPFRSKWGHVFKFIDTAIRPFTRFVPSFLHKKAYKAAL<br>DFIEPRLNGVDGLGAIYPPMSYSAVMYRALGIPDDDPRAATNWEALKGLLVIKEREAYCQACVS<br>PVVVDTALSGHALMEASFGPDGINADRTEKLIDRAAHWLRAHQVLNVVGDWAINNPNLQPGGW<br>AFQYGNDYYPDVDDTAVAAMLLHRQNLPENEEALDRARKWIIGMQSSNGGWGAFDIDNDKQI<br>LNDIPFADHGALLDPPTADVSARCISLLAELGHPEDRPVIERGIKYLRKEQEEDGSWFGRWGTN<br>YIYGAWSVLCAFNASGVPHDDPSVLKCVNFLKSVQREDGGWGESCETYEGSAHGVYTESLPS<br>QTAWAVLGLMASGRRTDPAVKRGIVVVLIQHQQDNGEWAEEPFNAVGFPRMFYLHYLGYKQF<br>FPLLALARYRHMEKSGTNNVSFAF<br><br>>seq_ID 11<br>MLPYNQDHHFGKVAENATMPPTLDEAIERSQDFLLSLQYPEGYVWVAELEANVTLTAQTIMLYKI<br>LGIDHKYPIHKMKTYILRTQRAHGGWEIFYGDGGCLSTTIGAYMALRILGVPKTDPVLQKALKLIH<br>SKGGVTKSRMFTKICLALLGCYDWKGIPSLPPWLVLLPSWFPFSLYDTASWVRGCVVPLTIIFD<br>KKPVYKLNPLLCLDELYSEGKGKARVHLSFIPGDWTSNFFVGLDHVFKYMENLGVVPFRQWGI<br>KEAERWTLERHEDSGDFHGIYPPMFYSIVSYSLLGYEITDPVVHRALESMRGFTVEREDECVV<br>QSCISPMWDTAFVIRSLAESGLQPDHPALQKAGEWLLQKQATQHGNWFYKKRTGRAGGWAF<br>QFFNRWYPDVDDSAAVSMALNAIKLQDDDVKKGAIKRCAEWISVMQCKDGGWAAYDCDNDR<br>EWLNCTPFGDLKAMIDPNTVDVTARVLEMVGRVKEAGDASAILPPRAIARGLAYLRREQETEG<br>CWYGRWGVNYIYGTSGALMALALVAPSTHKEEIERGARWLVEVQNKRGTKGANGYSHTNGA<br>REGGVAMNGNCKNMGAPEDGGWGETCFSYNDITLKGRNEVSTVSQTAWALQGLLAAGDALG<br>KYEVESIEHGVQYLLSTQRKDGSWCEKHFTGGGFPRFFYIRYHLYAGHFPLSALARYRDRVRA<br>GKMAK<br><br>>seq_ID 214<br>MDATAPLRDPGAPSAENCSVDRRELDDVIGESCRWLGERQNQDGHWVFELEADATIPAEYILL<br>NHFLDEIDDAREARIASYLRAIQGKHGGWPLFHDGDFDMSATVKAYYALKLTGDGVDEPHMVR<br>ARQAILEHGGAERTNVFTRFTLAMFDQVPWRACVPTPVEALLLPRFAPFHWSKVSYWSRTVM<br>TPLMILYSRRARAVNPRGIGVRELFRRDPEVIRDWLKNPTGHWIGDALIQIDKVLRVIEPAIHWAF<br>RDRAEKWALDFIEERLNGRDGLGGIYPAIANTLMAYHTLGYAKDHPGYRIAREAVDGLCTPHAK<br>GEYVQPCLSPVWDTCLASHAIQEAGQSAGDRAVDQSNAWLRERQVLDVVGDWKSNRGHLRP<br>GGWAFQYNNPHYPDVDDTAVVVMALARSKEDEANREAIARAEEWIIGMQSSNGGWGAFDAE<br>NEHDFLNHVPFADHGALLDPPTVDVSARCLGMLAQLGRPKTDPVVARGLDYLWREQEADGS<br>WFGRWGTNYIYGTWSALNAFNAVEWDMTDPRICKAVDWLKSRQRDDGGWGEDCATYWKER<br>RSVSKASTPSQTAWAVLGLMAAGEVDSPEVERGIRYLLEAPRDGGKWEEELYNAVGFPRIFYL<br>RYHGYSAYFPLWALARYRNLTSGNCKRTIHGM<br><br>>seq_ID 73<br>MPEEAILTETHPLDATTIETAITRARKALLGEQRADGHFVFELEADVSIPCEYILFYHFIGRPAPAE<br>LEAKIGHYLRARQSAEHDGWPLFQDGAFNISSSVKAYFALKAIGDTPDMPHMQRARTAILAHG<br>GAAAANVFTRSLLALFGLIPWHGIPVMPIE1MHLPEWFPFHIAKISYWGRTVLVPMMVVHALKPK<br>PANTCTIRIDELFVIPPDQVRHWPGSPGKRFPWTAIFAGIDKVLQIAEPYFPRRSRQSAIDKAVA<br>FVTKRLNGEDGLGAIYPAMAYSALMYLSIGRSLSDPHIQLVLKAIDKLVVVKDHEAYVQPCVSPV<br>WDTALASHALMEAGDGDKPILDSLKKGLAWLKPLQVTDIAGDWAWKKPDVKPGGWAFQYGN<br>AYYPDLDDTAVVVMAMDRARDRWPEIDEDNFRPSIARAREWIVGLQSENGGFGAFDADNDRD<br>YLNAIPFADHGALLDPPTADVTARCISMLTQLGEKPENSETLRRAIAYLFAEQEKDGSWFGRWG<br>LNYIYGTWSVLCSLNAAGIAHDAPEVRRAVAWLRTIQNEDGGWGEDAESYALDYAGYQQAPS<br>TSSQTAWAVLGLMAAGEKDDPAVARGIAYLTRTQGEDGFWTEKRFTATGFPRVFYLRYHGYS<br>KFFPLWAMARYRNLHNGNHASVLTGM<br><br>>seq_ID 103<br>MNDMTEMHTLDATAVPAAPAAADAPAPSAATTGLDAAVARATDALLAAQNADGHWVYELEAD<br>STIPAEYVLLVHYLGEEPNAELEQKIARYLRRIQQPDGGWPLFTDGAPNISASVKAYFALKVIGD<br>DENAEHMQRARRAIHAMGGAEMSNVFTRIQLALYGVVPWYAVPMMPVEIILLPQWFPFHLSKV<br>SYWARTVIVPLLVLNAKRPVAKNPRGVRIDELFKSAPVNTGLLPKQPHQHAGWFAFFRAVDGV<br>LRLADGLFPRYTRERAIRQAAAFVDERLNGEDGLGAIYPAMANAVMMYAALGYPEDHPNRAIA<br>RQSIEKLLVVGEEEAYCQPCLSPVVVDTSLAAHALLETGDERAREEAVRGLDWLVPRQILDVRG<br>DWISRRPHVRPGGWAFQYANAHYPDVDDTAVVVMAMDRVAKHDQTDAYRESIARAREWVVG<br>MQSSDGGWGAFEPENTQYYLNNIPFSDHGALLDPPTADVSGRCLSMLAQLGETSASSEPARR<br>ALDYMLKEQEPDGSWYGRWGMNYIYGTWTALCSLNAAGLGHDDPRVKRAAQWLLSIQNPDG<br>GWGEDGDSYKLDYRGYERAPSTSSQTAWALLGLMAAGEVDNPAVARGIGHLLGTQREHGLW<br>DETRFTATGFPRVFYLRYHGYRKFFPLWALARYRNLKRAGAARVTVGM |

Enzyme Sequences

>seq_ID 95
MNDMTEMHTLDAAAAPAADAPAVTAVTAGLDAAVARATDALLAAQNADGHWVYELEADSTIPA
EYVLLVHYLGEEPNAELEQKIARYLRRIQQPDGGWPLFTDGAPNVSASVKAYFALKVIGDDENA
EHMQRARRAIHAMGGAETSNVFTRIQLALYGVVPWYAVPMMPVEVMLLPQWFPFHLSKVSYW
ARTVIVPLLVLNAKRPVAKNPRGVRIDELFKSAPVNTGLLPKQPHQSTGWFAFFRAVDGVLRLV
DGLFPRYTRERAIRQAVAFVDERLNGEDGLGAIYPAMANAVMMYAALGYPEDHPNRAIARQSI
EKLLVVGEEEAYCQPCLSPVVVDTSLAAHALLETGDERARDAAVRGLDWLIPRQILDVRGDWIS
RRPHVRPGGWAFQYANPHYPDVDDTAVVVMAMDRVAKLDQSDAYREQIARAREWVVGMQS
SDGGWGAFEPENTQYYLNNIPFSDHGALLDPPTADVSGRCLSMLAQLGETNASSEPARRAFD
YMLKEQEPDGSWYGRWGMNYIYGTWTALCALNAAGLGHDDPRVKRAAQWLLSIQNQDGGW
GEDGESYKLDYRGYERAPSSSSQTAWALLGLMAAGEVDNPVVARGIDYLLGAQCEHGLWDET
RFTATGFPRVFYLRYHGYRKFFPLWALARYRNLKRANTTRVTVGM >seq_ID 106
MNDLTDMPTLAADSAAADLDAAVARATDALLAAQQADGHWVYELEADSTIPAEYILLVHYLGET
PNLELEQKIGRYLRRIQQPDGGWPLFTDGAPNISASVKAYFALKVIGDDENAEHMQRARRAIHA
MGGAEMSNVFTRIQLALYGAIPWRAVPMMPVEIMLLPQWFPFHLSKVSYWARTVIVPLLVLNAK
RPIAKNPRGVRIDELFIDPPVNAGLLPRQGHQSAGWFAFFRVVDHALRAVDGLFPSYTRERAIR
QAVAFVDERLNGEDGLGAIYPAMANAVMMYDALGYPEDHPNRAIARRSVEKLLVVHDDEAYC
QPCLSPVVVDTSLAAHALLETGDPRAEDAVVRGLEWLRPLQILDVRGDWISRRPNVRPGGWAF
QYANPHYPDVDDTAVVVMAMDRVEKLRHSDAYREAISRAREWVVGMQSSDGGWGAFEPEN
TQYYLNNIPFSDHGALLDPPTADVSGRCLSMLSQLGETAANSEAARRSLDYMLKEQEPDGSW
YGRWGMNYVYGTWTALCSLNAAGLGPDDPRVKRGAQWLLSVQNKDGGWGEDGDSYKLDY
RGYEQAPSTSSQTAWALLGLMAAGEVNHPAVARGIDYLIAEQKEHGLWDETRFTATGFPRVFY
LRYHGYRKFFPLWALARYRNLKRANATRVTVGM >seq_ID 87
MNDLTEMATLSAGAVPAGVDAAVARATDALLAAQQADGHWVYELEADSTIPAEYVLLVHYLGE
TPNLELEQKIGYLRRIQQADGGWPLFTDGAPNISASVKAYFALKVIGDDENAEHMQRARRAIH
AMGGAEMSNVFTRIQLALYGAIPWRAVPMMPVEIMLLPQWFPFHLSKVSYWARTVIVPLLVLNA
KRPLAKNPRGVRIDELFIDPPVNAGLLPRQGHQSPGWFAFFRVVDHALRAVDGLFPSYTRERAI
RQAVSFVDERLNGEDGLGAIYPAMANSVMMYAALGYAEDHPNRAIARKSVEKLLVVHDDEAYC
QPCLSPVVVDTSLAAHALLETGDARAQEAVLRGLEWLRPLQILDVRGDWISRRPNVRPGGWAF
QYANAHYPDVDDTAVVVMAMDRAQKLTQSDTYRESMARAREWVVGMQSSDGGWGAFEPEN
TQYYLNNIPFSDHGALLDPPTADVSGRCLSMLSQLGETPLNSEPARRALDYMLKEQEPDGSWY
GRWGMNYVYGTWTALCSLNAAGLTPDDPRMKRGAQWLLSIQNKDGGWGEDGSYKLNYRG
YEQAPSTASQTAWALLGLMAAGEVNNPAVARGVDYLVAQQNEEGLWDETRFTATGFPRVFYL
RYHGYRKFFPLWALARYRNLKRANATRVTVGM >seq_ID 107
MNDLTDMANLSAGTVPAGLDASVARATDALLAAQNADGHWVYELEADSTIPAEYVLLVHFLGE
TPNLELEQKIGRYLRRIQQADGGWPLFTDGAPNVSASVKAYFALKVIGDDENAEHMQRARRAI
HAMGGAEMSNVFTRIQLALFGAIPWRAVPMMPVEIMLLPQWFPFHLSKVSYWARTVIVPLLVLN
AKRPLAKNPRGVRIGELFIDPPVNAGLLPRQGHQSPGWFAFFRVVDHALRAADGLFPSYTRER
AIRQAVSFVDERLNGEDGLGAIYPAMANAVMMYDVLGYPEDHPNRAIARKSIEKLLVVHDDEAY
CQPCLSPVVVDTSLVAHALLETGDARAEQAVLRGLDWLRPLQILDVRGDWISRRPNVRPGGWA
FQYANAHYPDVDDTAVVVMAMDRAQKLQNTDTYRESIARAREWVVGMQSSDGGWGAFEPE
NTQYYLNNIPFSDHGALLDPPTADVSGRCLSMLAQLGESALSSEPARRALDYMLKEQEPDGS
WYGRWGMNYVYGTWTALCSLNAAGLGPEDPRVKRAAQWLLSIQNKDGGWGEDGDSYKLNY
RGFEPAPSTASQTAWALLGLMAAGEVNHPAVERGIGYLIAQQNDEGLWDETRFTATGFPRVFY
LRYHGYRKFFPLWALARYRNLKRANATRVTVGI >seq_ID 212
MESGNNKQPAAAIGALDASIESATNALLGYRQPDGHWVFELEADCTIPAEYVLLRHYLGEPVDA
ALEAKIANYLRRVQGAHGGWPLVHDGGFDMSASVKGYFALKMIGDDIDAPHMAKAREAIRSRG
GAIHSNVFTRFLLSMFGITTWRSVPVLPVEIMLLPMWSPFHLNKISYWARTTIVPLMVLAALKPR
AVNRLDIGLDELFLQDPKSIKMPAKAPHQSWALFKLFAGIDAVLRTIEPLFPKRLRDHAIKLAVDF
VEERLNGEDGLGAIYPPMANTVMMYKVLGFPEDHPPRAITRRGIDKLLVIGEDEAYCQPCVSPV
WDTALTCHALLEVGGEAAVPPAKRGMDWLLPKQVLDLKGDWAVKRPNLRPGGWAFQYNNAH
YPDLDDTAVVVMAMDRSRRATGSREYDEAIARAREWIEGMQSDDGGWAAFDVNNLEYYLNNI
PFSDHGAMLDPPTEDVTARCVSMLSQLGETAASSKAVADGVEYLRRTQLPDGSWYGRWGLN
YIYGTWSVLCALNAAGVDHQDPVIRKAVTWLASVQNPDGGWGEGAESYRLNYTRYEQAPTTA
SQTSWALLGLMAAGEVDSPVVARGVEYLKSTQTGKGLWDEQRYTATGFPRVFYLRYHGYAKF
FPLWALARYRNLRSTNSKVVGVGM >seq_ID 101
MNDLTEMATLSAGAVPAGVDTAVARATDALLAAQNADGHWVYELEADSTIPAEYVLLVHYLGE
TPNLELEQKIGKYLRRIQQADGGWPLFTDGAPNISASVKAYFALKVIGDDENAEHMQRARRAIH
AMGGAEMSNVFTRIQLALYGAIPWRAVPMMPVEIMLLPQWFPFHLSKVSYWARTVIVPLLVLNA
KRPLAKNPRGVRIDELFIDPPVNAGLLPRQGHQSAGWFAFFRVVDHALRAVDGLFPNYTRERAI
RQAVSFVDERLNGEDGLGAIYPAMANSVMMYDVLGYAEDHPNRAIARKSIEKLLVVQEDEAYC
QPCLSPVVVDTSLAANALLETRDARAEDAAIRGLEWLRPLQILDVRGDWISRRPHVRPGGWAF
QYANAHYPDVDDTAVVAVAMERAQQLKQNDAYRDSIARAREWVVGMQSSDGGWGAFEPEN
TQYYLNNIPFSDHGALLDPPTADVSGRCLSMLSQLGETPLNSEPARRALDYMLKEQEPDGSWY
GRWGMNYVYGTWTALCSLNAAGLTPDDPRVKRGAQWLLSIQNKDGGWGEDGDSYKLNYRG
FEQAPSTASQTAWALLGLMAAGEVNNPAVARGIDYLIAEQNAEGLWDETRFTATGFPRVFYLR
YHGYRKFFPLWALARYRNLKRDNTTRVTVGL

Enzyme Sequences

>seq_ID 112
MSAPSHVGNTLEHAAELATRKAMAYLTCLQERDGHWCAELTADTTLESDYILFQLWLYPPQDG
KWEPETRPLIRKAVNSILERQLPDGGFNICVGGPSEVSASVKAYVAMKLAGLPPEDDRMARLR
ERILALGGIQAANSYVKVNLSLFDLYPREFSPSIPPEVALLPFDLLYQMSAWTRAMSLGIVHAAN
PRRPAPAGFNLQELWLPGVSPEFRRDPSFFTWHNTFLTVDKALKLWERYGSKAVRRRAVEKA
KTWMIERLHHSDGLGAIYPPMMYSVMALDVLGYAKDDPLRVEALRHFNNLMVDDGDRFFFQP
CFSPVWDTAIGAYALVQADPSHEAIAPAADWLIAKEVRRKGDWSVKRPNTEPSGWAFEYSNE
YYPDIDDTAMVMLALGETRASNTEAQAAACKRGLAWLLAMQSSDGGWAAFDADNNWEFLSQ
VPFADHNAMLDPTCADITGRVLEALASQGLDRNHKAVRRGAEWLIRHQENDGSWYGRWGVA
YIYGTCFALRGLAASGENDREAHILRAGEWLRSIQNADGGWGESCKSYDNRIFTGGPSTPSQT
AWAILGLIAGGDANSLSVQHGIEYLLETQRSDGSWDEQFATGTGFPRVFYLNYHMYKDYFPLL
ALASFVKARAGSNG >seq_ID 83
MNDLTEMATLSAGTVPAGLDAAVASATDALLAAQNADGHWVYELEADSTIPAEYVLLVHYLGE
TPNLELEQKIGRYLRRVQQADGGWPLFTDGAPNISASVKAYFALKVIGDDENAEHMQRARRAI
HAMGGAEMSNVFTRIQLALYGAIPWRAVPMMPVEIMLLPQWFPFHLSKVSYWARTVIVPLLVL
NAKRPIAKNPRGVRIDELFVDPPVNAGLLPRQGHQSPGWFAFFRVVDHVLRAADGLFPSYTRE
RAIRQAVSFVDERLNGEDGLGAIYPAMANAVMMYDVLGYAEDHPNRAIARKSIEKLLVVHEDEA
YCQPCLSPVVVDTSLAAHALLETGDARAEEAVIRGLEWLRPLQILDVRGDWISRRPHVRPGGW
APFQYANAHYPDVDDTAVVAVAMDRVQKLKHNDTFRDSIALAREWVVGMQSSDGGWGAFEPE
NTQYYLNNIPFSDHGALLDPPTADVSGRCLSMLAQLGETPLNSEPARRALDYMLKEQEPDGS
WYGRWGMNYVYGTWTALCALNAAGLTPDDPRVKRGAQWLLSIQNKDGGWGEDGDSYKLNY
RGFEQAPSTASQTAWALLGLMAAGEVNNPAVARGVEYLIAEQKEHGLWDETRFTATGFPRVF
YLRYHGYRKFFPLWALARYRNLKRDNATHVTFGL >seq_ID 175
MLQTEAITTEGLRFRSLAPDDPLLPRVKQALKLSGQHSREEMHSDGHWCGEVKTNATTSAEH
VLLCQALDINLDADREAFISWFRCTQGADGGWSTAPDQAGDISVTVEAYLALKILGLSEDDAAM
RSARDFAIAAGGVARVRIFTRIYLAMFGLFPWAAVPELPPELILLPSRVPVSIYHWSAWARATVV
PLLIISHHRPIYALPGGKATCSDYLDELWCDPRNKMVPYNHDKPTAWRSDPFALIFTLADSILHR
LDGLRSFNPLRRFALRKCVDWILEHQEDMGDIGDIMPPLHGAMLALRLEGYPLHSDPIHRGLEA
IERFAYRDQQGKRIQTTVSAFWDTSLMLVALGDAGMASSPWLTRSLGWLQQHQRLGNYGDW
KVNNPGLKAGGFSFGYFNTWYPDVDDTASAVLAIIRQDERLVCSASVLDALNWLLGMQNTDG
GWGAFDRDNNKLFLNKIPPFSDMEAFCDPSTPDVTGHVLEAFGIFLAVSARQQSPTKADVLTDRI
VSASRRAICYLSDTHVSSGGWYGRWGCNYIYGTSAVLCALAYFGSKSDTLSGVRSVKDAVNQ
A1RWLETVQNQDGGWGETVNSYKDPSRAGSGPSTASQTAWAIMALLPYLPPSTEVIQRGVEYL
LRTQTKTASQGATWHEKAYTGTGFPKYFYMGYSFYCHYFPMMALGRYAYPCPEWHENWRPK
KE >seq_ID 88
MNDLTDMATLSAGAAPAADLDAAVARATDALLAAQNADGHWVYELEADSTIPAEYVLLVHYLG
ETPNLELERKIGRYLRRIQQADGGWPLFTDGAPNVSASVKAYFALKVIGDDENAEHMQRARRAI
HAMGGAEMSNVFTRIQLALYGAIPWRAVPMMPVEIMLLPQWFPFHLSKVSYWARTVIVPLLVL
NAKRPLAKNPRGVRIDELFIDPPVNAGLLPRQGHQSAGWFAFFRVNDHVLRAVDGLFPKYTRE
RAIRQAVSFVDERLNGEDGLGAIYPAMANAVMMYDVLGYAEDHPNRAIARKSIEKLLVVHDDEA
YCQPCLSPVVVDTSLAAHALLETGDPRAEDAALRGLEWLRPLQILDVRGDWISRRPNVRPGGW
APFQYANAHYPDVDDTAVVAMAMDRAQKLRQSDTYRESIARAREWVVGMQSSDGGWGAFEP
ENTQYYLNNIPFSDHGALLDPPTADVSGRCLSMLSQLGESALTSEPARRALDYMLKEQEPDGS
WYGRWGMNYVYGTWTALCALNAAGLGPDDPRVKRAAQWLLSIQNKDGGWGEDGDSYKLNY
RGYEQAPSTASQTAWALLGLMAAGEVNNPAVARGIDYLLAEQKEHGLWDEVRFTATGFPRVF
YLRYHGYRKFFPLWALARYRNLKRANATRVTVGM >seq_ID 92
MNDMTEMHTLDATAAPAGLDAAVARATDALLAAQQADGHWVYELEADSTIPAEYVLLVHYLGE
APNVELEQKIARYLRRIQQPDGGWPLFTDGAPNISASVKAYFALKVIGDDENAEHMQRARRAIH
AMGGAEMSNVFTRIQLALYGVVPWYAVPMMPVEIMLLPQWFPFHLSKVSYWARTVIVPLLVLN
AKRPVAKNPRGVRIDELFKGAPVSTGLLPKQPHQSAGWFAFFRAVDGVLRLVDGLFPRYTRER
AIRQAVAFVDERLNGEDGLGAIYPAMANAVMMYAALGYPEDHPNRAIARRSIEKLLVVGEQEAY
CQPCLSPVVVDTSLAAHALLETGDARAREAAVRGLDWLVPRQILDVRGDWISRRPHVRPGGWA
FQYANAHYPDVDDTAVVAMAMDRVAKLDRTDAYRESIARAREWVVGMQSSDGGWGAFEPEN
TQYYLNNIPFSDHGALLDPPTADVSGRCLSMLAQFGETSASSEPARRALDYMLKEQEPDGSW
YGRWGMNYIYGTWTALCSLNAAGLGHDDPRVKRAAQWLLSIQNADGGWGEDGDSYKLDYR
GYERAPSTSSQTAWALLGLMAAGEVDNPAVARGVDYLLGTQREHGLWDETRFTATGFPRVFY
LRYHGYRKFFPLWALARYRNLKRANAMRVTVGM >seq_ID 206
MTRKTIPASELDAAIVRARDALLDRQHPDGHWCFELECDATITAEYILMMHFVDEIDTALQARM
AKYLRAVQRLDGHGAWDLYFGGDLDISCSVKAYFALKAAGDPPDAPHMVRAREAILARGGAA
KSNVFTRILLATFGE1PWRGTPFMPVEFVLFPRWAPIHMDKVAYWARTTMVPLLVLCSIRAAAK
NPLGVHVQELFVTPPELEREYFPRKRGLQQAFLVADRVVRHLEPLIPRALRRRAIQRAVEWSEA
RMNGEDGFGGIFPPMVYSYEMMVLLDYPEDHPLRVECKAALKKLVVHRDDGSSYCQPCLSPV
WDTAWSVMALEQAPSDARTETAIARAYDWLTDRQVLDLRGDWENNAAPSTPPGGWAFQYEN
PYYPDIDDSAVVLAMLHARGKRTGQPGRYEMPVARCLDWIIGLQSRNGGFGAFDANCRDRFL
NAIPFADHGALLDPPTEDVSGRVLLALGITERPQDATARERCIQYLRDTQQPDGSVWVGRWGT
NYIYGTWSVLAGLGLAGVDRKLPMVRNGLQWLRGKQNADGGWGETNDSYARPELAGKHED

| Enzyme Sequences |
|---|

GSMAEQTAWAMLGQMAVGEGDADSVHRGAAYLLDAQNEDGFWMHPYHNAPGFPRIFHLKY
HGYTAYFPLWALGRYRRLAAARASAMQTAKAESAESMTAH

>seq_ID 96
MNDLSMTQTLGEVLPQTLIDDHAPVAAALATGAAPVDALDAAVTRATEAILAVQKDDGHWVYE
LEADATIPAEYVLLVHFLGETPNLELEQKIARYLRRIQLPNGGWPLFTDGAMDVSASVKAYFALK
MIGDPEDAAHMVRARECILANGGAEAANVFTRILLALFGVVTWYAVPMMPVEIMLLPKWFPFHL
SKVSYWARTVIVPLLVLNAKRPVARNPRGVRIDELFRGAPVTTGLLPRSGHQSKSWFAFFRAV
DGVLRVTDGLFPKASRERAIKAAVSFVDERLNGVDGLGAIFPAMANSVMMYDVLGYPADHPNR
AIARESIEKLLVVHEDEAYCQPCLSPVVVDTSLAAHALLETGDARAEEAAERGLAWLRPLQILDV
RGDWISRRPDVRPGGWAFQYNNAHYPDVDDTAVVAMAMHRSAAVTNSNVDANAIARAREWV
VGMQSSDGGWGAFEPENTQYYLNNIPFSDHGALLDPPTADVSGRCLSMLAQLGEMPATSEPA
RRAYDYLLKEQEDDGSWYGRWGMNYIYGTWTALCALNAAGISLEDARIKRAAQWLVSIQNAD
GGWGEDGTSYKLDYRGYEKAPSIPSQTAWALLGLMAAGYVDHPAVARGIDYLQREQRDHGL
WDEERFSATGFPRVFYLRYHGYRKYFPLWALARYRNLKRTGEKRVTVGM >seq_ID 104
MNDMTEMHTLDATAAPAAPTVATGLDAAVARATDALLAAQNADGHWVYELEADSTIPAEYVLL
VHYLGEAPNVELERKIARYLRRIQLPDGGWPLFTDGAPNISASVKAYFALKVIGDDENAEHMQR
ARRAIHAMGGAEMSNVFTRIQLALYGVVPWYAVPMMPVEIMLLPQWFPFHLSKVSYWARTVIV
PLLVLNAKRPVAKNPRGVRIDELFKSAPVNTGLLPKQPHQSAGWFAFFRAVDGVLRLTDGLFP
RYTRERAIRQAVAFVDERLNGEDGLGAIYPAMANAVMMYAALGYPEDHPNRAIARQSIEKLLVV
GEDEAYCQPCLSPVVVDTSLAAHALLETGDERAREAAVRGLDWLVPRQILDVRGDWISRRPHV
RPGGWAFQYANAHYPDVDDTAVVAMAMDRVAKLDRTDAYRESIARAREWVVGMQSSDGGW
GAFEPENTQYYLNNIPFSDHGALLDPPTADVSGRCLSMLAQFGETSASSEPARRALDYMLKEQ
EPDGSWYGRWGMNYIYGTWTALCSLNAAGLGHDDPRVKRAAQWLLSIQNPDGGWGEDGDS
YKLDYRGYERAPSTSSQTAWALLGLMAAGEVDHPAVARGIDHLLGTQREHGLWDETRFTATG
FPRVFYLRYHGYRKFFPLWALARYRNLKRANATRVTVGM >seq_ID 27
MAHQETMASETSISLHTLACDATKLAGTYALRQVREDGHWYGEMKSNATITAEYVFLAQALGF
SIEEDRDDLIKYFLSEQNTDGSWSLAYDFPGDVSVTAEAYFALCLLGLDRSHPAMASAREFTLS
KGGIAKVRVFTRMFFACFGLFPWSAVPELPAELILLPAAAPMSIYQLASWARATVVPMLVIRHH
RPIYALPNGRSSSNEYLDELWVDPTDKMVPYSPSLWSLWNDDLTAFGFTLADNILKALGGLRW
FPSRKIALRHCVAWILERQEPEGDIGGIFPPLHAALFALALEGYGLESSPVRRGIDALQNTYAWR
DSTGLRIQGCISPILDTILMTIGLIDSSLPAESPLVARSSRYLKAHQQLGNEGDWRVYNGNVPSG
GFNFEYFNSWYPDIDDTAAAILAMVKQDPNLLDLGPILSAVQWILGLQNDDGGWAAFDRENNY
LFLNKIPFSDMDSFCDPSTADVTGRVIECFGLNGKNPIPRFFIDDMSSATERAIDFLSTEQEADG
SWYGRWGSNYIYGTSAVLCGLVYHLEGWDDTYPVMEKRHKVDTHAALDWLKRHQNPDGGW
GERLESYYEPRLAGNGPSTASQTAWALMGLLAYLAPTDESITRGIQYLSRTQIKEGELAGSWKE
DHYTGTGFPNHFYLCYTLYSQYFPMMALGRYTSLSGYRPLENLESTVEDHKGNSSDC >seq_ID 28
MMTLREEGHKEGITPGKEQLTSDIEHSLKLATEYALSSIRSDGHWCGELRSNVTITAEYIFLRHA
LGLDLRTDNAAYCRYILSQQNCDGSWGLAPEYPGDVSTTTEAYLALKLLGTSPDMPAMQQAR
AFVRKAGGAEKVRVFTRIFLATFGLFPWDAVPQLPVELILLPSSCPINMYTLASWARGTIAPLLII
CHHQPVYALPEDYLDELWLDPTDKNVPYGSSLRDLLSRGDITGLAFSVVDNLLYYLNGLRSVPL
LRSYARRKCIQWILERQEPTGDWAGIFPPMHASIYAFVLEGYELNDPPVRLGIQALENFAWEDE
KGKRIQACVSPVVVDTALMSIGLCDAMSPDKQILQQAITWIRNRQLLKPCGDWRIYRSKLAPGGF
SFEYENSHYPDVDDTAAIILAQLKQDPQSVASDSVIAAATWILGMQNPDGGWAAFDVENDKLFL
NKIPFSDMDSLCDTSCADITGRILEAFGLMMKRELKRPVLSPMLRHACIRGITYLASTQESNGA
WFCRWGCNYIYGTCHALGLVAPALQWLKSKQNDDGGWGEPLLSYRTPGTQLQQQSTPSQTA
WALMGLLAHLPLTDPAIERGIRWLVCSQQPEKGNGASWPEAVYTGTGFPNHFYLGYDYYRHY
FPMMALGRYLQASQAQA >seq_ID 94
MNDLTDMATLSAGTVPAELDAAVARATDALLAAQNADGHWVYELEADSTIPAEYVLLVHYLGE
TPNLELEQKIGRYLRRIQQADGGWPLFTDGAPNISASVKAYFALKVIGDDENAEHMQRARRAIH
AMGGAEMSNVFTRIQLALYGAIPWRAVPMMPVEIMLLPQWFPFHLSKVSYWARTVIVPLLVLNA
KRPLAKNPRGVRIDELFIDPPVNAGLLPRQGHQSAGWFAFFRAVDHVLRAVDGLFPAYTRERAI
RQAVAFVDERLNGEDGLGAIYPAMANAVMMYDVLGYAEDHPNRAIARKSIEKLLVVHEDEAYC
QPCLSPVVVDTSLAAHALLETRDPRAEQAAVRGLDWLRPLQILDVRGDWISRRPHVRPGGWAF
QYANPHYPDVDDTAVVAMAMDRAQKLNQSDTYRESIARAREWVVGMQSSDGGWGAFEPEN
TQYYLNNIPFSDHGALLDPPTADVSGRCLSMLSQLGETALNSDAARRALDYMLKEQEPDGSW
YGRWGMNYVYGTWTALCALNAAGLGPDDARVKRAAQWLLSIQNKDGGWGEDGDSYKLNYR
GYEPAPSTASQTAWALLGLMAAGEVNNPAVKRGIDYLIAEQKEHGLWDEARFTATGFPRVFYL
RYHGYRKFFPLWALARYRNLKRDNTTRVTVGI >seq_ID 30
MERSSLLVPASIDSHSRESETTGLDQAIVRARAALLGRQGADGHWCFELESDCTITAEYILMMH
FTDEIDEDLQERMARYLRATQVQETHGGWPQYVGGAIDLSCTVKAYYALKAAGDSPEAPHMR
RAREAVLALGGAAKSNVFTRILLAMFEQVPWRAVPYLPVEIMLLPRWAPIHIEKMSYWARTTLV
PLTILCSLKARAANPKRVDIRELFVTAPEQERHYFLRGGLLNRIFLGLDKFARTLDRWMPKSLRQ
HAIRKAEAWFLPRMNGEDGLGAIFPPMVNCYEAMILLGYPKDHPARKTCLRSIQKLIVHRDDGS
AYCQPCVSPVVVDTAWSAMALIHSGDDTATQTAIARAGDWLVQRQELDCRGDWEAQAPQAAP
GGWAFQYANGYYPDIDDTALVAALLHISDRRRGQPGQHAFNIDRAVDWMLALQSRNGGFAAF
DADNTHYYLNAIPFADHGALLDPPTEDVSGRVAACLGILKRDQDRDGLRRCIDYLRTTQQPDG

Enzyme Sequences

SWWGRWGSNYIYGTWSALSGLALAGEDLRQPYLRKSVDWLRTRQHPDGGWGETNDSYIDP
HLAGTNAGISTPHSTAWAVLAQLAMGEVESDSVRRGIAFLLACQQTDGLWSHPSHNAPGFPR
VYYLKYHGYAAYFPLYALARYRHLLNRSREQR

>seq_ID 98
MNDMTEMHTLDATAAPAGLDAAVARATDALLAAQQADGHWVYELEADSTIPAEYVLLVHYLGE
APNVELEQKIARYLRRIQQPDGGWPLFTDGAPNISASVKAYFALKVIGDDENAEHMQRARRAIH
AMGGAEMSNVFTRIQLALYGVVPWYAVPMMPVEIMLLPQWFPFHLSKVSYWARTVIVPLLVLN
AKRPVAKNPRGVRIDELFKGAPVSTGLLPKQPHQSAGWFAFFRAVDGVLRLVDGLFPRYTRER
AIRQAVAFVDERLNGEDGLGAIYPAMANAVMMYAALGYPEDHPNRAIARRSIEKLLVVGEQEAY
CQPCLSPVVVDTSLAAHALLETGDARAREAAVRGLDWLVPRQILDVRGDWISRRPHVRPGGWA
FQYANAHYPDVDDTAVVAMAMDRVAKLDRTDAYRESIARAREWVVGMQSSDGGWGAFEPEN
TQYYLNNIPFSDHGALLDPPTADVSGRCLSMLAQFGETSASSEPARRALDYMLKEQEPDGSW
YGRWGMNYIYGTWTALCSLNAAGLGHDDPRVKRAAQWLLSIQNADGGWGEDGDSYKLDYR
GYERAPSTSSQTAWALLGLMAAGAVDNPAVARGVDYLLGTQREHSLWDETRFTATGFPRVFY
LRYHGYRKFFPLWALARYRNLKRANATRVTVGM >seq_ID 187
MTSDTASAAALDPRRLATSITRASRALHDVQQPDSHWVFELEADVTIPAEYVMMRHYFAEPVD
AEIEAKIAKYLRRMQNDNGGWSLFYGHEFDMSASVKAYYALKMIGDSPDAPHMKKAREAMLA
RGGASRANVFTRIMLALFGQVSWKAVPMMPVEIMLLPRWFPPFHLTKVSYWARTVIVPLLVLMT
LKPRAKNPRGIGVRELFLEDPQTVGPTPKAAHQSQLWFTSFDIIDRVLRITDPFFPKGMRKRAIA
KAEAFVTERLNGVDGLGAIFPAMVNSIMMYDVLGYPPNDPNRALARESVERLLVIKDDEAYCQP
CVSPVVVDTALAAHSMLESGEAADIEAAKAGLDWLLPRQVLDLKGDWADKRPDVRPGGWAFQ
YNNAHYPDLDDTAVVVMAMDRVRRLDGTTKYDEAIARATEWILGLQXSENGGWAAFDADNLEY
YLNNIPFADHGALLDPPTEDVTARCLSMLAQLGDTLETSEPMRRGVEYLRKTQLPDGSWFGR
WGINYVYGTWSVLCALNAVGVPHDDPMIAKAADWLESIQNEDGGWGEDGNSYKLNYKGYER
AATTASQTAWATLALMAAGRVDRDATQRGIDNLVQSQEADGFWGEPYYTGGGFPRVFYLRY
HGYSKFFPLWAMARYRNLRSSNSRFVGAGM >seq_ID 207
MNKHSGNRTAIDPAALEMSIASATEALLAYRHADGHWAFELEADSTIPSEYILLRHYLAEPIDVVL
EAKIGNYLRRTQGAHGGWPLVHDGPFDMSASVKSYFALKMICDSVDAAHMVKAREAIRARGG
AANSNVLTRFLLALYGVVSWRAVPVLPIEIVLLPIWSPFHLYKISYWARTTIVPLMVLAVLKPRAK
NPKGVGIEEELFLQDTKSVGMNPKAPHQSWGWFLLFRGIDCILRVIEPHLPKKLRERAIASALAFT
EERLNGEDGMGAIYPSMANIVMMYDALGKDDHFPPRAIARRAIDKLLVIGEEEAYCQPCLSPVW
DTALTCHALQEVGGANAVAKAKQGLDWLKPRQVLDVKGDWAVKAPNIRPGGWPFQYNNAHY
PDLDDTAVVVMAMDRAQRHAGSKEYATAIARGREWIEGMQSRDGGWAAFDVNNLEYYLNNL
PFADHGALLDPPTEDVTARCVSMLAQVGEFTQRSKAVAEGIAYLRRTQHAEGSWYGRWGLNY
IYGTWSVLCALNAAGIDHQDPMIRKAVEWLVSIQSWDGGWGEDAISYRLDYSGYEQAPSTSSQ
TAWALLGLMAAGEVEHPAVARGVNYLKNAQTENGLWDEQRYTATGFPRVFYLRYHGYSKFFP
LWALARYRNLRSTNV >seq_ID 29
MTTGHRQFDDGLSERERLIHEAGLTLQRSMDYAYNVVRSDGHWCGEMSSNVTITAEYIFLRQA
LGLDLKTDGAAYCRHILSQQNSDGSWGLAPEYPGDVSTTTEAYLALKMLGLSTDAPAMQQAK
AFVLNAGGVAKVRVFTRIFLATFGLFPWKAVPQLPVELILLPSACPINIYKFASWARGTIAPLLIIC
HHQPVYALPNGVFAENEYLDELWQDSTNKSEPYSPSIWELLSQGDITGLTFSLLDKLLYQLNGL
RSIPLLRSYALKQCMKWILERQEPTGDWAGIFPPMHASVYAFVLEGYKLEDPPVRLGIEALENF
AWEDAKGKRVQPCVSPVWDTTLMSIALSDAATPNHQIVDRAIQWIRDRQLLEPRGDWRVYRP
RLAPGGFSFEYTNSHYPDIDDSAAIILAQVKHDPISANSSSVIAAATWILGMQNPDGGWAAFDV
ENDKLFLNKIPFSDMDSLCDTSCADITGRILEAFGLLIRRVPDKDSSQLFQLLPAIRAACRRGIRY
LASTQEANGAWFGRWGCNYIYGTSHALCGLAYFLQEDQQVPAMVQPALQWLKSQQNDDGG
WGESLLSYQSPERKEQRSTASQTAWALMGLLAHLPHTDIVIERGIRWLVSSQRPVETLGSTWP
EPVYTGTGFPNHFYLGYDYYRHYFPMMALGRYLRGVQG >seq_ID 25
MLQTEAITTEGLRVRSLSPDDPLLPRIKQAIKLSGQHSRGEMHSDGHWCGEVKTNATTSAEHV
LLCQALGINLDADREAFISWFRCTQGADGGWSTAPDQAGDISVTVEAYLALKILGLSEDDAAMR
RARDFAIAAGGVAKVRIFTRIYLALFGLFPWAAVPELPPELILLPSRVPVSIYHWSAWARATVVPL
LIISHHRPIYALPGGGKGTSSDYLDELWCDPQNKMIPYNHDEPTAWRSDPFASIFTLADSILHRL
DGLRSFNPFRRFALQKCVDWILEHQEDMGDIGDIMPPLHGAMLALRLEGYPLHSGPIHRGLEAI
ERFAYRDKQGKRIQTTVSAFWDTSLMLIALGDAGMASKPWLTRSLGWLQQHQRLGNYGDWK
VNNHGLKAGGFSFGYFNTWYPDVDDTASAVLAMIRQDERLVHSASVLDALNWLLGMQNTDG
GWGAFDRDNDKHFLNKIPFSDMDALCDPSTPDVTGHVLEAFGLFLALSKADALADRVVAASRR
AIRYLSDTHVLSRGWYGRWGCNYIYGTSAVLCALAYFGSENDALSGVRVMKDAINQAIRWLET
VQNPDGGWGETVDSYKDPSRAGSGPSTASQTAWAIMALLPYLPPSTEVIQRGMEYLLRTQTK
TASQGATWHEKAYTATGFPKYFYMGYSLYAHYFPMMALGRYAYPCPAWHENWRLKRD >seq_ID 97
MNDLSQAQPLDAILPDFADAAPSAPAPAVTGEAPTASLDAAITRATEAILAAQKPDGHWVYELE
ADATIPAEYVLLVHYLGETPNLELEQKIARYLRRIQLPDGGWPLFTDGALDISASVKAYFALKMIC
DPADAEHMVRAREAILAHGGAETVNVFTRILLALFGVVSWRAVPMMPVEIMLLPMWFPFHLSK
VSYWARTVIVPLLVLNAKRPVARNPRRVRIDELFRGAPVNTGPRDRAPHQHAGWFRRFSGVD
VLLRAVDGLFPKSTREAVRQAVAFVDERLNGEDGLGAIFPAMANSVMMYDVLGYPADHPNR
AIARQSIDKLLVIKDDEAYCQPCLSPVVVDTSLAAHALLETGEAHAEQAAERGLAWLRPLQILDVR
GDWISRRPNVRPGGWAFQYNNAHYPDVDDTAVVAMAMQRSATVTQSDVDRDAIARAREWVV

| Enzyme Sequences |
|---|
| GMQSSDGGWGAFEPENTQYYLNNIPFSDHGALLDPPTADVSGRCLSMLAQLGELPQNSEPAQ<br>RAFDYMLKEQESDGSWYGRWGLNYIYGTWTALCSLNAAGLPHDDPRMKRAAQWLLSIQNED<br>GGWGEGGESYKLDYHGYERAPSTASQTAWALMGLMAAGEVNHEAVRGVAYLEREQREHG<br>LWDETRFTATGFPRVFYLRYHGYRKFFPLWALARFRHLKRNGLTRVAVGM<br><br>>seq_ID 176<br>MNSVNATVAPIDDAALGGSIGAATRGLLDLKQPDGHFVFELEADATIPSEYVLLRHYLGEPVDA<br>ALEAKIAVYLRRIQGAHGGWPLVHDGPFDMSASVKAYFALKMIGDSIDAPHMARAREAILSRGG<br>AANVNVFTRFLLSLFEVLTWRSAPVLPIEIMLLPMWSPFHINKISYWARTTMVPLMVLAALKPRA<br>RNPRGIGIRELFLQDPATVGTPKRAPHQSPAWFTLFNSLDWILRKIEPLFPKRLRARAIEKAIAFV<br>EERLNGEDGLGAIFPPMVNTVMMYDALGFPPEHPPRAVARRGIDKLLVIGKDEAYCQPCVSPI<br>WDTALTCHALLEAGGPEALSGAGKSLDWLLPKQELVLKGDWAVKRPDVRPGGWAFQYANAH<br>YPDLDDTAVVVMAMDRVRRNDRSDKYNEAIARGREWIEGMQSRDGGFAAFDADNLEYYLNNI<br>PFSDHAALLDPPTEDVTARCVSMLAQLGETVRSSPSMAAGVDYLRRTQLKEGSWYGRWGLN<br>YIYGTWSVVCALNAAGVDHQDPAMRKAVDWLVSIQNADGGWGEDAVSYRLDYKGFEGAPTT<br>ASQTAWALLALMAAGEVENPAVARGMKYLIDTQTKKGLWDEQRFTATGFPRVFYLRYHGYSR<br>FFPLWALARYRNLRSTNSKVVGVGM<br><br>>seq_ID 210<br>MDSGTFNPGGERGNTLDASIDAARAALLGYRRDDGHWVFELEADCTIPAEYVLLRHYLGEPID<br>AALEAKIAVYLRRTQGAHGGWPLVYDGEFDMSATVKGYFALKMIGDSIDAPHMAKAREAILSR<br>GGAVHANVFTRFLLAMFGILTWRAVPVLPVEIMLLPMWSPFHLNKISYWARTTIVPLMVLAALKP<br>RAVNRLGVGLDELFLQDPKSIGMPARGPHQNRGLFALFGAIDAVLRVIEPLIPKKLRKHAIDRAV<br>APFVEERLNGEDGLGAIYPPMANTVMMYKVLGYPEDHPPRAITRRGIDLLLVIGEEEAYCQPCVS<br>PIWDTSLTCHALLEAGGAEAAQPVREGLDWLLPKQVLDLKGDWAVKAPNVRPGGWAFQYNN<br>AHYPDLDDTAVVVMALDRARRDQPSAAYDNAIARGREWIEGMQSDDGGWAAFDVNNTEYYL<br>NNIPFSDHGAMLDPPTEDVTARCVSMLAQLGETEQTSKAVARGVAYLRKTQLPDGSWYGRW<br>GMNYIYGTWAVLCALNAAGVDHQDPAIRKAVAWLASIQNADGGWGEDGVSYRLDYRGYETAP<br>STASQTAWALLSIMAAGEVDHPAVARGIEYLKGTOTEKGLWDEQRHTATGFPRVFYLRYHGYS<br>KFFPLWGLARYRNLRATNSKVVGVGM<br><br>>seq_ID 23<br>MTTGHRQFDDGLSERERLIHEAGLTLQRSMDYAYNVVRSDGHWCGEMSSNVTITAEYIFLRQA<br>LGLDLKTDGAAYCRHILSQQNSDGSWGLAPEYPGDVSTTTEAYLALKMLGLSTDAPAMQQAK<br>AFVLNAGGVAKVRVFTRIFLATFGLFPWKAVPQLPVELILLPSACPINIYKFASWARGTIAPLLIIC<br>HHQPVYALPNGVFAENEYLDELWQDPTNKSEPYSPSIWELLSQGDITGLTFSLLDKLLYQLNGL<br>RSIPLLRSYALKQCMKWILERQEPTGDWAGIFPPMHASVYAFVLEGYKLEDPPVRLGIEALENF<br>AWEDAKGKRVQPCVSPVWDTTLMSIALSDAATPNHQIVDRAIQWIRDRQLLEPRGDWRVYRP<br>RLAPGGFSFEYTNSHYPDIDDSAAIILAQVKHDPISANSSSVIAAATWILGMQNPDGGWAAFDV<br>ENDKLFLNKIPFSDMDSLCDTSCADITGRILEAFGLLIRRVPDKDSSQLFQLLPAIRAACRRGIRY<br>LASTQEANGAWFGRWGCNYIYGTSHALCGLAYFLQEDQQVPAMVQPALQWLKSQQNDDGG<br>WGESLLSYQSPERKEQRSTASQTAWALMGLLAHLPHTDIVIERGIRWLVSSQRPVETLGSTWP<br>EPVYTGTGFPNHFYLGYDYYRHYFPMMALGRYLRGVQG<br><br>>seq_ID 91<br>MNDLSQAHVLGAAMPETAGEAQNAQAAANSAAAAAEASAVLAPSLDAAITRATDAILAAQKPD<br>GHWVYELEADATIPAEYVLLVHYLGETPNVELEQKIARYLRRIQLPNGGWPLFTDGAIDISASVK<br>AYFALKMIGDPVDAEHMVRAREAILAHGGAETVNVFTRILLALFGVVSWRAVPMMPVEITLLPM<br>WFPFHLSKVSYWARTVIVPLLVLNAKRPLARNPRRVRIDELFRGAPVNTGMPARAPHQHVGWF<br>GFFRVVDTVLRAVDGLFPKATRERAVREAVAFVDQRLNGEDGLGAIFPAMANSVMMYDVLGY<br>PADHPNRAIARRSIEKLLVIKDDEAYCQPCLSPVWDTSLAAHALLETGDARAEQAAERGLAWLR<br>PLQILDVRGDWISRRPNVRPGGWAFQYNNAYYPDVDDTAVVAMAMHRSEALTHSGADREAIA<br>RAREWVVGMQSSDGGWGAFEPENTQYYLNNIPFSDHGALLDPPTADVSGRCLSMLAQLGEF<br>PQNSEPAQRALDYMLKEQEADGSWYGRWGLNYIYGTWTALCSLNAAGLPHDDPRIRRAAQW<br>LLSIQNEDGGWGEGGESYKLDYRGYERAPSTASQTAWALMGLMAAGEVDHEAVARGIEYLQR<br>EQREHGLWDETRFTATGFPRVFYLRYHGYRKFFPLWALARYRHLKRNGLTRVAVGM<br><br>>seq_ID 213<br>MDSGSYTTGVERNALEASIDAARSALLNYRRDDGHWVFELEADCTIPAEYVLLRHYLGEPVDA<br>ELEAKIAVYLRRIQGAHGGWPLVHDGDFDMSASVKGYFALKMIGDSIDAPHMVRAREAIRSRG<br>GAIHSNVFTRFLLTLYGVTTWRAVPVLPVEIMLLPSWSPFTLTKISYWARTTMVPLLVLCALKPQ<br>AKNPKGVGIDELFLQDPKTIGMPVKAPHQNWALFKLFGSIDAVLRVIEPVMPKGIRKRAIDKALA<br>FIEERLNGEDGMGAIFPPMANAVMMYEALGYPEDYPPRASQRRGIDLLLVDRGDEAYCQPCVS<br>PVWDTALASHAVLEADGHEGAKSVRPALDWLLPRQVLDVKGDWAVKAPNVRPGGWAFQYNN<br>AHYPDLDDTAVVVMALDRARKDQPNPAYDAAIARAREWIEGMQSDDGGWGAFDINNTEYYLN<br>NIPFSDHGAMLDPPTEDVTARCVSMLAQLGETMDSSPALARAVGYLRDTQLAEGSWYGRWG<br>MNYIYGTWSVLCALNAAGVPHADPMIRKAVAWLESVQNRDGGWGEDAVSYRLDYRGYESAP<br>STASQTAWALLALMAAGEVDHPAVARGIEYLKSTOTEKGLWDEQRYTATGFPRVFYLRYHGY<br>SKFFPLWALARYRNLQATNSKVVGVGM<br><br>>seq_ID 196<br>MSMTSREDHDASSLISQVEHALKLSNDYALGLVHPDGHWYGEMNTNVTVTAEYVFLRQALRL<br>DLKTDIAAYCHYLLSQQNSDGSWGLAPEYPGDVSTSTEAYLALKILGTSPHTPAMRNARAFVLK<br>AGGIARVRIFTRIFLATFGLFPWSAVPELPVELMLLPSICPINIYKFASWARGTIAPLLIICHHQPVY<br>SLPNGKSTDNDYLDELWVDCTNKSVPYGLPLWDLMSQGEFAGLAFGVLDKVLYQLNGLRSIPL<br>IRAYARKQCIQWILERQEKTGDWAGIFPPMHANMYAFTLEGYKLDDDPVRLGFQALERFAWED<br>EKGKRIQACVSPVWDTALMTIGLCDAMSPNKQTIDHALAWIRARQLLEPRGDWRVYRPQLAPG |

| Enzyme Sequences |
|---|
| GFSFEYENSWYPDVDDTAAIILAQVKHDNGSIGSNSVIAAATWILGMQNPDGGWAAFDVENDK<br>LFLNKIPFSDMDSLCDTSCADITGRILEAYGLMMMKYFSAKSDADPLLHTLRAACMRGMHYLAS<br>TQEPNGSWYGRWGCNYIYGTSHVLCGLAYFVEKRLVCVMVKSALQWLKSRQNDDGGWGES<br>LLSYQSPDREQQASTPSQTAWALMGLLSHLPVTDDAIERGIRYLVSSQRPEKGIGSSWPQAEY<br>TGTGFPNHFYLGYDYYRHYFPMMALGRYLQGSRGLN<br><br>>seq_ID 99<br>MNDLSQTQPLAAVLPEAADAPAVADASATAAPEPVQAASPSALDASITRATDTILAAQKPDGH<br>WVYELEADATIPAEYVLLVHYLGETPNLELEQKIARYLRRIQLPNGGWPLFTDGALDISASVKAY<br>FALKMICDPVDAEHMVRARDAILAHGGAERANVFTRILLALFGVVSWRAVPMMPVEIMLLPVVVF<br>PPHLSKVSYWARTVIVPLLVLNAKRPLARNPRKVRIDELFRAAPVNTGMNERAPHQHAGWFGF<br>FRCVDTVLRAVDGLLPKATRERAIRAAVAFVDERLNGEDGLGAIFPAMANSVMMYDVLGYPAD<br>HPHRAIARKSLDKLLVIKDDEAYCQPCLSPVWDTSLAAHALLETGEARAEQAAERGLAWLRPL<br>QILDVRGDWISRRPNVRPGGWAFQYNNAHYPDVDDTAVVAMAMHRSAALTQSDVDREAIARA<br>REWVVGMQSSDGGWGAFEPENTQYYLNNIPFSDHGALLDPPTADVSGRCLSMFAQIGELPQS<br>SEPARRAFDYMLQEQEPDGSWYGRWGLNYIYGTWTALSSLNAAGMPHDDPRMRRAAQWLV<br>SIQNEDGGWGEGGESYKLDYHGYERAPSTASQTAWALLGLMAAGEVNHEAVARGIDYLQRE<br>QREHGLWDETRFSATGFPRVFYLRYHGYRKFFPLWALARFRHLKRHGLTRVTVGM<br><br>>seq_ID 85<br>MIRRMNKSAPSPWSALDAAIARGRDALVRLQQPDGSWCFELESDATITAEYILMMHFMDRIDD<br>VRQERMARYLRANQRLDTHGAWDLYVDGAPDVSCSVKAYFALKAAGDSEHAPHMIRARDAIL<br>KLGGAARSNVFTRILLATFGQVPWRAAPFMPIEFVLFPKWVPISMYKVAYWARTTMVPLLVLCS<br>LKARARNPRNVSIRELFVTPPEQERHYFLPARGMRRLFLALDRTVRPIEPLLPKRLRQRAIRHAE<br>AWCAERMNGEDGLGGIFPPIVYSYQMMQVLGYPDDHPLRRDCENALEKLLVTRPDGSMYCQ<br>PCLSPVVVDTAWSTMALEQARGVAAPETGDTASGALRELDERIARAYDWLATRQVNDLRGDWI<br>ENAPADVEPGGWAFQYANPYYPDIDDTALVTAMLDRRGRTHRGADGTHPYASRVARALDWM<br>RGLQSRNGGFAAFDADCDRMYLNAIPFADHGALLDPPTEDVSGRVLLCFGVTKRAADRASLAH<br>AIDYVKRTQQPDGSWWGRWGTNYLYGTWSVLAGLALAGEDKSQPYITRALDWLRARQHADG<br>GWGETNDSYIDPKLAGTNDGESTSNCTAWALLAQMAFGDCESDSVKRGIAYLQSVQQEDGF<br>VWVHRSHNAPGFPRIFYLKYHGYTAYFPLWALARYRRLAGAKDADATRSPASATPATDNALA<br><br>>seq_ID 93<br>MIRAMNKSALSPWSALDTAIARGRDALARLQQPDGSWCFELESDATITAEYILMMHFMDRIDDA<br>LQERMARYLRAIQRLDTHGAWDLYVDGAPDVSCSVKAYFALKAAGDSEHAPHMIRAREAILKL<br>GGAARSNVFTRILLATFGQVPWRATPFMPIEFVLFPKWVPISMYKVAYWARTTMVPLLVLCSLK<br>ARARNPRNVAIPELFVTPPPDQERHYFPPTRGMRRAFLILDRVVRHVEPLLPKRLRRRAIRHAEA<br>WCAQRMNGEDGLGGIFPPIVYSYQMMDVLGYPEDHPLRRDCENALAKLLVTRPDGSVYCQPC<br>LSPVWDTAWSTMALEQARSVAVPESDESARALDELDARIARAYDWLATRQVNDLRGDWIENA<br>PADTQPGGWAFQYANPYYPDIDDSAVVTAMLDRRGRTHRNADGSHPYAARVARALDWMRAL<br>QSRNGGFAAFDADCDRLYLNAIPFADHGALLDPPTEDVSGRVLLCFGVTRRAEDRASLARAID<br>YVKRTQQPDGSWWGRWGTNYLYGTWSVLAGLTLAGEDPSQPYIARALEWLRAHQHADGGW<br>GETNDSYLDPALAGTNGGESTSNCTAWALLAQMAFGDCASDSVKRGIAYLQSVQQDDGFVWV<br>HRSHNAPGFPRIFYLKYHGYTAYFPLWALARYRRLAGAAEARARASSGRAPHAADTALA<br><br>>seq_ID 168<br>MGKVETLHRMSTQDITLDDVERRVSLASKALMRLAGPDGHWCFELEADATIPSEYILYHHFRG<br>SIPSAELEGKIANYLRRTQSAQHDGWSLVHDGPFDMSATVKAYFALKMICDSIEAPHMRRARE<br>AILRRGGAAHANVFTRTLLALYGEVPWSAVPVMPVEMLLPRWFPFHLDKVSYWARTLTVMVPLF<br>VLQAKKPRARNPRGIGIQELFVEPPERVKRWPAGPQESSPWRPVFAAIDKVLQKVEGSFPAGS<br>RARAIDKAVAFVSERLNGEDGLGAIFPAMVNAVLMYEALGYPEDHPLVATARSSVEKLVTVKEH<br>EAYVQPCLSPVVVDTALSAHALMEAGGVEAERHAKRALDWLKPLQVLDIKGDWAASKPNVRPG<br>GWAFQYANPHYPDLDDTAVVVMAMDRAQVRRSPGPDAADYGQSIARAREWVEGLQSRDGG<br>WAAFDADNTYHYLNYIPFSDHGALLDPPTADVTARCVSMLAQLGETRESCPPLDRGVAYLLAD<br>QEADGSWYGRWGMNYIYGTWSVLCALNAAGVDPASEPVRRAVNWLTTIQNPDGGWGEDAA<br>SYKLEYRGYERAPSTASQTAWALLGLMAAGEADSPAVARGINYLTRSQGADGLWTEDRYTAT<br>GFPRVFYLRYHGYAKFFPLWALARYRNLQQSNSRRVAVGM<br><br>>seq_ID 184<br>MKKFGGMARTSLQAQSPGSNNTPSMDEKMLKAGLEAARGALLAQQREDGHWCFPLEADCTI<br>PAEYILMMHFMDEVDLDLEVRIARFIREKQDVAHGGWPLYYGGEFDLSCSVKAYYALKIVGDSP<br>DAPHMVRARAAILKHGGAARANVFTRLLLAMYDQLPWRGVPFVPVEIILFPKWFPFHTSKVAY<br>WSRTVMVPLSILCSLKARAANPRKVAIRELFTVPPGEERNYFPVRTALNRVFLLIERTLSLLEPFI<br>PQGVRRLALRRAESWIVERLNGDSGLGAIFPAMVNAGEALALLGYPYDHPAREQCRKALRLLL<br>VEEGERTWCQPCVSPVWDTVLTCLAFQEDTEVDQKPIRKALDWLVPCQVLDAPADWQEDHP<br>GLPGGGWAFQYANPHYPDLDDTAAVAWALYQADPKAYQESISRAADWLAGMQSSNGGFAAF<br>DSDNTYYYLNElPFADHGALLDPPTSDVSARCAGFLALYGQSRHKQALERSLAYLFNEQEASG<br>AWFGRWGSNYIYGTWSVLEAFRLAGIDAGHPAIRRAVHWLKSVQREDGGWGESNDSYLSPQ<br>QAGQFHTSTSFHTAWALLALMGAGEWRSHEVHRGIAYLLREQDSDGLWHEPWFTAPGFPRV<br>FYLKYYGYTKYFPVWALTRFHALNRKFPG<br><br>>seq_ID 12<br>MMYNNQWYFNQFNDIFCFPEQQKEYFPPTGTNISLNLKKRPDRQLLAHGASDLNGPFHLSQH<br>NAFSAMLLAEVQKVLRLAVGHSLDLQRTDGAWCGEVHSNATFTAQYVFLQQQLGLPLDPTEIE<br>GLSRWLFSQQNEDGSWGLGPGLGGDVSTTTETYLALKILGVSPEDPRMAAARSSIIKAGSLPA<br>TRMFTRVFLASFGLIPWSAVPPLPAELILLPTLFPVNIYNLSSWARATCVPLLLIRHHEPLHSLPN<br>GRHAENDFLDELWTKDIPRDFCYTTPLSRMWRLGDYAGIFFTSADHGLRFLGQYFNSPLRNLS |

Enzyme Sequences

RRKIINWILDHQEQSGEWAGYWPPQHNNIWALSLEGYSLDHPVLRRGIAAVKSFVLHDVTGMR
AQVTVSQVWDTALMSIALSDSAPSTGIISPTQAIDWLMHHEVASHRGDWRVLRPKLATGGFCF
EEFNTLYPDVDDTAAVIMALIKSNPAHLISGCVRRAAQWILGMQNRDGGWGAFDWNNDKFFLN
KIPFSDMDSLCDPSTPDVTGRIIECFGMMMAGRHGYSLDGPLESRLRASSSQLAIAYLLGCQENN
GSWWGRWGVNYLYGTSNVLCGLAYYYDRSGLSKGDGKSNSHIVSAVDRASEWLKARQHSN
GGWGEGPESYDSAQLAGCGQPTASQSAWVTMALLNYLSPTDEVIQRGISYLVRSQVKYGDES
RATWPLERYTATGFPGHLYMEYDYYRHYFPIMALGRYVNKLSESHKLL

>seq_ID 100
MIRRMTTPTPSPWSALDTAIARGRDALVRLQQPDGSWCFELESDATITAEYILMMHFMDKIDDL
RQEKMARYLRANQRLDTHGGWALYVDGDPDVSCSVKAYFALKAAGDSEHAPHMVRARDAILK
LGGAARANVFTRILLATFGQVPWRAAPFMPIEFVLFPKWVPISMYKVAYWARTTMVPLLVLCSL
KARARNPRNISIRELFVTPPDEERQYFPPARGMRKLFLALDRTVRHVEPLMPKGLRQRAIRHAE
AWCAERMNGEDGLGGIFPPIVYCYQMMEVLGYPDDHPLRRDCENALEKLLVTRPDGSMYCQP
CLSPVWDTAWSTMALEQARGVAVAEDGEPGDARRALDERITRAYDWLAERQVNDLRGDWIE
NAPADVQPGGWAFQYANPYYPDIDDTAVVTAMLDRRGRTHANADGTNPYATRVARALDWMR
GLQSRNGGFGAFDADCDRLYLNAIPFADHGALLDPPTEDVSGRVLLCFGVTKRADEHASLARC
DYVKRTQQPDGSVWVGRWGTNYIYGTWSVLAGLALAGEDKSQPYIARAIEWLRARQHADGG
WGETNDSYIDPKLGGTNGGESTSNFTAWALLAQMAFGDCESDSVKRGIAYLQSVQQEDGFW
WHRSHNAPGFPRIFYLKYHGYTAYFPLWALARYRRLAGVANKRVSTADKTADAMA >seq_ID 84
MIRRMNQSAPSSWSALDAAIARGRDALVRLQQPDGSWCFELESDATITAEYILMMHFMDRIDD
VRQEKMARYLRANQRLDTHGAWDLYVDGAPDVSCSVKAYFALKAAGDSEHAPHMIRARDAIL
KLGGAARSNVFTRILLATFGQVPWRAAPFMAVEFVLFPKWVPISMYKVAYWARTTMVPLLVLC
SLKARARNPRNVSIRELFVTPPEQERHYFPPARGMRRLFLALDRTVRPIEPLLPKRLRQRAIRH
AEAWCAERMNGEDGLGGIFPPIVYSYQMMQVLGYPDDHPLRRDCENALEKLLVTRPDGSMYC
QPCLSPVVVDTAWSTMALEQARGVAAPETGDTATGAPRDLDGRIARAYDWLATRQVNDLRGD
WIENAPADVEPGGWAFQYANPYYPDIDDTALVTAMLDRRGRTHRAADGTHPYASCVSRALDW
MRGLQSRNGGFAAFDADCDRMYLNAIPFADHGALLDPPTEDVSGRVLLCFGVTKRAADRASL
ARAIDYVKRTQQPDGSVWVGRWGTNYLYGTWSVLAGLALAGEDKSQPYIARALDWLRARQHA
DGGWGETNDSYLDPKLAGTNGGESTSNCTAWALLAQMAFGDCESDSVKRGIAYLQSVQQED
GFVWVHRSHNAPGFPRIFYLKYHGYTAYFPLWALARYRRLAGAKDAGATRSGASGASATSVTD
DALA >seq_ID 86
MIRRMNKSAPSPWSTLDTAIARGRDALVRLQQPDGSWCFELESDATITAEYILMMHFMDRIDD
VRQEKMARYLRANQRLDTHGAWDLYVDGAPDVSCSVKAYFALKAAGDSEQAPHMIRARDAIL
KLGGAARSNVFTRILLATFGQVPWRAAPFMPIEFVLFPKWVPISMYKVAYWARTTMVPLLVLCS
LKARARNPRNVSIRELFVTPPEQERRYFPPARGMRRLFLALDRAVRHIEPLMPKRLRQRAIRHA
QAWCAERMNGEDGLGGIFPPIVYSYQMMQVLGYPDDHPLRRDCENALEKLLVTRPDGSVYCQ
PCLSPVVVDTAWSTMALEQARGVAAPETGETAAGTLRELDERIARAYDWLAARQVNDLRGDWI
ENVPADVEPGGWAFQYANPYYPDIDDSALVTAMLDRRGRTHRHADGTNPYAPRVARALDWM
RGLQSRNGGFAAFDADCDRMYLNAIPFADHGALLDPPTEDVSGRVLLCFGVTKRAEDRASLAR
CIDYVKRTQQPDGSWWGRWGTNYLYGTWSVLAGLALAGEDKSQPYIARALDWLRARQHADG
GWGETNDSYLDPTLAGTNGGESTSNCTAWALLAQMAFGDCESDSVKRGIAYLQSVQQEDGF
VWVHRSHNAPGFPRIFYLKYHGYTAYFPLWALARYRRLAGAAAAPPAALVAADTALA >seq_ID 80
MIRRMNKPAPSPWSALDTAIARGRDALMRLQQPDGSWCFELESDATITAEYILMMHFMDKIDD
ARQEKMARYLRAIQRLDTHGGWDLYLDGDPDLSCSVKAYFALKAAGDSEHAPHMVRARDAIL
KLGGAARSNVFTRILLATFGQVPWRATPFMPIEFVLFPKWVPISMYKVAYWARTTMVPLLVLCS
LKARARNPRNIAIPELFVTPPDQERQYFPPARGMRRAFLALDRVVRHVEPLLPKRLRQRAIRHA
QAWCAERMNGEDGLGGIFPPIVYSYQMMDVLGYPDDHPLRRDCENALEKLLVTRPDGSMYC
QPCLSPVVVDTAWSTMALEQARGVAVPEAGAPAGALDELDARIARAYDWLAERQVNDLRGDW
IENAPADTQPGGWAFQYANPYYPDIDDSAVITAMLDRRGRTHRNADGSHPYAARVARALDWM
RGLQSRNGGFAAFDADCDRMYLNAIPFADHGALLDPPTEDVSGRVLLCFGVTKRADDRASLA
RAIDYVKRTQQPDGSWWGRWGTNYLYGTWSVLAGLALAGEDPSQPYIARALAWLRARQHAD
GGWGETNDSYIDPALAGTNAGESTSNCTAWALLAQMAFGDGESESVKRGIAYLQSVQQDDGF
VWVHRSHNAPGFPRIFYLKYHGYTAYFPLWALARYRRLAGGASSAGAHTVPASTGADAALA >seq_ID 82
MNKPAPSPWSALDTAIARGRDALMRLQQPDGSWCFELESDATITAEYILMMHFMDKIDDVRQE
KMARYLRAIQRLDTHGGWDLYVDGDPDVSCSVKAYFALKAAGDSEHAPHMVRARDAILALGG
AARSNVFTRILLATFGQVPWRATPFMPIEFVLFPKWVPISMYKVAYWARTTMVPLLVLCSLKAR
ARNPRNIAIPELFVTPPDEERHYFPPARGMRRAFLALDRVVRHVEPLLPKRLRQRAIRHAQAWC
AERMNGEDGLGGIFPPIVYSYQMMDVLGYPDDHPRRRDCENALEKLLVTRTDGSMYCQPCLS
PVWDTAWSTMALEQARAVAVPEAGARASALDELDARIARAYDWLAERQVNDLRGDWIENAPA
DTQPGGWAFQYANPYYPDIDDTAVVTAMLDRRGRTHRNADGSHPYAARVARALDWMRGLQS
RNGGFAAFDADCDRMYLNAIPFADHGALLDPPTEDVSGRVLLCFGVTKRAADRASLARAIDYV
KRTQQPDGSVWVGRWGTNYLYGTWSVLAGLALAGEDPSQPYIARALAWLRARQHADGGWGE
TNDSYIDPTLAGTNAGESTSNCTAWALLAQMAFGDCESESVRRGIAYLQSVQQDDGFWWHRS
HNAPGFPRIFYLKYHGYTAYFPLWALARYRRLASGVSSAGVHAVPASTGADAALA >seq_ID 108
MNDLSQTQPRDAVLPEAAGAVPPASAPAPAAASEAPAASLDTAITRATDAILAAQKPDGHWVY
ELEADATIPAEYVLLVHYLGETPNVELEQKIARYLRRIQLPDGGWPLFTDGAPDVSASVKAYFAL

| Enzyme Sequences |
|---|

KMIGDPADAEHMVRAREAILANGGAEAVNVFTRILLALFGWSWRAVPMMPVEIMLLPMWFPF
HLSKVSYWARTVIVPLLVLNAKRPLARNPRRVRIDELFRGAPVNTGPRDRAPHQHAGWFRFFS
GVDMLLRAVDGLFPKATRERAVRAAVAFVDERLNGEDGLGAIFPAMANSVMMYDVLGYPADH
PNRAIARQSIEKLLVIKDDEAYCQPCLSPVVVDTSLVAHALLETGEARAEQAAERGLAWLRPLQIL
DVRGDWISRRPNVRPGGWAFQYNNDYYPDVDDTAVVVMAMHRSAALTHSEVDREAIARARE
WVVGMQSSDGGWGAFEPENTQYYLNNIPFSDHGALLDPPTADVSGRCLSMLAQLGELPQGS
EPAQRAFAYMLKEQEPDGSWYGRWGLNYIYGTWTALCSLNAAGMPHDDPRMKRAAKWLLSI
QNEDGGWGEGGESYKLDYHGYERAPSTASQTAWALMGLMAAGEVNHEAVARGVAYLQREQ
REHGLWDETRFTATGFPRVFYLRYHGYRKFFPLWALARFRHLKRHGLTRVAVGM

>seq_ID 169
MREAAVSKVETLQRPKTRDVSLDDVERGVQNAARALTEMTQTDGHICFELEADATIPSEYILFH
QFRGTVPRDGLEAKIGNYLRRTQSKVHGGWALVHDGPFDMSATVKAYFALKMICDDIEAPHM
RAARKAILQRGGAANANVFTRILLALYGEVPWAAVPVMPVEVMHLPKWFPFHLDKVSYWARCT
MVPLFVIQAKKPRAKNPRGIGVAELFVTPPDSVRTWPGSPHATWPWTPIFGAIDRVLQKTQDH
FPKVPRQRAIDKAVAWVSERLNGEDGLGAIFPSMVNSVLMYEVLGYPPDHPQVKIALEAIEKLV
AEKDDEAYVQPCLSPVWDTALTSHAMLETGGAAAEANARAGLDWLKPLQILDIKGDWAETKPN
VRPGGWAFQYANPHYPDLDDTAVVVMAMDRAQRQHGLVSGMPDYSASIARAREWVEGLQS
ADGGWAAFDADNNHHYLNHIPFSDHGALLDPPTADVTARVVSMLSQLGETRETSRALDRGVT
YLLNDQEKDGSWYGRWGMNFIYGTWSVLCALNAAGVDPQSPEIRKAVAWLIRIQNPDGGWG
EDASSYKLNPEFEPGYSTASQTAWALLALMAVGEVDDPAVARGVNYLMRTQGQDGLWNEER
YTATGFPRVFYLRYHGYPKFFPLWAMARFRNLKKGNSRQVQFGM >seq_ID 163
MREAAVSKVETLQRPKTRDVSLDDVERGVQSAARALTDMTQADGHICFELEADATIPSEYILFH
HFRGTEPRAGLEAKIGNYLRRTQSKVHGGWALVHDGPFDMSASVKAYFALKMIGDDIEAPHM
RAVRKAILQRGGAANANVFTRILLALYGEVPWTAVPVMPVEVMHLPKWFPFHLDKVSYWARCT
MVPLFVIQAKKPRAKNPRGVGVAELFVTPPDSVRTWPGSPHATWPWTPIFGAIDRVLQKTQDH
FPKVPRQRAIDKAVAWVSERLNGEDGLGAIFPSMVNSVLMYEVLGYPPDHPQVKIALEAIEKLV
AEKDDEAYVQPCLSPVWDTALTSHAMLEVGGTQAEANARAGLDWLKPLQILDIKGDWAETKP
NVRPGGWAFQYANPHYPDLDDTAVVVMAMDRAQRQHGLVSGMPDYSTSIARAREWVEGLQ
SADGGWAAFDADNNHHYLNHIPFSDHGALLDPPTADVTARVVSMLAQLGETRETSRALDRGV
TYLLNDQEKDGSWYGRWGMNFIYGTWSVLCALNAAGVDPQSPEIRKAVAWLIRIQNPDGGWG
EDASSYKLNPEFEPGYSTASQTAWALLALMAVGEVDDPAVARGVNYLMRTQGADGLWNEER
YTATGFPRVFYLRYHGYPKFFPLWAMARFRNLKRGNSRQVQFGM >seq_ID 105
MKPNHTFSPAALDAAILRGRDTLSGLQQPDGSWCFELESDATITAEYILMMHFMDKIDEVRQAQ
MARYLRAIQRVETHGAWDLYVDGAPDISCSVKAYFALKAAGDSEHAPHMIRAREAILKLGGAAR
SNVFTRILLATFGQVPWRAAPFMPVEFVLFPKWVPISMYKVAYWARTTMVPLLVLCSLRARAR
NPRNVSIAELFVTPPDEERHYFPPAKGMRKLFLALDRTVRHLEPLLPRRLRQRAIRHAEAWCAE
RMNGEDGLGGIFPPIVYSYQMMEVLGYPEDHPLRRDCEDALEKLLVTRADGSVYCQPCLSPV
WDTAWSTMALEQARGATPAAPDTQVSERELDARIARAYDWLATRQVNDLEGDWRENARPGT
LPGGWAFQYANPYYPDIDDSAVVTAMLDRRGRAQARASGENPYAERVTRALDWMRGLQSRN
GGFGAFDADCDRLYLNAIPFADHGALLDPPTEDVSGRVLLCFGVTKRPADRAAAARAIEYVKRT
QQPDGSVWVGRWGTNYLYGTWSVLAGLALSGEDKSQPYIARALDWLRAHQHADGGWGETN
DSYADPRLRATNYGESTSNCTAWALLAQMAFGDWQSDSVRRGIAYLLSVQQDDGFWWHRSH
NAPGFPRIFYLKYHGYTAYFPLWALARYRRLAGAQAAPSSPGPGTAATIADPAVA >seq_ID 211
MTSGTTILGAERGRTLDASIDAARAALLGYRRDDGHWVFELEADCTIPAEYVLLRHYLGEPVDA
ALEAKIAVYLRRTQGAHGGWPLVHDGEFDVSATVKAYFALKMIGDSIDAPHMAKAREAILARGG
AlHVNVFTRFLLSMFGILTWRSVPVLPVEIMLLPMWAPFHLNKISYWARTTIVPLMVLAALKPRA
VNKLDIGLDELFLQDPQSIGMPAKAPHQSWGLFTLFGSIDAVLRVIEPLIPKKLRSYAIGRAVAFIE
ERLNGEDGLGAIYPPMANTVMMYKVLGYGEDHPPRAITRRGIDLLLVVGEEEAYCQPCVSPIW
DTSLTCHALLEAGGAEAALPVRKGLDWLIPKQVLDLKGDWAVKAPNVRPGGWAFQYNNAHYP
DLDDTAVVVMALDRARRDQPSAAYDNAIARGREWIEGMQSDDGGWAAFDVNNTEYYLNNIPF
SDHGALLDPPTEDVTARCVSMLAQLGETAETSSALARGVAYLRKTQLAEGSWYGRWGLNYIY
GTWSVLCALNAAGVAHQDPAMRKAVAWLASIQNADGGWGEDAVSYRLDYRGYESAPSTASQ
TAWALLALMAAGEVDHPAVARGVEYLKGTQTEKGVVVDEQRYTATGFPRVFYLRYHGYSKFFP
LWALARYRNLRATNSKVVGVGM >seq_ID 76
MDSVNATAREAKESKISESEILESSIASATQGVLGFQQSDGHWVFELEADCTIPAEYVLLRHYLA
EPVDTVLEAKIGNYLRRVQGAHGGWPLVHDGEFDMSASVKAYFALKMIGDSIDAPHMVRAREA
IHARGGAIHSNVFTRFMLAMFGIVTWRAVPVLPIEIMLLPFWSPFHINKISYWARTTMVPLMVIAA
LKPRAKNPKGVGIDELFLQDPRSIGMTAKAPHQSMAWFLLFRSLDAILRVIEPLFPKSLRKRAID
TALAFSEERLNGEDGMGAIYPPMANLVMMYDALGKDENYPPRAVTRRGIDKLLVIGDDEAYCQ
PCVSPVVVDTTLTAHALLEAGGDKAGPAAKHGLDWLIPKQELEVKGDWAVKRPDVRPGGWAF
QYNNAYYPDLDDTAVVVMSMDRMRREHGVTGYDSAIDRGREWIEGMQSDDGGWAAFDVNN
LEYYLNNIPFSDHGALLDPPTEDVTARCVSMLAQLGETAKTSKHVADGVAYLRKTQHPEGSWY
GRWGMNFIYGTWSVLCALNMAGVRHDDPMIRKAADWLASIQNKDGGWGEDTVSYRLDYKG
WEAAPSTASQTAWALLALMAAGEVDHPAVARGVEYLIATQNEKGLWDEQRYTATGFPRVFYL
RYHGYSKFFPLWGLARYRNLRNTNSRVVGVGM

| Enzyme Sequences |
| --- |

>seq_ID 179
MEQQPELISGGVGGVAYPWDLGSQAIEEAILAARAALLAHLHPDGYWCFELEADCTIPAEYIMM
MHYTGELEAALELKLARYIRECQLQEGGWPLYYGGAMDISCSVKAYFALKLAGDDPEAAHMRR
ARKAVLERGGAVNANVFTHIALALFGEIPWRGVPFMPPEILLLPRWFPFHLSKVSYWSRTVMVP
LFILAAHKPRARNPRAIHISELFVTDPQLETGYFKARSRLNRLFITLDALGRRIEPFIPRAVRAKAL
RRAAEWFITRLNGEHGLGAIFPAMVNSYEALELLGYAADHPLRQQVRKGLRDLVVEQADRAYC
QPCLSPIWDTALACLALQEADRGSSSAQVRHALDWLQARQLLDTPGDWSEQHPSLPGGGWP
FQFRNDHYPDLDDTAIVAWAMQRASDPERYGAAIRRATVWLLGMQSANGGFAAFDSDNTRYY
LNEIPFADHGALLDPPTSDVTARVVALLGSLDGEVHDRSALNRAVAFLHREQEAEGCWYGRW
GTNYIYGTWSVLTALEQLGYDFNAPWVRKAVIWLKSVQRDDGGWGESNDTYLDHRPQDRQA
DESTPFQTAWAVLALIAAGECRSPEVVRGVEYLLRHQRPDGLWYCPWFTAPGFPRVFYLKYH
GYDAYFPLMALARYRNCVLDNDA >seq_ID 81
MIRRMNKPAPSPWSALDAAIARGRDALMRLQQPDGSWCFELESDATITAEYILMMHFMDKIDD
ARQEKMARYLRAIQRLDTHGGWDLYVDGDPDVSCSVKAYFALKAAGDSEHAPHMVRARDAIL
ALGGAARSNVFTRILLATFGQVPWRAAPFMPIEFVLFPKWVPISMYKVAYWTRTTMVPLLVLCS
LKAHARNPRNIAIPELFVTPPDQERHYFPPARGMRRAFLALDRVVRHAEPLLPKRLRQRAIRHA
QAWCAERMNGEDGLGGIFPPIVYSYQMMDVLGYPADHPLRRDCENALEKLLVTRPDGSMYC
QPCLSPVVVDTAWSTMALEQARGVAVHEAGAPASALDELDARIARAYDWLAERQVNDLRGDWI
ENAPADTQPGGWAFQYANPYYPDIDDSAVVTAMLDRRGRTHRNADGTHPYAARVARALDWM
RGLQSRNGGFAAFDADCDRMYLNAIPFADHGALLDPPTEDVSGRVLLCFGVTKRADDRASLA
RAIDYVKRTQQPDGSWWGRWGTNYLYGTWSVLAGLALAGEDPSQPYIARALAWLRARQHAD
GGWGETNDSYIDPALAGTNAGESTSNCTAWALLAQMAFGDGESESVKRGIAYLQSVQQDDGF
VWVHRSHNAPGFTRIFYLKYHGYTAYFPLWALARYRRLAGGASSAGAHAVPASTAADAALA >seq_ID 22
MATLTTMATTATMATTEASQPLEAQARTALTKATSYAWEIISNRHWCGELESNVTVTCEHIFFL
YVLYQHIDPDEGSQYRQWLLSQQNADGSWGIAPNYPGDVSTSAEAYLALRIIGMSPDSPELFQ
ARTFIRAAGGLSKMRMFTRIFFAEFGLVPWTAIPQLPAEFILVPAHFPISIYRLASWARSNVVPLLI
1AHHRPLYPLPNGLHKQNPFLDELWLDPATKPLPYGSLDPTDPLSFVFTILDKALSYLGGLRRCP
TRGYARRRCIQWILQHQEKAGDWAGIIPPMHAGIKALWLEGYLHRDEPIQLGLAAIERFTWTDN
RGKRLQCCISPVWDTVLMIRALQDTPASLGIKSDPRIADALAWTAENQHRGPEGDWRVYQPNI
PVGGWAFEYSNTWYPDIDDTAAAVLAFLTHDPATARSRLVRDAVLWIVGMQNADGGWAAFDH
ENNRLFLNKIPFSDMESLCDPSTPDVTGRTIECLGMLRDLLMLPAEKAGKKGEKYGYPDGERD
AAADSHLLKIINTACARAIPYLIRTQEATGAWYGRWAVNYVYGTCLVLCGLQYFKHDPTFAPEID
TMATRAVKWLRQIQNSDGGWGESVLSYREPWRAGCGPSTPSQTAWALMGLLTVCGGEDRS
VQRGVRHLVDTQDDILSKGEGGAAAWTEREFTSTGFPNHFYISYTLYRVYFPITALGRYLSLVE
GGKKENGGGA >seq_ID 178
MNSINATAAPIDDNVLGDRIGAATRGLLSLKQSDGHFVFELEADATIPSEYILMRHYLGEPVDTV
LEAKIAAYLRRIQGAHGGWPLVHDGPFDMSASVKAYFALKMAGDSIDAPHMARAREAILSRGG
AANVNVFTRFLLSFFGELTWRSVPVLPVEIMLLPMWSPFHLNKVSYWARTTMVPLMVLAALKP
RARNPRGIGIRELFLEDPATVGTPKRAPHQSPGWFALFTGFDRVLRLIEPLSPKWLRARAMKKA
IAFVEERLNGEDGLGAIFPPMVNTVMMYDALGFPPEHPPRAVTRRGIDKLLWGENEAYCQPC
VSPIWDTALSCHALLEAGGPEAVNSAGKCLDWLLLKQELVLKGDWAVKRPDVRPGGWAFQYA
NGHYPDLDDTAVVVMAMDRVRRNGPNGRYDEAIARGREWIEGMQSRDGGFAAFDADNLEYY
LNNIPFSDHAALLDPPTEDVTARCVSMLAQLGETVDSSSSMAAGVEYLRRTQLAEGSWYGRW
GLNYIYGTWSVLCALNVAGVDHQDPVIRRAVNWLVSIQNADGGWGEDAVSYRLDYKGFEGAP
TTASQTAWALLALMAAGEVENPAVARGIKYLIDTQTKKGLWDEQRYTATGFPRVFYLRYHGYS
KFFPLWALARYRNLRSTNSKAVGVGM >seq_ID 177
MNATVAQICDAVLEDRIGSATRGLLNLKQSDGHFVFELEADATIPSEYILLRHYLGEPVDTVLEA
KIAAYLRRIQGAHGGWPLVHDGPFDMSASVKAYFALKMIGDSVDAPHMARAREAILSRGGAAN
VNVFTRFLLSFFEVLTWRSVPVLPVEIMLLPMWSPFHLNKISYWARTTMVPLMVLAVLKPRARN
PRDVGIRELFLQDPATVRTPKRAPHQSPAWFALFSSLDWILRRIEPLFPKRLRARAMEKAIAFVE
ERLNGEDGLGAIFPPMVNTVMMYDALGFPPEHPPRAVTRRGIDKLLVIGEDEAYCQPCVSPIW
DTALSCHALLEAGAPEALNSAGKCLDWLLPKQELVLKGDWAAKRPDVRPGGWAFQYANGHY
PDLDDTAVVVMAMDRVRRNGRGDKYDEAIERGREWIEGMQSRDGGFAAFDADNLEYYLNNIP
FSDHAALLDPPTEDVTARCVSMLAQLGATVDGSSSMAAGVEYLRRTQLAEGSWYGRWGLNYI
YGTWSVLCALNAAGVDHQDPAIRKAVDWLLSIQNEDGGWGEDAVSYRLDYKGFEGAPTTASQ
TAWALLALMAAGEVENPAVTRGIKYLIDTQTKKGLWDEQRYTATGFPRVFYLRYHGYSKFFPL
WALARYRNLRSTNSKVVGVGM >seq_ID 170
MREAVSKVEALQRSKTQGISLEDVERGVAQATRALTALAHDDGHICFELEADATIPSEYILFHHF
RGTQVPGDLEAKIGNYLRRTQGRHGGWALVHEGPFDMSCTVKAYFALKMIGDDIEAPHMRRA
REGILSRGGAANANVFTRFMLALYGEVPWRAVPVMPVEVMFLPKWFPFHLDKISYWARTTVVP
LFVLQATKPRARNPRGISVQELFVTPPESVRSWPGSPHATWPWTPIFGFIDRVLQRVENHLPR
KSRQRAMEMARAWVSERLNGEDGLGAIFPAMVNSVLMYEVMGYRPDHPQVRVACDAIEKLV
VEKADEAYVQPCVSPVWDTALASHALLEAGGPEAEAQARAGLDWLKPRQVLDIVGDWAARKP
KVRPGGWAFQYANAHYPDLDDTAVVVMAMDRAMHQHGLVAGMPDYKASIARAREWVEGLQ

| Enzyme Sequences |
|---|
| SEDGGWAAFDADNNHMYLNHIPFSDHGALLDPPTADVTARVVGMLSQLGETRETSRALDRGV<br>NYLLNDQEEDGSWYGRWGMNFIYGTWSVLCALNAAGVDPADPRIQKAVSWLIRIQNPDGGW<br>GEDASSYKIDPAFEPGSSTASQTAWALLALMAAGAVDDPAVTRGINFLTRTQGADGFWKEERY<br>TATGFPRVFYLRYHGYPKFFPLWAMARFRNLKRGNSRRVQFGM<br><br>>seq_ID 14<br>MLLAEVQKALRLAVGHSLDLQRADGAWCGEVHSNATFTSQYVFLQQQIGLPLDPTEIEGLSRW<br>LFSQQNEDGSWGLGPGLGGDVSTTTETYLALKILGVSPEDPRMAAARTSIIKAGSLPATRMFTR<br>VFLASFGLIPWSAVPPLPAELILLPTLFPVNIYNLSSWARATCVPLLLIRRHEPLHSLPNGRHAEN<br>DFLDELWTKDIPRDFCYTTPLSRMWRLGDYAGIFFTSADHGLRFLGQYFHSPLRNLSRRKIINWI<br>LDHQEQSGEWAGYVVPPQHNNIWALSLEGYSLDHPVLRRGIAAVKSFVLHDATGMRAQVTVSQ<br>VVVDTALMSIALSDSAPSTGIISPTQAIDWLMHHEVASHRGDWRVLRPKLATGGFCFEEFNTLYP<br>DVDDTAAVIMALIKSNPAHLISGCVRRAAQWILGMQNRDGGWGAFDWNNDKFFLNKIPFSDMD<br>SLCDPSTPDVTGRIIECFGMMMAGRHGYSLDCQLENRLRASSQLAIAYLLGCQENNGSVWVGR<br>WGVNYLYGTSNVLCGLAYYYDRSSLSKGDVKSNSNIVSAVDRASEWLKARQHSNGGWGEGP<br>ESYDNAQLAGCGQPTASQSAWVTMALLNYLSPTDEVIQRGVSYLVRNQVKYGDESRATWLLE<br>RYTATGFPGHLYMEYDYYRHYFPIMALGRYVNKLSGSHKLL<br><br>>seq_ID 180<br>MTRALRQAPESAGAIGIAAASPATETSGQDTHPREISGAITAARDALLKLQQADGHWCFMLEAD<br>CTIPAEYILWTHFTGELEPEIERKLAARLRAKQASHGGWPLYEGGDLDISCSVKVYYALKLVGD<br>DPNAPHMRRAREAILAQGGGARANVFTRLALAMFSQIPWRGVPFIPVEIMLLPRWFPFHLSKVS<br>YWSRTVMVPLAILYSLKAQAQNPRNVHIQELFTVPPEQERHYFPVRSRLNKILLSVERTARLLEP<br>LIPSMLRRRALKKAETWFTERLNGEDGLGGIFPAMVNAHESLILLLGYSPDHPWRVQAKKALQNL<br>VIEEKNSASCQPCLSPIWDTGLAALALQETEGGHTTAPVIRALDWLKERQILEQSGDWQVQHP<br>NLKGGGWAFQYNNSYYPDLDDTALVAWSMDQAATPERYGEAIGRACDWLCGMQSRNGGFA<br>AFESDNTHYYLNEIPFADHGALLDPPTADVTARCIVLLGRLNKPQYAETLQRALDYLRREQEPN<br>GSWFGRWGTNYIYGTWSALTALEQANIDPQEGFIRKAVEWLKQVQRLDGGWGEDNYSYFDS<br>SLAGRYQESTPVHTAWALLALMAVGEANSEAVKKGIAYLLQIQQEDGLWDHPAFNAPGFPRVF<br>YLKYHGYDKFFPLWALARYRNHLNRQC<br><br>>seq_ID 155<br>MMANATDTIELPPSRAADRIVPMTDIDQAVDAAHAALGRRQQDDGHWVFELEADATIPAEYVLL<br>EHYLDRIDPALEERIGVYLRRIQGDHGGWPLYHGGKFDVSATVKAYFALKAIGDDIDAPHMARA<br>RAAILDHGGAERSNVFTRFQLALFGEVPWHATPVMPVELMLLPRKALFSVWNMSYWSRTVIAP<br>LLVLAALRPRAINPRDVHVPELFVTPPDQVRDWIRGPYRSQLGRLFKYVDIALRPAERLIPDATR<br>QRAIKAAVDFIEPRLNGEDGLGAIYPAMANTVMMYRALGVPDSDPRAATAWEAVRRLLVELDG<br>EAYCQPCVSPIWDTGLAGHAMIEAASGPKGIRPEDTKKKLAAAAEWLRERQILNGEGRLGDQL<br>PRRAPRRLGLPVQQRLLPRRGRHGSGRHVLHREGDPANDEALERARQWIIGMQSSNGGWGA<br>FDIDNNLDFLNHIPFADHGALLDPPTADVTARCISFLAQLGHPEDRPVIERGIAYLRTDQEREGC<br>WFGRWGTNYIYGTWSVLCAYNAAGVAHDDPSVVRAVDWLRSVQREDGGWGEDCASYEGAT<br>PGIYTESLPSQTAWAVLGLMAVGLRDDPAVMRGMAYLTRTQKDDGEWDEEPYNAVGFPKVFY<br>LRYHGYRQFFPLLALSRYRNLASSNSRHVAFGF<br><br>>seq_ID 8<br>MNRMLQPLHSGAGIFRSSLDRVIAQARQALGGRQAEDGHWCFEFEADCTIPAEYILMQHYMD<br>ERDEALEARIAVYLRGKQADHGGWPLYYGGHFDLSASVKVYYALKLAGDDPELPHMRRAREAI<br>LAHGGAERSNVFTRITLALFAQVPWRAVPFIPVEIMLLPRWFPFHIYKVASWSRTVMVPLFILCS<br>LKARAKNPLQVHIRELFRRPPDQITDYFSHARRGIVAYIFLSLDRFWRLMEGWIPHGIRRRALKK<br>AEAWFTARINGEDGLNGIFPAMVNAHEALELLGYPPDHDYRRQTGAALRKLVVERANDAYCQP<br>CVSPVVVDTCLALHALLEEDGEVSPAVQNGIRWLKNRQIGAEPGDWRESRPHLAGGGWAFQY<br>ANPYYPDLDDTAAVGWALARAGRAEDRDSIEKAANWLAGMQSRNGGFGAYDVDNTHYYLNEI<br>PFADHKALLDPPTADVTGRWAFLAHLARPRDRDVLRRAVAYLLREQESSGAWFGRWGTNYIY<br>GTWSVLMALAELNDPSLKPTMERAAYWLRAVQQGDGGWGESNDSYSDPGLAGMGQTSTAA<br>QTAWACLGLMAAGDRDSVALHRGIAWLQAHQEGDGCWQAPFFNAPGFPKVFYLIYHGYAFYF<br>PLWALARYRNLGCMAHE<br><br>>seq_ID 203<br>MSMNEAVLAAPRAAVATAAPALQAPIEALSPLDAGICHAVDALLAQQNADGHWVYELEADATIP<br>AEYVLMVHYLGETPDLSLEARIARYLRRIQNADGGWPLFHEGRSDISASVKAYFALKMAGDDP<br>QAAHMARAREVILAMGGAETSNVFTRTLLALYGVMPWQAVPMMPVEIMLLPQWFPFHLSKVS<br>YWARTVIVPLLVLNSLRPQARNPRKVGIDELFLGSRDAVRLPPRAPHQHKGWHALFHGADVLL<br>RTAEHVMPRGLRRRAIDAAKAFVRERLNGEDGLGAIFPAMANSVMMFDVLGVPPDDPDRAIAR<br>RSIDKLLVVHGDEAYCQPCLSPVVVDTALAAHALLEASEPRATAAVTRALDWLRPLQVLDVRGD<br>WTVRRPDVRPGGWAFQYANPHYPDVDDTAVVVAAMHRAARTDHSGRADPNAEATARAIEWI<br>VGMQSANGGWGAFEPENTHLYLNNIPFADHGALLDPPTADVSARCLSMLCQTGATPDKSEPA<br>ARALQYLLAEQLPDGSWFGRWGTNYIYGTWSALCALNAAGLGPDAPPLRRAAEWLVAIQNPD<br>GGWGEDGDSYKLEYRGYETAPSVASQTAWALLALMAAGQAAHPAVTRGIDYLLRTQQADGL<br>WHEPRFTAVGFPRVFYLRYHGYARYFPLWALARYRNLERSGNRQVAWGL<br><br>>seq_ID 165<br>MREAAVSKVETLQRPKTRDVSLDDVERGVQSATRALTEMTQADGHICFELEADATIPSEYILFH<br>QFRGTEPRPGLEAKIGNYLRRTQSKVHGGWALVHDGPFDMSASVKAYFALKMIGDDIEAPHM<br>RAVRKAILQRGGAANANVFTRILLALYGEVPWAAVPMPVEVMHLPKWFPFHLDKVSYWARCT<br>MVPLFVIQAKKPRAKNPRGVGVAELFVTPPDSVRTWPGSPHATWPWTPIFCCIDRVLQKTQDH<br>FPKVPRQRAIDKAVAWVSERLNGEDGLGAIFPAMVNSVLMYEVLGYPPEHPQVKIALEAIEKLV<br>AEKEDEAYVQPCLSPVWDTALNSHAMLEAGGHQAEANARAGLDWLKPLQILDIKGDWAETKP |

Enzyme Sequences

NVRPGGWAFQYANPHYPDLDDTAVVVMAMDRAQRQHGLVSGMPDYSESIARAREWVEGLQ
SADGGWAAFDADNNHHYLNHIPFSDHGALLDPPTADVTARVVSMLSQLGETRATSRALDRGV
TYLLNDQEKDGSWYGRWGMNFIYGTWSVLCALNTAGVDPQSPEIRKAVAWLIRIQNPDGWG
EDASSYKLNPEFEPGYSTASQTAWALLALMAAGEVDDPAVARGVNYLVRTQGQDGLWSEER
YTATGFPRVFYLRYHGYPKFFPLWAMARFRNLKRGNSRQVQFGM

>seq_ID 181
MSISPTFSGSSLQKSSLSDHSTISEPFTVVDRVNGISAVALDDAITRARSALLAQQREDGHWCF
SLEADCTIPAEYILMMHFMDEIDTALERRIANFLRNRQVTDGHGGWPLYYGGDFDMSCSVKVY
YALKLAGDSPEAAHMVRARNAILERGGAARSNVFTRLLLAMYRQIPWRGVPFVPAEIMLLPRW
FPFHLSKVAYWSRTVMVPLSILCTLKAKAANPRNIHVRELFTVDPEMEKNYFPVRTPLNHLLLYL
ERLGSKLEPLIPSFIRRRALKKAEQWTIERLNGRDGLGAIFPAMVNAYEALTLLGYDHDHPLLQQ
CRLALRELLVNEGEDITWCQPCVSPVVVDTVLASLALQEDERADNGPVRHALDWLVPLQALDQ
PGDWRNSRPDLPGGGWAFQYANPHYPDLDDTAAAAWALCQADTEDYRTSITRAADWLAGM
QSSNGGFAAFDIDNVHYYLNEIPFADHGALLDPPSSDVTARCIGLLALNGEARHQETVKRGLTF
LFNEQEPSGAWFGRWGTNYVYGTWSVLEALKLARVDHDHQAVKRAVQWLKSVQRADGGWG
ETNDSYLDSELAGQLETSTSFQTAWAVLGLMAAGEVGSTAVRNGIDYLIRTQSAAGLWEEPWF
TAPGFPKVFYLKYHGYSKYFPLWALNRYRAMNSRSVV >seq_ID 110
MILFPAGFYFSIYEISYWSRCIWPLSIAIARKPHVTVGDDLLKELYLVPREDVVYRIERDQDGFC
WYNFFIDADSIFRRYEQHPIKFIRRIAKKMAEKWLLEHMEKSGGLGAIWPAMINSIFAMKCLDYP
DDHPALTAQMKEVEALVIYEGDMLYLQPCVSPVVVDTAWSIIAMNDSGIPGSHPVLQKAGKWLL
SKEVRDFGDWKLKCKVEEPSGWYFQYANEFYPDTDDTGAVLMALQRVSLPEDMHKEKTLLRA
LRWLQAMQCDDGGWGAFDRNNNKTILNNIPFADFNALLDPSTSDVTGRCIEFFGRIGFNKTYL
NIKKAVEFLKKEQDEDGSWFGRWGSNYIYGTWSVISGLIAVGEDINKAYIKKAIAWLKSVQNSD
GGWGETIKSYEDSALKGIGKSTPSQTAWALLTLITAGEIKSSSTERGIDFLLSTQKEDGSWDER
EFTATGFPKVFYLKYHMYRNYFPLMALGRYRHFTHKLATSQ >seq_ID 182
MSISQAFFRTLIQKSSLSDSSLVSENFPADDVAGNEANEISAVTLDEAITRAYTALLAQQREDGH
WCFPLEADCTIPAEYILMMHFMDEVDTVLERKIANFLRTRQVTDGHGGWPLYYGGDFDMSCS
VKTYYALKLAGDSPEAAHMVHARNAILERGGAARSNVFTRLLLAMYRQIPWRGVPFVPAEIMLL
PRWFPFHLSKVAYWSRTVMVPLSILCTLKAKAINPRNVHVQELFVVDPVKEKNYFPVRTSLNRL
LLYVERLASKLEPFIPSFIRRRAVKKAEQWVIERLNGNDGLGAIFPAMVNAYEALTLLGHDRDHP
LLQQCRQSLRELLVDEGEEITWCQPCVSPVVVDTVLATLALQEDKQADSEPIRRALDWIVPLQIL
DEPGDWRDSRPNLLGGGWAFQYANPHYPDLDDTAAVAWALIQTGAEDYRVSITRAADWLAG
MQSSNGGFAAFDIDNAYYYLNEIPFADHGALLDPPTSDVSARCVGLLALNGEVRHQEAVKRGL
DFLFNEQESSGAWFGRWGSNYIYGTWSVLEAFRLARVDKGHQAVQRAIQWLESVQRADGGW
GETNDSYLDPQLAGQLEASTSFQTAWAVLGLMAAGEVENTAVRKGIDYLLRTQIATGLWEEPW
FTAPGFPRVFYLKYHGYSKYFPLWALNRYRTLSSKSAV >seq_ID 162
MSPFLQASDDNNPLFKESCQALDHATEFARDTLVNKEHWCGWVLSNVTVTAEWIFLQYILGLE
MSNEDRRGFLKHFTSSQRPDGSWSLATQTTTGGELSCTIEAYLALKILGVSPEEDYMVRARDY
VRSHGGAEKMRMLSRFHLAMFGLIPWAAVPQMPPELIFMPSWSLVNIYKFSSWARCNIVGLCM
LRVHEPLYALPNGKQLDNDYLDELWLDPYHKAIPYTVPYLQLMQTSPLGVLFQLGDLFLWLLSF
LGFWFLRRWAVSSSIQWTLDHQEPSGDWGGIYPPMHHNILALMLEGWSQDDPVIQRGIGACQ
RFLAEDPAHGKWMQPSVSPVWDTFLMIRAVADAKTTDDADKLLVKPVDWVLAQQIDDDHIGD
WRIYRPDIPAGGFAFEYFNKWYPDVDDTAVGVVALMRHDPSLVNDDRILKAAAWTLGMQNRD
FGWAAFDADNNAFYLHATPFSDMDSLTDSSTPDVTGHVLEMLGLMYRLERQGRVKSPEMLAF
LSQSHGACDRGLGYLLGSQEAFGGWYGRWGVNYIFGTSAALCALAYFADRKGVRGKMAAGA
DWLRSRQNPDGGWGELLESYDNKALAGRGRSTPSQTAWALQGLLELEDPRGEVVEAGVNW
LLRHQVTSPSRNSGRVSATWPEDDYTATGFPGHFYLKYELYCHYFPMMALARYRSCIQDGA >seq_ID 172
MDDRVGAATFEAQPRAGFGSVEAAISRAREALLAVQKPDGHFVFELEADVSIPAEYILFRHFLG
DPAKTEIERKIGVYLRRRQTAAGGWPLFAEGVFNVSSSVKAYFALKIIGDDPNAPHMAKARNAIL
AHGGAAQSNVFTRSLLALYGEVPWRAVPAMPVEIMHLPRWFPFHLSKVSYWGRTVIAPLIVVH
ALKPRAKNPRKISVSELFVAPAETVSRWPGAPHKSFPWTTIFGAIDRVLHKTEPLLPARSHQTAI
DKAVAFVTARLNGEDGLGAIYPAMAYSAMMFFALGAPLSDPRIVQIRKAIDRLLVIKDGEAYCQP
CVSPVVVDTALASHALMESAGQRPEARTAPAAAAVFEALDWLKPLQVLDVKGDWATQNPDVR
PGGWAFQYANPHYPDLDDTAVVVLAMDRAVKTSPLIAGEEETAYVEAISRAREWILGLQSANG
GFGAFDADNDRDYLNYIPFADHGALLDPPTADVTARCVSMLGQLGERPETSPALARAIDYLLSE
QEEEGSWFGRWGMNYIYGTWSVLSAFNAVERPADCAATRKAAAWLKRIQNPDGGWGEDGE
SYALGYKGYNPAPSTASQTAWALLALMAAGEVDAPEVALGLDYLVSTQADDGFWDEARFTAT
GFPRVFYLRYHGYAKFFPLWAMARYRNLKSGNRLKTQFGM >seq_ID 24
MLGAIREPPIDVQIALHSRDDNQTGLVLRGTRRTVDRVLKGLCSSPCFFCSVSLTMATLTTTMA
TTATMATTEASKPLEAQARTALTKATNYAWEIFSNRHWCGELESNVTVTCEHIFFLYVLYQHID
PGEGSQYRQWLLSQQNSDGSWGIAPNYPGDISTSAEAYLALRIIGMSTDSPELYRARTFIRAAG
GLSKMRMFTRIFFAEFGLVPWTAIPQLPAEFILVPAHFPISIYRLASWARSNVVPLLIIAHHRPLYP
LPNGLHKQNPFLDELWLDPATKPLPYGSSDPTDPVAFVFTILDKALSYLGGLRRSPTRGYARRR
CVQWILQHQEKAGDWAGIIPPMHAGIKALLLEGYKLHDEPIQLGLAAIERFTWADNRGKRLQCC
ISPVVVDTVLMIRALQDTPASLGIKLDPRIADALAWTAENQHRGPEGDWRVYKPNIPVGGWAFE
YHNTWYPDIDDTAAAVLAFLTHDPATARSRLVRDAVLWIVGMQNADGGWAAFDHENNQLFLN

| Enzyme Sequences |
|---|
| KIPFSDMESLCDPSTPDVTGRTIECLGMLRDLLMRPAENAENGEKYGYPDGEGDAAADAHLLQ<br>IINTACARAIPYLIRSQEATGTWYGRWAVNYVYGTCLVLCGLQYFKHDPKFAPEIQAMAARAVK<br>WLKQVQNSDGGWGESLLSYREPWRAGCGPSTPSQTAWALMGILTVCGGEDRSVQRGVRHL<br>VDTQDDTLSQGDGGAAAWTEREFTIREPLHEASQRIGSD<br><br>>seq_ID 26<br>MATLTTTMATTATMATTEASKPLEAQARTALTKATNYAWEIFSNRHWCGELESNVTVTCEHIFF<br>LYVLYQHIDPGEGSQYRQWLLLQQNSDGSWGIAPNYPGDISTSAEAYLALRIIGMSTDSPELYR<br>ARTFIRAAGGLSKMRMFTRIFFAEFGLVPWTAIPQLPAEFILVPAHFPISIYRLASWARSNVVPLLI<br>IAHHRPLYPLPNGLHKQNPFLDELWLDPATKPLPYGSSDPTDPVAFVFTILDKALSYLGGLRRS<br>PTRGYARRRCVQWILQHQEKAGDWAGIIPPMHAGIKALLLEGYKLHDEPIQLGLAAIERFTWAD<br>NRGKRLQCCISPVVVDTRVYKPNIPVGGWAFEYHNTWYPDIDDTAAAVLAFLTHDPATARSRLV<br>RDAVLWIVGMQNADGGWAAFDHENNQLFLNKIPFSDMESLCDPSTPDVTGRTIECLGMLRDLL<br>MRPAENAENGEKYGYPDGEGDAAADAHLLQIINTACARAIPYLIRSQEATGTWYGRWAVNYVY<br>GTCLVLCGLQYFKHDPKFAPEIQAMAARAVKWLKQVQNSDGGWGESLLSYREPWRAGCGPS<br>TPSQTAWALMGILTVCGGEDRSVQRGVRHLVDTQDDTLSQGDGGAAAWTEREFTSTGFPNH<br>FYISYTLYRVYFPITALGRYLSLIEGGQEKKKKGGGT<br><br>>seq_ID 171<br>MGKVETLHRTSTQDITLDDVERRVTLASKALMRLANADGHWCFELEADATIPSEYILYHHFRGSI<br>PTAELEGKIAAYLRRTQSAQHDGWALIHDGPFDMSATVKAYFALKMVGDPIDAPHMRRARDAIL<br>RRGGAAHANVFTRIMLALYGEVPWTAVPVMPEVMLLPRWFPFHLDKVSYWARTVMVPLFVL<br>QAKKPRARNPRGIGIRELFVEAPERVKRWPAGPQESSPWRPVFAAIDKVLQKVEGFFPPAGSRA<br>RAIDKAVAFVSERLNGEDGLGAIFPAMVNTVLMFEALGYPDDHPFAVTARSSVEKLVTVKEHEA<br>YVQPCLSPVVVDTALAAHALMEAGGTEAERHAKRAMDWLKPLQVLDIKGDWAASKPDVRPGG<br>WAFQYANPHYPDLDDTAVVMAMDRVQSRRSPGPDAADYGLSIARAREWVEGLQSRDGGW<br>AAFDADNTYHYLNYIPFSDHGALLDPPTADVTARCVSMLSQLGETRETCPPLDRGVAYLLADQ<br>EADGSWYGRWGMNYIYGTWSVLCALNAAGIDPACEPVRRAVTWLTAIQNPDGGWGEDASSY<br>KLEYRGYERAPSTASQTAWALLALMAAGEADNPAVARGINYLTRTQGADGLWAEDRYTATGF<br>PRVFYLRYHGYAKFFPLWALARYRNLQRGNSLKVAVGM<br><br>>seq_ID 173<br>MLREATAISNLEPPLTASYVESPLDAAIRQAKDRLLSLQHLEGYWVFELEADCTIPAEYILMMHF<br>MDEIDAALQAKIANYLRHHQSADGSYPLFRGGAGDISCTVKVYYALKLAGDSIDAPHMKKARE<br>WILAQGGAARSNVFTRIMLAMFEQIPWRGIPFTPVEIMLLPKWFPFHLDKVSYWSRTVMVPLFIL<br>CSHKVTARNPSRIHVRELFTVEPQKERHYFDHVKTPLGKAILALERFGRMLEPLIPKAVRKKATQ<br>KAFDWFTARLNGVDGLGAIFPAMVNAYEALDFLGVPPDDERRRLARESIDRLLVFQGDSVYCQ<br>PCVSPIWDTALTSLTLQEVARHTADLRLDAALSKGLKWLASKQIDKDAPGDWRVNRAGLEGGG<br>WAFQFGNDYYPDVDDSAVVAHALLGSEDPSFDDNLRRAANWIAGMQSRNGGFGAFDADNTY<br>YYLNSIPFADHGALLDPPTADVSARCAMFLARWVNRQPELRPVLERTIDYLRREQEADGSWFG<br>RWGTNYIYGPGAVLLAYEGRRVPNDDPSVRRAVAWLKSIQREDGGWGEDNFSYHDPSYRGR<br>FHTSTAFQTGFALIALMAAGEXGSPEVQAGVDYLLRQQRPDGFWNDECFTAPGFPRVFYLKY<br>HGYDKFFPLWALARYRNERYALA<br><br>>seq_ID 117<br>MNETAFANPAPQVGPAQRQPAAPQEAPAARLPAPALDRGIDRALDALLHQQRPDGHWVYELE<br>ADATIPAEYVLMVHYLGEDPDRDLEARIARYLRRIQNPDGGWPLFHQGRSDISASVKAYFALKM<br>AGDDPQSAPMQRARQAIHAMGGAEATNVFTRTLLALYGVLPWKAVPMMPVEIMLLPRWFPFH<br>LSKVSYWARTVIVPLLVLNSLRPQARNPRGVGINELFVGNCHTVGLPPRAAHQHAGWYTVFRG<br>LDALLRLAEPLFPRTLRRRAIAAAQRFVRERLNGEDGLGAIFPAMANSVMMFDVLGVPPEDPAR<br>AVARRSIERLLVEHGDEAYCQPCLSPVVVDTALATHALLETGEARAAQAAGRALDWLRPLQVLD<br>LRGDWAVRRPLVRPGGWAFQYANAYYPDVDDTAVVAAAMDRFMRAHHAPGRYGEAVARAT<br>EWIVGMQSGNGGWGAFEPENTHLYLNNIPFADHGALLDPPTADVSARCLSMLCQTGATPANS<br>EPAARALRYLLAEQMPDGSWFGRWGTNYIYGTWSALCALNAAGLPPEAPELCRAVAWLARIQ<br>NADGGWGEDSSYRLDYSGYEPAPSVASQTAWALLALMAAGAAQHPAVARGIDYLLRTQQP<br>GGLWHEPRFTAVGFPRVFYLRYHGYARYFPLWALARYRNLQRGLGDHGGNSGQVAWGL<br><br>>seq_ID 204<br>MSMNETAFATAVPRIAPASAGDSPAPRDAAQALDQGIGRAIDALLHQQRPDGHWVYELEADAT<br>IPAEYVLMVHYLGEAPDLELEARLARYLRRIQNPDGGWPLFHEGRSDVSASVKAYFALKMAGD<br>DPQAAHMQRARRAVHALGGAEASNVFTRTLLALYGVMPWLAVPMMPVEIMLLPQWFPFHLSK<br>VSYWARTVIVPLLVLNSLRPQARNPRGVGINELFVGNCHTVGLPPRAAHQHAGWYTVFRGLDA<br>LLRVAEPLVPRTLRRRAIAAAQAFVRERLNGEDGLGAIFPAMANSVMMFDVLGVPPDDPARAL<br>ARQSVERLLVEHGDEAYCQPCLSPVVVDTALAAHALLETGEARATAAAGRGLDWLRPLQVLDV<br>RGDWAVRRPLVRPGGWAFQYANAYYPDVDDTAVVAAAMNRYMRAHDVPGRYDEAVARAAE<br>WIVGMQGGDGGWGAFEPENTHLYLNNIPFADHGALLDPPTADVSARCLSMLCQIGATPGKSE<br>PAARALRYLLAEQMPDGSWFGRWGTNYIYGTWSALCALNATGLAPEAPEMRRAVAWLEQIQN<br>ADGGWGEDGSSYRLDYRGYEPAPSVASQTAWALLALMAAGAAQHAAVARGIDYLLRTQQSG<br>GLWHEPRFTAVGFPRVFYLRYHGYARYFPLWALARYRNLQRGGAHQVPWGL<br><br>>seq_ID 79<br>MRIGTTTNPSMPFPLSSSGAVFYREVNELREVQQEINRIQAFLLQRQQEDGTWRFCLESSPMT<br>DSHMIILLRTLGIHDERLMEKLTAHITALQHDNGAWKLYPDEQEGHLSTTIDSYYALLLSGKYTK<br>NEPRMALARSFILEKGGLTQANMLTKFATALTGQYQWPSHFLVPVEIALLPPSFPVSFYDFVGY<br>ARVHLAPMMIVADRNYVKKPDNAPDLSDLYADTPISRGLYPHRFLENFLKEGQSFLATIHDSLQ<br>QLPFLPGQLHKLALRRLEQYILARIEPDGTLYNYSTSTFFMIFALLARGFSPKDPLIQKAMQGLTG<br>SVYDYENGAHLQLATSAVVVDTALLTFSLQKSGLSPTHPAIQKANRYLLRKQQHTYGDWKIRNP |

| Enzyme Sequences |
| --- |
| NGKPGGWGFSDYNTMNPDIDDTTAALRSLRLLARTDVTAATAWKRGLEWLLSMQNDDGGWP<br>AFERNTDADFIRHLPIEGADTVSTDPSSADLTGRTLEFLGNYAGRTLTDLHVEKGVRWLLKHQE<br>SDGSWYGRWGIAYLYGTWAAITGLMAVGFSPTEPAIQKAVAWLVANQNPDGGWGESCQSDL<br>KKTYVPLGASTPSQTAWAIDALIAVSSKPTAELQRGIRYLLTHNQANDWTTRYPTGGGRPGGT<br>YFAYHSYRWIWPLLALSHYQVKYANT<br><br>>seq_ID 70<br>MLLYDKVHEEIERRTTALQTMQRQDGTWQFCFEGALLTDCHMIFLLKLLGRNDEIEPFVKRLVS<br>LQTNEGTWKLYEDEKGGNLSATIQAYAALLASEKYSKEDMNNRRAEMFIKEHGGVSRAHFMT<br>KFLLAIHGEYEFPALFHFPTPILFLQDDSPLSIFGLSSSARIHLIPMMICMNKRFRVEKKLLPNLNHI<br>AGGGGQWFREERSPLIQSFLGDVKKVISYPLSLHHKGYEEVERFMKERIDENGTLYSYASATF<br>YMIYALLALGHSIQSPIIEKAVTGLKSYIWKMDRGSHLQNSPSTVVVDTALLSYSLQEAKVTNENK<br>MIQRATEYLLQKQQTKKVDWSVHASSLVAGGWGFSDVNTTIPDIDDTTAALRALARSRGNDRV<br>DDAWGRGVEWVKGLQNNDGGWGAFERGVTSKLLSNLPIENASDMITDPSTPDITGRVLELFG<br>TYAPNELLEEQKKKAIKWLMDVQEQNGSWYGKWGICYIYGTWATMTGLRALGVPSTHPALKK<br>AASWLEHLQHEDGGWGESCQSSVEKKFISLPFSTPSQTAWALDALISYYDQETPIIRKGISYLLA<br>QSTMNEKYPTGTGLPGGFYIRYHSYGHIYPLLALAHYVKKYRK<br><br>>seq_ID 140<br>MAGERSALITALKRSQAADGSWRFPFETGISTDAYMIILLRTLDINDEPLIQALVERIESRQEANG<br>AWKLFADEGDGNVTATVEAYYALLYSGYRQPTDRHMQKAKRRILDMGGLDRVHLFTKVMLAL<br>TGQYPWPGRFPLPLEFFLLPPSFPLNMYDLSVYGRANMIPLLIAADSRYSRKTDKSPDLSDLFA<br>SRGDWGMPESRSLLTYVKRSLIGLPAQLHQAAKQRAVRYLFEHIEPDGTLYSYFSSTFLFIFALL<br>ALGYRNDDPRIRQAVRGLRSLRTTIDGHVHLQYTTASVVVNTALASYTLQEAGVPMTDRAIEKA<br>NRYLLSRQNVRYGDWAVHNPYSTPGGWGFSDVNTMNPDVDDTTAALRAIRQAAAKETAFRH<br>AWDRANQWLFSMQNDDGGFAAFEKNVSSRFWRYLPIEGAEFLLMDPSTADLTGRTLEYFGTF<br>AGLTKDQRAVSRAVDWLLSHQERNGSWYGRWGICYIYGTWAAITGLTAVGVPAHHPALQKAV<br>RWLLSIQNDDGGWGESCKSDGAKTYVPLGDSTPVHTAWALDALVAAAERPTLEMKAGFRALF<br>RLLHHPDWTASYPVGQGMAGAFYIHYHSYRYIFPLLALAHYEQKFGPLDD<br><br>>seq_ID 137<br>MAGERSALITALKRSQAADGSWRFPFETGISTDAYMIILLRTLDINDEPLIQALVERIESRQEANG<br>AWKLFADEGDGNVTATVEAYYALLYSGYRQPTDRHMQKAKRRILDMGGLDRVHLFTKVMLAL<br>TGQYPWPGRFPLPLEFFLLPPSFPLNMYDLSVYGRANMIPLLIAADSRYSRKTDKSPDLSDLFA<br>SRGDWGMPESRSLLTYVKRSLIGLPAQLHQAAKQRAVRYLFEHIEPDGTLYSYFSSTFLFIFALL<br>ALGYRNDDPRIRQAVRGLRSLRTTIDGHVHLQYTTASVVVNTALASYTLQEAGVPMTDRAIEKA<br>NRYLLSRQNVRYGDWAVHNPYSTPGGWGFSDVNTMNPDVDDTTAALRAIRQAAAKETAFRH<br>AWDRANQWLFSMQNDDGGFAAFEKNVSSRFWRYLPIEGAEFLLMDPSTADLTGRTLEYFGTF<br>AGLTKDQRAVSRAVDWLLSHQERNGSWYGRWGICYIYGTWAAITGLTAVGVPAHHPALQKAV<br>RWLLSIQNDDGGWGESCKSDGAKTYVPLGDSTPVHTAWALDALVAAAERPTLEMKAGFRALF<br>RLLHHPDWTASYPVGQGMAGAFYIHYHSYRYIFPLLALAHYEQKFGPLDD<br><br>>seq_ID 136<br>MVADERSALIDALKRSQSVDGSWRFPFETGISTDAYMIILLRTLGIHDEPLIQALVERIESRQDAN<br>GAWKLFADEGDGNVTATVEAYYALLYSGYRKKTDSHMQKAKARILEVGGLERVHLFTKVMLAL<br>TGQHSWPRRFPLPLVFFLLPPSFPLNMYDLSVYGRANMVPLLVVAERRYSRKTDNSPDLSDLA<br>ASRNDWRLPDTEALWSYVKRSLTGLPAWLHRAAEQRAVRYMLEHIEPDGTLYSYFSSTFLLIFA<br>LLALGYPKDDPHIARAVRGLRSLRTEIDGHTHMQYTTASVVVNTALASYALQEAGVPPTDRTIEK<br>ANRYLLSRQHIRYGDWAVHNPYGVPGGWGFSDVNTMNPDVDDTTAALRAIRRAAAKETAFRH<br>AWDRANRWLFSMQNDDGGFAAFEKNVGKRFWRYLPIEGAEFLLMDPSTADLTGRTLEYFGTF<br>AGLTKDHSAIARAIDWLLDHQEADGSWYGRWGICYVYGTWAAVTGLSAVGVPIDHPAMQKAV<br>RWLLSIQNDDGGWGESCKSDGAKTYVPLGASTPVHTAWALDALIAAAERPTPEMKAGVRALV<br>RMLHHPDWTASYPVGQGMAGAFYIHYHGYRYIFPLLALAHYEQKFGPFVD<br><br>>seq_ID 49<br>MLLYEKVYEEIARRTTALQTMQRQDGTWRFCFEGAPLTDCHMIFLLKLLGRDKEIEPFVKRLAS<br>LQTNEGTWKLYEDEVGGNLSATIQSYAALLASEKYTKEDANMKRAEMFINERGGVARAHFMTK<br>FLLAIHGEYEYPSLFHLPTPIMFLQNDSPLSIFELSSSARIHLIPMMLCLNKRFRVGKKLLPNLNHI<br>AGGGGEWFREDRSPVFQTLLSEVKKIITYPLSLHHKGYEEVERFMKERIDENGTLYSYATASFY<br>MIYALLALGHSIQSPIIQKAITGIASYIWKMERGSHLQNSPSTVVVDTALLSYALQEAQVPKASKVI<br>QNASAYLLRKQQTKKVDWSVHAPNLFPGGWGFSDVNTMIPDIDDTTAVLRALARSRGDENVD<br>NAWKRAVNWVKGLQNNDGGWGAFEKGVTSRILANLPIENASDMITDPSTPDITGRVLEFFGTY<br>AQNELPEKQKQSAINWLMNVQEENGSWYGKWGICYIYGTWAVLTGLRSLGIPSSDPSLKRAAL<br>WLEHIQHEDGGWGESCQSSVEKRFVTLPFSTPSQTAWALDALISYYEKETPIIRKGISYLLSNPY<br>VNEKYPTGTGLPGGFYIRYHSYAHIYPLLTLAHYTKKYRK<br><br>>seq_ID 62<br>MNIVIRISKGWVSNLLLDEKAHEEIVRRATALQTMQWQDGTWRFCFEGAPLTDCHTIFLLKLLG<br>RDKEIEPFVERVASLQTNEGTWKLYEDEVGGNLSATIQSYAALLASKKYTKEDANMKRAENFIQ<br>ERGGVARAHFMTKFLLAIHGEYEYPSLFHVPTPIMFLQNDSPFSIFELSSSARIHLIPMMLCLNKR<br>FRVGKKLLPNLNHIAGGGGEWFREDRSPVFQTLLSDVKQIISYPLSLHHKGYKEIERFMKERIDE<br>NGTLYSYATASFYMIYALLALGHSLQSSMIQKAIAGITSYIWKMERGNHLQNSPSTVVVDTALLSY<br>ALQEAQVSKDNKMIQNATAYLLKKQHTKKADWSVHAQALTPGGWGFSDVNTTIPDIDDTTAVL<br>RALARSRGNKNIDNAWKKGVNWIKGLQNNDGGWGAFEKGVTSKLLAKLPIENASDMITDPSTP<br>DITGRVLEFFGTYAQNELPEKQIQRAINWLMNVQEENGSWYGKWGICYIYGTWAVMTGLRSLG<br>IPSSNPSLTRAASWLEHIQHEDGGWGESCHSSVEKRFVTLPFSTPSQTAWALDALISYYDTETP<br>AIRKGVSYLLSNPYVNERYPTGTGLPGAFYIRYHSYAHIYPLLTLAHYIKKYRK |

Enzyme Sequences

>seq_ID 59
METLIDPEISRLTQRLLEDQEEDGAWRYCFENSLMTDAYMIVLIRSLGIKKERLVQELADRLLSQ
QEEKGFWKIYRDEVEGNLSATVEAYFALLWSGAVKEKDENMVKARDCILSGGGLDKVHSMTK
FMLAAHGQYPWDRFFPVPVEVILLPTYFPVSFTDFSAYARVHLAPLLLLKSERYIRKTSTTPDLS
YLLKDQEDFSFFREEERSFIEYVTSGVEAIAAFPANLNDLAKKTALNYMLARLEPDGSLYSYFSS
SFYMIIALLSQGYSRKDPLVVNAIKALISYQCKGDGYPHIQNSPSTIWDTALISHALQSSGVDSRN
AQILKASHYLYRHQHTQKGDWASEAPQTAPGGWGFSESNTINPDVDDTTAALRALKLDAYTDP
VKRMAWNRGVKWALSMQNKDGGWPAFEKNKNKDILSWVPMDGAEDAALDRSCADLTGRTL
EFLGNDAGMGRENSQVLKGIEWLMNNQENDGSWYGKWGICYIYGTWAALTGMMAAGMSAD
HQSIIKAIKWLYQIQNSDGGWGESCRSDKERKYISLGASTPSQTAWALDALISINDHPTKEIDRGI
ESLVRLLNTDDWRKEYPTGAGLPGRFYIHYHSYPYIWPLLALSNYKTKFLEVR >seq_ID 51
MVLYGRVCAEIERTITALHTMQQQDGAWRFCFEGSPLTDCHMIFLLRLLEKEEEIEPFVARLTSI
QTNEGTWKLYEDERAGNVSTTIQAYAALLASGMYTKEDVNMKRAEAFIQERGGIARSHFMTKF
LLALHGGYEYPRMFYFPTPILFLPEDSPLSIFELSSSARIHLIPMMICMNKRFTVSKTILPNLDHIS
GSSKSEWFREDRSSLFETILGEVKKFVTYPLSLHHKGDKEAERFMIERIDRNGTLYSYASATFY
MIYALLALGHHIQSPLIQQAVAGLRTYKWHMEAGIHLQNSPSTVVVDTALLSYALQEANVNESTP
MIQTATEYIWQRQHHEKKDWSLHAPTLSPGGWGFSDVNTTIPDVDDTTAALRALARSRKRNR
RIEEAWKKGVNWVKGLQNKDGGWAAFEKGVTNRFLTHLPLENSGDMMTDPSTADITGRVLEF
FGTYAPNELQDHQKNRAITWLMDVQENNGSWYGKWGVSYIYGTWAALTGLRAVGVANTHPA
LKKAVMWLERIQHRDGGWGESCRSSIEKRFVPLSFSTPSQTAWAIDALISYYDEETPVIRKGISY
LLEHAASHQEYPTGTGLPNGFYIRYHSYSYMYPLLTFAHYINKYRK >seq_ID 32
MLLYEKAHEEIVRRATALQTMQWQDGTWRFCFEGAPLTDCHMIFLLKLLGRDKEIEPFVERVA
SLQTNEGTWKLHEDEVGGNLSATIQSYAALLASKKYTKEDANMKRAENFIQERGGVARAHFMT
KFLLAIHGEYEYPSLFHLPTPIMFLQNDSPFSIFELSSSARIHLIPMMLCLNKRFRVGKKLLPNLN
HIAGGGGEWFREDRSPVFQTLLSDVKQIISYPLSLHHKGYEEIERFMKERIDENGTLYSYATASF
YMIYALLALGHSLQSSMIQKAIAGITSYIWKMERGNHLQNSPSTVVVDTALLSYALQEAQVSKDN
KMIQNATAYLLKKQHTKKADWSVHAPALTPGGWGFSDVNTTIPDIDDTTAVLRALARSRGNKNI
DNAWKKGGNWIKGLQNNDGGWGAFEKGVTSKLLAKLPIENASDMITDPSTPDITGRVLEFFGT
YAQNELPEKQIQRAINWLMNVQEENGSWYGKWGICYLYGTWAVMTGLRSLGIPSSNPSLTRA
ASWLEHIQHEDGGWGESCHSSVEKRFVTLPFSTPSQTAWALDALISYYDTETPAIRKGVSYLLS
NPYVNERYPTGTGLPGAFYIRYHSYAHIYPLLTLAHYIKKYRK >seq_ID 31
MSTIHENVRSRQKKTISLLRETQNADGSWSFCFEGPILTNAFLILLLTSLGDNDKELIAELAEGIR
AKQRPDGTFANYPDDRKGNVTATVQGYAGLLASGLYSRSEAHMIQAERFIISNGGLRNVHFMT
KWMLAANGLYPWPALHLPLSFLVIPPTFPLHFYQFSTYARIHFVPMAVTLNKRFSLKNPNVSSL
AHLDRHMTKNPFTWLRSDQDENRDLSSLFAHWKRLLQIPAAFHQLGLRTAKTYMLDRIEEDGT
LYSYASATIFMVYGLLALGVSRHSPVLRKALAGTKALLTSCGNIPYLENSTSTVVVDTALLNYALM
KSGISDNDQMITSAARFLRERQQKKVADWAVHNPHAEPGGWGFSNINTNNPDCDDTAAVLKAI
PRKLYPASWERGLSWLLSMQNSDGGFSAFEKNVHPLVRLLPLESAEEEAAIDPSTSDLTGRVL
HCLGEAGLSSDHPQIEKAVQWLIRHQEEDGSWYGRWGVCYIYGTWAALTGMKACGVSQNHP
AVKKAIRWLKSIQNEDGSWGESCKSAEEKTYVPLSYGTLVQATAWAAEALLQYEKTHHQAVTKG
ISFLIENRHYEGAAFSYPTGIGLPKQFYIRYHSYPYVFSLLALSTFMKMSEKEEEK >seq_ID 48
MLLYEKAHEEIARRATALQTMQRDGTWRFCFEGAPLTDCHMIFLLKLLGRDKEIEPFVKRLAS
LQTNEGTWKLYEDEVGGNLSATIQSYAALLASKKYTKEDANMKRAENFIKERGGVARAHFMTK
FLLAIHGEYEYPSLFHLPTPIMFLQNDSPLSIFELSSSARIHLIPMMVCLNKRFRVGKKLLPNLNHI
AGGGGEWFREDRSPLFQTLLSDVKQIISYPLSLHHKGYEEVERFMKERIDENGTLYSYATASFY
MIYALLALGHSLQSSLIQKAIAGITSYIWKMERGSHLQNSPSTVVVDTALLSYALQEAHVPKDHKM
IQQTITYLLKKQHTKKADWSVHALALTPGGWGFSDVNTTIPDVDDTTAVLRALARSRGNENIDN
AWKKGVNWIKGLQNNDGGWGAFEKGVTSKLLANLPIENASDMITDPSTPDITGRVLELFGTYT
QNELPKKQKQSAINWLMNVQERNGSWYGKWGICYIYGTWAVMTGLRSLGIPSNNPSLKRAAL
WLEHIQHEDGGWGESCQSSVEKRFVTLPFSTPSQTAWALDALISYYDKETPTIRKGVSYLLAN
PYVNEKYPTGTGLPGGFYIRYHSYAQIYPLLTLAHYTKKYQK >seq_ID 34
MNIVIRISKGWVSNLLLYEKVHEEIARRTTALQSMQRDGTWRFCFEGAPLTDCHMIFLLKLLG
RDKEIEPFVKRLASLQTNEGTWKLYEDEVGGNLSATIQSYAALLASEKYTKEDANMKRAEMFIN
ERGGVARAHFMTKFLLAIHGEYEYPSLFHLPTPIMFLQNDSPLSIFELSSSARIHLIPMMLCLNKR
FRVGKKLLPNLNHIAGGGGEWFREDRSPVFQTLVSDVKKIITYPLSLHHKGYEEVERFMKERID
ENGTLYSYATASFYMIYALLALGHSLQSSMIQKAIAGITSYMWKMESGNHVQNSPSTVWDTALL
SYALQEAHVLKDNKMLQNATAYLLKKQHTKKADWSVHAPALTPGGWGFSDVNTTVPDVDDTT
AVLRVLARSRGNEKVDHAWQKGINWVKGLQNNDGGWGAFEKGVTSHILANLPIENASDMITD
PSTPDITGRVLEFFGTYAQNELPEKQKQSAINWLMNVQEENGSWYGKWGICYIYGTWAVLTGL
RSLGIPSSDPSLKRAALWLEHIQHEDGGWGESCQSSVEKRFVTLPFSTPSQTAWALDALISYY
DKETSVIRKGISYLLSNPYINETYPTGTGLPGGFYIRYHSYAHIYPLLTLAHYAKKYRK >seq_ID 47
MLLYEKVHEEIVRRATALQTMQWQDGTWRFCFEGAPLTDCHMIFLLKLLGREKEIEPFVERIAS
LQTNEGTWKLYEDEVGGNLSATIQSYAALLASKKYTKEDANMKRAENFIKERGGVARAHFMTK
FLLAIHGGYEYPSLFHLPTPIMFLQNDSPLSIFELSSSARIHLIPMMLCLNKRFRVGKKLLPNLNHI

Enzyme Sequences

AGGGGEWFREDRSPVFQTLISDVKQIISYPLSLHHKGYEEIERFMKERIDENGTLYSYATASFY
MIYALLALGHSPQSSMIQKAIAGLTSYIWKMGRGSHLQNSPSTVVVDTALLSYALQEARVSKDNK
MIQNATAYLLKKQHTKKADWSVHAPALIPGGWGFSDVNTTIPDIDDTTAVLRALARSRGNKNID
NAWQKGVNWIKGLQNNDGGWGAFEKGVTSKLLANLPIENASDMITDPSTPDITGRVLEFFGTY
AQNGLPEKQKQSAINWLMNAQEENGSWYGKWGICYIYGTWAVMTGLRSLGIPSSNPSLKRAA
SWLEYIQHEDGGWGESCHSSVEKRFVTLPFSTPSQTAWALDALISYYDTETPAIRKGVSYLLSN
PYVNERYPTGTGLPGAFYIRYHSYAHIYPLLTLAHYLKKYRK

>seq_ID 52
MRSILEDVKAFRQKTLAELQNRQRSDGSWRFCFEGPVMTDSFFILMLTSLGDQDSSLIASLAER
IRSRQSEDGAFRNHPDERAGNLTATVQGYTGMLASGLYDRKAPHMQKAEAFIKDAGGLKGVH
FMTKWMLAANGLYPWPRAYIPLSFLLIPSYFPLHFYHFSTYARIHVPMAITFNRRFSLKNNQIG
SLRHLDEAMSKNPLEWLNIRAFDERTFYSFNLQWKQLFQWPAYVHQLGFEAGKKYMLDRIEE
DGTLYSYASATMFMIYSLLAMGISKNAPVVKKAVSGIKSLISSCGKEGAHLENSTSTVVVDTALIS
YAMQESGVPEQHSSTSSAADYLLKRQHVKKADWAVSNPQAVPGGWGFSHINTNNPDLDDTA
AALKAIPFQRRPDAWNRGLAWLLSMQNKDGGFAAFEKDVDHPLIRNLPLESAAEAAVDPSTAD
LTGRVLHLLGLKGRFTDNHPAVRRALRWLDHHQKADGSWYGRWGVCFIYGTWAALTGMKAV
GVSANQTSVKKAISWLKSIQREDGSWGESCKSCEAKRFVPLHFGTVNQSSWALEALLQYERP
DDPQIIKGIRFLIDEHESSRERLEYPTGIGLPNQFYIRYHSYPFVFSLLASSAFIKKAEMRETY >seq_ID 188
MRSELLQLQSADGSWRLCFDSGTMPDSYFIIILRMLGYSQDEALIRQIASRILSRQLPNGTWKIY
PDEEDGNLDATAEAYFALLYSGFLTKLDPRMQLAKQFILSKGGLSKIRSLLTQAIFAAAGQASWP
KSMRIPLEVFFSDNGIGIDLFSLSGHARVHIVPIIMLANAQFVQHSASMPDLSDLFAGSSKRFEN
DSPWIAALATLIGSLSLSELLPFESPTPQEKAVQFLFDRLEPDGTLLTYTTATMFMILVLLMLGYS
SSSPLIHRMVSGIHSVICANSHVQIASSEVVVDTAMLVHALRKAGVNPTSTALENAGAYLRQRQQ
TQLGDWAIRNPGTPAGGWGFSNVNTLYPDVDDTTAALRAIQPYSSRTPELQADWQRGLNWVL
TMRNDNGGWPAFERQGSRLPITFFNFEGAKDIAVDPSTVDLTSRTLQFLGQELGMNAGNSWIE
STLRWVLSQQESNGSWYGRWGITYVHGTSAALQGLTAVGIAEDHPAVKKGVDWLLQVQNED
GGWGESCISDKVRRYVPLNFSTPSQTAWALDGLTAALPKPTPALERGVDALLQSLDRHDWTY
TYPTGGALPGSVYAHYASNNYIWPLLALSNIWQKYS >seq_ID 60
MGTLQEKVRRFQKKTITELRDRQNADGSWTFCFEGPIMTNSFFILLLTSLDEGENEKELISSLAA
GIHAKQQPDGTFINYPDETRGNLTATVQGYVGMLASGCFHRTEPHMKKAEQFIISHGGLRHVH
FMTKWMLAANGLYPWPALYLPLSLMALPPTLPIHFYQFSSYARIHFAPMAVTLNQRFVLINRNIS
SLHHLDPHMTKNPFTWLRSDAFEERDLTSILLHWKRVFHAPFAFQQLGLQTAKTYMLDRIEKD
GTLYSYASATIYMVYSLLSLGVSRYSPIIRRAITGIKSLVTKCNGIPYLENSTSTVVWDTALISYALQ
KNGVTETDGSVTKAADFLLERQHTKIADWSVKNPNSVPGGWGFSNINTNNPDCDDDTAVLKAI
PRNHSPAAWERGVSWLLSMQNNDGGFSAFEKNVNHPLIRLLPLESAEDAAVDPSTADLTGRV
LHFLGEKVGFTEKHQHIQRAVKWLFEHQEQNGSWYGRWGVCYIYGTWAALTGMHACGVDRK
HPGIQKALRWLKSIQNDDGSWGESCKSAEIKTYVPLHRGTIVQTAWALDALLTYENSEHPSVVK
GMQYLTDSSSHSADSLAYPAGIGLPKQFYIRYHSYPYVFSLLAVGKYLDSIEKETANET >seq_ID 56
MQDFKTKVNVYMDELHMQMQHRQREDGAFVFCFEGSMMTNAFLIMLLKAVGDTDQALVHQL
AEAIREKQNEDGSFSLYHDQAGHVTATVQGYCGMLVSGRYQQDEPHMEKAARYIRSKGGLKD
VHFMTKWMLAVNGMHPWPYFYAPLSFLLIPTYFPLHFYHLSAYARIHFVPMMIALNKRYTSHEQ
FPSLSHLDANMSKNPFDWFMAREERSTHHFLAYMRSYTALDSRFDFFGYEAAKRYMFDRLEK
DGTLYSYLSASIFMVYALMSLGYSPGHHLILKAVKGMKQLVTDCGGKKYAENSTSTVVVDTALV
SYASQRAGRTQDDPVIKKSFTYLLNRQQMKKADWAIHNRHAAPGGFGFSDLNTNNPDCDDTQ
IVLKAIPQTYAPVQWKRGFDWLLSMQNRDGGFSAFEKNQDHFLLRHLPLESAEDAAIDPSTPDI
TGRVLHLIASEENDKSPLMQRQKDHCVKWLLDHQEKDGSWYGRWGVCYIYGTWAALTGLKA
SCIPSSHPAVQKACRFLKTIQLEDGSFGESCKSSEVKRYVPLPFGTVVQTAWAAEALLQYVQP
DDKSILKAISFLIQHQHSSKALHYPVGIGLPKQFYITYHSYPFVFPMMACSTFLEEMRRKNE >seq_ID 58
MKNRNKGAGCMQLVKSEIERLKQQLLSEQTPDGSWNHPFDTGCMTDIYMIVLLRTLEEEDEEE
LIKELAKGILSRQGKDGAWRLFHDHHEGSLSLTIEAYYALLYSGYYEKNHPALVKARRVITGGG
LKKAGMYTKIMLALTGQYPWPLLFPVPMEVILLPRSFPLNMYDISVFGRSNLIPVILLGNKKFSRK
TALSPDLGDLSVRDDDDPWPELRSAEWRSLTSFLAAGVKALVGIPRQIRAWSIEKAREYMQSH
TEPDGTLYNYFSSTFYMIFALLALGGGPEEPAIRNAVAGLKRMTVKADGRTHIQYTTAAVWNTA
LISHALQEAGVVPPKENAIQKANQYLAGQQHRRFGDWIVHNTKAEPGGWGFSRFNTINPDVDDT
TAALRSLYQPAREKPHYDDIWKKGLLWTLSMQNRDGGWPAFERNVDKKLLHLLPIQGAEFILT
DPSTADLTGRTLEFLGKAGYADASLPPIKKAVKWLKKHQEPNGSWYGRWGICYIYGTWAAVTG
MAAVGVTLEDKSMKKGIDWLLSIQNEDGGWGESCRSDMEKKYIPLKESTLTQTAWAVDALAAA
GMADSTPSRKGAAFLVREGKRKDWTADYPMGQGMANFFYIHYHSYRCIWPLLALSHYIEKSEA
PD >seq_ID 57
MQDFKTKVNEYIDELHMQLQRRQREDGAFVFCFEGPMMTNAFLIMLLKAVGDSDQALVHQLA
EAIREKQNEDGSFSLYHDQAGHVTATVQGYCGMLVSGRYQQDEPHMEKAAHFIRSNGGLKDV
HFMTKWMLAVNGMHPWPYFYAPLSFLLIPTYFPLHFYHLSAYARIHVPMMIALNKRYTSHEQF
PSLAHLDANMSKNPFDWFMAREERSTHHFLAYMRSYTALDSRLDFFGYEAAKRYMFDRLEKD
GTLYSYLSASIFMVYALMSLGYSPGHHLILKAVKGMKQLVTDCGGRKYAENSTSNVVVDTALVS
YASQQAGRTQDDPVIKKSFTYLLNRQQMKKADWAIHNRHAAPGGFGFSDLNTNNPDCDDTQI
VLKAVPQTYAPVQWKRGFDWLLSMQNDGGFSAFEKNQNHFLLRHLPLESAEDAAIDPSTPDI

| Enzyme Sequences |
|---|
| AGRVLHLIALEENSMSPLMQRQKDHCVKWLLDHQEKNGSWFGRWGVCYIYGTWAALTGLKT<br>AGISSSHSAVQKACRFLKTIQLEDGSFGESCKSAEVKRYVPLPFGTVVQTAWAAEALLQYVQP<br>DDKVILKAISFLIQHQSSEALHYPVGIGLPKQFYITYHSYPFVFPMMACSTFLEEMRRKNE |

>seq_ID 61
MGTLQEKVRRFQKKTITELRDRQNADGSWTFCFEGPIMTNSFFILLLTSLDEGENEKELISSLAA
GIHAKQQPDGTFINYPDETRGNLTATVQGYVGMLASGCFHRTEPHMKKAEQFIISHGGLRHVH
FMTKWMLAANGLYPWPALYLPLSLMALPPTLPIHFYQFSSYARIHFAPMAVTLNQRFVLINRNIS
SLHHLDPHMTKNPFTWLRSDAFEERDLTSILLHWKRVFHAPPAFAFQQLGLQTAKTYMLDRIEKD
GTLYSYASATIYMVYSLLSLGVSRYSPIIRRAITGIKSLVTKCNGIPYLENSTSTVVVDTALISYALQ
KNGVTETDGSVTKAADFLLERQHTKIADWSVKNPNSVPGGWGFSNINTNNPDCDDTTAVLKAI
PRNHSPAAWERGVSWLLSMQNNDGGFSAFEKNVNHPLIRLLPLESAEDAAVDPSTADLTGRV
LHFLGEKVGFTEKHQHIQRAVKWLFEHQEQNGSWYGRWGVCYIYGTWAALTGMHACGLTESI
PVYKRLCVGSNPYKMMTEAGENPAKAPKSKHMYRFIEEPLYKRPGL >seq_ID 50
MAEAISYPRRVHIITTKFPVNFYDFSVFGRSNIAPILLLADSKFQIPKTTETPDISHLYVRELYVWVS
EDRGWNGFTKAINKGVNNLIGLPNELHTLGRKQAENYMLDRLEDDGTLLSYYSSTFFMIYALLS
VGYTKDHKVIKKAARGLLSMNTTVKDTIHIQYTTAHIWNTSLISHALQTAGASPDDTMVMRANH
YLLQRQHTKFGDWAIYQPNLGPGGWGFSHSNTFNPDVDDTTASLRSIQNSLHSHPNYQSSWY
RGLSFTLGMQNQDGGFPAFEKGVDKTFPLHLLPVQGAEFLLTDPSTPDLTGRTLEFLGESAHLY
KDSGAIKRGVNWLIENQRRDGSWYGRWGICYIYGTWAALTGLQAVGVSKEHPSVQEGIDWLK
SIQQDDGGWGESCESDSQKTYIPLSKSTVTQTAWAVDALIAYEKEETVEIKKGMEYLLENWNH
EDWTMDYPMGQGMAKAFYIHYSYRYVFPLLTMGHYMRKFM >seq_ID 199
MSETISCQRIQAAYQRSRAELLSLRNSTGHWTGELSTSALSTATAIMALEMIRRKRLPADLSLNT
YIDNGIRWLAEHQNSDGGWGDTVKSFSNISTTMLCHAVFHATKSTEQYVSHVVNARQYIDRVG
GVEAVVARYGKDKTFSVPILTHCALAGLVKWKTIPALPFELACLPARFYKTVRLPVVSYALPALIA
IGQVRHHFCKPRNPITRLIRKLAVKRSLKKLISIQPSNGGFLEAAPLTSFVTMSLAGMGLTDHPV
VQKGLQFLLDSVRPDGSWPIDTNLATWTTTLSVNALEGTLAEFEKTPIREWLLQQQYKELHPYT
SAEPGGWAWTDLPGGVPDADDTPGAILALLNLQPDEPDTQQPADLQVALRNGVKWLLDLQNS
NGGWPTFCRGWGALPFDQSAADISAHVIRALQAWLQTEPESAEAELRLRAERAVRKCFKYLAT
VQRPDGSWLPLWFGNQHVENDENPVYGTARVLAAYAQGEQCGSIQAEQGILFLKSVQNLDG
GWGGATSAPSSVEETALAVDTLLALGLEPADPVVAQGLNWLSGRVENGTYTETTPIGFYFAKL
WYFEQLYPIIFTVSALHRAETVLKKSADDNLRLSLEEEDYPIMSVKEK >seq_ID 75
MDQDRLQRCYAIARDDLLAQRNGQGHWTGELSTSALSTATAVSALQLVVRHDPAQSERLMPLI
EGGVRYLTEHQNPDGGWGDTDRSYSNIATTMLAVAALTIAERREALFEQLAFAENYIEAQGGIP
GLRRRYGKDKTFAVPILTNYALAGLVDWREVSPLPFELACLPQKFYKLVKLPVVSYAIPALVAIG
QARYFHRPPFNPLMRGLRGAAVKKSLAVLERMQPASGGYLEAAPLTSFWMSLASIGNASHPV
AQNGVQFLVDSVREDGSWPIDSNLANWVTTLSISALATGGDDIAELDCLPWVLANQYQETHPF
TGADPGGWGWTDLSGSVPDADDTPGAMLAIAHFFHSPRADNETRRQIASAAISGARWLLDLQ
NSDGGWPTFCAGWGTQPFDRSGSDLTAHAIRALHAWRSELGDLPVERAIERGLRYLQKQQR
DDGSWLPLWFGNQDIHDDENPIYGTVKVLLAYRDLGKMSSETAQRGAAWLAARQNEDGGFG
GGPSISTLCGGPGESSVEETALAIEALFAAENSNISAEIVPPAVGWLCQRVEEGSYVNCTPIGFY
FSKLWYYEKLYPRVMTVTSLGAALQANASVPPAPETVTTSSDH >seq_ID 325
MATSDPSLAEAIQNTRAHLLSLRNARGHWEGHLSNSALSTATAIVALHLVDAPLHSARIAQGVR
WLVLHQNKDGGWGDTTLSKSNLSTTLLCWSALSLCEPDRTEPIQHCEAWIKERTGSLEPEVIC
RAVVARYGKDKTFSVPILMLCAIGGRLGPEKEAWSRVLALPFELAAMPREWFGAIGLPVVSYAL
PALIAIGYARFYHAPPSLLNPLHALRKALWPRISPMLKLLQPSTGGYLEATPLTSFVTMALASAG
EKFHPCVPEAVRFLEDSQRPDGSWPIDTNLATWGTTLSTKALTATSEGREALDIPALKSWLLEQ
QYQEIHPFTNAAPGGWAWTDLPGGVPDADDTSGALVALWHLCEDEAERQALAPAVAKGVQW
LMDLQNRDGIPTFCRGWGTLPFDRSTPEITAHALHAWGLWQVNLPEELQQEVSLRIPRAIAFI
ARPPSRGAPGFNHVPLWFGNEHAKEEENHVYGTAQIMNHLLSSGLNTPEIKVILETGHRNLLA
WQQLDGGWSGSETGPASLEETAVSVAALALHTLHAGNRTRSSAEDAVAKGTQWLVQHTATG
TTFPSAPIGLYFARLWYHEQLYPVIWTLGALHAVETLSAAALPLRARASAPPQHPGVVRTKPIHI
APPSDP >seq_ID 135
MIPAERLRTAYRTARAALLAERVPEGHWVGELSTSALSTATAVMALHLVNPFTHRELIDAGRKW
LAEHQNADGGWGDTVKSFSNISTTMLCRAAFKLAGEKEYPETVQRVEEYLSRNAGALPTARAA
AIRARYGKDHTFSVPILMTCAVAKLVPWDEVPRLPFELACLPQSWYRFAKLPVVSYALPALIAIG
QCIHHHRRSQNPIRNTVRRLARGLSLKVLRRIQPTSGGYLEATPLTSFVVMALSSIRRRRAAAE
QQVIDEGVRFLVASVRPDGSWPIDTNLATWVTTLSVNALATAGDLEALDTKEQILAWLLKQQYK
ERHPYTGADPGGWAVVTDLPGGVPDCDDTPGALIALAHLDPKSDPQAVLSGLRWVLRLQNGD
GGAPTFCRGWGTLPFDRSGADLTAHSVRSLASWYRVVVGAGPPPIEHLRHRLKDLEFPLSGLF
WDVARRNPRFVRYLKKQQRSDGSWLPLWFGNQHAPDDINPVYGTARVLAAYRDLELKDAPE
CRRGIEFLLSVQNADGGWGGAKGCPSSVEETALAVEVLLDLADGDAVQKGVAWLAEAVESDR
FRDASPIGFYFAKLWYFEKLYPIIFTVAALGRAVKITSPAPAAESA >seq_ID 115
METLSRSRLEAALAKATQALLTELNPAGHWSGELSSSALSTATAIVALGAVDREQQRELIAGGM
RWLAQHQNADGGWGDTVKSRSNISTTALCWAAVSTSTEHAESAAKAEAWLTRAAGSMAQLV

Enzyme Sequences

PAIEARYGKDRTFSVPILMHLAICGRVSWSQIPALPFELAALPHQLFGALQLPVVSYALPALIAIG
QAIHHHAPPTNPLLNGLRKSARARTLEVLESIQPQNGGFLEATPLTSFVTMALASAGEAQHPVA
RRGVSFLQASVQRDGSWAIDTNLATWVTTLSIKALAHQPGALSPERALTLREWLLGQYVVEH
PYTHAAPGGWAWTDLPGGVPDADDTPGALLALLHLGVNDAPTRQAGQIGVRWLLDLQNRDG
CIPTFCRGWGALPFDRSSPDLTAHTLRAWTAWLPQLDESLKRRTLRAVTKAIHFLATHQRTDG
SWLPLWFGNEHAPDDENPLYGTAKVVIALRELLNRDFTLPNGMLERALCWLVERQDISGGWS
GAKNGPVSVEETALAVEALAGTGHVSATDRGAAWLTEQIEADTWREPAPIGFYFAKLWYYERL
YPQIWTVGALGRVAALRVGESESDTPAGLHRATSET

>seq_ID 208
MMAVVENSVSEVLDRRELRGTLDLLRGELLAQRTKDGHWTGELSASALSTATAISAMSAAVRS
GKLAGADKAALLEQIQSGRRWLADQQNDDGGFGDTDRSHSNIATSYLVLAAWTLSDQVTGET
TDANAISRLRNWIQLAGELDGLRRRYGKDKTFVVPILTNMAIAGLVPWKKVSALPFEAAVVPQS
MYRFVGMPVVSYAVPALVAIGQVKFLEGGGCLPPWSLVRRAAIEPSMKVLRSMQPSSGGYLE
ATPLTAFWMSLSASGRADHEVTQNGLRFLRDSMLPDGSWPIDTNLANWATSLATTALTMDPD
DDRSWSTNELIQWQRGCQYQERHPFTGADPGGWGWTDLTGSVPDADDTPGAIISLRMQATT
RPDPLCDDYSRDWPASDSSGSVSANALDTWKACDRGVDWLLGLQNRDGGWPTFCRGWGKL
PFDRSSNDLTAHALRAIACLPKRESAKRSRAVQRGLRFLRKNQQADGSWLPLWFGNQDRPEE
DNPIYGTSRVLVDVSPALGHDAISRGLYYLINSQNSDGGWGGGESVRETFGLPEGFISSVEETA
LAVEALVSVWVGRIPGNEGGQAAENDIPDGSPWDASMRSALRAAILSGTRWLIDAVQRERHQV
AWPIGFYFAKLWYYERLYPLVYTTAALGRVMQRDELLR >seq_ID 247
MEIQDEVDLLEPQESLTASADSAVDRALFWLLDAQYEDGYWAGILESNACMEAEWLLCFHVLG
IANHPMSRGLVQGLLQRQRADGSWDVYYGARAGDINTTVEVYAALRCQGYAADHPDIKRARD
WIQLQGGVKQVRVFTRFWLALIGEWPWEETPNLPPEILFFPRWFPFNIYHFAAWARATLVPLCI
LSARRMVVPLNKKSCLQELFPEDRSAVVALGKKAGAWSTFFYHADRALKKYQRTFKRPPGRQ
QAIKMCLEWILRRQDADGAWGGIQPPWIYSLMALKAEGYPVTHPVMAKGLAALDAHWSYERP
GGARFVQACESPVVVDTLLSSFALLDCGFSCTSSSELRKAVDWILDQQVLLPGDWQQKLPTVS
PGGWAFERANVHYPDVDDTAVALIVLAKVRPDYPDTARVNLAIERGLNWLFAMQCRNGGWGA
FDKDNDKDLLTKIPFSDFGETIDPASVDVTAHVLEALGLLGYRTTHPAVAKALEFIRSEQENDGC
WFGRWGVNYIYGTAAVLPALASLNMNMNQEFIRRAANWILGKQNNDGGWGESCASYMDDTQ
RGRGPSTASQTAWAMMSLLAVDGGTYAESLLRAEAYLKTTQTPEGTWDEPYYTGTGFPGYGI
GRREIKRQRSLQQHAELSRGFMINYNLYRHYFPLMALGRLAALRGA >seq_ID 148
MTSPFKHPISHALTSFNGIVTEPEQSVEQKAGAKVHQFPASLWKSKPGKAKSPLDIAIEGCRDF
FFREQLPKGYWWAELESNVTITAEYIMLFNFLSLVDHERQRKMSNYLLSKQTEEGFWTIYYGG
PGDLSTTVEAYFALKLTGYPADHPAMVKARAFILEKGGVIKSRVFTKIFLALFGEFDWLGVPSMP
VELNLLPNWAYVNVYEFSSWARATIIPLSIVMLKRPVHKLPPSQRVQELFVRPPRAIDYTFTKED
CIFTWKNFFIGLDHMLKVYERSPVRPFKKRAMGKAEEWVLEHQEETGDWGGIQPAMLNAVLA
LSALGYDNGHPAVAHGLKALENFCIESDEQIVLQSCISPVVVDTALALKALVDAGVPSDHPSLVK
GAQWLLEREVRRPGDWRVKSPDLEPGGWAFEFLNDWYPDVDDSGFVMIALKGVEVKDRKAM
NAAVKRGIDWCLGMQSKNGGWGAFDKDNTRHILNKIPFADLEALIDPPTADLTGRMLELMGTF
GYAKTYPAAQRALKFLKENQEPEGPWWGRWGVNYLYGTWSVLCGLAAIGEDLEQPYIKKAVN
WIKSRQNMDGGWGETCESYHDPTLAGMGESTASQTGWALLGLMAAGEVHSATVVRGVQYLI
STQSQDGTWDETQYTGTGFPKYFMIKYHIYRNCFPLMALGTYRTLTGGTA >seq_ID 149
MTSPFKHPISNALTSFNGNFAEPEQCVEQQTGAKVHHLPASIWKRKMGKAKSPLDVAIEGSRD
FFFQEQLPKGYVWVAELESNVTITAEYIMLFHFLGLVDRERQRKMSNYLLSKQTEEGFWPIYYG
GPGDLSTTIEAYFALKLSGYPADHPALAKARAFILEQGGVVKSRVFTKIFLALFGEFEWQGVPS
MPVELNLLPDWAYINIYEFSSWARATIVPLSVVMHSRPVRRVPPSARVQELFVRQPTAADYSFA
KNDGIFTWENFFLGLDRVLKVYEKSPLRPFKNMALAKAEEWVLEHQEPTGDWGGIQPAMLNA
VLALNVLGYQNDHPAVEQGLRALANFCIETEDQLVLQSCVSPVVVDTALALKALLDAGVPPDHP
SLVKGAQWLLDKEVTRPGDWRVKSPALEPGGWAFEFLNDWYPDVDDSGFVMIALKGIQVKDR
KSMDAAIKRGINWCLGMQSKNGGWGAFDKDNTRHVLNKIPFADLEALIDPPTADLTGRMLELM
GTFNYPITLPAAQRAIEFLKKNQEPEGPVWVGRWGVNYLYGTWSVLCGLAAIGEDMDQPYIRKA
VNWIKSRQNIDGGWGETCQSYHDRTLAGVGESTPSQTGWALLGLLAAGEMHSATVVRGVQY
LISTQNSDGTWDEQQYTGTGFPKYFMIKYHIYRNCFPLMALGTYRTLTRTQP >seq_ID 216
MTDVLTRELSPNSTRDRVRSCVSSARQYLLSLQHEEGWWKGELDTNVTMEAEDLLLRQFLGIS
DEQVTQETARWIRSCQREDGTWATFHGGPPDLSTTVEAYVALRLAGDAMDAAHLRKAREYIL
DSGGIESTRVFTRIWLALFGEWPWSRLPVLPPEMMLLPDWFPLNIYDWASWARQTVVPLTIVG
SLRPTRDLGFSVRELRTGIQRRDLESPLSWAGVFHGLDSVLHRLEKLPLKPLRKVALARAEQWI
LDRQESDGGWGGIQPPWVYSILALHLRGYPLDHPVLRKALDGLDGFTIRHRTENGWIRKLEAC
QSPVWDTALAMTALLDSGTPPNDPALVRAADWILRQEIRVSGDWRVRRPALEPSGWAFEFAN
DHYPDTDDTAEVVLGLQRVRHPEPHRVNAAVERATAWLVGMQSSDGGWGAFDADNTRTLCE
KLPFCDFGAVIDPPSADVTAHIVEMLAARGMADSESARRGVRWLLEHQEVDGSWFGRWGAN
HVYGTGAVVPALVACGISPQHEAVRAAVQWLVAHQNADGGWGEDLRSYVDRTWVGRGTSTP
SQTAWALLALLAAGERGEVVRRGVEWLMAAQRPDGGWDEPQYTGTGFPGDFYISYHMYRIV
FPLTALGRYLGRGGDVGTG >seq_ID 229
MTATTDGSTGASLRPLAASASDTDITIPAAAAGVPEAAARATRRATDFLLAKQDAEGVWVKGDL
ETNVTMDAEDLLLRQFLGIQDEETTRAAALFIRGEQREDGTWATFYGGPGELSTTIEAYVALRL

| Enzyme Sequences |
|---|
| AGDSPEAPHMARAAEWIRSRGGIASARVFTRIWLALFGVWVKWDDLPELPPELIYFPTWVPLNI
YDFGCWARQTIVPLTIVSAKRPVRPAPFPLDELHTDPARPNPPRPLAPVASWDGAFQRIDKALH
AYRKVAPRRLRRAAMNSAARWIIERQENDGCWGGIQPPAVYSIALYLLGYDLEHPVMRAGLE
SLDRFAVVREDGARMIEACQSPVVVDTCLATIALADAGVPEDHPQLVKASDWMLGEQIVRPGD
WSVKRPGLPPGGWAFEFHNDNYPDIDDTAEVVLALRRVRHHDPERVEKAIGRGVRWNLGMQ
SKNGAWGAFDVDNTSAFPNRLPFCDFGEVIDPPSADVTAHVVEMLAVEGLAHDPRTRRGIQW
LLDAQEADGSWFGRWGVNYVYGTGSVIPALTAAGLPTSHPAIRRAVRWLESVQNEDGGWGE
DLRSYRYVREWSGRGASTASQTGWALMALLAAGERDSKAVERGVAWLAATQREDGSWDEP
YFTGTGFPWDFSINYNLYRQVFPLTALGRYVHGEPFAKKSRAADAPAEAAPAEVKGS >seq_ID 113
MTDVIDKAVAATGPADPSQGAAATLQAAADHLLGLQDDAGWWKGELETNVTMDAEDLLLRQF
LGIRTEEVTREAGDWIRSQQRADGTWANFFDGPADLSTTIEAYTALRMAGDAKDAEHMRAART
YILDSGGIEASRVFTRIWLALFGEWQWSDLPVMPPELIYLPKWFPLNVYDWACWARQTVVPLTI
VNALRPVRPLGFDLKELRTGRRAPAQRGLFSTLDRALHVYERKPLRSVRDAALRRSADWIIAR
QEADGSWGGIQPPWVYSLMALNLLGYGVDHPVMRKGIEGLDRFTIRDERGRRLEACQSPVVV
DTVLAMTALRDAELPENHPALVKAADWVLGEEITNPGDWSVRRPRVAPGGWAFEFDNDGYPD
VDDTAEVVLALNRVAHPDAPAAIRRGVDWLEGMACKDGGYGAFDADNTRTLALKLPFCDFGA
VIDPPTADVTAHTLEAYAALGLANSRASQRALEWLVKAQERDGSWFGRWGANHVYGTGAVVP
AMVAVGVDPEDEMIRRAVRWLEEHQNDDGGWGEDLRSYRDKSWIGRGVSTASQTAWALLAL
LAAGEERGTAVEQGVRFLIRTQRADGTWDEDHYTGTGFPGDFYLNYHLYRLVFPISALGRYVR
AVGAAGDGGDAGHAGHAGTVS >seq_ID 236
MTATTDGGGAITGGADPRHDSTAAPAAAAAGPSGGGTGLPEGVREAVDRATAELLARQDPAG
VWVKGDLQTNVTMDAEDLLLRQFLGIRDEAVTRAAALFIRGEQQGDGTWATFHGGPPELSATIE
AYVALRLAGDPPDAPHMTRASAWIRAHGGIAAARVFTRIWLALFGVWVSWDRLPELPPELVFLP
PWVPLNIYDFGCWARQTIVPLTVNSALRPVRSAPFALDELHTDARDPVPAKPLPPLASWDGAF
QRMDKALHLYRRVAPRRLRKAAMAAAGRWIVERQENDGCWGGIQPPAVYSVIALHLLGYDLG
HPVMRAGLESLDRFAVWREDGARMEACQSPVVVDTCLAAIALADAGLPPDHPALVRAADWM
LGEEIRRPGDWAVRRPGLAPGGWAFEFHNDNYPDIDDTAEVVLALRRIRHPQPGGVEAAIARG
VSWTLGMQSKNGAWGAFDADNTSPFPNRLPFCDFGEVIDPPSADVTAHVVEMLAAEGRAADP
RARRGIAWLLAEQEPDGPWFGRWGTNYVYGTGSVVPALTAAGIAPSHPAVRRAVRWLESVQ
NEDGGWGEDQRSYRDRSWAGKGASTASQTAWALMALLSAGERDGDAVARGLAYLVETQRP
DGTWDEPYFTGTGFPWDFSINYHLYRQVFPLTALGRYLHGEPFGPERRNVPPAGES >seq_ID 134
MSLTSDPSPATPATQPTSARPGSLSDRRSRSGGSAVAGPVLVTTRPVAPVAKSGAVTPTATSG
AVTSTATSGPALLPDLATDLADPTGPLAGAASATVRAAGGAGTRTQQTGQLGSTELAGPQAD
QVADRAAAVLGRARDHLLGLQSEAGVWVKGELETNVTMDAEDLMLRQFLGILPPELAAETGRW
IRSKQQDDGGWPTFHGGPSDLSTTFEAYVGLRLAGDLPDAPHMLAAASFVRAHGGLAATRVF
TRIWMALFGEWPWDEVPVLPPELVLLPSWVPLNVYDFGCWARQTVVALTIVGHFRPVRSLGF
SIDELRVAAVRPDRAPLVSWTGVFQRLDAGLRRYQRHPVKTLRELALRRATEWVLARQEADG
GWGGIQPPWVYSIMALHLMGYSMDHPVLVAALDGLETFTVREQVREGDEVVTVRRLEACQSP
VVVDTALAVVALADAGLDARHPAMRKAGEWLVREEVTVPGDWRVRRPNLEPGGWAFEFANDI
YPDVDDTAEVVLAVRRLLGSGWDDVDPTFAKQARASVERAVNWSVGMRSANGAWGAFDAD
NVRELATKIPFCDFGEVIDPPSADVTAHMVEMLADLGRADHPVTQRAVRWLLDDQEPGGSWF
GRWGVNHVYGTGAVVPALISAGVAADHPAIRSAVRWLAHQHPDGGWGEDLRSYQDDAWV
GRGEPTASQTAWALLALLAADPMNEAVGRGVRWLCDTQLPNGTWDEPYYTGTGFPWDFSIN
YHLYRLVFPLTALGRYVTLTGRSAA >seq_ID 225
MTATTDGSTGAALPPRVTAASDTDTDIPVAAGVPDIAARAMRRATDFLLSRQSDQGVWVKGDL
ETNVTMDAEDLLLRQFLGIRDEGTTRAAALFIRGEQREDGTWATFHGGPGDLSATIEAYVALRL
AGDPPDAPHLARASAWIREQGGIAASRVFTRIWLALFGVWVKWEDLPELPPELIWFPAWVPLNI
YDFGCWARQTIVPLTIVSAERPVRPAPFPLDELHTDPARPNPPRALAPVTGWDGAFQRLDKAL
HVLRGAVPRRLRRAAMNTAARWIIERQENDGCWGGIQPPAVYSIIALHLLGYDLNHPVMRAGL
ESLDRFAVWREDGARMIEACQSPVVVDTCLATIALADAGLPADHPQLVKAADWMLGEQIVRPG
DWSVRRPHLPPGGWAFEFHNDNYPDIDDTAEVVLALRRVAHHDPERVDNAIGRGVRWNLGM
QSRNGAWGAFDVDNTSPFPNRLPFCDFGEVIDPPSADVTAHVVEMLAAEGLAHDPRTRRGVQ
WLLAEQEPNGSWFGRWGVNYLYGTGSVVPALTAAGISGSHPAIRRAVAWLESVQNDDGGWG
EDLRSYRDARGWSGRGASTASQTAWALMALLAAGERESRAVERGVEWLAATQHEDGSWDE
PYFTGTGFPWDFSINYHLYRQVFPLTALGRYVNGEPLAGKPRAAGAATAREDTGQEQSLAEAK
GS >seq_ID 223
MTATTDGSTGAANITGAPADDPTDTRTAANDVTDIARRAAERSVEHLLGRQDEQGVWVKGDLA
TNVTMDAEDLLLRQFLGIQDPATTRAAALFIRGEQLGDGTWNTFYGGPGDLSATIEAYVALRLA
GDRPDEPHMARASGWIRDQGGIAAARVFTRIWLALFGVWVKWDDLPELPPELMFFPKWVPLNI
YDFGCWARQTIVPLTIVSAKRPVRPAPFALDELHTDPDHPNPPRKLAPPTSWDGLFQRLDKGL
HLYHKVAPRPLRRIAMNVAARWIIERQENDGCWGGIQPPAVYSVIALHLLGLDHPVMKAGLA
SLDRFAVHREDGARMIEACQSPVVVDTCLATIALADAGLRPDHPALVKAADWMLAEEITRPGDW
SVRKPELAPGGWAFEFHNDNYPDIDDTAEVVLALRRVRHPDPARLEAAIARGVRWNLGMQSR
NGAWGAFDADNTSPFPNRLPFCDFGEVIDPPSADVTGHVVEMLAVEGLANHPRTREGIEWLLA
EQEACGAWFGRWGVNYVYGTGSVVPALITAGLPAGHPAIRRAVDWLESVQNDDGGWGEDLR
SYQEEKWIGHGESTASQTAWALLALLAAGRRDTASVTRGVWLTEAQQADGSWDEPYFTGT
GFPWDFSINYHLYRQVFPLTALGRYVHGDPFADRTDAAEGV |

Enzyme Sequences

>seq_ID 226
MTATTDGSTGAALPPRVTAASENDTDIPEAAGVPDIAAHAMRRATDFLLSRQDDQGVWVKGDL
ETNVTMDAEDLLLRQFLGIRDEDTTRAAALFIRGEQREDGTWATFHGGPGELSTTIEAYVALRL
AGDPPEAPHMARASAWIRERGGIAAARVFTRIWLALFGVWVKWEDLPELPPELIWFPSWVPLNI
YDFGCWARQTIVPLTIVSAKRPVRPAPFPLDELHTDPRRPRPPRPHAPPNTWDGAFQRLDRAL
HALRRAVPRRVRQAAMNAAARWIIERQENDGCWGGIQPPAVYSIALHLLGYDLRHPVMRAGL
ESLDRFAVWREDGARMIEACQSPVVVDTCLAAIALADAGLPADHPSLVKAADWMLGEQIVRPG
DWSVRRPHLPPGGWAFEFHNDNYPDIDDTAEVVLALRRVRHHDPERMDSAIGRGVRWSLGM
QSKNGAWGAFDVDNTSPFPNRLPFCDFGEVIDPPSADVTAHVVEMLAVEGLAHDPRTRRGIQ
WLLAEQEPDGSWFGRWGVNYLYGTGSVVPALAAAGIPGSHPAIRRAVAWLEKVQNDDGGWG
EDLRSYRHVREWSGRGASTASQTAWALMALLAAGERDSGAVERGVAWLAATQREDGSWDE
PYFTGTGFPWDFSINYHLYRQVFPLTALGRYVHGEPFSKKQTAARNGSAQPLAGVKGSR >seq_ID 219
MDPALSRAVDWLLEHQDPAGWWCGEFETNVTITAEHILLLRFLGLDPSPLRDAVTRYLLGQQR
EDGSWALYYEGPADLSTSIEAYAALKVLGLDPTSEPMRRALQVIHDLGGVAQARVFTRIWLAMF
GQYPWDGVPSMPPELIWLPPSAPFNLYDFACWARATITPLLIILARRPVRPLGCDLGELVLPGS
EHLLTRVPGSGPFVWVGDKVLKRYDHLVRHPGRDRACQRIVEWIIARQEADGSWGGIQSAWV
MSLIALHLEGLPLDHPVMRAGLAGFDRVALEDERGWRLQASTSPVVVDTAWAVLALRRAGLPR
EHPRLALAVDWLLQEQIPGGGDWQVRTGTIPGGGWAFEFDNDHYPDIDDTAVVVLALLEAGH
EDRVRNAVERAARWILAMRSTDGGWGAFDRDNAREVIHRLPIADFGTLIDPPSEDVTAHVLEM
LARLSFPSTDPVVARGLEFLQQTQRPDGAWFGRWGVNYIYGTWCAVSALTAFADTDATARAM
VPRAVAWLLDRQNADGGWGETCGSYEDPNLAGVGRSTPSQTAWAVLALQAAGLGQHPACR
RGLDFLRERQVGGTWEEREHTGTGFPGDFFINYHLYRHVFPTMALAGAATGMDSPR >seq_ID 220
FLGIRDEATTRSAALFIRGEQREDGTWATFHGGPPDLSTTVEAYVALRLAGDSPDAPHMTRAA
HWVRSQGGIAEARVFTRIWLALFGVWVPWDRLPELPPELIFLPPWAPLNIYDFGCWARQTIVPL
TVVSAKRPVRPAPFPLDELHTDPADPAPRARFAPLASWNGAFQRLDRALHAYRKVAPRALRRA
AMATAGRWIVERQENDGCWGGIQPPAVYSMIALHLLGYDLGHPVMRAGLESLDRFTLTREDG
SRMVEACQSPVVVDTCLATIALADAGVPADHPQLVRAADWMLDEQIERPGDWSVRRPHLAPG
GWAFEFHNDNYPDIDDTAEVVLALRRVRHPDTARMERAISLGVRWNLGMQSKNGAWGAFDV
DNTSSLPNRLPFCDFGEVVDPPSADVTAHVVEMLAAEGLAADPRTRRAVDWLLAEQEPSGAW
FGRWGVNYLYGTGSAVPALVDAGLPTTHPAIRRAVAWLESVQNDDGGWGEDLRSYREQGRM
ARGASTASQTGWALMALLAAGERESRAARRGVTFLAETQHEDGSWEEPYYTGTGFPWDFSIN
YHLYRQVFPLTALGRYTRGAAPEGA >seq_ID 125
MQTQNRVTSTQKVELSNLTQAIIASQNYILSRQYPEGYWWGELESNITLTAETVLLHKIWKTDKT
RPFHKVETYLRRQQNEQGGWELFYGDGGELSTSVEAYMALRLLGVTPEDPALIRAKDFILSKG
GISKTRIFTKFHLALIGCYDWKGIPSIPPWIMLFPDNFPFTIYEMSSWARESTVPLLIVFDKKPIFEI
EPAFNLDELYAEGVENVKYALPRNHNWSDIFLGLDKLFKWTEKNNLVPFHKKSLQAAEKWMLN
HQQESGDWGGIMPPMVNSLIAFKVLNYDVADPSVQRGFEAIDRFSIEEEDTYRVQACVSPVVVD
TAWVIRALVDSGLKPDHPSLVKAGEWLLDKQILEYGDWAIKNQGKPGGWAFEFINRFYPDLD
DSAVVVMALNGIKLPDENRKKAAINRCLEWMATMQCKPGGWAAFDVDNDQAWINEIPYGDLK
AMIDPNTADVTARVLEMVGSCGLKMDENRVQKALFYLEKEQESDGSWFGRWGVNYIYGTSGV
LSALAVIAPNTHKPQMEKAVNWLISCQNEDGGWGETCWSYNDSSLKGTGISTASQTAWAIIGL
LDAGEALETLATDAIKRGIDYLLATQTPDGTWEEAEFTGTGFPCHFYIRYHLYRHYFPLIALGRY
WKIGLKTPSVIPLN >seq_ID 228
MLARRATDRAVRHLLSRQDEQGVWVKGDLETNVTMDAEDLMLRHFLGIQNPDVLDAAGRYIRS
QQAADGTWATFHGGPPELSATVEAYVALRLAGDPPDAPHMAAASAWVRNNGGVASSRVFTRI
WLALFGVWVRWEDLPELPPEIIYFPPWLPLNLYDFGCWARQTIVPLTVVSAKRPVRPAPFSLDE
LHADPRRPNPPRPAAPLASWDGAFQRLDRALHLYRKVALRPLRRAALRSCARWIVERQENDG
CWGGIQPPAVYSVIALHLLGYDLDHPVMRAGLESLDRFAVVVREDGSRMIEACQSPVVVDTCLA
VIALADAGLAPDHPALVKSADWMLAEEIDRPGDWSVKRPRLAPGGWAFEFDNDNYPDIDDTAE
VILALRRVDHPRPERIAAAVRRGVRWTLGMQSRNGAWGAFDVDNTSPLPNRLPFCDFGEVIDP
PSADVTAHVVEMLAHEGGARDPRTRRAVGWLLAEQEPSGAWFGRWGTNYVYGTGSVVPALV
AAGLPATHPAIRRAVRWLESVQNEDGGWGEDQRSYPDPEWIGHGASTASQTAWALLALLAAG
ERESKAVERGVGWLAATQDQDGSWDEPYFTGTGFPWDFSINYHLYRLVFPLTALGRYVSGEA
TGARPRRT >seq_ID 241
MTATTDGSTGALPPRADAASEHDIETPEAAGVREAAVRAARRATDFLLSRQDAQGVWVKGDLE
TNVTMDAEDLMLRQFLGVLDEKTAQAAALFIRGEQREDGTWASFYGGPGELSTTIEAYVALRL
AGDAPDSPHLAKASAWIREQGGIAAARVFTRIWLALFGVWVKWEDLPELPPELIWFPKWVPLNI
YDFGCWARQTIVPLTIVSAKRPVRPAPFPLDELHTDPARPNPPRPLAPAFSWDGAFQRMDKGL
HALRKVAPRGLRRAAMNAAARWIIERQENDGCWGGIQPPAVYSIIALHLLGYDLQHPVMREGL
ASLDRFAVWREDGARMVEACQSPVVVDTCLAAIALVDAGLPADHPQLVKAADWMLGEEIVRPG
DWSVRRPGLPPGGWAFEFHNDNYPDIDDTAEVILALRRITHHDPVRVDKAVGRGVRWTLGMQ
SKNGAWAAFDVDNTSPFPNRLPFCDFGEVIDPPSADVTAHVIEMLAVEGLAHDPRTRRGIEWL
LAEQEPDGSWFGRWGVNYVYGTGSVVPALVAAGLPGAHPAIRRAVSWLESVQNDDGGWGE
DLRSYKYVKEWSGRGASTASQTAWALMALLAAGERDSKAVERGVEWLAATQREDGSWDEPY
FTGTGFPWDFSINYHLYRQVFPLTALGRYVHGEPFADRLKGS

| Enzyme Sequences |
|---|

>seq_ID 238
MHEGEAMTATTDGSTGAATPPATTASAPLHLSPEARETHEATARATRRAVDFLLARQSDEGW
WKGDLATNVTMDAEDLLLRQFLGIRDEATTRAAALFIRGEQQEDGTWNTFYGGPGDLSATIEG
YVALRLAGDSPEAPHMRKASAFVRAQGGVARARVFTRIWLALFGVWVKWEDLPEMPPELMFF
PKWAPLNIYDFGCWARQTIVPLIVVCAQRPVRPAPFALEELHTDPADPDPAQPAPPVVSWDNV
FHKLDKLLHGYRRIAPRRVREAAMRAAATWIVERQENDGCWGGIQPPAVYSIMALNLLGYDLD
HPVLRAGLASLDRFAVWREDGARMIEACQSPVVVDTCLATVALADAGVPADHPQMIKAADWML
AEQIVRPGDWVVRRPDLPPGGWAFEFHNDNYPDIDDTAEVVLALRRVAHPDATRVDKAVRRA
VDWNVGMQSKNGAWGAFDADNTSPFPNRLPFSDFGEVIDPPSADVTAHVVEMLAEEGLAHH
PRTRRGIEWLLKNQEGNGSWFGRWGVNYVYGTGAVVPALVAAGLPASHPAIRRSVSWLGQV
QNEDGGWGEDLRSYQDSAWHGRGHSTASQTAWALLALLAAGERETEQVRRGIAYLVETQTE
DGTWDEPWFTGTGFPWDFTINYHLYRQVFPVTALGRYLNGTGPGEN >seq_ID 237
MRRRRSPRGPGAGPEADYGPARASAPDRLRGDAARGDAARRVQDATARAIRNLLGRQDPAG
VWVKGDLETNVTMDAEDLLLRQFLGIRDEAVTQAAALFIRREQREDGTWATFHGGPPELSATIE
AYVALRLAGDAPDAPHMATASAWIRAHGGLAAARVFTRIWLALFGVWVDWENLPELPPELVLLP
PWVPLNIYDFGCWARQTIVPLTWSAMRPVRPAPFALDELHTDARVPVPPRRMAPPTTWNGA
FQWMDRALHVYRRFAPRRLREAAMASAGRWIIERQENDGCWGGIQPPAVYSVIALHLLGYDL
GHPVMRAGLESLDRFAVWREDGSRMIEACQSPVVVDTCLAAIALADAGVRPDHPALVKAADW
MLGEEIVRTGDWAVRRPGLAPGGWAFEFHNDTYPDIDDTAEVVLALRRIRHPDPARVEAAIAR
GVSWNLGMQSRGGAWGAFDADNTSPFPNRLPFCDFGEVIDPPSADVTAHVVEMLAAEGRAA
DPRTRRGIAWLLAEQEPEGPWFGRWGTNYVYGTGSVVPALTAAGLSPGHPAIRRAVLWLESV
QNPDGGWGEDQRSYQDRAWAGKGESTPSQTAWALMALLSAGERDAKTVERGIAYLVETQLA
DGGWDEPHFTGTGFPWDFSINYHLYRHVFPLTALGRYLYGEPFGHDGRHIGAHLGDRTGVPA
EGV >seq_ID 239
MDFLLDRQSDEGWWKGDLATNVTMDAEDLLLRQFLGIRDEATTQAAALFIRGEQQEDGTWNT
FYGGPGDLSATIEGYVALRLAGDSPEAPHMRKASAFVRAGGGVARARVFTRIWLALFGWWKW
EDLPEMPPELMFFPKWAPLNIYDFGCWARQTIVPLIVVCAQRPVRPAPFALEELHTDPADPNP
AQPAPPVASWDNVFHKLDKMLHGYRKVAPRRVREAAMRAAATWIVERQENDGCWGGIQPPA
VYSIIALHLLGYDLDHPVLRAGLESLDRFAVVVREDGARMIEACQSPVVVDTCLATVALADAGVPA
DHPQMIRAADWMLAEQIVRPGDWVVRRPDLPPGGWAFEFHNDNYPDIDDTAEVVLALRRVAH
PDATRVDKAVRRAVDWNAGMQSKNGAWGAFDADNTSPFPNRLPFSDFGEVIDPPSADVTAH
VVEMLAEEGLAHHPRTRRGIEWLLENQEANGSWFGRWGVNYVYGTGAVVPALVAAGIPAAHP
AIRRSVSWLGQVQNEDGGWGEDLRSYQDTAWHGRGHSTASQTAWALLALLAAGERDSEQV
RRG1AYLVETQTEDGTWDEPWFTGTGFPWDFTINYHLYRQVFPVTALGR >seq_ID 235
MTQTVPRTAASAPAARTAADTVAAAVQFLRREQDRAGVWVKGELATNVTMDAEDLLLRHFLGI
LTPQIAEESARWIRSQQRADGTWANFPDGPADLSTTVEAWVALRLAGDPADAPWLATAAEWI
REHGGIEATRVFTRIWLAMVGQWSWDDLPSLPPELIFLPSWFPLNVYDFACWARQTIVPLTIVG
TLRPARKLPFDVAELRTGKRPPKPRAPWTWDGVFQNLDTALHAYAKLPLNPVRKLALKQAAE
WILARQEADGSWGGIQPPWVYSILALHLLGYSLDHPALKAGIAGLDGFTIREKTDQGWVRRLEA
CQSPVVVDTALAMTALLDAGVSPGDESLVRAAEWMLGEEIRVPGDWAVRRPSLKPGGFAFEFA
NDGYPDTDDTAEVVLALRRMGKPDHLRIREAVDRSVAWLEGMQSSDGGWGAFDADNTQVLT
TRLPFCDFGAVIDPPSADVTAHVVEMLAAEGKADTRECRRGIRWLWDNQEADGSWFGRWGA
NYVYGTGAVVPALVAAGVPGTDPRIRRAVRWLAEHQNDDGGWGEDLRSYDDRSWAGRGDS
TPSQTAWALLALLAAGERESTWARGVEWLCERQRPDGGWDEDKHTGTGFPGDFYLSYHLY
RVVFPLSALGRYVRGGS >seq_ID 159
MSGQSNFTGGKKMTPAEGSSSPAPALLEKAAPSIELDERSDPLSRTLARAVSWLVAAQDGAG
HWVAPLEADATIPSEYVFLHEVLGRPLDPVRRDKIVRAILSVQGKEGAWPLFHDGDPDISATVK
AYQALKLCGFDPSHPALVRAREWVLSQGGAGKVNVFTRIALAIFGQYSWTKIPALPAEMVLLPS
WFPFSIYSVSYWSRTVIVPLLFIYHHKPLVRLSPERGISELFDPARPDGESFAPSPDFFSLRNLFL
LLDKVLQWVNRHPPGFLRKKALSFAMEWMVPRLKGEGGLGAIYPAMANSAVALSLEGYELDH
PLMQRVLASIDDLLIEGEKEVLVQPCVSPVVVDTALAMGALIEAGISPDSPTVDRAMEWFCAREV
RTRGDWAIRAPDCEPGGWAFQFENDYYPDVDDTAMVLMGMAKILPARPDLAARMEGVFRRA
TLWVMAMQGTDGGWGAFDRDNDLLFLNHIPFADHGALLDPSTADLTGRVLELLGALGYGPDF
PPAARAIRYLRREQEEDGSWFGRWGVNYIYGTWSVVAGLKSIGVPMSEPWVMRSMEFLLAR
QNPDGGWGEDCLSYASRDFAGRGASTPSQTAWALIALLHGGHAGHMAVRQGVDYLIQQMTP
EGTWNEELFTGTGFPRVFYLRYHMYRHYFPLWALALYRNMTERGRALGHERVDFWKTAPYA
PIARSV >seq_ID 232
MTATTDGSTGALPPRAPSASDTDHGTPVAAGVQEAALHAVGRATDFLLSRQDAQGVWVKGDL
ETNVTMDAEDLLLRQFLGIRDDATTRAAALFIRGEQRPDGTWATFYGGPPDLSATVEAYVALRL
AGDDPAAPHMAKASAWIRARGGIAAARVFTRIWLALFGVWVKWDDLPEMPPEIVYFPTWMPLNI
YDFGCWARQTIVPLTVVSAKRPVRPAPFPLDELHTDPGRPNPPRPLDRLGSWEGAFQRLDRA
LHGYHKVALKRLRRAAMNRAARWIVERQENDGCWGGIQPPAVYSVIALHLLGYDLGHPVMRA
GLESLDRFAVVVREDGARMIEACQSPVVVDTCLATIALADAGLPPDHPQLVKAADWMLGEEIVRP
GDWSVKRPQLPPGGWAFEFHNDNYPDIDDTAEVVLALRRVRHPDPERVERAVRRGVRWTLG

| Enzyme Sequences |
|---|
| MQSGNGAWAAFDADNTSPFPNRLPFCDFGEVIDPPSADVTAHVVEMLAAEGLSHDPRTRRGI<br>EWLLAEQEPGGAWFGRWGVNYVYGTGSVVPALVTAGLPAAHPAIRRAVAWLETVQNDDGG<br>WGEDLRSYPDPAEWGGKGASTASQTAWALLALLAAGERDGKATERGVAWLARTQREDGSW<br>DEPYFTGTGFPWDFSINYHLYRQVFPLTALGRYVHGEPAVLKPGTR |

>seq_ID 224
MTATTDGSTGAANLRAAAASDPTESTSAAPDMMAVARHAAERSVEHLLGRQDEQGWWKGDL
ATNVTMDAEDLLLRQFLGIQDPETVKAAARFIRGEQLGDGTWNTFYEGPPDLSATVEAYVALRL
AGDRPDDPHMIRAAGWVREQGGIAESRVFTRIWLALFGVWVKWDDLPELPPELMFFPKWVPL
NIYDFGCWARQTIVPLTIVSAKRPVRPAPFALDELHTDPACPNPSRPTAPAASWDGVFQRLDKA
LHLYHKVAPRRLRRIAMNEAARWIIERQENDGCWGGIQPPAVYSVIALHLLGYDLDHPVMRAGL
ESLDRFAVWREDGARMIEACQSPVVVDTCLATIALADAGVSPDHPALVRAADWMLGEEIVRPG
DWAVRKPGLAPGGWAFEFHNVNYPDIDDTAEVALALRRVRHPDPARVDAAIERGVRWNLGM
QSRNGAWGAFDADNTSPFPNRLPFCDFGEVIDPPSADVTGHVVEMLAVEGRAHDPRTRRGV
EWLLAEQEASGAWFGRWGVNYIYGTGSVVPALIAAGLPAAHPSVRRAVDWLRSVQNDDGGW
GEDLRSYREEKWIGHGSSTASQTGWALLALLAAGERETRSVERGVAWLAATQQADGSWDEP
HFTGTGFPWDFSINYHLYRQVFPLTALGRYVYGDPFATATAIGAGTGKGA >seq_ID 243
MSISALQTDRLSQTLTQSVVAAQQHLLSIQNPEGYVVWANLESNASITAEVVLLHKIWGTLDSQP
LAKLENYLRAQQKTHGGWELYWNDGGELSTSVEAYMGLRLLGVPASDPALVKAKQFILHRGG
VSKTRIFTKFHLALIGCYRWQGLPSLPAWVMQLESPFPFSIYELSSWARGSTVPLLIVFDKKPVY
PLQPSPTLDELFTESAENVRWELEEKGDWSDAFLWLDKAFKLAESVDLVPFREESIRKAEKWV
LERQEPSGDWGGIIPAMLNSMLALRALGYSVSDPVVRRGFQAIDNFMVESETECWAQPCISPV
WDTGLAVRSLTDSGLSPNHPALVKAGEWLLDKQILSYGDWSVKNPQGQPGGWAFEFENSFY
PDVDDTAVVAMALQDITLPNEPLKRRAIARAVRWIATMQCKTGGWAAFDINNDQDWLNDIPYG
DLRAMIDPSTADITGRVLEMHGRFAADLDLANSYAADLSPYRLSRGLNYLIKEQELDGSWFGR
WGVNYIYGTGQALSALALIAPERCRIQIERGIAWFVSVQNADGGWGETCESYKDKSLKGKGIST
ASQTAWALLGLLDVSFCLDPAAKIAVDRGIQYLVSTQSEGTWQEEESFTGTGFPQHFYLRYRLY
CHYFPLMALGRYQRVINSSAGI >seq_ID 197
MTSGTFGAKRVDLLAAFEHSAPAEKTRETCVGLQTAIARTRQYLLDQQHSEGFFVAELEGDTIL
ESEYILLLAFLNEGQSPDAQAAARYLLTKQNTDGSWSNFPGGPIDVSCAVKAYLALRITGHAAD
EPALIRAREAILQAGGVERVNSFTRFYLAMLGLIPYSLCPAVPPEVVLLPDWFPINLSQMSAWSR
TIWPLSLLWAFQPAVELNDADGHQITIEELYASPEKQLPRFIRGVNHESNSNGWMNWSRFFFR
VDQCLKSIESYGIKPLRSRAVRKCVQWILDRQEMSDGLGAIFPPIVWTLIGLKCAGFDDQHPMV
QKQRDELNRLMLREQDALRLQPCLSPVVVDTAISIIALRESGVEPDHPALSKARNWLLSKEVRHA
GDWSKAHPETPVSGWYFEFNNEFYPDVDDTAMVLIALASTLPEEATPLAISHGVLPVQTGWSA
ESTSRVQALKQLENHRPVLEAMGRGVQWLKALQSKDGGWGAFDSDINKELLTKVPFADHNAM
LDETNADISARVLEAYAAVGISFNDPSVQRALEFIWNDQEDDHAWYGRWGVNYIYGTWQVLV
GLTAIGISAHDPRLVRAAGWLKSKQQACGGWGETPATYDNPTLRGQGTPTASQTAWAVLGLIA
AGEQNSIECQRGVEFLLKTQKHNGTWDEEEFTGTGFPRVFYLRYHYYPLYFPLMALGRFARA
GGRVNFAG >seq_ID 158
MTTNAAATSARSGEDAIRQVSGQQLETAIASARNSLLALQRPDGHFVFELEADATIPAEYVLMR
HYLAEPVDAVLEEKIARYLRRIQSDDGGWPLFRDGASNISASVKAYYALKMIGDAPNAPHMQKA
RAWILAQGGASHSNVFTRNLLALFGAIPWSGVPVMPVEIMLLPKWFPPFHIDKISYWARTVLIPLT
VLNALKPVARNPKGVGIAELFVTPPDQVRNWPKGPHQKFPWSQVFGGIDRVLRLFEPAFPKSL
RKKSIDKAVAFATERLNGEDGLGGIFPPAMVNALLVYDALGYPHDHPDYVTARGSIEKLLVIKDDE
AYCQPCLSPVWDTALAVHALMESGVAQADQNVDRALAWLKPLQVLDTVGDWAASRPGVRPG
GWAFQYANAYYPDVDDTAVVVMAMDRAAGGDAAKRDHYRESMARGREWVAGVQSKNGGW
GAFDADNTYEYLNQIPFSDHGALLDPPTADVSARCVSMLAQLGERRETSPVLDKAMRYLESTQ
EKDGSWYGRWGMNYIYGTWSVLCALNAAGVAPSAPSMRKAADWLLSIQNSDGGWGEDGES
YSLDYKGYEPAPSTASQTAWALMGLMAAGEVDHPAVQRGVAYLAAKQGSDGFWGEERFTAT
GFPRVFYLRYHGYSKFFPLWALARYRNLNAANSKSVLVGM >seq_ID 77
MAADGSALSESRLSSEALDRAVLSAHTALSQAQQDDGHWVYELEADATIPAEYILLEHFMDRID
DALEQKIAIYLRRIQSEEHGGWPLYHNGKFDLSATVKAYFALKAVGDDINAPHMQRAREAILDH
GGAERSNVFTRSQLALFGEVPWRATPVMPVELMLLPAKAFFSVVVNMSYWSRTVIAPLLVLAAL
RPVAANPRQVHVRELFVTPPEKVQDWIRGPYRSAWGYVFKGLDSVLRPVVPPIPEKTHKKAIQ
AALDFIEPRLNGKDGLGAIYPAMANVVMMYRAMGVPDEDPRAKTAWEAVQALIVEKDDEAYC
QPCVSPIWDTGLSGHAMIEAASGPNGIAPEKTVAELKKASAWLRSKQILNVKGDWAVRNPNLA
PGGWAFQYGNDYYPDVDDTAVVGMLLHREGDPTNAEAIERARTWIVGMQSTDGGWGAFDID
NNKDVLNHIPFADHGALLDPPTADVTARCISFLAQLRNPEDEPVIQRGLEYLRKEQEKDGSWFG
RWGTNYIYGTWSALCALNAAGVSHDDPAVVKAVEWLRSVQRADGGWGEGCESYEGGPHGT
YGESLPSQTAWAVLGLMAAGRRDDPAVTRGIAWLADQQDANGEWHEDPYNAVGFPKVFYLR
YHGYKQFFPLMALARYRNLESSNTRRVSFGF >seq_ID 6
MTVSTSSAFHHSSLSDDVEPIIQKATRALLEKQHQDGHWVFELEADATIPAEYILLKHYLGEPED
LEIEAKIGRYLRRIQGEHGGWSLFYGGDLDLSATVKAYFALKMIGDSPDAPHMLRARNEILARG
GAMRANVFTRIQLALFGAMSWEHVPQMPVELMLMPEWFPVHINKMAYWARTVLVPLLVLQAL
KPVARNRRGILVDELFVPDVLPTLQESGDPIWRRFFSALDKVLHKVEPYWPKNMRAKAIHSCV
HFVTERLNGEDGLGAIYPAIANSVMMYDALGYPENHPERAIARRAVEKLMVLDGTEDQGDKEV

Enzyme Sequences

YCQPCLSPIWDTALVAHAMLEVGGDEAEKSAISALSWLKPQQILDVKGDWAWRRPDLRPGGW
AFQYRNDYYPDVDDTAVVTMAMDRAAKLSDLHDDFEESKARAMEWTIGMQSDNGGWGAFDA
NNSYTYLNNIPFADHGALLDPPTVDVSARCVSMMAQAGISITDPKMKAAVDYLLKEQEEDGSW
FGRWGVNYIYGTWSALCALNVAALPHDHLAIQKAVAWLKNIQNEDGGWGENCDSYALDYSGY
EPMDSTASQTAWALLGLMAVGEANSEAVTKGINWLAQNQDEEGLWKEDYYSGGGFPRVFYL
RYHGYSKYFPLWALARYRNLKKANQPIVHYGM

>seq_ID 89
MNDLTNSSAPGARPDDATPSAAGPTPAEAAGGAVAPSRAVQPADTQTAATGAAGAAAAVGAT
PAELAATAPASSGTPAGASAAPAPSGTPSVDAPAELASAAPAPSGATPAATATAATAPAPARA
ASIDAPALAAADLDAAITRATDALLAAQQADGHWIYELEADSTIPAEYVLLVHYLGETPNLELERK
IARYLRRVQLPGGGWPLFTDGAPDVSASVKAYFALKMICDDANAEHMVRARNAIHAMGGAEM
SNVFTRIQLALFGWPWFAVPMMPVEIMLLPQWFPFHLSKVSYWARTVTVPLLVLSAKRPLARN
PRGVRVDELFVAPPVNAGLLPRAGHQSPAWFACFRLLDGLLRLTDGLFPRYTRERAIRQALQF
VDERLNGEDGLGAIYPAMANSVMMYAALGYPEDHPNRATARRAIEKLLVIHDDEAYCQPCLSP
VVVDTSLAAHALLETGEPRAEAAAIRGLDWLRPLQILDVRGDWISRRPDVRPGGWAFQYANPH
YPDVDDTAVVTLAMDRVAKLAQTDAYRDAIARAREWVVGMQSSDGGWGAFEPENTHQYLNSI
PFSDHGALLDPPTADVSGRCLSMLAQLGETAANSAPARRALDYLLAEQGADGSWYGRWGMN
YIYGTWSALGALNAAGLPFDDPRVKRAAQWLLSIQNPDGGWGEDGDSYKLDYRGYERAASTA
SQTAWALLGLMAAGEVEHPAVARGIAWLAAQQREHGLWDEARFTATGFPRVFYLRYHGYRKF
FPLWALARYRNLRRTGTRRVTVGM >seq_ID 201
MLPYNQNSYKEALHGGHAAHNPPTLEEAIKRSQEFLLAHQHPEGFVWVGDLECNVTSASHTLIL
YKILGIADRYPLHKFEKYLRRMQCSHGGWEMSFGDGGYLSATIEAYICLRLLNVPQSDPALQRA
LKNILARGGVTKARVFTKVCLALLGGFDWAALPSLPPWLMLFPAWFPWNIYEAASWARGCVVP
LIVLLEKKPVFQVKPEVSFDELYVEGRAHACKALPFSAHDWVSNIFVAADRAFKLMERFGAVPF
RQWSIKEAKKWVLDRQEEMGDFIGYNPPMLYFAVCLKLWGYEVTDPLLQRALLAHKKLTVETE
DECWLQSSQSPVVVDTALVIPALVESGLPPDHPALQKAGQWLLEKQILKHGDWALKTGGGRMQ
DDIGGGWAFQFVNSWYPDVDDSAAVVIALNCIKMPDEDVKNGAIARCLKWIAFMQGRNGGWA
AFDRDSNQRWMDATPFSDIEAMLDVSTADVTARVLEMVGLMRLKHAAQPANNSLGKAHRHIS
TESIARGVDYLTKEQEKEGCWWGRWGVNYIYGTRGALMGLSQVAAKTHKKEIARGAAWLKV
QNKKNEKKQGAQDGGWGEACFSYDDPATKGQNSRSTASQTGWAMQGLLAAGEVLGRKYEM
EAVEEGVQFLLDTQRKDGSWSEAEFTGGGFPKHYYLKYHYFAQHFPLSALARYRARLLQLSR
PKNQA >seq_ID 183
MDGSQRISDMSQQPEGIAVSDEISSAYSVSSLNQDEINVDELENKLTQARSAMLSLQKPDGHW
CFPLEADCTIPAEYILMMHFMDEIDVILENKIARFIREKQDLTHGGWPLYYGGAFDISCTIKSYYA
LKLVGDSPDAAHMVRAREAILERGGAAKANVFTRLLLAMYEQIPWSGVPWPTELMLLPSWFP
FHISKVSYWSRTVMIPLSILCTIKARAINPRNVDIRELFIVPPEQEKNYFPQADTWLKRAFMLVER
VLSRVEPKLPQAIRQYSIRKAENWTLERLNGECGIGAIFPAMVNAHESLALLGYAYDHPSRVQC
RNALRGLLVDEGERAWCQPCTSPVVVDTVLTCLALQEDPAADQGPVLKALDWLVDQQVLDEP
GDWRDKRPDLLGGGWAFQYANPHYPDLDDTAAVAWALDQSDAQRYQKPLDRAANWLAGMQ
SRNGGFAAFDIDNTYHYLNEIPFADHGALIDPPTSDVTARCVGLLQGKEVVVRGISFLLR
EQEKNGSWFGRWGTNYIYGTWSVLEAFQLANFDMQHTSVRRAVKWLESVQRVDGGWGETN
DSYLDIQLAGQFPQTSTTFQTAWAVLGLMAAGEVNSKSVRRGINYLLHNQADDHLWEDPWFT
APGFPRVFYLRYHGYSKFFPIWALVRYRALTKERVS >seq_ID 102
MNDLSQTQPLDAVLPEAADAASNLAEAAVVANAPAVADALATATPSPMQTAGASPLDVSITRA
TDAILAAQQPDGHWIYELEADATIPAEYVLLVHYLGETPNLELEQKIARYLRRIQLPNGGWPLFT
DGALDISASVKAYFALKMICDPVDAEHMVRARDAILAHGGAEHANVFTRILLALFGVVSWRAVP
MMPVEIMLLPMWFPFHLSKVSYWARTVIVPLLVLNAKRPLARNPRKVRIDELFRGAPVNTGMN
ERAPHQHAGWFGFFRCVDTVLRAVDGLLPKASRERAIRAAVAFVDERLNGEDGLGAIFPAMAN
SVMMYDVLGYPADHPNRAIARKSLDKLLVIKEDEAYCQPCLSPVVVDTSLVAHALLETREARAE
QAAERGLAWLRPLQILDVRGDWISRRPNVRPGGWAFQYNNAHYPDVDDTAVVAMAMHRSAA
LTKSDVDREAIARAREWVVGMQSSEGGWGAFEPENTQYYLNNIPFSDHAALLDPPTADVSGR
CLSMFAQIGELPQNSEPAQRAFDYMLQEQESDGSWYGRWGLNYIYGTWTALCSLNAAGMSH
DDPRMRRAVQWLLVSIQNEDGGWGEGGESYKLDYRGYERAPSTASQTAWALLGLMAAGEVD
HDAVARGIDYLQREQREHGLWDETRFTATGFPRVFYLRYHGYRKFFPLWALARFRHLKRNGL
TRVTVGM >seq_ID 90
MIRPMKNSDLPLPSLLDAAILRGRDALAQRQSADGSWCFELESDATITAEYILMMHFMGKIDEA
RQARMARYLRGIQRLATHGAWDLYVDGAPDVSCSVKAYFALKAAGDSEDAPHMARARETILKL
GGAAKSNVFTRILLATFGQVPWRATPFMPVEFVLFPKWVPISMYKVAYWARTTMVPLLVLCSL
KARAKNPRNVSIRELFVTAPEAERHYFARGGFVRNLFLGIDRALRPLDALIPKALRRRAIRHAEA
WCAERMNGEDGMGGIFPPIVYSYQMMDVLGYPEDHPLRRDCENALDKLLVERPDGSVYCQP
CLSPVWDTAWSTMALEQARAVPDPRDAPPVSDAQLQRCIAASYEWLAGKQVTQVRGDWVEN
APAATPAGGWAFQYENPYYPDIDDSAVVAAMLHRRGRLLARSTGTDPYAQVVARGLDWMRG
LQSRNGGFGAFDADCDRLYLNLIPFADHGALLDPPTEDVSGRVLLCLGVTGRDEDKPALARAIE
YVKRMQRADGCWWGRWGTNYIYGTWSVLAGLALAGENPSQPYIARAIAWLRACQNADGGW
GETNDSYLDPALAGTNGGESASNVTAWALLAQMAFGDWQSESVQRGIRYLLSVQQADGFWW
HRSHNAPGFPRIYYLKYHGYTAYFPLWALARYRRLSQAGAARDVTDGAALAAS

| Enzyme Sequences |
| --- |

>seq_ID 167
MREAAVSKVETLQRPKTRDVSLDDVERGVQSATRALTEMTQADGHICFELEADATIPSEYILFH
QFRGTEPRPGLEAKIGNYLRRTQSKVHGGWALVHDGPFDMSASVKAYFALKMIGDDIEAPHM
RAVRKAILQRGGAANANVFTRILLALYGEVPWVAVPVMPVEVMHLPKWFPFHLDKVSYWARCT
MVPLFVIQAKKPRAKNPRGVGVAELFVTPPDSVRTWPGSPHATWPWTPIFCCIDRVLQKTQDH
FPKVPRQRAIDKAVAWVSERLNGEDGLGAIFPAMVNSVLMYEVLGYPPEHPQVKIALEAIEKLV
AEKEDEAYVQPCLSPVWDTALNSHAMLEAGGHQAEANARAGLDWLKPLQILDIKGDWAETKP
NVRPGGWAFQYANPHYPDLDDTAVVVMAMDRAQRQHGLVSGMPDYSESIARAREWVEGLQ
SADGGWAAFDADNNHHYLNHIPFSDHGALLDPPTADVTARVVSMLSQLGETRATSRALDRGV
TYLLNDQEKDGSWYGRWGMNFIYGTWSVLCALNAAGVDPQSPEIRKAVAWLIRIQNPDGGWG
EDASSYKLNPEFEPGYSTASQTAWALLALMAAGEVDDPAVARGVNYLVRTQGQDGLWSEER
YTATGFPRVFYLRYHGYPKFFPLWAMARFRNLKRGNSRQVQFGM >seq_ID 133
MTTTDETALAAGTPKAAFAPAPRGAADDLVARTVAVEAPPSPAPASDDTLARAVAHLKSLQDE
AGWWKGDLETNTTMDSEDLMLRHWLGIWNPEQAERTARFIRSKQYADGSWPIYHAGPGDLN
ATVESYVALRMVGDSPQDPHMRAAAAWARARGGVPATRIFTRIWLALFGVWVRWEDLPVLPP
ELIFVPAKMPLSIYKFASWGRQTIVAIMVLMAHRPAGTPPFPIAELFPPPATKKKAAAQRKAQKK
AGHAGGPTAWRDSSIDDMFTEPAPGTDTLRQPAALAIGPARPAPAKGRRGKGQPAAPDVMG
RAKDGGGPGLPLPARLVSRVGFRTRRALRQAALDHVNWNLLFGGIDRFLHVYHRHPIRPVRSL
ALGLAERWIVVRQEADGCFGGIQPPTVYSIMALRVLGYPMDHPVMTAALRSLDEYSVTLPDGA
RMQEACQSPVVVDTCLATIALADAGVPRDDPSLVRAADWMLAEEVRERRGDWSVPIPDVPTG
GWSFEFDNDTYPDVDDSAEVMLALMRVAHPRPEKVVAATYRGLQWVFGMQCADGGWGAFD
VDNAGELVVKIPFADFGMLTDPPSADVTAHVVELLGELGLGDDPRTKRGVEWLLHSQEADGS
WYGRWGVNHLYGTGGVVPALRAAGLPASHPAIQRAADWLVAKQNPDGGWGESCYSYDEMS
TAGVGVSTASQTAWALLALIAAGRVGDGVTGEAAARGVAWLAETQTAEGTWDEDYFTGTGFA
GYFYINYHLYRLVVVPVMALGRYQAALAGKGH >seq_ID 7
MNPVVHNLTRPHRSAEPRPSALQRSIAAAQAALLQHQAADGHWCFEFEADCTIPAEYILMMHY
MDERDAALEAKMAAYLRRKQENHGGWSLYHGGHFDMSASVKAYFALKLAGDDPEAAHMRRA
RSAILAHGGAERANVFTRITLALFGQVPWRAVPFIPVEILLFPRWFPMHIYKVASWSRTVMVPLF
ILCSLKPQAKNPLGVHIRELFTRPPEDIDDYFAHALQGWVSRIFLWFDRLGRALESWIPQALRRR
AIARAEAWFIERLNGEDGLNGIFPAMVNAHEALALLGYAAEHPYRQQTRAALTKLVVERAGEAY
CQPCVSPVVVDTCLAHHALLEADGDVSEAARRSMQWLLDRQITDAPGDWRERRPHLAGGGWA
FQYANPYYPDLDDTAAVAWALARARRPEDRPAVERAANWLAGMQSRNGGFGAYDVDNTYYY
LNEIPFADHKALLDPPTADVSGRVLAFLAILDREQDAPVRARLIQYLLREQEPSGAWFGRWGTN
YIYGTWSVLMGMAELRDPGAEVRDAMARAAHWLRSVQQDDGGWGESNDSYADPGLAGLGQ
ESTAAQTAWACLALMAAGDSDSESLRRGIQWLQRHQEQPGDWQDPYFNAPGFPRVFYLTYH
GYKIYFPLWALARYRNITERHCA >seq_ID 190
MALSNGEIREEIQRLSEELIQRQEPDGSWRFCFENGITIDACTIILLRTLNVDKEELIRQLHDRIVA
AQQPEGCWRWYHDDKEGHLSATVEAYYALLCSGYSRPEDEPIQRAKRYILDRGGIGQARSLF
TKAILAATGQRKWPASLSLIPIEILLLPESLPLNFYDFSGYSRVHLVPLLIMAERNFRTRSVRTPDL
SELFLDARNGEEDPLTLTPESREPLKLIQSGLAHLVGTPRRIRQAAVNRAEQYMLDRIEGDGTL
YTYASCTVLMVFALLALGYEPQHPVIQRAVEGLSQMKFTVDSTGQGGTRYVTIQNSPSTVVVDT
ALISYALQEAGVSSSHPAIQRAADYLRNRQHRRPGDWQIHNPGIVPGGWGFSETNTFVPDVDD
TTAALRALSALHGSEPAVLGAWNRGLNWVVVSMQNNDGGWPAFEKNTNKEMLTWLAIEGAKS
AATDPSEADLTGRTLEYLGNFAKLSVRQDWVARGADWLLSHQEADGSWYGRWGICYIYGTW
AALTGLMAVGMPADHPGIAKAANWLIRIQNADGGWGESCRSDQVRRYVPLHASTPSQTAWAL
DALIAVHDRRAPEIERGVARLIALLHEDDWPSTYPTGAGLPGYFYVHYSYRYIWPLLALSHYV
NKYGDSSP >seq_ID 45
MSGVLLYDKVREEIERRTTALQTMQRQDGTWSFCFEGALLTDCHMIFLLKLLGRNDEIEPFVKR
LASLQTNEGTWKLYEDENGGNLSATIQAYAALLASEKYSKEDINMRRAEMFIKEHGGVSRAHF
MTKFLLAIHGEYEFPTLFHFPTPILFLQDDSPLSIFELSSSARIHLIPMMICMNKRFRVEKKLLPNL
NHIAGEGGQWFREERSPLFQSFVGDVKKVIAYPLSLHHKGYEEVERFIGERIDENGTLYSYASA
TFYMIYALLALGHSIQSPIIEKAVIGLKSYIWKMDRGSHLQNSPSTVVVDTALLSYSLQEANVMKE
NKMIQKATEYLLQRQQTKRMDWSVHAPSIMAGGWGFSDVNTTIPDVDDTTAALRALARSRGS
SRVDSAWERGVEWLKGLQNNDGGWGAFERGVTSRILANLPIENASDMITDPSTPDITGRVLEF
FGTYAPNELPEEQKKKAVKWLMDVQELNGSWYGKWGICYIYGTWAAMTGLRALGVPSSHPSL
KKAASWLEHLQYEDGGWGESCQSSVEKKFISLPFSTPSQTAWALDALISYYDQETPIIRKGISYL
LAQPTMNEKYPTGTGLPGGFYIRYHSYGHIYPLLALAHYIKKYKK >seq_ID 53
MSGVLLYDKVHEEIERRTTALQTMQRQDGTWQFCFEGALLTDCHMIFLLKLLGRNDEIEPFVKR
LVSLQTNEGTWKLYEDEKGGNLSATIQAYAALLASERYSKEAMNMRRAEMFIKEHGGVSRAHF
MTKFLLAIHGEYEFPALFHFPTPILFLQDDSPLSIFGLSSSARIHLIPMMICMNKRFRVEKKLLPNL
NHIAGGGGQWFREERSPLFQSFLGDVKKVISYPLSLHHKGYEEVERFMKERIDENGTLYSYAS
ATFYMIYALLALGHSIQSPIIEKAVTGLKSYIWKMDRGSHLQNSPSTVWDTALLSYSLQEAKVTN
ENKMIQRATEYLLQKQQTKKVDWSVHASSLVAGGWGFSDVNTTIPDIDDTTAALRALARSRGN
DRVDDAWGRGVEWVKGLQNNDGGWGAFERGVTSKLLSNLPIENASDMITDPSTPDITGRVLE
LFGTYAPNELLEEQKKKAIKWLMDVQEQNGSWYGKWGICYIYGTWATMTGLRALGVPSTHPA
LKKAASWLEHLQHEDGGWGESCQSSVEKKFISLPFSTPSQTAWALDALISYYDQETPIIRKGIS
YLLAQSTMNEKYPTGTGLPGGFYIRYHSYGHIYPLLALAHYVKKYRK Enzyme Sequences >seq_ID 44
MSGVLLYDKVHEEIERRTTALQTMQRQDGTWQFCFEGALLTDCHMIFLLKLLGRNDEIEPFVKR
LASLQTNEGTWKLYEDEKGGNLSATIQAYAALLASEKYSKEDMNMRRAEMFIKEHGGVSRAHF
MTKFLLAIHGEYEFPALFHFPTPILFLQDDSPLSIFGLSSSARIHLIPMMICMNKRFRVEKKLLPNL
NHIAGGGGQWFREERSPLFQSLLGDVKKVISYPLSLHHKGYEEVERFMKERIDENGTLYSYAS
ATFYMIYALLALGHSIQSPIIEKAVTGLKSYIWKMDRGSHLQNSPSTVWDTALLSYSLQEAKVTN
ENKMIQRATEYLLQKQQTKKVDWSVHASSLVAGGWGFSDVNTTIPDIDDTTAALRALARSRGN
DRVDDAWGRGVEWVKGLQNNDGGWGAFERGVTSKLLSNLPIENASDMITDPSTPDITGRVLE
LFGTYAPNELLEEQKKKAIKWLMDVQEQNGSWYGKWGICYIYGTWATMTGLRALGVPSTHPS
LKKAASWLEHLQHEDGGWGESCQSSVEKKFISLPFSTPSQTAWALDALISYYDQETPIIRKGITY
LLAQSTMNEKYPTGTGLPGGFYIRYHSYGHIYPLLALAHYVKKYRK >seq_ID 64
MSNLLLYEKVHEEIARRTTALQTMQRQDGTWRFCFEGAPLTDCHMIFLLKLLGRDKEIEPFVKR
LASLQTNEGTWKLYEDEAGGNLSATIQSYAALLASEKYTKEDANMKRAEMFINERGGVARAHF
MTKFLLAIHGEYEYPSLFHLPTPIMFLQNDSPLSIFELSSSARIHLIPMMLCLNKRFRVGKKLLPNL
NHIAGGGGEWFREDRSPVFQTLLSDVKKIITYPLSLHHKGYEEVERFMKERIDENGTLYSYATA
SFYMIYALLALGHSIQSPIIEKAITGITSYIWKMERGSHLQNSPSTIWDTALLSYALQEAQVPKASK
VIHNASAYLLRKQQTKKVDWSVHAPDLFPGGWGFSDVNTTIPDIDDTTAALRALARSRGNENV
DNAWKRAVNWVKGLQNNDGGWGAFEKGVTSRILANLPIENASDMITDPSTPDITGRVLEFFGT
YTQNELPEKQKQSAINWLMNVQEENGSWYGKWGICYIYGTWAVMTGLRSFGIPSSNPSLKRA
ALWLEHIQHEDGGWGESCQSSVEKRFVTLPFSTPSQTAWALDALISYYDKETPVIRKGISYLLS
NSYINEKYPTGTGLPGGFYIRYHSYAHIYPLLTLAHYAKKYKK >seq_ID 68
MLLYEKVHEEIARRTTALQTMQRQDGTWRFCFEGAPLTDCHMIFLLKLLGKDKEIEPFVKRLAS
LQTNEGTWKLYEDEVGGNLSATIQSYAALLASEKYTKEDVNMKRAEMFINEHGGVARAHFMTK
FLLAIHGEYEYPSLFHLPTPIMFLQNDSPLSIFELSSSARIHLIPMMLCLNKRFRVGKKLLPNLNHI
AGGGGEWFREDRSPVFQTLVSDVKKIITYPLSLHHKGYEEVERFMKERIDENGTLYSYATASFY
MIYALLALGHSIQSPIIQKAITGITSYIWKMERGSHLQNSPSTVWDTALLSYALQEAQVPKASKVI
HNASAYLLRKQQTKKVDWSVHAPDLFPGGWGFSDVNTTIPDIDDTTAALRALARSRGNENVDT
AWKRAVNWVKGLQNNDGGWGAFEKGVTSRILANLPIENASDMITDPSTPDITGRVLEFFGTYT
QNELPEKQKQSAINWLMNVQEENGSWYGKWGICYIYGTWAVLTGLRSLGIPSSDPSVKRAAL
WLEHIQHEDGGWGESCQSSVEKRFVTLPFSTPSQTAWALDALISYYDKETPVIRKGISYLLSNS
YINEKYPTGTGLPGGFYIRYHSYAHIYPLLTLAHYAKKYRK >seq_ID 41
MSNLLLYEKVHEEIARRTTALQTMQRQDGTWQFCFEGAPLTDCHMIFLLKLLGRDKEIEPFVKR
LASLQTNEGTWKLYEDEMGGNLSATIQSYAALLASEKYTKEDANMKRAEMFINERGGVARAHF
MTKFLLAIHGEYEYPSLFHLPTPIMFLQNDSPLSIFELSSSARIHLIPMMLCLNKRFRVGKKLLPNL
NHIAGGGGEWFREDRSPVFQTLVSDVKKIITYPLSLHHKGYEEVERFMKERIDENGTLYSYATA
SFYMIYALLALGHSIQSPIIQKAITGITSYIWKMERGSHLQNSPSTVWDTALLSYVLQEAQVPKAS
KVIHNASAYLLRKQQTKKVDWSVHAPDLFPGGWGFSDVNTTIPDIDDTTAALRALARSRGNEN
VDTAWKRAVNWVKGLQNNDGGWGTFEKGVTSRILANLPIENASDMITDPSTPDITGRVLEFFG
TYTQNELPEKQKQSAINWLMNVQEENGSWYGKWGICYIYGTWAVLTGLRSLGIPSSDPSVKRA
ALWLEHIQHEDGGWGESCQSSVEKRFVTLPFSTPSQTAWALDALISYYDKETPVIRKGISYLLS
NSYINEKYPTGTGLPGGFYIRYHSYAHIYPLLTLAHYAKKYRK >seq_ID 66
MSNLLLYEKVHEEIARRTTALQTMQRQDGTWQFCFEGAPLTDCHMIFLLKLLGRDKEIEPFVKR
LASLQTNEGTWKLYEDEMGGNLSATIQSYAALLASEKYTKEDANMKRAENFIKERGGVARAHF
MTKFLLAIHGEYEYPSLFHLPTPIMFLQNDSPLSIFELSSSARIHLIPMMLCLNKRFRVGKKLLPNL
NHIAGGGGEWFREDRSPVFQTLASDVKKIITYPLSLHHKGYEEVERFMKERIDENGTLYSYATA
SFYMIYALLALGHSIQSPIIEKAIMGITSYIWKMERGSHLQNSPSTIWDTALLSYALQEAQVPKAS
KVIQNASAYLLRKQQTKKVDWSVHAPDLFPGGWGFSDVNTTIPDIDDTTAVLRALARSRGNEN
VDNAWKRAVNWVKGLQNNDGGWGAFEKGVTSRILANLPIENASDMITDPSTPDITGRVLEFFG
TYGQNELPEKQKQSAINWLTNAQEENGSWYGKWGICYIYGTWAVLTGLRSLGIPSSDPSLKRA
ALWLEHIQHEDGGWGESCHSSVEKRFVTLPFSTPSQTAWALDALISYYDKETPVIRKGISYLLS
NPYINEKYPTGTGLPGGFYICYHSYAHIYPLLTLAHYAKKYRK >seq_ID 138
MVADERSALIDALKRSQSVDGSWRFPFETGISTDAYMIILLRTLGIHDEPLIQALVERIESRQDAN
GAWKLFADEGDGNVTATVEAYYALLYSGYRKKTDSHMQKAKARILEVGGLERVHLFTKVMLAL
TGQHSWPRRFPLPLVFFLLPPSFPLNMYDLSVYGRANMVPLLVVAERRYSRKTDNSPDLSDLA
ASRNDWRLPDTEALWSYVKRSLTGLPAWLHRAAEQRAVRYMLEHIEPDGTLYSFVSSTFLLIFA
LLALGYPKDDPHIARAVRGLRSLRTEIDGHTHMQYTTASVVVNTALASYALQEAGVPPTDRTIEK
ANRYLLSRQHIRYGDWAVHNPYGVPGGWGFSDVNTMNPDVDDTTAALRAIRRAAAKETAFRH
AWDRANRWLFSMQNDDGGFAAFEKNVGKRFWRYLPIEGAEFLLMDPSTADLTGRTLEYFGTF
AGLTKDHSAIARAIDWLLDHQEADGSWYGRWGICYVYGTWAAVTGLSAVGVPIDHPAMQKAV
RWLLSIQNDDGGWGESCKSDGAKTYVPLGASTPVHTAWALDALIAAAERPTPEMKAGVRALV
RMLHHPDWTASYPVGQGMAGAFYIHYHGYRYIFPLLALAHYEQKFGPFVD >seq_ID 69
MLLYEKVHEEIARRTTALQTMQRQDGTWRFCFEGAPLTDCHMIFLLKLLGRDKEIEPFVKRLAS
LQTNEGTWKLYEDEVGGNLSATIQSYAALLASEKYTKEDANMKRAEMFINERGGVARAHFMTK
FLLAVHGEYEYPSLFHLPTPIMFLQNDSPLSIFELSSSARIHLIPMMLCLNKRFRVGKKLLPNLNHI

| Enzyme Sequences |
| --- |
| AGGGGEWFREDRSPVFQTLLSEVKKIITYPLSLHHKGYEAVERFMKERIDENGTLYSYATASFY<br>MIYALLALGHSIQSPIIQKAITGITSYIWKMERGSHLQNSPSTVWDTALLSYALQEAQVPKASKGI<br>QNASAYLLRKQQTKKVDWSVHAPDLFPGGWGFSDVNTTIPDIDDTTAVLRALARSRGNENVD<br>NSWKRAVNWVKGLQNNDGGWGAFEKGVTSRILANLPIENASDMIPDPSTPDITGRVLEFFGTY<br>AQNELPEKQKQSAINWLMNIQEENGSWYGKWGICYIYGTWAVLTGLRSLGIPSSDPSLKRAAL<br>WLEHIQHEDGGWGESCQSSVEKRFVTLPFSTPSQTAWALDALISYYEKETPVIRKGISYLLSNP<br>YVNEKYPTGTGLPGGFYIRYHSYTHIYPLLTLAHYAKKYRK<br><br>>seq_ID 67<br>MSNLLLYEKVHEEIARRTTALQTMQRQDGTWRFCFEGAPLTDCHMIFLLKLLGRDKEIEPFVKR<br>LASLQTNEGTWKLYEDEVGGNLSATIQSYAALLASEKYTKEDANMKRAEMFINERGGVARAHF<br>MTKFLLAIHGEYEYPSLFHLPTPIMFLQNDSPLSIFELSSSARIHLIPMMLCLNKRFRVGKKLLPNL<br>NHIAGGGGEWFREDRSPVFQTLLSEVKKIITYPLSLHHKGYEEVERFMKERIDENGTLYSYATA<br>SFYMIYALLALGHSIQSPIIQKAITGIASYIWKMERGSHLQNSPSTVVVDTALLSYALQEAQVPKAS<br>KVIQNASAYLLRKQQTKKVDWSVHAPNLFPGGWGFSDVNTMIPDIDDTTAVLRALARSRGDEN<br>VDNAWKRAVNWVKGLQNNDGGWGAFEKGVTSRILANLPIENASDMITDPSTPDITGRVLEFFG<br>TYAQNELPEKQKQSAINWLMNVQEENGSWYGKWGICYIYGTWAVLTGLRSLGIPSSDPSLKRA<br>ALWLEHIQHEDGGWGESCQSSVEKRFVTLPFSTPSQTAWALDALISYYEKETPIIRKGISYLLSN<br>PYVNEKYPTGTGLPGGFYIRYHSYAHIYPLLTLAHYTKKYRK<br><br>>seq_ID 35<br>MSNLLLYEKAHEEIVRRATALQTMWQDGTWRFCFEGAPLTDCHMIFLLKLLGRDKEIEPFVER<br>VASLQTNEGTWKLYEDEVGGNLSATIQSYAALLASKKYTKEDANMKRAENFIQERGGVARAHF<br>MTKFLLAIHGEYEYPSLFHLPTPIMFLQDDAPFSIFELSSSARIHLIPMMLCLNKRFRVGKKLLPN<br>LNHIAGGGGEWFREDRSPVFQTLLSDVKQIISYPLSLHHKGYEEIERFMKERIDENGTLYSYATA<br>SFYMIYALLALGHSLQSSMIQKAIAGITSYIWKMERGNHLQNSPSTVVVDTALLSYALQEAQVSK<br>DNKMIQNATAYLLKKQHTKKADWSVHAPALTPGGWGFSDVNTTIPDIDDTTAVLRALARSRGN<br>KNIDNAWKKGGNWIKGLQNNDGGWGAFEKGVTSKLLAKLPIENASDMITDPSTPDITGRVLEFF<br>GTYAQNELPEKQIQRAINWLMNVQEENGSWYGKWGICYIYGTWAVMTGLRSLGIPSSNPSLKR<br>AASWLEHIQHEDGGWGESCHSSVEKRFVTLPFSTPSQTAWALDALISYYDTETPAIRKGVSYLL<br>LNPYVNERYPTGTGLPGAFYIRYHSYAHIYPLLTLAHYLKKYRK<br><br>>seq_ID 43<br>MNALLLYEKVHEEIARRTTALQTMQRQDGTWRFCFEGAPLTDCHMIFLLKLLGRDKEVEPFVK<br>RLASLQTNEGTWKLYDDEMGGNLSATIQSYAALLASKKYTKEDANMKRAEMFITERGGVARAH<br>FMTKFLLAIHGEYEYPSLFHLPTPIMFLQNDSPLSIFELSSSARIHLIPMMLCLNKRFRVGKKLLP<br>NLNHIAGGGGEWFREDQSPMFQTLLGNVKQIISYPLSLHHKGNEEVERFMKERIDENGTLYSY<br>ASASFYMIYALLALGHSIQSPMIQKAITGITSYIWKMERGNHLQNSPSTVWDTALLSYALQEARV<br>SKESKMIQNASAYLLKKQHKKADWSVHAPVLIPGGWGFSDVNTTVPDVDDTTAVLRALAQSR<br>GNGNVDDAWKKGTNWIKGLQNNDGGWGAFEKGVTSKLLANLPIENASDMITDPSTPDITGRVL<br>EFFGTYTQNELPEKQKQSAINWLMNEQEENGSWYGKWGICYIYGTWAVMTGLRALGITSAHP<br>SLKRATLWLEHIQHEDGGWGESCQSSVEKRFATLPFSTPSQTAWALDALISYYDKETPAIRKGI<br>SYLLANPYVNEKYPTGTALPGGFYIHYHSYAHIYPLLTLAHYAKKYKK<br><br>>seq_ID 33<br>MNIVIRISKGWVSNLLLYEKVHEEIARRTTALQTMQRQDGTWQFCFEGAPLTDCHMIFLLKLLG<br>RDKEIEPFVKRLASLQTNEGTWKLYEDEVGGNLSATIQSYAALLASKKYTKEDANMKRAEMFIN<br>ERGGVARAHFMTKFLLAIHGEYEYPSLFHLPTPIMFLQNDSPLSIFELSSSARIHLIPMMVCLNKR<br>FQVGKKLLPNLNHIAGGGGEWFREDRSPMFQTLLSDVKQIISYPLSLHHKGYEEVERFMKERID<br>ENGTLYSYATASFYMIYALLALGHSLQSSMIQKAIAGITSYIWKMEKGNHLQNSPSTVVVDTALLS<br>YTLQEAHASKDNKMIQHAAAYVLKKQHTKKADWSVHAPGLIPGGWGFSDVNTTIPDVDDTTAV<br>LRALARSRGNENVDNAWKKGVNWVKGLQNNDGGWGAFEKGVTSNLLANLPIENASDMITDPS<br>TPDITGRVLELFGTYAQNELPEKQKQSAINWLMNVQEENGSWYGKWGICYIYGTWAVMTGLR<br>SLGIPSSNPSMKRAALWLEHIQHEDGGWGESCQSSVEKRFITLPFSTPSQTAWALDALISYHDE<br>ETPAIRKGISYLLANPYVNEKYPTGTGLPGGFYIHYHSYAYIYPLLTLAHYIKKYRK<br><br>>seq_ID 36<br>MSNLLLYEKVHEEIARRATALQTMQRQDGTWRFCFEGAPLTDCHMIFLLKLLGRDKEIEPFVKR<br>LASLQTNEGTWKLYEDEVGGNLSATIQSYAALLASQKYTKEDANMKRAENFIKERGGVARAHF<br>MTKFLLAIHGEYEYPSLFHVPTPIMFLQNDSPLSIFELSSSARIHLIPMMVCLNKRFRVGKKLLPN<br>LNHIAGGGGEWFREDRSPLFQTLLSDVKQIISYPLSLHHKGYEEVERFMKERIDENGTLYSYAT<br>ASFYMIYALLALGHSLQSSMIQKAIAGITSYIWKMERGSHLQNSPSTVVVDTALLSYALQEAQVPK<br>DHKMIQQTITYLLKKQHTKKADWSVHAPALTPGGWGFSDVNTTVPDVDDTTAVLRVLARSREN<br>EKVNNAWQKGIDWVKGLQNNDGGWGAFEKGVTSKLLANLPIENASDMITDPSTPDITGRVLEL<br>FGTYTQNELPEKQKQSAINWLMNAQEENGSWYGKWGICYIYGTWAVMTGLRSLGIPSNNPSL<br>KRAALWLEHIQHEDGGWGESCQSSMEKRFITLPFSTPSQTAWALDALISYYDTETPAIRKGISY<br>LLANPYVNEKYPTGTGLPGGFYIRYHSYAQIYPLLTLAHYTKKYRK<br><br>>seq_ID 42<br>MSNLLLYEKVHEEIARRTTALQTMQRDGTWRFCFEGAPLTDCHMIFLLKLLGRDKEIEPFVKR<br>LASLQTNEGTWKLYEDEVGGNLSATIQSYAALLASEKYTKEDANMKRAEMFINERGGVARAHF<br>MTKFLLAIHGEYEYPSLFHLPTPIMFLQNDSPLSIFELSSSARIHLIPMMLCLNKRFRVGKKLLPNL<br>NHIAGGGGEWFREDRSPVFQTLVSDVKKIITYPLSLHHKGYEEVERFMKERIDENGTLYSYATA<br>SFYMIYALLALGHSIQSPIIEKAIMGITSYIWKVERGSHLQNSPSTIWDTALLSYALQEAQVPKASK<br>VIQNASAYLLRKQQTKKVDWSVHAPDLFPGGWGFSDVNTTIPDIDDTTAVLRALARSRGNEHV<br>DNAWKRAVNWVKGLQNNDGGWGAFEKGVTSRILANLPIENASDMITDPSTPDITGRVLEFFGT<br>YTQNELPEKQKQSAINWLMNVQEENGSWYGKWGICYIYGTWAVLTGLRSLGIPSSDSSLKRAV |

| Enzyme Sequences |
| --- |

```
LWLEHIQHEDGGWGESCQSSVEKRFVTLPFSTPSQTAWALDALISYYDKETPVIRKGISYLLSN
PYINEKYPTGTGLPGGFYIRYHSYAHIYPLLTLAHYAKKYRK

>seq_ID 65
MSNLLLYEKVYEEIARRTTALQTMQRQDGTWRFCFEGAPLTDCHMIFLLKLLGRDKEIEPFVKR
LASLQTNEGTWKLYEDEVGGNLSATIQSYAALLASEKYTKEDANMKRAEMFINERGGVARAHF
MTKFLLAIHGEYEYPSLFHLPTPIMFLQNDSPLSIFELSSSARIHLIPMMLCLNKRFRVGKLLPNL
NHIAGGGGEWFREDRSPVFQTLVSDVKKIITYPLSLHHKGYEEVERFMKGRIDENGTLYSYATA
SFYMIYALLALGHSIQSPIIEKAIMGITSYIWKMERGSHLQNSPSTIWDTALLSYALQEAQVPKVS
KVIQNASAYLLRKQQTKKVDWSVHAPDLFPGGWGFSDVNTTIPDIDDTTAVLRALARSRGNEN
VDNAWKRAVNWVKGLQNNDGGWGAFEKGVTSRILANLPIENASDMITDPSTPDITGRVLEFFG
TYTQNELPEKQKQSAINWLMNVQEENGSWYGKWGICYIYGTWAVLTGLRSLGIPSSDSSLKRA
VLWLEHIQHEDGGWGESCQSSVEKRFVTLPFSTPSQTAWALDALISYYDKETPVIRKGISYLLS
NPYINEKYPTGTGLPGGFYIRYHSYAHIYPLLTLAHYAKKYRK >seq_ID 39
MNNLLLYEKVHEEIARRATALQTMQQQDGTWRFCFEGAPLTDCHMIFLLKLLGRDKEIEPFVKR
LASLQTNEGTWKLYEDEVGGNLSATIQSYAALLASKKYTKEDANMKRAENFIKERGGVARAHF
MTKFLLAIHGEYEYPSLFHLPTPIMFLQNDSHLSIFELSSSARIHLIPMMLCLNKRFRVGKKLLPSL
NHIAGGGGEWFREDRSPLFQTLVSDVKQIISYPLSLHHKGYEEVERFMKERIDENGTLYSYATA
SFYMIYALLALGHSLQSTMIQKAITGITSYIWKMESGNHLQNSPSTVWDTALLSYALQEAHVPKD
NKMIQHAATYLLKKQHTQKADWSVHAPALTPGGWGFSDVNTTIPDVDDTTAVLRALARSRGNE
KVDNAWPKGINWVKGLQNNDGGWGAFEKGVTSNILANLPIENASDMITDPSTPDITGRVLEFF
GKYAQNELPEKQKQSAINWLMNVQEENGSWYGKWGICYIYGTWAVMTGLRSLGIPSSNPSMK
RAALWLEHIQHEDGGWGESCHSSVEKRFVTLPFSTPSQTAWALDALISYYDKETSIIRKGISYLL
ANPYVNEKYPTGTGLPGGFYIRYHSYAHIYPLLTLAHYIKKYRK >seq_ID 63
MSNLLLYEKAHEEIARRATALQTMREDGTWRFCFEGAPLTDCHMIFLLKLLGRDKEIEPFVKR
LATLQTNEGTWKLYEDEVGGNLSATIQSYAALLASGKYTKEDANMKRAENFIKERGGVARAHF
MTKFLLAIHGEYEYPSLFHVPTPIMFLQNDSPLSIFELSSSARIHLIPMMLCLNKRFRVGKKLLPN
LNHIAGGGGEWFREERSPLFQTLLSDVKQIISYPLSLHHKGYEEVERFMKERIDENGTLYSYAT
ASFYMIYALLALGHSLQSSMIQKAIAGITSYIWKMESGNHVQNSPSTVVVDTALLSYALQEAHVP
KDNKMLQNATAYLLKKQHTKKADWSVHAPALTPGGWGFSDVNTTVPDVDDTTAVLRVLARSK
GNEKLDHAWQKGINWVKGLQNNDGGWGAFEKGVTSRILANLPIENASDMITDPSTPDITGRVL
EFFGTYAQNELPEKQKQSAINWLMNAQEENGSWYGKWGICYIYGTWAVMTGLRSFGIPSSNP
SLKRAALWLEHIQHKDGGWGESCHSSVEKRFVTLPFSTPSQTAWALDALISYYDTETPVIRKGI
SYLLANPYVNEKYPTGTGLPGGFYIRYHSYAHIYPLLTLTHYIKNIENKPRDISRFIFLGSRSLLKRI
RLCFPYFSVDWRF >seq_ID 37
MSNLLLYEKAHEEIARRATALQTMREDGTWRFCFEGAPLTDCHMIFLLKLLGRDKEIEPFVKR
LASLQTNEGTWKLYEDEVGGNLSATIQSYAALLASGKYTKEDANMKRAENFIKERGGVARAHF
MTKFLLAIHGEYEYPSLFHVPTPIMFLQNDSPLSIFELSSSARIHLIPMMLCLNKRFRVGKKLLPN
LNHIAGGGGEWFREERSPLFQTLLSDVKQIISYPLSLHHKGYEEVERFMKERIDENGTLYSYAT
ASFYMIYALLALGHSLQSSMIQKAIAGITSYIWKMESGNHVQNSPSTVVVDTALLSYALQEAHVP
KDNKMLQNATAYLLKKQHTKKADWSVHAPALTPGGWGFSDVNTTVPDVDDTTAVLRVLARSK
GNEKLDHAWQKGINWVKGLQNNDGGWGAFEKGVTSRILANLPIENASDMITDPSTPDITGRVL
EFFGTYAQNELPEKQKQSAINWLMNAQEENGSWYGKWGICYIYGTWAVMTGLRSFGIPSSNP
SLKRAALWLEHIQHKDGGWGESCHSSVEKRFVTLPFSTPSQTAWALDALISYYDTETPVIRKGI
SYLLANPYVNEKYPTGTGLPGGFYIRYHSYAHIYPLLTLTHYIKKYRK >seq_ID 46
MLLYEKVHEEVKEKMAALQAMQQQDGTWRFCFEGSPLTDCYMIFLLTLLGQDQEIEPFVARLA
ALQTNEGTWKLYEDEPDGNLSATIQAYAALLVSKMYKKEDINMKRAEVFIRKQGGITKAHFMTK
FLLALHGGYEYPPLFHFPTPILFLSEDSPLSIFELSSSARIHLIPMMLCMNKRFTVSKKMLPNLDYI
SGGSKEQWFREERSPLFQTLLRDVTKFLSYPLSLHYKGDKAAERFMIERIDTNGTLYSYASATF
YMIYALLALGHSIQSPLISNAVLGLKTYVWNMDRWAHLQNSPSTVVVDTALLSYSLQEARVPHD
NEMIQKAINYLLQKQHKEKKDWSVHAPTLDAGGWGFSDVNTTIPDVDDTTAVLRALAGSRQGN
PKVESAWRKGIEWVKGLQNSDGGWAAFEKGVTSKVLTHLPLDNSGDWITDPSTVDITGRVLEF
FGTYAPNELQGDQKDRAIRWLIYTQEKNGSWHGKWGVCYIYGTWAALTGLRAVGVPSNHIAL
QKAATWLESIQHSDGGWGESCRSSVEKKFISLPFSTPSQTAWALDALIACYDSETPTIRKGISYL
LKHSTKHQEYPTGTALANGFYIRYHSYHHIFPLLTFAHYIKKYRK >seq_ID 40
MSNLLLYEKVHEEIARRTTALQTMQRRDGTWRFCFEGAPLTDCHMIFLLKLLGRDKEIEPFVKR
LASLQTNEGTWKLYEDEVGGNLSATIQSYAALLASKKYTKEDANMKRAEMFINERGGVARAHF
MTKFLLAVHGEYEYPSLFHLPTPIMFLQSDSPLSIFELSSSARIHLIPMMLCLNKKFRIRKKLLPNL
NHISGGGGEWFRGNRSPLFQTLVSDVKQIISYPLSLHHKGNEEVERFMKERIDENGTLYSYATA
SFYMIYALLALGHSLQSTMIQKAITGITSYIWNMESGNHLQNSPSTVVVDTALLSYALQEAHVPKD
TNMLQHATAYLLKKQHTKKADWSVHAPALAPGGWGFSDVNTTIPDVDDTTAVLRALARSRGS
EKVDYVWEKGINWVKGLQNNDGGWGAFEKGVTSNLLANLPIENASDMITDPSTPDITGRVLEL
FGTYAQNELPEKQTQSAINWLMNVQEKNGSWYGKWGICYIYGTWAVMTGLRSLGIPSSNPSL
KRAALWLEHIQHEDGGWGESCHSSVEKRFVTLPFSTPSQTAWALDALISYYDKETPAIRKGISY
LLANRYVNEKYPTGTGLPGGFYICYHSYAHIYPLLTLAHYIKKYRK
```

| Enzyme Sequences |
| --- |

>seq_ID 38
MSNLLLYEKAHEEIARRATALQSMQWQDGTWRFCFEGAPLTDCHMIFLLKLLGRDKEIEPFVK
RLASLQTNEGTWKLYEDEVGGNLSATIQSYAALLASGKYTKEDANMKRAENFIKERGGVARAH
FMTKFLLAVHGEYEYPSLFHLPTPIMFLQNDSPLSIFELSSSARIHLIPMMLCLNKRFRVGKKLLP
NLNHIAGGGGEWFREERSPLFQTLVSDVKQIISYPLSLHHKGYEEVERFMKERIDENGTLYSYA
TASFYMIYALLALGHSLQSSIIQNAITGITSYIWKMESGNHLQNSPSTVVVDTALLSYALQEAHVPK
DNKMLQNATAYLLKKQHTKKADWSVHASALTPGGWGFSDVNTTVPDVDDTTAVLRVLARSRG
NEKVDHAWQKGINWVKGLQNNDGGWGAFEKGVTSNILAKLPIENASDMITDPSTPDITGRVLE
FFGTYAQNELPEKQKQSAINWLMNVQEENGSWYGKWGICYIYGTWAVMTGLRSFGIPSSNPS
LKRAALWLEHIQHKDGGWGESCHSSVEKRFVTLPFSTPSQTAWALDALISYYDTETPIIRKGISY
LLANPYVNEKYPTGTGLPGGFYIRYHSYAHIYPLLTLAHYIKKYRK >seq_ID 55
MLLYEKVRQEVERKVTALRTMQYQDGAWRFCFEGSPLTDCHMIFLLRLLGQNGEMEPFVTRV
ASLQTNEGTWKLYEDESVGNLSTTINAYVALLASGRYTKEDINMKRAEAFIRRQGGITKAHFMT
KFLLALHGGYEYPSLFHFPTPMLFLPEDSPLSIFELSSSARIHLIPMMICMNKRFTVSKTILPNLDY
ISGGSKKQWFREERSSLFQRLLGDVKKFLSYPLSLQHKGYKEAERFMIERIETNGTLYSYASAT
FYMIYALLALGHSIQSPLISNAVLGLKSYIWNMNKGTHLQNSPSTVVVDTALLSYSLQEAGVPND
NQMIQKATDYLLQKQHKEKKDWSVHAPSLDAGGWGFSDVNTTIPDIDDTTAALRAIARSREGN
QRIEEAWRKGIEWVKGLQNIDGGWAAFERGVTSHFLTHLPLDNAGDMTTDPSTSDITGRVLEF
FGTYAPHQLKDDQKDRAIKWLMQAQEKNGSWYGKWGVCYIYGTWAALTGLRAVGVPSNHTA
LQKAATWLERIQHNDGGWGESCRSSIEKHFISLPFSTPSQTAWALDALITFYDTETPVIRKGISY
LLAHLNQNQDYPTGIGLPDGFYIRYHSYHHIFPILTFAHYIKKYMK >seq_ID 54
MLLYEKVRQEVERKVTALRTTQYQDGAWRFCFEGSPLTDCHMIFLLRLLGQNGEMEPFVTRV
ASLQTNEGTWKLYEDESVGNLSTTINAYVALLASGRYTKEDINMKRAEAFIRRQGGITKAHFMT
KFLLALHGGYEYPSLFHFPTPMLFLPEDSPLSIFELSSSARIHLIPMMICMNKRFTVSKTIFPNLDY
ISGGSKKQWFREERSPLFQTLLGDVKKFLSYPLSLQHKGYKEAERFMIERIETNGTLYSYASAT
FYMIYALLALGHSIQSPLISNAVLGLKSYIWNMNKGTHLQNSPSTVVVDTALLSYSLQEAGVPND
NQMIQKATDYLLQKQHKEKKDWSVHAPSLDAGGWGFSDVNTTIPDIDDTTAALRAIARSREGN
QRIEEDWRKGIEWVKGLQNIDGGWAAFERGVTSHFLTHLPLDNAGDMTTDPSTSDITGRVLEF
FGTYAPHQLKDDQKDRAIKWLMQAQEKNGSWYGKWGVCYIYGTWAVLTGLRAVGVPSNHTA
LQKAATWLERIQHNDGGWGESCRSSIEKHFISLPFSTPSQTAWALDALITFYDTETPVIRKGISY
LLAHLNQNQDYPTGIGLPDGFYIRYHSYHHIFPILTFAHYIKKYMK >seq_ID 189
MRSELLQLQSADGSWRLCFDSGTMPDSYFIIILRMLGYSQDEALIRQIASRILSRQLPNGTWKIY
PDEEDGNLDATAEAYFALLYSGFLTKLDPRMQLAKQFILSKGGLSKIRSLLTQAIFAAAGQASWP
KSMRIPLEVFFSDNGIGIDLFSLSGHARVHIVPIIMLANAQFVQHSASMPDLSDLFAGSSKRFEN
DSPWIAALATLIGSLSLSELLPFESPTPQEKAVQFLFDRLEPDGTLLTYTTATMFMILVLLMLGYS
SSSPLIHRMVSGIHSVICANSHVQIASSEVVVDTAMLVHALRKAGVNPTSTALENAGAYLRQRQQ
TQLGDWAIRNPGTPAGGWGFSNVNTLYPDVDDTTAALRAIQPYSSRTPELQADWQRGLNWVL
TMRNDNGGWPAFERQGSRLPITFFNFEGAKDIAVDPSTVDLTSRTLQFLGQELGMNAGNSWIE
STLRWVLSQQESNGSWYGRWGITYVHGTSAALQGLTAVGIAEDHPAVKKGVDWLLQVQNED
GGWGESCISDKVRRYVPLNFSTPSQTAWALDGLTAALPKPTPALERGVDALLQSLDRHDWTY
TYPTGGALPGSVYAHYASNNYIWPLLALSNIWQKYS >seq_ID 200
MALPFNQDSYKGDDEADVSKGAAKSPPSLEEAIQRSQEFLLAQQFPEGFWFGELEANVTIISHT
VILYKLLGIEENFPMYKFERYLRRMQCSHGGWEIAYGIGSYLSATIEAYIALRLLNVPQSDPALQK
ALRVILDSGGVTKARIFTKICLALLGSFDWRGIPSLPPWLILCPTWFPLSIYEVSSWARGCIVPLL
VILDKKPVFKVSPEVSFDELYAEGREHACKIIPISGDWTSKFFITVDRVFKMMERLRVVPFRQW
CIREAEKWILERQEESGDYVNIFPAMFYSVMCMKVLGYETDPVVQRALLGFKGFTIETADECK
VQSTVSPIWDTAFIVRALVDSGIPPDHPALQKAGQWLLQKQILKHGDWAFKDRQNPVNQRGFA
CLQRDSQIETADECRVQSTLSPVWDTAFVVKALVDSGIPPNHPALQKAGQWLLQNQTLTHGD
WAFKTQSGHLAAGGWAFQSHNRWYPDADDSAAVMMALDCIELPDEDVKNGAIARGLKWISAL
QSRNGGWAGYDKNCDQQWINKVPFNDLNGILDVPTADVTARVLEMVGRLSRLGAVGTPYSPR
HCTLVESIPHLLLPETIARGLAYLRREQEGEGCVWVGKWGVNYIYTCGALLALSQVAPTTHQE
EIARGAKWLAQVQNRCDKQKAAQGPRDGGWGESCFSYDDPALKGQNDASTASQTAWAVQG
LLAAGDALGKYEVEAIEQGVQYLLATQRKDGTWHEAHFTGSCFAQHFYVRYHYYAQHFPLSAL
GLYRTRILQHQ >seq_ID 139
MVADERSALIDALKRSQSVDGSWRFPFETGISTDAYMIILLRTLGIHDEPLIQALVERIESRQDAN
GAWKLFADEGDGNVTATVEAYYALLYSGYRKKTDSHMQKAKARILEVGGLERVHLFTKVMLAL
TGQHSWPRRFPLPLVFFLLPPSFPLNMYDLSVYGRANMVPLLVVAERRYSRKTDNSPDLSDLA
ASRNDWRLPDTEALWSYVKRSLTGLPAWLHRAAEQRAVRYMLEHIEPDGTLYSYFSSTFLLIFA
LLALGYPKDDPHIARAVRGLRSLRTEIDGHTHMQYTTASVVVNTALASYALQEAGVPPTDRTIEK
ANRYLLSRQHIRYGDWAVHNPYGVPGGWGFSDVNTMNPDVDDTTAALRAIRRAAAKETAFRH
AWDRANRWLFSMQNDDGGFAAFEKNVGKRFWRYLPIEGAEFLLMDPSTADLTGRTLEYFGTF
AGLTKDHSAIARAIDWLLDHQEADGSWYGRWGICYVVGTWAAVTGLSAVGVPIDHPAMQKAV
RWLLSIQNDDGGWGESCKSDGAKTYVPLGASTPVHTAWALDALIAAAERPTPEMKAGVRALV
RMLHHPDWTASYPVGQGMAGAFYIHYHGYRYIFPLLALAHYEQKFGPFVD

Enzyme Sequences

>seq_ID 13
MAQMASSLGSPRLLLRMGREAAQQQHLASGTEVQKALRLAVGHSLDLQRTDGAWCGEVHSN
ATFTAQYVFLQQQIGLPLDPTEIEGLSRWLFSQQNEDGSWGLGPGLGGDVSTTTETYLALKILG
VSPEDPRMAAARTSIIKAGSLPATRMFTRVFLASFGLIPWSAVPPLPAELILLPTLFPVNIYNLSS
WARATCVPLLLIRHHEPLHSLPNGRHAENDFLDELWTKDIPRDFCYTTPLSRMWRLGDYAGIFF
TSADHGFRFLGQYFNSPLRNLSRRKIINWILDHQEQSGEWAGYWPPQHNNIWALSLEGYSLDH
PVLRRGIAAVKSFVLHDATGMRAQVTVSQVVVDTALMSIALSDSAPSTGIISPTQAIDWLMHHEV
ASHRGDWRVLRPKLATGGFCFEEFNTLYPDVDDTAAVIMALIKSNPAHLISGCVRQCFGMMMA
GRHGYSLDCQLETRLRASSQLAIAYLLGCQENNGSVINVGRWGVNYLYGTSNVLCGLAYYYDR
SSLSKGDGKSNSNIVSAVDRASEWLKARQHSNGGWGEGLESYDNAQLAGCGQPTASQSAW
VTMALLNYLSPTDEVIQRGVSYLVRNQVKYGDESRATWPLERYTATGFPGHLYMEYDYYRHYF
PIMALGRYVNKLSGSHKLL >seq_ID 198
MEDLTQKLQQALQLASRALLNERVRPGLAHWEGELSTSALSTATAVMALFQYAKCQQASGRL
QKVFDGKSEGDWRLIEQGLAWLLQHQLADGGWGDTDKSISNISTTMLAHATLVACREAVRQK
SLVLNASDIDAAIERSGRLIEELGGIQAIRDRYGKDHTFSVPILTHAALAGLVSWNEIPALPYELAL
LPHRFFEVIQLPVVSYALPALIAIGQTLHLRQRTWNPWWIMVRRAAIPGTLQKLQSIQPESGGFL
EATPLTSFVTMCLASVGRVDHPVTQAGLKFIRDSVRPDGSWPIDTNLATWVTTLSINHLGAEAF
SSDEREALMRWLLQQQYRTMHPYTNAAPGGWAWTNLSGGVPDADDTPGAMLALMELDRVS
VSSQESLSIEQALYQAALWLIKLQNRDGGWPTFCRGWGALPFDRSSNDITAHCLRALIQYERRL
NDVTVDATGDTTSRPLAVEVPSPKLREQMQRSIQQGFEYLEKTQREDGSWLPLWFGNQHSPD
DENPLYGTARVLLAYADAGLEGSSAALRGCDWLVRHQHADGAWGPGTSIETADTSDAESDVE
GEPASIEETALALMALCRFDATHNVLHRGASWLITKVENETWREPTPIGFYFAKLWYYEKLYPQ
VFTVGALKALALRLGSALTTVSENEPAPSSAEPPIPPIATDRVADSMHLQRTSPSINLANGGITLA >seq_ID 252
SPVVVDTVLTLLALDDCGYNDCYSEEVDKAVQWVLDQQVLSKGDWSVKLPNVEPGGWAFEYA
NTRYPDTDDTAVALIVLSQFKDDPKWKERGINQAIERGVNWLFEMQCKNGGWGAFDKDNDKT
LLTKIPFCDFGEALDPPSVDVTAHIVEAFGKLGYSKDHPKIAHAIEYLKEEQEADGAWFGRWGV
NYVYGTGAVLPALEAIGEDMSQPYIRKAANWLVLHQNEDGGWGE >seq_ID 253
SPVWDTVLTLLAFDDCDKNEAYQASVEKAVQWTLDNQVLRKGDWSVKLPDVEPGGWAFEYA
NTFYPDTDDTAVALIVLSQFRDVEKWQEAGIEKAIERGVNWLFAMQSKNGGWGAFDKDNDNN
FITKIPFCDFGEALDPPSVDVTAHCIEAFGKLGLSRARPEIARGLDYLKSEQEADGAWFGRWGV
NYVYGTGAVLPALEAIGEDMSQPYIRKAANWLILRQNEDGGWGE >seq_ID 257
SPVWDTXLTLLALDDCDLNERQSKEVEKAVQWVLNQQVLRPGDWCVKVPKVQPGGWAFEYK
NYFYPDTDDTAVALIVLSQFRDDPKWQEKNIEQAIDRGLNWLIGMQCKGGGWGAFDKDNDKT
YLTKIPFCDFGEALDSPSVDVTAHIVEAFGKLGLGKSHPAMIRAIDYLKAEQEQDGAWFGRWGV
NYIYGTGAVLPALEAIGEDMRAPYIAKACDWLIAVQQEDGGWGE >seq_ID 254
SPVVVDTLLTLLAYDDSGQNERKADEVEKAVDWVLAXQVLRPGDWKVKAPNLEPGGWAFEYA
NYFYPDTDDTAVALIVLSQFRNDAAWKEKGIEQAIEKGVNWLFGMQCKGGGWGAFDKDNDKQ
FLTKIPFCDFGEALDPPSVDVTAHIVEAFGKLKFSKDHPNIRRAIDYMKDEQEADGAWFGRWGV
NYIYGTGAVLPALEAIGEDMFAPCIGRACDWLVSRQNDDGGWGE >seq_ID 255
SPVVVDTLLTLLAYDNSGHNARKASEVEKAVDWVLAQQVLRPGDWNVKAPNLEPGGWAFEYA
NYFYPDTDDTAVALIVLSQFRNDAAWKDKGIEQAIEKGVNWLFGMQCKGGGWGAFDKDNDR
QFLTKIPFCDFGEALDPPSVDVTAHIVEAFGKLKFSKDHPNIRRAIDYTKDEQEDDGAWFGRWG
VNYIYGTGAVLLALEAIGEDMSAPYIGRACDWLVSRQNDDGGWGE >seq_ID 256
SPVVVDTLLTLLAIEDSGQSVKRAQEVEKAVDWVLSQQVLRPGDWKVRAPHLEPGGWAFEYAN
YFFPDTDDTAVALIVLSQFRNDAAWKAKGIETAIEKGVNWLLGMQCKGGGWGAFDKDNDKTYL
TKIPFCDFGEALDPPSVDVTAHIVEAFGKLGFSKDHPNIARAIEYLKSEQESDGXWFGRWGVNY
VYGVGAVLPALEAIGEDMSAPYIGRACDWLVSKQNSDGGWGE >seq_ID 258
SPVVVDTVLTMLAIHDCGADKQYAPQMDKAIDWLLANEVRHKGDWAVKLPDVEPGGWAFEYS
NACYPDLDDTAVALIVLAPYRNDPKWQARDIEGAVERAVDWTLAMQCKNGGWGAFGKDNDK
AILTKIPFCDFGEALDPPSVDVTAHVLEALAALGYDNSHPAVARAIRYLRDEQEPDGSWWGRW
GVNYIYGTAAVLPALKAMGVDMNEPFVHKAADWIGSVQNEDGGWGE >seq_ID 302
SPVVVDTSLVLVAMQEAGVPVDHPALVKAAQWLLDREVRLKGDWRVKSPDLEPGGWAFEFLN
DWYPDVDDSGFVMLALKDIKVRDKKQKSQAIKRGIAWCLGMQSANGGWGAFDKDNTKYLLNK
IPFADLEALIDPPTADLTGRMLELMGTFNYPKSHVAVVRALGFLKSVQEPEGPWWGRWGVNYI
YGTWSVLGGLDAIGEDMSQPYIRKAVNWLKSKQNLDGGWGEVCETYEDRSLMGCGPSTPSQ
TSWALLSLFSAGElNAKAVLRGIKYLVETQNQDGSWDEDAYTGTGFP

| Enzyme Sequences |
|---|

>seq_ID 271
SPVVVDTAISVISLAXSGMERGHPALVRAAXWLMSKEIKTAGDWKVTNPAGPVGGWAFEFNNA
FYPDIDDSAMVMMALRHVHLDEHTAHRREKACLRGLNWLLSMQSRTGGWAAFDKDNTKVIMT
KIPFADHNAMIDPPWADITGRVLEFLGYIGYDQSYPAVARAARFLREEQEEDGSWFGRWGVNY
IYGTWQVLRGLAAIDEDMSQPYIRRAAEWLRSVQPPDGGWGETCATYHDPSLKGKGPATPAQ
TAWAVMGLMAAGIYDESVSRGIDYLVRTQRPDGTWDETEYTGTGFP >seq_ID 299
SPVWDTALVLVAMQEAGVPVDHPALIKSAQWLLDLEVRRKGDWHVKSPDLEPGGWAFESLND
WYPDVDDSGFVMLFIKDIKVRDKKLKDQAIKCGIAWCLGMQSENGGWAFDKDNTKHLLNKIP
FADLEALIDPPTADLTGRMLELMGNFNYPKSHQAAVKALDFLKVEQEGPVWVGRWGVNYIY
GTWSVLCGLEAIGEDMSQPYIKKAVNWLKSKQNLDGGWGEVCDSYADRSLMGCGPSTASQT
SWALLSLFAAGEVSSKAALRGVEYLLSTQKLDGTWDEDAFTGTGFP >seq_ID 314
SPVVVDTALAVRALAAAGVPPEHPAMVKASEWLLTQQIFKPGDWSIKCPDLPPGGWAFEFVNN
WYPDVDDSSMVLVALKDGLADAAKHQAALQRGINWCLGMQSKNGGFASFDKDNTKEWLNSL
PFGDLKALVDPPTEDITARILEMMGAFGHGLDHPVAARALAYLHQTQRPEGPVWVGRWGVNYI
YGTWSVLVALKRIGEDMSRPYVRRAVDWVKAHQNPDGGWGEFCESYRNPELMGKGPSTAS
QTAWALLGLFAAGEVHAPEVTAGVDYLVKTQDSLGRWDEEQFTGTGFP >seq_ID 251
SPVVVDTVLTMLSVQDCDADENSENAPAIEKAIEWLLANEVRTGGDWQEKVKGVEPGGWAFEY
KNASYPDTDDTAVAMMALAPYRTEEKWKKKGLPEALKRAAEWNIAMQCSNGGWGAFDKDND
KTILCKIPFCDFGEALDPPSVDVTAHVLEGLAALDYPPEHPAIQRAVQFIKDEQEPDGSVWVGR
WGVNFIYGTAAALPALKAVGEDMRAPYIDRAAKWIVDHQNEDGGWGE >seq_ID 312
SPVWDTALAVRALAAAGVPPEHPAMVQASEWLLTQQIFKPGDWSVKCPDLPPGGWAFEFVN
NWYPDVDDSSMVLVALKDGLADAAKHQAALQRGINWCLGMQSKNGGFASFDKDNTKEWLNA
IPFGDLKALVDPPTEDITARILEMMGAFGHGLDHPVAVRAMAYLHETQRPEGPWWGRWGVNYI
YGTWSVLVALKRIGEDMSRPYVRRAVDWVKAHQNLDGGWGECCESYRNPELMGRGPSTAS
QTAWALLGLFASGEVHTPEVKAGVDYLVKTQNSLGRWDEEQFTGTGFP >seq_ID 250
SPMWDTVLTTLAVQDAGVDQEPEFKPAMERTLEWLLKNEVRTGGDWQQKTRGVEPGGWAF
EYANASYPDNDDTAVALIVLAPFRHDPKWQARGIQHVIDRAVNWMFAMQCDNGGWAAFDLDN
DKAILTRIPFCDFGEALDPPSVDVTAHVLEALAALGYSREHPAVRRAIAFLKEDQEPDGSWFGR
WGVNFIYGTAAALPALKAMDEDMTQDWITRAADWMRSRQNDDGGWGE >seq_ID 260
SPVVVDTVLTLLAIQDADKQDDMAAEVDRAIGWLLSKEVRTNGDWSVKLPDVEPGGWAFEHEN
ARYPDTDDTAVAVMVLAPYRHHPKWRKRGLPEALDRAISWMRAMQCRNGGWGAFDKDNDN
AFLCVIPFCDXGEALDPPSIDVTAHALEAFAAMGFGPEDTTVARALDYMSKEQEADGSWWGR
WGVNYIYGTAAALPAYKAFGQDMRDPKLMKAADYLRAKQNADGGWGE >seq_ID 259
SPVVVDTVLTLLAMEDCEATEEHAAAIEQAIEWLLENEVRTPGDWQMKVPDADPGGWAFEYAN
AAYPDVDDTAVAILVLARYRDDPKWQAKGLPQAIDRAVAWVLAMQCSNGGWAAFDKDNDKSI
LCKIPFCDFGEALDPATVDVTAHVLEALAAVGYGPDHPAVRRGLDFLYAEQEADGSVWVGRWG
VNYVYGTGAALPAFKAIGADMRDPRMLKAADWILRCQNKDGGWGE >seq_ID 261
SPVVVDTVLTLLAIQDADKQEEMAGEIDKAIGWLLSKEVRTKGDWSVKLPRVEPGGWAFEHENA
RYPDIDDTAVAIMVLAPYRDHPKWKKRGLPEALDRAIAWMRAMQCRGGGWGAFDKDNDKQIL
CTIPFCDFGEALDPPSIDVTAYALEAFAAMGYGPDDKTVARALKYMSKEQEADGSVWVGRWGV
NYIYGTAAALPAYKALGQDMRDPGLMKAADYLRDKQNADGGWGE >seq_ID 262
SPVVVDTVLTLLAMQDADRTDKHKAAVDKAIQWVLDQEVRTPGDWCVQTPDVEPGGWAFEYE
NARYPDVDDTAVAIMVLAPYQDDPKWRKRGLPDALARAIAWIRAMQCKNGGWGAFDRDNDN
SMLTVIPFCDFGEALDPPSVDVTAHALEAFHMMGYGPEDPTVARALAYLDAEQEQDGSVWVGR
WGVNFIYGTSAALPALKAMGRDMRDPRYTKAADYLRAVQNDDGGWGE >seq_ID 275
SPVVVDTLLALLALQDCDRELTAEMSRALDWVLANEVRYHGDWTKKVKGVEPSGWAFERANL
NYPDIDDTAVALIVLARLPRAWLDEPRIRATIDRVLGWTLAMQSSNGGWAAFDKDNDRPIITKIP
FCDFGEALDPPSADVTAHVLEALGLLGFDRRHPAVERGLRFLRSEQEADGSWFGRWGVNYVY
GTAAVLPGLAAIGEDMTQDYIRRANDWLIAHQNPDGGWGE >seq_ID 280
SPVWDTLLSLVALQDCGKELTPARERALEWILGREIRTRGDWAKKVKNVEASGWAFERANLHY
PDIDDTAVALIMLARLPRAWLDQPRIRAVIDRALGWTLAMQSSSGGWAAFDKDNDRLIITKIPFC
DFGEALDPPSADVTAHVLEALGILGFDRQHAAVRHGLKFLRSEQEADGSWFGRWGVNHVYGT
GAVLPALAAIGEDMAQDYVRRAADWLVAHQNADGGWGE

| Enzyme Sequences |
| --- |

>seq_ID 277
SPVWDTLLALLAMQDCERELTPQMERALDWVLANEVRYYGDWSKKVRGVEPSGWAFERANL
NYPDIDDTVVALIVLARLPRALLDQPRIRAVIDRALGWTLAMQSSNGGWAAFDKDNDHLIITKIPF
CGFGEALDPPSADVTAHVLEALGLLGFDRHHPAVARGYQFLRKEQEADGSWFGRWGVNHIY
GTAAVLPALAAIGEDMSQPYIRAAAEWIIAHQNADGGWGE >seq_ID 300
SPVVVDTALVLVAMQXAGVPVXHPALVKSAQWLLDLEVXXKGDWQVKSPELEPGGWAFXFLN
DWYPDVDDSGFVMLSIKXIKVRDKKHKEQAIKRGISWCLGMQSDNGGWAAFDKNNTKYLLNKI
PFAXLEALIDPPTAXLTGRMLELMGNFNYPKTHKAAVQALEFLXMEXEPXGPVWVGRWGVNYIY
GTWSVLCGLEAIGEDMAQPYIKKSINWLKSKQNMDGGWGEVCESYGDRSLMGCGPSTASQT
SWALLSLFAAGEVHSKAATRGIEYLLATQKLDGTWDEDAYTGTGFP >seq_ID 279
SPVVVDTLLXLLAMQDCERESTPSMERALDWXXANEVRYYGDWSKKVRGVEPSGWAFXRANL
NYPDIDDTDVALIVLARLPRALLDQSRVHAVIDRALGWTLXMQSSNGGWAAFDKDNNHLIITKIP
FCDFXEALDPPSADVTAHVLEALGLLGFNRNHPAVERGYRFLRSEQETDGSWFGRWGVNHVY
GTXAVLPALAAIGEDMTQPYIRSAAEWIIAHQNADGGWGE >seq_ID 264
SPVVVDTLLTLEALLDCNLSPKTFTGMQAAVDWILSKQIVTPGDWQIKVPGVSCGGWAFERANT
FYPDMDDTAVAMIVLARIRRYYNDSSRIDRALACATDWILSMQCSNGGWAAFDLDNTNDLVTRI
PFSDFGEMLDPPSVDVTAHVVEALGCLGRTRNDPAVARAVAYILDEQEPEGSWFGRWGVNHI
YGTGAVLPALAAVGTDMSAGYITRAADWVATHQNADGGWGE >seq_ID 19
GGWMFQASISPIWDTGLTVLALRSAGLPPDHPALIKAGEWLVSKQILKDGDWKVRRRKAKPGG
WAFEPHCENYPDVDDTAMVVLALNGIQLPDEGKRRDALTRGFRWLREMQSSNGGWGAYDVD
NTRQLTNRIPFCNFGEVIDPPSEDVTAHVLECFGSFGYDEAWKVIRKAVEYLKAQQRPDGSWF
GRWGVNYVYGIGAVVPGLKAVGVDMREPWVQKSLDWLVEHQNEDGGWGE >seq_ID 278
SPVVVDTLLSLLAMQDCERGFTPSMERALDWVLANEVRYYGDWSKKVRGVEPSGWAFERANL
NYPDIDDTAVALIVLARLPRAQLDQPRIREVIDRALGWTLAMQSSNGGWAAFDKDNDHLIITKIP
FCDFGEALDPPSADVAAHVLEALGLLGFERKHPAVERGLKFIRSEQEADGSWFGRWGVNHIY
GTAAVLPALXAIGEDM >seq_ID 315
SPVVVDTALAVRALAAAGLPPDHPFMTQATSWLLTQQIFKPGDWCIKCPDLPPGGWAFXFHNN
WYPDVDDSSMVLVALKDGLPDTARHQAALQRGINWCLGMQSKNGGFASFDKDNTKEWLNAL
PFGDLKALVDPPTEDITARILEMMGAFGHGLDHPTADRALAFLRRTQHPEGPVWVGRWGVNYL
YGTWSVLVALKRIGXDMSRPYVQRAVNWIKSHQNPDGGWGEVCESYRHPELMGQGPSTASQ
TAWALLGLLAAGEIQAAEVKAGVDYLVKTQNAQGRWDEKYFTGNWLP >seq_ID 297
SPVVVDTALVLQAMQEASIPLDHPALVKAAQWLLDREVRIKGDWKIKSPGLEPGGWAFEFQND
WYPDVDDSAAVLIAIKDIQVKNNKAKQGAVRRGIDWCLGMQSKNGGWGAFDKDNTKHLLNKIP
FADLEALIDPPTADLTGRMLELMGNFGYDKHHPQAVHALEFLKKEQEPEGPWFGRWGVNYIY
GTWYVLIGLEAIGEDMNQPYIKKAANWIKSRQNIDGGWGE >seq_ID 17
QASISPVVVDTGLAVLALRAAGLPADHDRLVKAGEWLLDRQITVPGDWVVKRPNLNPGGFALQF
DNVYYPDVDDTAVVIWALNTLRLPDERRRDAMTKGFRWIVGMQSSNGGWGAYDVDNTSDL
PNHIPFCDFGEVTDPPSEDVTAHVLECFGSFGYDDAWKVIQRAVAYLKREQKPDGSWFGRW
VNYIYGTGAVVSALKAVGIDMREPYIQKALDWVEQHQNPDG >seq_ID 303
SPVVVDTALVLVAMQEAGVPLDHPALVKAAQWLLDREVRIKGDWRIKSPDIEPGGWAFEFLND
WYPDVDDSGFVMLAIKDVKVRDKKKKEQAIKRGINWCLGMQSANGGWGAFDKDNTKYLLNKI
PFADLEALIDPPTADLTGRMLELLGTFNFPKDHHAIERALEFIQLEQEPEGPVWVGRWGVNYIYG
TWSVISGLEAIGEDMSQPYIRKTVNWLKSKQNMDGGWGE >seq_ID 298
SPVVVDTTLVLVAMQEAGVPVDHPALVKSAQWLLDLEVRRKGDWQVKSPDVEPGGWAFEFMN
DWYPDVDDSGFVMLAIXNIRVRDKKHQEQAIKRGIAWCLEMQSENGGWGAFDKDNTKYLLNKI
PFADLEALIDPPTADLTGRMLELMGNFDYSASYPAAVRALEFLKKEQEPEGPVWVGRWGVNYIY
GTWSVLCGLEAIGEDMSQPYIRKAVNWLKSKQNLDGGWGE >seq_ID 301
SPVVVDTALALVAMQEAGVPKDHPALVKAAQWLLDLEVRRKGDWQIKSPELEPGGWAFEFLND
WYPDVDDSGFVIMAIRDIKAPDKKHKEQAIKRGIAWCLGMQSKNGGWGAFDKDNTKHLLNKIP
FADLEALIDPPTADLTGRMLELMGSFDYPMDHPAAARALEFLKKEQEPEGPWWGRWGVNYIY
GTWSVLCGLESIGEDMSQPYIKKAVNWLKSKQNMDGGWGE >seq_ID 276
SPVVVDTLLTLLAMEDCDRGLTPSMQRALEWVLAQEVRYAGDWSKKVKGVEPSGWAFERANL
NYPDIDDTAVALIVLARLPRAWLDEPRIRATIDRVLGWTLAMQSSNGGWAAFDKDNDRPIITKIP

| Enzyme Sequences |
| --- |

FCDFGEALDPPSADVTAHVLEALGLPGFDRRHPAVERGYKFLRSEQEADGSWFGRWGVNHIY
GTAAVLPALASIXEDM

>seq_ID 283
SPVVVDTCLTSNALVESGGDTSAPHVHRSVQWLLNQEIRNHGDWSVKAPKVGPSGWAFEFAN
KVYPDVDDAAEVIIALANYSNDSGTAPPDAIARGVRWISGMQSSNGGWGSFDKNNTSFFVTRL
PFFDFGEVIDPPSVDVTAHVIEALAVAGWQEKASKQIQKALDYIWSEQEADGPWFGRWGINYIY
GTCAVLSALEAIGYDMADARVVKALKWIEECQNADGGWGE >seq_ID 307
SPVVVDTPWMIEALLETGVPPGDPALLRAGRWLMSKQITGVRGDWAMKSPKGKPGGWAFEFE
NDYYPDVDDTIQVLTALCKLSIPWREKEKAVMQGIDWLISMQNDDGGWGAFDRNQTRWIVNRI
PFSDHKACLDPSSPDITGRMVEFLMRRNYSTSHPSVKKALKYIRETQEDFGAWFARWGINYIY
GTWCVLTALAAMGICHTDSRVAKAVAWLSSVQRPDGGFSEAADTYHPHKPFESYSESVPSQS
AWALMGLVAGGAVHSPAAARAACYLINNRNLNNGWDERHYTGTGFP >seq_ID 267
SPVVVDTAISVIALAESGLHRGHPSLVQATEWLVANEIRRGGDWQVKNPTAPISGWAFEFKNDF
YPDVDDTAMVLLALRHVHLYNDDVSQDREKSYLRGLNWMLSMQCKNGGWAAFDRDNVKTIF
EKIPFADHNAMIDPPSVDITGRVLELLGYVGYDKSYPCVTKALEYIKKDQEADGSWYGRWGVN
YIYGTWQVLRGLAAIGEDMQSEYVQKAVRWMKSVQNPDGGWGE >seq_ID 309
SPVVVDTVLSITALADADLPRTHPAMRRAVAWVLGKQVLCEGDWRVKNRRGEPGGWSFEFNN
NFYQDNDDTAAVLIALHKARLPDEAKGEAMQRGLRWLLSMQCDDGGWSAFDVNNNKRLLNKI
PFADLESMLDPSTCDLTGRTLEALGSIGFPFTHRIVQHAVRFIRQHQEADGAWYGRWGVNYIY
GTCHVLCGLLSVGEDMHQPYVQRAVQWLIEHQNADGGWGE >seq_ID 202
MVYSYEMMVLLDYPEDHPLRVECKAALKKLVVHRDDGSSYCQPCLSPVWDTAWSVMALEQA
PSDARTETAIARAYDWLTDRQVLDLRGDWENNAAPSTPPGGWAFQYENPYYPDIDDSAVVLA
MLHARGKRTGQPGRYEMPVARCLDWIIGLQSRNGGFGAFDANCDRDFLNAIPFADHGALLDP
PTEDVSGRVLLALGITERPQDATARERCIQYLRDTQQPDGSWWGRWGTNYIYGTWSVLAGLG
LAGVDRKLPMVRNGLQWLRGKQNADGGWGETNDSYARPELAGKHEDGSMAEQTAWAMLG
QMAVGEGDADSVHRGAAYLLDAQNEDGFWMHPYHNAPGFPRIFHLKYHG >seq_ID 306
SPVVVDTPWTVMALLEAGVPSNDPALLRSGRWLLAKQITDTKGDWAIKNKNTAPGGWSFEFEN
KYFPDVDDTIEVLHCLHKLAIPWREKEKPCRLGIDWLLSMQNDDGGWGAFDKNQKRQVVNRIP
FSDHGACLDPSSPDITGRMIEFLATQKFNSEYESVKRALKYIWKTQEDFGGWHARWGINYIYGT
WCVLTGLRAIGFNMTDRRVQKALNWLESIQNKDGGFGESPASYEECRYIPWKESVPSQTAWA
LMALVAGGGAGSAPAENAATFLINYRNSNGVVVDEECYTGTGFP >seq_ID 281
SPVVVDTLLLTLLAYQDCELEMNDSAGRALDWILSQENSYRGDWAHRNKKLEPSGWAFERANLH
YPDIDDTSVALIVLARLPQAVRSRPDIKSAIDRALAWTLGMQCRNGGWAAFDRDNDKLIITMIPF
CDFSEALDPPSADVTAHVVEAMAHLGFDRSHKAVEKAYQYLLAEQEDDGSWFGRWGVNHIY
GTAAVLPALAALGEDATVPHVKRAADWISAHQNTDGGWGE >seq_ID 310
SPVVVDTALAVRALAAAGLPPEHPAMVKASEWLLTQQIFKPGDWSVKCPDLPPGGWAFEFVNN
WYPDVDDSSMVLVALKEGLADAAKHQAALQRGINWCLGMQSKNGGFASFDKDNTKEWLNAIP
FGDLKALVDPPTEDITARILEMMGAFGHGLDHPVAVRGLAYLHQTQRPEGPVWVGRWGVNYIY
GTWSVLVALKRIGEDMSRPYVRRAVDWVKAHQNPDGGWGE >seq_ID 311
SPVVVDTALAVRALAAAGLPPEHPAMVKASEWLLTQQIFKPGDWSVKCPDLPPGGWAFEFVNN
WYPDVDDSSMVLVALKDGLVDAAKHQAALQRGINWCLGMQSKNGGFASFDKDNTKEWLNAI
PFGDLKALVDPPTEDITARILEMMGAFGHGLDHPVAVRALAYLHQTQRPEGPVWVGRWGVNYI
YGTWSVLVALKRIGEDMNRPYVRRAVDWVKAHQNLDGGWGE >seq_ID 290
SPIWDTAKAVNALHESGLPSDHPQLKAAARWLVEKEVRKPGDWKMRVPHVDVGGWPFQFRN
EFYPDVDDTAAVVMALGRVDERDVPGIKDSITRGINWVTQMQCSCGGWAAFDVDVKREFLTK
VPYADHNAMLDPPCPDITGRCLEMYGRFPGVRKDADVQRVIEKGIEYLKKTQEPDGSWYGRW
GVNYIYGTWQSLKGLAAVGEDPSQPYIQKAAHFLKTHQNSDGGWGE >seq_ID 292
SPVVVDTAKAVNALHESGLPSDHPQLKAAARWLVEKEVRKPGDWKMRVPHVDVGGWPFQFR
NEFYPDVDDTAAVVMALGRVDERDVPGIKDSITRGINWVTQMQCSCGGWAAFDVDVKREFLT
KVPYADHNAMLDPPCPDITGRCLEMYGRFPEVRKDANVQNVIAKGIEYLKKTQEPDGSWYGR
WGVNYIYGTWQSLKGLAAVGEDPSQPYIQKAAHFLKTHQNSDGGWGE

| Enzyme Sequences |
| --- |

>seq_ID 293
SPVVVDTCLSLAALTEAGAQNDHPAVKQAVEWLLDHQIFVEGDWCAQASGLEPGGWAFQYEN
DKYPDVDDTGMVLMSLLRAGVHDKEHKRKRVNQALNWVLGMQNPDGSWGAFDIENNYEYLN
KIPFADHGALVDPGTADLTARCVELLAMLGYDATFPPVKRALEFLEHDQEEDGSWYGRWGVN
YIYGTWSVLCALGAIGEDVAKPYVRKSVQWLQDTQNEDGGWGE >seq_ID 313
SPIWDTALAVRALTAAGMPPEHPAMVKASEWLLTQQIFKPGDWSVKCPDLPPGGWAFEFVNN
WYPDVDDSSMVLVALKEGLADTAKHQAALQRGINWCLGMQSKNGGFASFDKDNTKEWLNAIP
FGDLKALVDPPTEDITARILEMMGAFGHGLDHPVAVRALAYLHETQRPGGPVWVGRWGVNYLY
GTWSVLVALKRIGEDMSRPYVRRAVDWVKDHQNLDGGWGE >seq_ID 304
SPVVVDTPWMVMALLEAGVPTDXPGLLRAGRWLISKQITGVHGDWAVKNRHALPGGWSFEFE
NDYFPDVDDTIEVLHVIHRLAIPWEEKSECCRLGLDWLLSMQNDDGGWGAFDRNQTLVMVNRI
PFSDHAACLDPSSPDIVGRVLEFLASRSFSREHPAVKRALDYIWREQSPFGGVWVARWGIDYLY
GTWCVLTGLRAIGWDMEDPRVRKAVAWLESVARPDGGYGESPESYRDHSYVEWKRSVPSQT
AWALMGLVAGGVGHGKAARGAADYLLTSRNAQGGWDEMDYTGTGFP >seq_ID 291
SPMWDTAKAVNALHESGLPSDHPQLKAAARWLVEKEVQKPGDWKMRVPYVDVGGWPFQFR
NEFYPDVDDTAAVVMALGRVDERDVPGIKDSITRGINWVTQMQCSCGGWAAFDVDVKREFLT
KVPYADHNAMLDPPCPDITGRCLEMYGRFPEVRKDVDVQRVIEKGIEYLKKTQEPDGSWYGR
WGVNYIYGTWQSLKGLAAVGEDPSQPYIQKAAHFLKTHQNSDGGWGE >seq_ID 318
SPVWDTGLALHALLESGMDPDDPAIAKAMHWLDEREITDVAGDWAEQRPGLAPGGWAFQYR
NDHYPDVDDTAVVGMAMHRANPQARPETLERTRAWIEGMQSQNGGWGAFDADNTHYHLNHI
PFADHGAMLDPPTADVSARCLGMLSQMGYDRDHPSIQRAIAYLKNDQEEDGSWFGRWGTNYI
YGTWSVLSALNAAGEDMSQPYIRKAVDYLTNFQREDGGWGE >seq_ID 294
SPVVVDTCLSLAALTEAGAQNDHPAVKQAVEWLLDHQIFVEGDWCDQAPGLEPGGWAFQYEN
NKYPDVDDTGMVLMSLLRAGVHDKEHKRKRVNQALNWVLGMQNPDGSWGAFDIENNYEYLN
RIPFADHGALVDPGTADLTARCVELLAMLGYDATFPPVKRALEFLEQDQEEDGSWYGRWGVN
YIYGTWSVLCALGATGEDVAKPYVRKSVQWLQDTQNEDGGWGE >seq_ID 320
SPVWDTCLGLHALLEAGEPREAPSVKKAVDWLLEREITETYGDWVVVRRPHLKPSGWAFQYW
NNYYPDVDDTAVVVMALDRVGDPRCRPAIERACEWIIGMQSTSGGWGSFDPENEFTYLNHIPF
ADHGALLDPPTVDVTARCISMLAQVGYRHDHPAIRKSVXFILREQEKDGSWYGRWGTNYVYG
TWSALSALNAVGEDMSSPVVRKGVAWLEAFQQPDGGWGE >seq_ID 295
SPVVVDTCLSLTAMTESGAHPEHPAVKQAVEWLLDQQIFVKGDWADQAKNLEPGGWAFQFEN
DRCPDVDDTGMVLMALLRAGVQDKEHKIKRINQAVNWVLGMQNPDGSWGAFDIGNDHEYLN
NIPFADHGALVDPGTADLTARCVELLAMLGYGPDFPPIQRAVAFLERDQEEFGAWYGRWGVN
YIYGTWSVLSAIGILGEDYAKPYVRKAVEWLKEIQNDDGGWGE >seq_ID 324
SPVVVDTSLAAHALLEAGEPNDPEVIGLLDWLKDKQILTTVGDWSARRPNLRPGGWAFQYENP
HYPDVDDTAVVAMAMHRQGDPKYAEAIARACEWLAGMQSSSGGWGAFDPENEHFYLNSIPF
ADHGALLDPPTVDVTARCVGCLAQVDAERFASEIQAGIDYIKREQEEDGSWFGRWGANYVYG
TWSALVALNKAGEDMNTPYIRRAVDWLKARQRPDGGWGE >seq_ID 296
SPVVVDTCLSLNALTEADMPANDPRVRAAVQWLFDRQIFVRGDWSENAPELEPGGWAFQYEN
DKYPDVDDTGMVLMSLLRANAHEHDAQRKRMNQALNWVLGMQNSDGSWGAFDIDNHYTYL
NNIPFADHGALVDPGTADLTGRCIELFGMLGYDKNFTPARRGIEFLKRDQHPCGGWYGRWGV
NYLYGTWSVLTALGAIGEARDAPYLRRAVEWLYSVQNDDGGWGE >seq_ID 305
SPVVVDTPWMVMALLEAGCPANDPXLIRAGRWLKAKXITEVRGDWAVKNRKALPGGWSFEFE
NDYFPDVDDTIEVLSVIHRLSIPWNEKAKSCRLGLEWXLSMXNRDGGWGAFDREQXFKVVNRI
PFSDHAACLDPSSPDITGRMVEFLASXNFSKGHVAVRRALDYIWKQQAXFGGWWARWGIDYL
YGTWCVLTGLASLGFXMDDPRARKAADWLESIQHADGGFGESPESYREDSFVDWKRSVPSQ
TAWALMGLVAAGRASGAAAQRAAAWLLDNRNTNGSWDEQDYTGTGFP >seq_ID 282
SPMWDTSLAAHALMEADGRGDPKDNPRLISAMDWLADKQILDHVGDWAVRRPDVRPGGWAF
QYENPDYPDVDDTAVVVMAMHRADPERYEMSIDRACEWLVGMQSKNGGWGAFEPENEHYY
LNSIPFADHGALLDPPTVDVTARCVGALAQVDRDRYAAEIANGIRSIRREQEDDGSWFGRWGA
NYVYGTWSALVALKGAGEDMQQPYIRRAVDWLKARQRSDGGWGE >seq_ID 316
SPVVVDTAWAVIGLCESGMERTHPAVRSAIRWLYSMQILRPGDWAVKNPLTEPGGWAFEFHND
FYPDNDDTAAVLMGLLFSDLNDEENHRAFERGVRWLLSMQNNDSGWGAFERNVDNKIFDQIP

| Enzyme Sequences |
| --- |
| FNDQKNMLDPSTADVTGRVVELLGRIGRRLGGSFSDEPYVRQAIEFLKNEQEPEGCWFGRWG
VNYIYGTWSVLVALEAIGESMRAPYIRKAVNWVKKVQNPDGGWGE >seq_ID 266
SPIWDTGIVLHSLVESGVSPDHEALLRSVSWLLAKEVTHEGDWKVKCPDAPVGGWYFEYANE
FNPDCDDTAKVLMATSRFSSVDFPDAGRLRDARNRGLQWLLHMQNKDGGWAAFDKGCDNEL
LTYIPFADHNAMIDPSTEDITGRVLETLAREGFDNTHPVVKRAIQYLHKTQDAEGPWYGRWGS
NFIYGTWLVLQGLKAVGEDMTXPRYQRAANWLLNVQNXNGSWGE >seq_ID 323
SPMWDTSLAAHAFLESGDREDPRLIRALDWLVDKQILDHVGDWAVRRPGLRPGGWAFQYEN
PDYPDVDDTAVVAMAMHRTDPERYAENIDRACEWLAGMQSKNGGWGAFDPENEHYYLNSIP
FADHGALLDPPTVDVTARCIGCLAQVDAEAFADNIKRGIGFIKREQEPDGSWFGRWGANYIYGT
WSALVALKGAGEDMSQPYIRKSVAWLKGRQGPDGGWGE >seq_ID 274
SPVVVDTILSMQALLDTKEVFQPSPTLKKAMEWLLEQQVRAWGDWKVYVSDARGGGWAFQRA
NSFYPDVDDTIMVMMALRNVSPRGESKVVDEAIERALFWVLGMQCEDGGWAAFDRDNAKAFL
TKVPFADHNAMIDPSTADLTSRTFEMFAMIAPEVFTIHHPVVRRGLEFLKKDQCKDGSWFGRW
GVNYMYGTWQVLRGLRLIGEDMSKGYVRKGVEWFKSVQLEDGGWGE >seq_ID 284
SPVVVDTVAQLHALIASGLARRDEALRRAASWLLTRQSRTHGDWSGRNPAEPGGFYFEFRNEF
YPDVDDTAMALMVLTQAEANVATDVQHAAIARALAWMLGMQNRDGGWAAFDRDNDKHFLTQ
VPFADHNAMIDPSTADITGRVLGALSHVPSYGPDHPSVRRAIAFLQRDQEPDGSWYGRWGVN
YLYGTGQVLRGLRAIGFDMQQPFVRRAARFLSAHQNDDGGWGE >seq_ID 285
SPVVVDTAITIIALAESGLPKNHPAFEQAATWLEKKEIRFKGDWAVRMPGVEPSGWAFEHENKY
YPDTDDTMMVLMALRHVQSRNSAERCEQFDRALKWLLAFQCQDGGWAAFDKDVTASWLEH
VPFADHNAILDPTCSDLTARVLELLGSISFDRQSAIVRRAVAMMRRTQETDGSWYGRWGVNYI
YGTWQALRGLAAIGENMDQEWIRRGRDWLESCQNDDGGWGE >seq_ID 308
SPVVVDTAIAGYALGESGCAPQSALRRMADWLLTKEVRRKDDWSVKRPDVEPSGWYFEFANE
FYPDTDDTAMVLLSLLHGRATNPAAQEACAKRAVNWLLAMQSKDGGWAAFDVDNDWKPLSY
VPFADHNAMLDPSCPDITGRVLEALCKYGVSQEHPAVLRAIDYLIQTQEQDGSWHGRWGVNY
VYGTFLALRGLKAAGVSDREAYVLRAGEWLDLIQNPDGGWGE >seq_ID 288
SPVVVDTAITAVSLAESGLEPDHPALQKSAEWLLDKEVRIQGDWAIKNRHGEASGWAFEFNNEF
YPDVDDTLKVLLALRLIKTRDEETKREAMERALGWVMSFQCSDGGWAAFDKDVTQRWLEDVP
FADHNAILDPTCSDITARCLELLGKMGCTSDHPAVRRALRMVRETQEPDGTVWVGRWGVNYIY
GTWQILRGLSALKIDMNQDWIVRAKEWLESCQNPDGGWGE >seq_ID 287
SPVVVDTAITSVALTSSGVKPDHPQIQKAADWLLDREVVMRGDWKVKNPYPHASGWAFEFNND
FYPDADDTFKVLLALMKMKSSDPERQRKIMDRALDWARSFQCKDGGFAAFDKDVTKKWLEHV
PFADHNAILDPSCSDITARGLECMGKLGWPRTDRVIRRAIRYLKKTQEEDGSWWGRWGVNYIY
GTWQSLRGLEAIGEDMNQDWVVRARNWLESCQNPDGGWGE >seq_ID 289
SPIWDTAIVTMAIAESGQDPNDPRLQKAADWLLEREIGFRGDWRENCDFPEATGWAFEFNND
WYPDVDDTFQVILGLKPLSASDSRRQEQTLDRAIRWCRAMQCREGGFAAFDKDINDAWLNEV
PFADHNAILDPPCSDITGRALETLSLMGFDREDPVVRRARQYLMETQLEDGSWFGRWGVNYIY
GTGHALRGLHAIGEDINGSAMQRARNWLENCQNDDGGWGE >seq_ID 286
SPVVVDTAINVISLAESGLLSDHPALQKAADWLVNKEVRFRGDWSVNNSYPQVSGWAFEYNNV
YYPDTDDTAMVLMALRLIRPKDPQALNELFRRALDWQLSFQCRDGGWAAFDKNVTTPWLEDM
PFADHNAILDPTCSDLTARTLELLGYTGFDPKAQSVRDALQYLIDTQDEDGSWYGRWGVNYIY
GTWQVLRGLRAMGQDMTQDWILRGRDWLESCQNSDGGWGE >seq_ID 270
SPVVVDTALAMSALLEGDTAPDDEALQRGCRWLLGKEVRHRGDWQVNVGAEPGGWFFEYEN
EFYPDCDDTAEVLAVLERVRLSDPEEDQRRRDALDRALAWQLGMQSTNGGWGAFDKDCDHR
ILELVPFADHNAMIDPPTVDVTSRSIEAALAMGVPASDAAIRRAVRFLYSEQEADGSWYGRWG
SNYLYGTWLALCALRSAGEDLTSPAVQRAVEWLLSVQQEDGGWGE >seq_ID 322
SPVVVDTGIAAHALGEAGHASAMQSTADWLLTKEVRRKGDWSVKRPDVEPSGWYFEFANEFY
PDIDDTAQVLLGLAHAKASDPAKQKACMDRAVAWLLAMQGSDGGWAAFDVDNNWEFLSSVP
FADHNAMLDPTCPDITGRVLEALAACGVPNSHPAVKRGVEFLRNSVEKDGSWYG RWGVNYIY
GTYLALRGLRASGEDDREAHILRAGEWLRAIQNADGGWGE |

Enzyme Sequences

>seq_ID 263
SPVVVDTSLILNALLAGSEKTETDPKILKAGQWLLDREVREIGDWKIKNNRGPVGGWYFEYANE
FYPDCDDTAEVITVLNQMQFSDPEKEKAKQVAQQRGLDWLLSMQNKDGGWPAFDKNCDKQS
LTYMPFADHNAMIDPSYEDITGRTLEALASLGFSEDDPIVRRAVDFLKSKQLPDGTWYGRWGC
NFLYGTWLAIScLYHAGEDLNEERYQSLLSWLEQCQNEDGGWGE >seq_ID 268
SPVVVDTCLILNSMLEHLEPDHPRVQKAAEWLLSKEVTEPGDWQVKCPEAPVGGWYFEYANEF
YPDCDDTAEVLAALQRVQFTDADREAQKRGAIQRGLGWLLAMQNQDGGXAAFDRECTREALT
YVPFADHNAMIDPSNGDITGRVLKALDYAGYSPDDPIVRGGVDFLLANQEPDGTWYGRWGCN
HLYGSWLVVVVGLKHAGVNLQQTQFTQVMSWLESCQNADGGWGE >seq_ID 265
SPVVVDTTNAMTAVLDAGLPGNHPAVLRAARWLLSKEVRMPGDWRLWYKNGEPGGWFFEYN
NEFYPDADDTAEALHCLCRVVFDCEDEMDRCRAAIKRGLNWQFACQNPDGGWPAFDKECDD
EYLTFIPFADHNAMIDPSCCDITGRSLQALSKLGYTTNDVDVKRAIDYLLDAQEDDGTWYGRWG
INYIYGTWLAVQGLRAIGVDLSEKRFQKVTKWLRKKQNPDGGWGE >seq_ID 269
SPVVVDTCLILNSLLEHLEPDHPRLQHAAEWLLSKEVTEPGDWQVKCPEAPIGGWYFEYANEFY
PDCDDTAEVLAALQRVRFSDADREAQKHAAIERGLGWLLAMQNGDGGWAAFDRECTREALT
YVPFADHNAMIDPSNGDITGRVLKALDYSGRSPQDPVVQGGVHFLLANQEPDGTWYGRWGC
NHLYGSWLAIWGLKHAGVDSQQSQFMRLLSWLESCQNPDGGWGE >seq_ID 319
SPVVVDTSLSAHALMEAGLEENDKRLEGLLDWLKDLQILDVKGDWVARRPDVRPGGWAFQYR
NDHYPDVDDTAVVAMAMHRQGDEKYKEAIDRAAEWIVGMQSSSGGWGAFDPENEHFYLNSI
PFADHGALLDPPTEDVTARCVGFLAQLDPDAYAEPIKRGVEFLKRTQQEDGSVWVGRWGANF
VYGTWSVLCALNAAGEDPKSPYIQKAVAWLKSRQREDGGWGE >seq_ID 321
SPVVVDTGIACQALQEVGGPAADAGVQRALDWLVERQLRDEPGDWRRDRPDLEGGGWAFQY
NNPHYPDLDDTSMVAWVMQVADHGRYREEIRRAAKWVNGMRSEGGGFASFEVDNTYYYLNH
IPFADHGXLLDPPTXDVTARCIAVLAITDRAQHETVIREAIDFLFVDQEEDGSWFGRWGTDYIYG
TWSVLSXLDVVGFDMRDARVRXSVEWLFXQQNPDGGWGE >seq_ID 272
SPVVVDTGLVALALQEVDKHNSQDALQRNLKQAYSWLLSKQLKDEPGDWRISKPTLTGGGWAF
QFNNPHYPDVDDTAVVAFALAQAEHTELDESIHLATRWIEGMQSQNGGYGAFDVDNTFYYLNE
IPFADHGALLDPPTADVSARCAMLMARVAKDHEEYLPALERTIQYLRSEQEADGSWFGRWGT
NYVYGTWSVLLGLEQTNVPKTDPLFTKAAQWLKSVQRPDGGWGE >seq_ID 273
SPVVVDTGLVALALPEVDKHNSQDALQPNLKQAYSWLLSKQLKDQPGDWRISKPTLTGGGWAF
QFNNPHYPDVHDTAVLAFALAQAEHTELDESIHLATRWIEGMQSQNGGYGAFDVDNTFYYLNE
IPFADHGALLDPPTADVSARCAMLMARVAKGHEEYLPALERTIQYLRSEQEADGSWFGRWGT
NYVYGTWSVLLGLEQTNVPKTDPLFTKAAQWLKSVQRPDGGWGE >seq_ID 317
SPVVVDTILGMIGLVDCGHDGKDPLLVTARDWIVKRQLLVNYGDWKVYNPNGPSGGWSFEYDN
SWYPDVDDTAAIVIGFLKQDYEFRHSEVVKRACDWIASMQNQXGGWAAFDINNDKTFLNEIPF
SDMESLCDPSSPDVVGRVLEAFGILNDPKYAEVCRRGIEYLRRTQESEGSWFGRWGVNYVYG
TSNVLCSLKRQDVAXKDPMVTRALTWLKKVQNKDGGWGE >seq_ID 215
MGRQTRNLTRREPAAEAEERGFRLLDAHRRADSSWVGELSSSALATAMSALALRLLGHPAES
GPVAGGLAWLAATRNPDGGWGDAPGEPSNMNATSIAAAALARCAPRRYREEVAGGRRWVE
EHGGFAALNDPRTTTLSGPGRTLWALAGLVPPERVRKLPTEMILLPRRIRRTVSTTFPAFLSLSL
LHERFRPSPRWRRPLRRRAEREALAWLRRAQGPNGSYEESAFLTSLIAAALTAAGAEGGDIVR
RALPFVLRSRRPDGSWPIDRDLENFDTTQAILAHHEAGRPLREAGRVREWLLDNQFRRPFFPT
SSPPGGWAWAYPAGWPDTDDTACALRSLRLLGVPAGHPSIRLGLRWLYRMQNRDGSWPTFV
RGSRMPFDHGCPYITSQVLSALALMGPEARRGAPLRRALAYLRRAQRPDGSLGSLWFRPHTR
GTAAAVEAFSDLGLSGDPLVGRAARWLAEHQNPDGGWGDGHGAPSTAEETAWASAALLRLG
GGEAARKGVRWLVEHQDPGGWKPAVIGLYYASLSYSDTFYALSYPLVALARHRRLSR >seq_ID 191
MIKKILVLILLMMTSKVDIERVQTVIRDAREICWNELTDNEWVYPTYLGTLFLSEYYFELKALGI
QNSQFEESKFTQILLGSQLPDGSWVQVEDAYIQTGQLDATIFNYWYLKAVGIDIHTDTMKKAQE
WIKANGGIEKAQTMTKFKLAMFGQYPWKKLFKIPLILFYKKFNPLYIKDITAQWVYPHMTALAYL
QNQRIIFNVAVSISELYKNKAPKIKNHQKKGRPSFFINNLVQEMLKLRQPMGSFGGYTVSTLLSM
LALNDYTGRTNKHKSEISDALKKGLDFVEFNYFNFRQAYHGSLDDGRWWDTILISWAMLESGE
DKEKVRPIVENMLQKGVQPNGGIEYGYDFGYAPDADDTGLLLQVLSYYGTDYADAMDKGAEF
VYSVQNTDGGFPAFDKGKMGKNPLYKYAFKIAGIADSAEIFDPSSPDVTAHILEGLISSDRSNYD
VVVKSLKYFMDTQENFGSWEGRWGINYIYAAGAVLPALKKMNNGWAKAVNWLVSKQNADGG
FGETTLSYRDPKKYNGIGVSTVTQTSWGLLGLLAVEDHYDVKEAIEKARDGEFKDISVVGTGHR
GLLYLQYPSYARSFPVISLGRFLDQQR

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10190112B2). An electronic copy of the "Sequence Listing" will also be available from the USPTO upon request and payment of the fee set forth in 37 CFR 1.19(b)(3).

The invention claimed is:

1. An enzyme mutant with cyclase activity which is a mutant of a wild-type enzyme comprising the amino acid sequence of SEQ ID NO: 209 with a mutation at a position corresponding to position F445 of the amino acid sequence of SEQ ID NO: 209, wherein up to 10% of the amino acid residues in said enzyme mutant are altered relative to the amino acid sequence of SEQ ID NO: 209 by deletion, insertion, substitution, addition, inversion, or a combination thereof, and wherein said enzyme mutant catalyzes at least the cyclization of a citronellal isomer to at least one isopulegol isomer.

2. The enzyme mutant of claim 1, wherein up to 5% of the amino acid residues in said enzyme mutant are altered relative to the amino acid sequence of SEQ ID NO: 209 by deletion, insertion, substitution, addition, inversion, or a combination thereof.

3. The enzyme mutant of claim 1, wherein the mutation at the position corresponding to position F445 of the amino acid sequence of SEQ ID NO: 209, is a substitution selected from the group consisting of F445N, F445Q, F445L, F445M, F445E, F445G, F445S, F445V, F445T, F445C, F445I and F445A.

4. The enzyme mutant of claim 1, wherein said enzyme mutant is a single mutant comprising F445X, with X=N, Q, L, M, E, G, S, V, T, C, I, or A of the amino acid sequence of SEQ ID NO: 209.

* * * * *